(12) United States Patent
Goswami et al.

(10) Patent No.: US 8,722,930 B2
(45) Date of Patent: May 13, 2014

(54) PROTEASE INHIBITORS

(75) Inventors: Rajeev Goswami, Uttaranchal (IN);
Anil Kumar Vuppala, Andhra Pradesh (IN); Ramesh Veludandi, Andhra Pradesh (IN); Ramesh Sistla, Karnataka (IN); Chakshusmathi Ghadiyaram, Karnataka (IN); Muralidhara Ramachandra, Bangalore (IN)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 13/321,078

(22) PCT Filed: May 18, 2010

(86) PCT No.: PCT/FI2010/000031
§ 371 (c)(1),
(2), (4) Date: Jan. 31, 2012

(87) PCT Pub. No.: WO2010/133748
PCT Pub. Date: Nov. 25, 2010

(65) Prior Publication Data
US 2012/0136002 A1     May 31, 2012

(30) Foreign Application Priority Data

May 18, 2009  (IN) .............................. 758/KOL/2009

(51) Int. Cl.
*C07C 233/65*   (2006.01)
*A61K 31/165*   (2006.01)

(52) U.S. Cl.
USPC ............... 564/164; 514/253.13; 514/255.01; 514/307; 514/311; 514/314; 514/318; 514/330; 514/348; 514/349; 514/395; 514/522; 514/540; 514/620; 544/365; 544/389; 544/391; 558/416; 548/307.4; 560/34; 546/146; 546/168; 546/171; 546/194; 546/226; 546/293; 546/297

(58) Field of Classification Search
USPC ........ 564/164; 514/620, 253.13, 255.01, 307, 514/311, 314, 318, 330, 348, 349, 395, 522, 514/540; 560/34; 558/307.4; 548/307.4; 546/146, 168, 171, 194, 226, 293, 297
See application file for complete search history.

(56) References Cited

U.S. PATENT DOCUMENTS 5,691,364 A    11/1997   Buckman et al.

FOREIGN PATENT DOCUMENTS

| WO | WO 96/28427 A1 | 9/1996 |
| WO | WO 01/97794 A2 | 12/2001 |
| WO | WO 2009/027450 A1 | 3/2009 |

OTHER PUBLICATIONS

Taha et al., Eur. J. Med. Chem., 40(7), 701-727, 2005.*
Phillips et al, J. Med. Chem., 1999, 42(10), 1749-56.*
Gary Phillips, et al.; "Design, Synthesis, and Activity of 2,6-Diphenoxypyridine-Derived Factor Xa Inhibitors;" Journal of Medicinal Chemistry; vol. 42; pp. 1749-1756; Apr. 24, 1999.
J. Enyedy, et al.; "Structure-Based Approach for the Discovery of Bis-Benzamidines as Novel Inhibitors of Matriptase;" Journal of Medicinal Chemistry, ACS; vol. 44, No. 9; pp. 1349-1355; Apr. 26, 2001.
International Search Report for PCT/FI2010/000031, dated Sep. 1, 2010.

* cited by examiner

*Primary Examiner* — Shailendra Kumar
(74) *Attorney, Agent, or Firm* — Finnegan, Henderson, Farabow, Garrett & Dunner, LLP

(57) ABSTRACT

A compound of formula (I) wherein $R_1$ to $R_{15}$, $P_1$, $P_2$, A, B and Q are as defined in the claims and pharmaceutically acceptable salts and esters thereof, are disclosed. The compounds of formula (I) possess utility as matriptase inhibitors and are useful in the treatment of matriptase dependent conditions, particularly cancer.

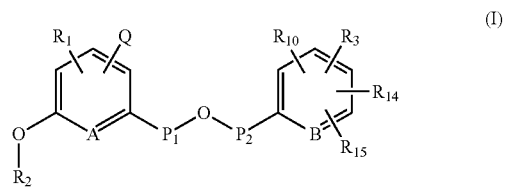

11 Claims, No Drawings

PROTEASE INHIBITORS

This is a national stage application under §371 of international Application No. PCT/FI2010/000031, filed on May 18, 2010, which claims the benefit of priority of Indian Patent Application No. 758/kol/2009, filed on May 18, 2009.

TECHNICAL FIELD

The present invention relates to therapeutically active compounds and pharmaceutically acceptable salts and esters thereof useful in the treatment of conditions involving matriptase activity, particularly cancer.

BACKGROUND OF THE INVENTION

Cancer drug discovery has traditionally focused on targeting DNA synthesis and cell division, resulting in drugs such as antimetabolites and DNA alkylating agents. Although these drugs show efficacy, their lack of selectivity for tumor cells over normal cells can lead to severe side effects. The recent recognition that certain genes are associated with cancer has resulted in several rational and targeted drugs for cancer therapy. However, many of the available targeted cancer treatments inhibit only a specific aspect of cancer progression such as proliferation, angiogenesis or metastasis. This limits their utility and necessitates their use in combination with traditional chemotherapeutic agents. Examples of such targeted cancer drugs include erlotinib (Tarceva®) and bevacizumab (Avastin®). Erlotinib inhibits cell proliferation, while bevacizumab is an anti-angiogenesis drug. These drugs target kinases or proteins involved in kinase signaling pathways. Recent findings indicate that matriptase, a transmembrane serine protease, plays a role in triggering the formation of tumor cells. Unlike kinases, the localization of matriptase on the cell surface makes it more accessible to a potential inhibitor. Matriptase is over-expressed (up to several hundredfold) in all phases of cancer in multiple cancer types and has also been shown to play a role in invasion and metastasis. Therefore, a matriptase inhibitor could comprise a potential first-in-class drug with a broad spectrum of anti-tumor activity including anti-proliferative and anti-invasive activities.

Matriptase is a multi-domain 80-kDa type II transmembrane serine protease and belongs to the S1 trypsin-like family. Matriptase is involved in matrix remodeling/degradation, regulation of cell growth and survival, cell motility, cell morphogenesis, and activation of other membrane bound proteins. It is also called the membrane-type serine protease-1 (MT-SP1), the tumor-associated differentially expressed gene-15 (TAGD-15), or epithin in mouse. Matriptase is over-expressed in a vast array of human tumors of epithelial origin including prostate, ovarian, uterine, colon, epithelial-type mesothelioma, cervical and head and neck squamous cell carcinoma. Epidemiological studies have revealed that increased expression of matriptase relative to HAI-1 correlates with the grade of the tumor and results in poor prognosis in breast and ovarian cancer.

The role of matriptase has been well established in pathways involved in cancer even though the exact function of human matriptase has not been elucidated. Matriptase enhances tumor cell proliferation through phosphatidylinositol 3-Kinase signaling and invasion through the HGF/cMet and uPAR activation. Glycosylation of matriptase by UDP-GlcNAc alpha-mannoside beta1-6-N-acetylglucosaminyl-transferase (GnT-V) plays a key role in metastasis by increasing the stability of degradation-resistant active form of the enzyme. Furthermore, matriptase activates other proteases such as receptor-bound urokinase-type plasminogen activator (uPA). Overexpression of uPA or its receptor (uPAR) is a feature of malignancy and plays a critical role in angiogenesis, tumor invasion and metastasis. Down-regulation of matriptase inhibits tumor invasion through suppression of uPAR activation.

Several other "trypsin like serine proteases" such as uPA, trypsin, plasmin, hepsin and kallikrein play a critical role in cancer affecting various pathways leading to angiogenesis, invasion and metastasis. Urokinase-type plasminogen activator (uPA) plays a major role in extracellular proteolytic events associated with tumor cell growth, migration and angiogenesis. Many cancer cells secrete pro-uPA and its receptor uPAR. Binding of pro-uPA to uPAR leads to its activation, with subsequent generation of plasmin by the uPA-catalyzed hydrolysis of extracellular plasminogen. The increased production of plasmin leads to degradation of extracellular matrix both by plasmin itself and by other proteases that are activated by plasmin. The surface location of bound uPA provides directionality to the degradation of matrix, thereby assisting the directional migration of cancer cells. uPA in complex with uPAR also affects other biological processes including signaling pathways that influence cell proliferation. Hepsin is another type II transmembrane serine protease (TTSP) expressed on the surface of epithelial cells. It has been implicated in ovarian cancer and prostate cancer, where several gene expression studies have identified it as one of the most highly induced genes. Hepsin over-expression was associated with basement membrane disruption and was shown to be connected the HGF/c-Met pathway and uPA pathway connecting hepsin to the pathways leading to basement membrane disruption and tumor progression.

Therefore, inhibitors of matriptase and other related serine proteases could be of significant therapeutic value because of the following reasons:

potential to be used as a 'mono-therapy' due to wide expression and activity of matriptase and other proteases in both early and late stages of cancer superior safety profile due to localization of matriptase, uPA and hepsin at the cell membrane which avoids the need of cellular entry of the drug superior efficacy profile due to tumor-specific expression potential for reducing morbidity due to a larger therapeutic window that results from fewer therapy-related side effects typically associated with cytotoxic agents Matriptase inhibitors have been described earlier e.g. in Enyedy, I. et al., J. Med. Chem., 2001, 44, 1349-1355; and in international patent publications WO 01/97794, WO 2004/058688, WO 2004/101507, WO 2008/085608, WO 2008/107176, WO 2008/097673, WO 2008097676 and WO 2008/107176. Other benzamidine compounds have been described earlier e.g. in Phillips, G. et al., J. Med. Chem., 1999, 42, 1749-1756; Phillips, G. et al., J. Med. Chem., 1998, 41, 3557-3562; and EP 0 813 525.

SUMMARY OF THE INVENTION

It has been found that compounds of formula (I) are serine protease inhibitors. In particular, it has been found that the compounds of formula (I) are potent and selective matriptase inhibitors. The compounds of the invention are able to inhibit invasion and metastasis of various tumor cells and inhibit tumor growth. Compounds of the invention provide also good safety, and are therefore particularly useful in the treatment of cancer.

The compounds of the present invention have a structure represented by formula (I)

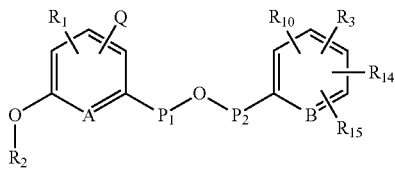

wherein
$P_1$ and $P_2$ are, independently a bond or $C_{1-3}$ alkyl;
A is CH or N;
B is CH or N;
$R_1$ is hydrogen, amino, —NH—$SO_2$—$ZR_9R_{13}$, —$NR_4$—CO—$ZR_9R_{13}$, —CO—$NR_7R_8$, —CO—O—$ZR_9R_{13}$, —CO—$NR_4$—$R^X$—$ZR_9R_{13}$ or a group of formula

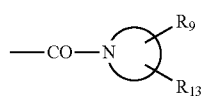

wherein the ring portion in formula (II) is a 5-12 membered saturated, partially saturated or aromatic ring which may be monocyclic or bicyclic, and which may contain 1-3 further heteroatoms selected from N, O, S or combinations thereof;

$R_3$ is —C($NR_{17}$)$NH_2$, or in case A is CH, $R_3$ can also be amino $C_{1-7}$ alkyl;

$R_{10}$, $R_{14}$ and $R_{15}$ are independently hydrogen, halogen, hydroxy, $C_{1-7}$ alkyl, halogen $C_{1-7}$ alkyl or —C($NR_{17}$)$NH_2$;

Q is hydrogen or halogen, with a proviso that $R_1$ and Q are not simultaneously hydrogen;

$R_4$ is hydrogen or $C_{1-7}$ alkyl;

Z is a 5-12 membered saturated, partially saturated or aromatic ring which may be monocyclic or bicyclic, and which may contain 1-3 heteroatoms selected from N, O, S or combinations thereof;

$R_9$ and $R_{13}$ are, independently, hydrogen, halogen, hydroxy, carboxy, $C_{1-7}$ alkyl, carboxy $C_{1-7}$ alkyl, hydroxy $C_{1-7}$ alkyl, $C_{1-7}$ alkoxycarbonyl, $R^A NH_2$ or —COR$^B NH_2$;

$R^A$, $R^B$ and Rx are, independently, a bond or $C_{1-7}$ alkyl;

$R_7$ and $R_8$ are, independently, hydrogen, amino $C_{1-7}$ alkyl, carboxy $C_{1-7}$ alkyl, or in case A is CH, $R_7$ and $R_8$, independently, can also be $C_{1-7}$ alkyl, with a proviso that $R_7$ and $R_8$ are not simultaneously hydrogen;

$R_2$ is $C_{1-7}$ alkyl, amino $C_{1-7}$ alkyl, carboxy $C_{1-7}$ alkyl, $C_{1-7}$ alkoxycarbonyl $C_{1-7}$ alkyl, $C_{1-7}$ alkylamino, carboxy $C_{1-7}$ alkylamino, $R^D$C($NR_{17}$)$NH_2$, or a group of formula (III)

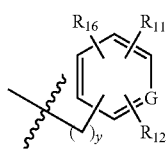

y=0-2; $R^D$ is a bond or $C_{1-7}$ alkyl; G is CH or N; $R_{11}$ is hydrogen, halogen, amino, carboxy, amino $C_{1-7}$ alkyl, $C_{1-7}$ alkoxycarbonyl, halogen $C_{1-7}$ alkoxy, —C($NR_{17}$)$NH_2$, —NHCOR$^G NH_2$, R$^J$NHCOOR$^U$ or —CONR$_{19}R_{20}$;

$R^G$ is $C_{1-7}$ alkyl; $R^J$ is a bond or $C_{1-7}$ alkyl; Ru is hydrogen or $C_{1-7}$ alkyl;

$R_{12}$ and $R_{16}$ are, independently, hydrogen, halogen or $C_{1-7}$ alkyl; or $R_{12}$ and $R_{16}$ form, together with the carbon atoms to which they are attached, a 5 or 6 membered saturated, partially saturated or aromatic ring which may contain 1-3 heteroatoms selected from N, O, S or combinations thereof, which ring can be substituted;

$R_{17}$ is hydrogen, —OH, $C_{1-7}$ alkoxy, —O(CO)OR$_8$ or —(CO)OR$_{18}$;

$R_{18}$ is $C_{1-7}$ alkyl;

$R_{19}$ and $R_{20}$ are, independently, hydrogen, $C_{1-7}$ alkyl or $C_{1-7}$ alkoxy;

or a pharmaceutically acceptable salt or ester thereof.

In one class of preferred compounds are compounds of formula (I), wherein A is CH and B is CH. A subclass of these preferred compounds are compounds wherein $R_3$ is —C($NR_{17}$)$NH_2$ and $R_{10}$, $R_{14}$ and $R_{15}$ are hydrogen. In one class of preferred compounds are compounds wherein $R_2$ is a group of formula (III) wherein G is CH, y is 0-1, $R_{11}$ is —C($NR_{17}$)$NH_2$ or amino $C_{1-7}$ alkyl, $R_{12}$ and $R_{16}$ are hydrogen. In still another class of preferred compounds are compounds of formula (I), wherein $P_1$ and $P_2$ is a bond. In still another class of preferred compounds are compounds of formula (I), wherein $P_1$ is a bond and $P_2$ is —$CH_2$—.

In one class of preferred compounds are compounds of formula (I), wherein $R_1$ is a group of formula (II). In another class of preferred compounds are compounds of formula (I), wherein the ring portion of formula (II) is a 6 or 10 membered saturated, partially saturated or aromatic ring, which may be monocyclic or bicyclic, and which may contain one further heteroatom N. Examples of particularly preferred compounds are those, wherein the ring portion of formula (II) is piperidinyl, piperazinyl, nonahydro-quinolinyl or 3,4-dihydro-1H-quinolinyl. In another class of preferred compounds are compounds of formula (I), wherein $R_1$ is —$NR_4$—CO—$ZR_9R_{13}$, —CO—O—$ZR_9R_{13}$, or —CO—$NR_4$—$R^X$—$ZR_9R_{13}$. Z is suitably a 6 or 10 membered saturated, partially saturated or aromatic ring, which may be monocyclic or bicyclic, and which may contain 1 or 2 N atoms. Examples of particularly preferred compounds are those, wherein Z is cyclohexyl, piperidinyl, phenyl, naphthyl or quinolinyl. In a subclass of preferred compounds are compounds, wherein Z is cyclohexyl or piperidinyl, $R_4$ is hydrogen, $R^X$ is a bond, $R_9$ is $R^A NH_2$ and $R_{13}$ is hydrogen.

In another class of preferred compounds are compounds of formula (I), wherein A is N and B is CH.

The present invention also provides a pharmaceutical composition comprising a compound of formula (I) together with a pharmaceutically acceptable carrier.

The present invention provides further a method for the treatment of a matriptase dependent condition, comprising administering to a subject in need thereof a therapeutically effective amount of a compound of formula (I).

The present invention provides a compound of formula (I) for use in the treatment of a matriptase dependent condition.

The present invention provides further a method for the treatment of cancer, comprising administering to a subject in need thereof a therapeutically effective amount of a compound of formula (I).

The present invention provides a compound of formula (I) for use in the treatment of cancer.

DETAILED DESCRIPTION OF THE INVENTION

The compounds of the invention can be prepared according to the following Schemes. It should be noted that any appropriate leaving groups, e.g. N-protecting groups, such as t-butoxycarbonyl (t-BOC) group, can be used in well known manner during the syntheses in order to improve the selectivity of the reaction steps.

Compounds of formula (I), wherein $R_1$ is —NH—SO$_2$—ZR$_9$R$_{13}$, $R_3$ is —C(NR$_{17}$)NH$_2$, $R_2$ is a group of formula (III) and $R_{11}$ is —C(NR$_{17}$)NH$_2$ can be prepared according to the Scheme 1 or Scheme 2 by sulfonylating the amino group of the compound of formula (IV) with suitable sulfonylchloride Cl—SO$_2$—ZR$_9$R$_{13}$ using a base such as sodium hydride, TEA, DIPEA or combinations thereof along with solvents such DMF, THF and the like at temperatures ranging from about 0° C. to 80° C. The reaction affords the sulfonamide of formula (V).

SCHEME 2.

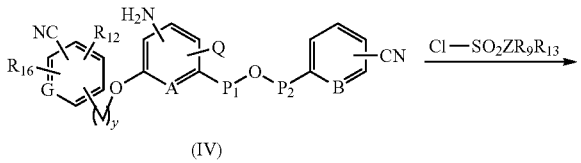

(IV)

SCHEME 1.

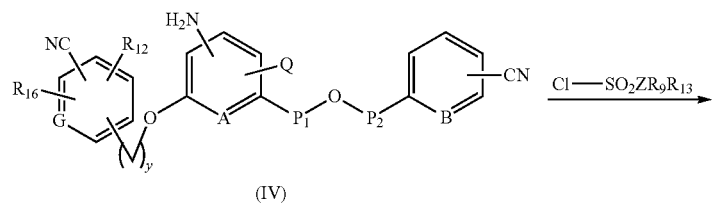

(IV)

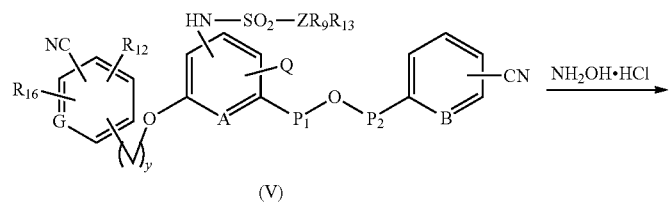

(V)

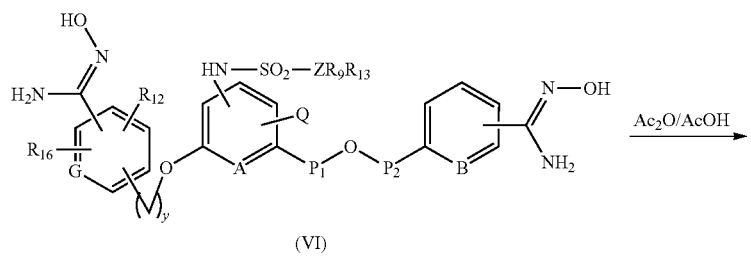

(VI)

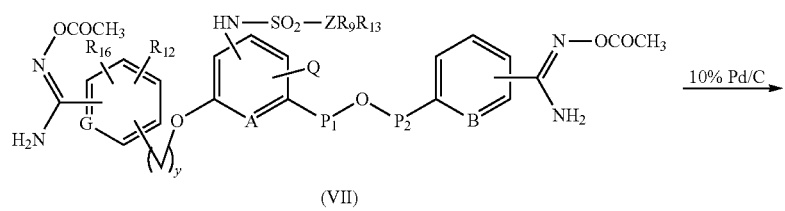

(VII)

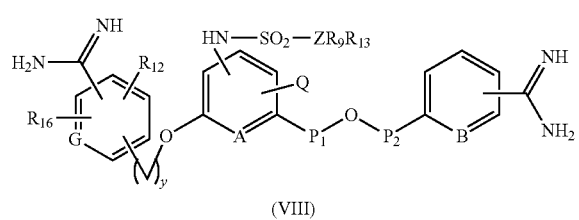

(VIII)

-continued

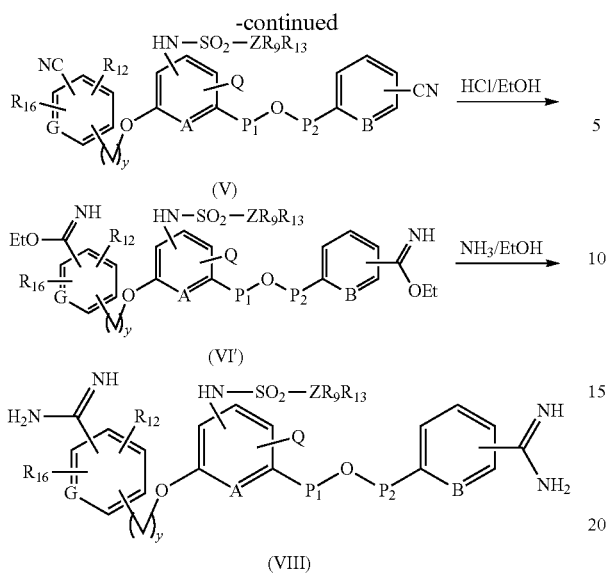

Compound of formula (V) is converted to the corresponding imidate (VI') or hydroxyamidine (VI) derivative as explained below.

Using the method of Scheme 1, the nitrile group of the compound (V) is reacted with hydroxylamine hydrochloride with a suitable base such as TEA or DIPEA in solvent such as DMF, THF and the like at temperatures ranging from about 20° C. to 100° C. to afford the hydroxyamidine compound (VI). This compound is either first acetylated using acetic anhydride in solvents such as acetic acid at RT and then reduced using a reducing agent such as Zn, Pd/C and the like in solvents such as methanol, ethanol or acetic acid at temperatures ranging from about 20° C. to 50° C. to afford the corresponding amidine compound (VIII). Alternatively the hydroxyamidine (VI) is directly reduced with a reducing agent such as Pd/C in solvents such as methanol or acetic acid at a temperature ranging from about 40° C. to 70° C. to afford the corresponding amidine compound (VIII).

Subsequent to the above step, deprotection of the product from any protecting groups such as t-BOC, where applicable, is carried out with appropriate reagents such as HCl-TFA or the like to afford the required final compounds.

Using the method of Scheme 2, the nitrile group of the compound of formula (V) is allowed to react with alcoholic HCl for approximately 15 to 48 h at a temperature ranging from about 0° C. to about RT to afford the corresponding imidate ester (VI'). This compound is then subjected to reaction with alcoholic ammonia to get the corresponding amidine compound (VIII).

Compounds of formula (I), wherein $R_1$ is —CO—$NR_7R_8$, and $R_2$ is a group of formula (III) and $R_{11}$ is —C($NR_{17}$)$NH_2$, can be prepared according to the Scheme 3 by coupling the carboxylic group of compound (IX) with amine $HNR_7R_8$. The reaction is carried out in the presence of suitable coupling reagents, such as PyBOP, EDC.HCl or HOBt and the like, and a base such as DIPEA, TEA and the like in a solvent of such as THF, DMF and the like under inert atmosphere at a temperature ranging from about 0° C. to 40° C. The reaction affords the desired amide compound of formula (X). Starting from compound (X) and following the last steps of Scheme 1 or 2 affords the final product.

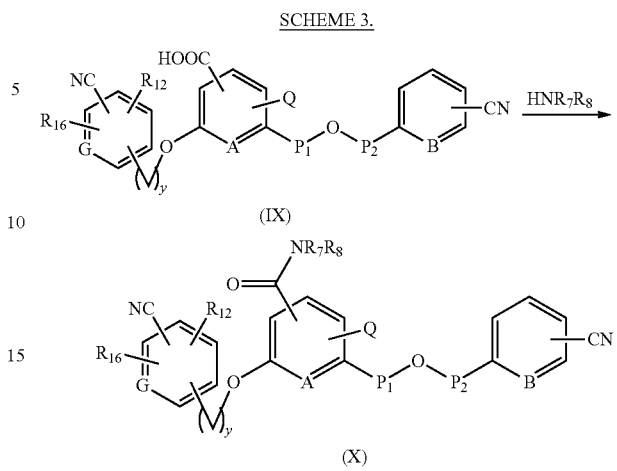

Compounds of formula (I), wherein $R_1$ is —CO—$NR_4$—$R^X$—$ZR_9R_{13}$, $R_2$ is a group of formula (III) and $R_{11}$ is —C($NR_{17}$)$NH_2$, can be prepared according to the Scheme 4 such as to obtain first a compound of formula (XI) and following then the last steps of Scheme 1 or 2 to obtain the final product.

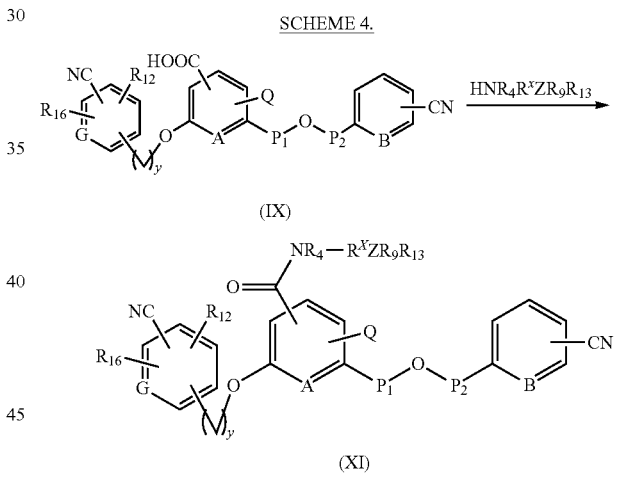

Compounds of formula (I), wherein $R_1$ is —CO—O—$ZR_9R_{13}$, and $R_2$ is a group of formula (III) and $R_{11}$ is —C($NR_{17}$)$NH_2$, can be prepared according to the Scheme 5 such as to obtain first a compound of formula (XXXII) and following then the last steps of Scheme 1 or 2 to obtain the final product.

SCHEME 5.

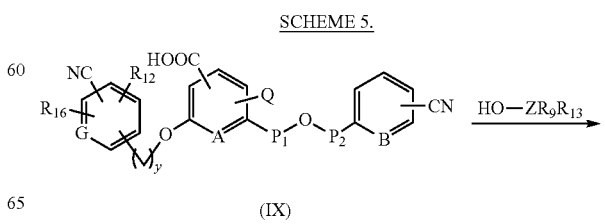

-continued

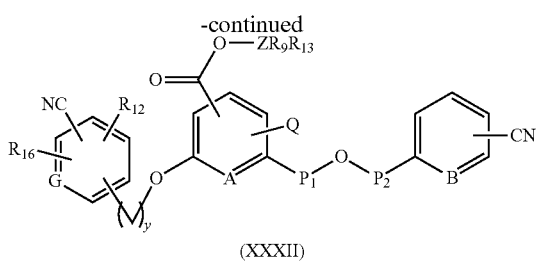

(XXXII)

Compounds of formula (I), wherein $R_1$ is —NH—CO—$ZR_9R_{13}$, and $R_2$ is a group of formula (III) and $R_{11}$ is —C(NR$_{17}$)NH$_2$, can be prepared according to the Scheme 6 such as to obtain first a compound of formula (XXXI) and following then the last steps of Scheme 1 or 2 to obtain the final product.

SCHEME 6.

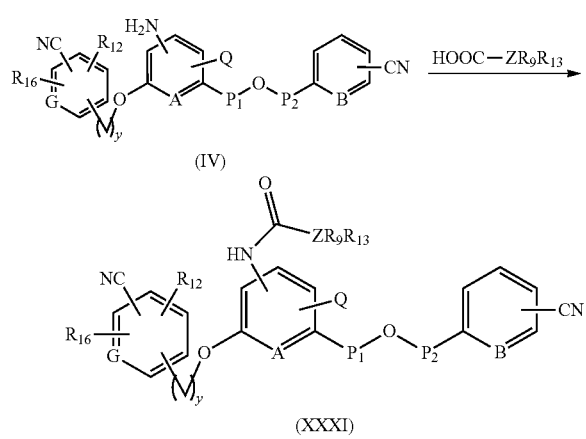

Compounds of formula (I), wherein $R_1$ is a group of formula (II), and $R_2$ is a group of formula (III) and $R_{11}$ is —C(NR$_{17}$)NH$_2$, can be prepared according to the Scheme 7 such as to obtain first a compound of formula (XII) and following then the last steps of Scheme 1 or 2 to obtain the final product.

SCHEME 7.

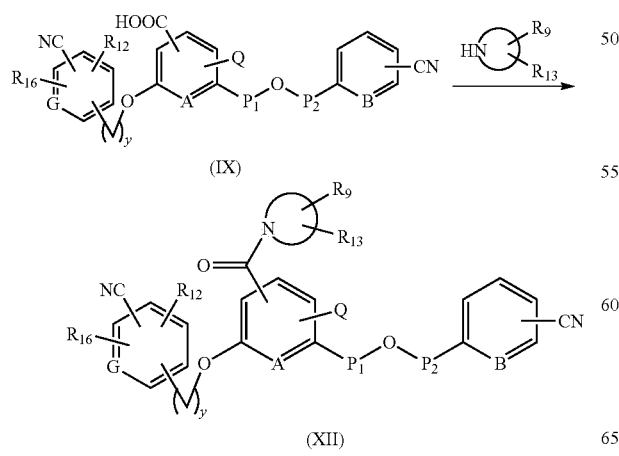

Compounds of formula (I), wherein $R_1$ is a group of formula (II), $R_2$ is a group of formula (III), and $R_9$ or $R_{13}$ is —COR$^B$NH$_2$ group linked to a nitrogen atom of the ring portion of formula (II), can be prepared according to the Scheme 8 such as to obtain first a compound of formula (XV) by a acid coupling reaction and following then the last steps of Scheme 1 or 2 to obtain the final product. L is an acid labile protection group such as a t-BOC group.

SCHEME 8.

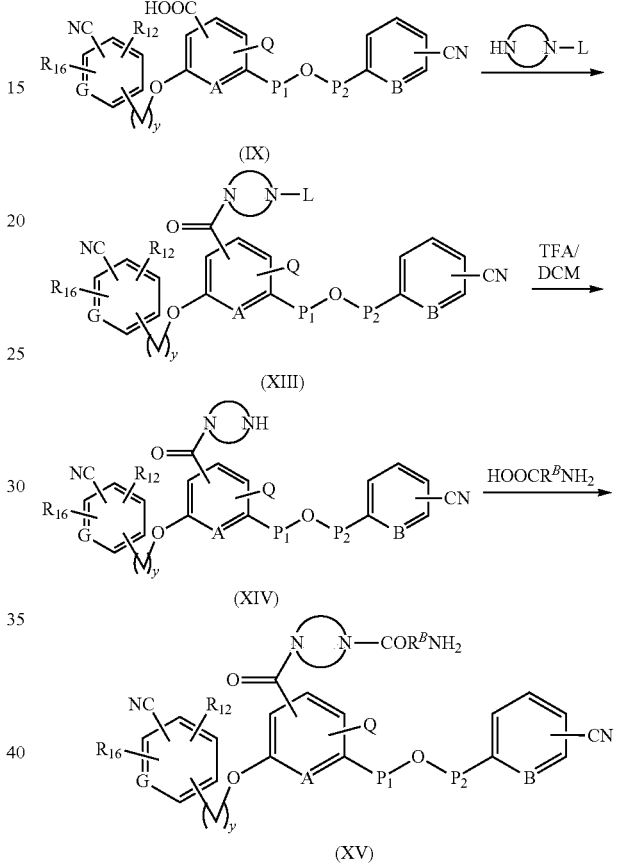

Similarly, compounds of formula (I), wherein $R_1$ is —CO—NR$_4$—R$^X$—ZR$_9$R$_{13}$, $R_2$ is a group of formula (III), and $R_9$ or $R_{13}$ is —COR$^B$NH$_2$ group linked to a nitrogen atom of the ring portion Z, may also be prepared by reacting compound of formula (IX) with a compound of formula HNR$_4$—R$^X$—Z-L, wherein L is an acid labile protection group, such as a t-BOC group, attached to the nitrogen atom of the ring portion Z. After deprotection, the amino moiety of the Z ring is coupled with HOOCR$^B$NH$_2$ by acid coupling reaction to obtain first a compound of formula (XVI)

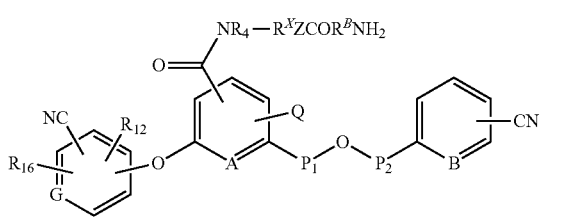

(XVI)

and following then the last steps of Scheme 1 or 2 to obtain the final product.

Compounds of formula (I), wherein $R_1$ is a group of formula (II), $R_2$ is a group of formula (III), and $R_9$ or $R_{13}$ is carboxy $C_{1-7}$ alkyl or $R^A NH_2$ group linked to a nitrogen atom of the ring portion of formula (II), may be prepared according to the Scheme 9 such as to obtain first a compound of formula (XVII) by an alkylhalide reaction and following then the last steps of Scheme 1 or 2 to obtain the final product.

SCHEME 9.

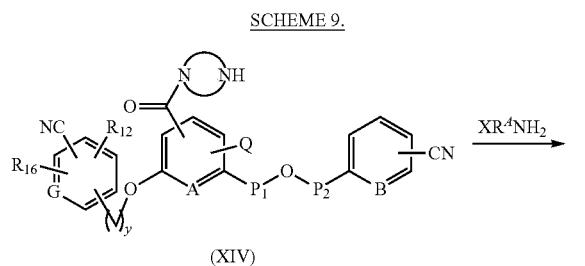

(XIV)

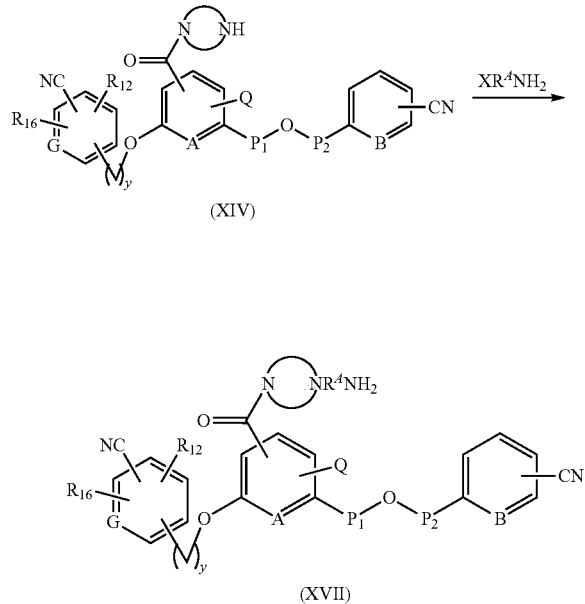

(XVII)

Similarly, compounds of formula (I), wherein $R_1$ is —CO—$NR_4$—$R^X$—$ZR_9 R_{13}$, $R_2$ is a group of formula (III), and $R_9$ or $R_{13}$ is carboxy $C_{1-7}$ alkyl or $R^A NH_2$ group linked to a nitrogen atom of the ring portion Z, can be prepared by coupling the amino moiety of the Z ring with a suitable alkylhalide, e.g. $XR^A NH_2$, wherein X is halogen, to obtain a compound of formula (XVIII)

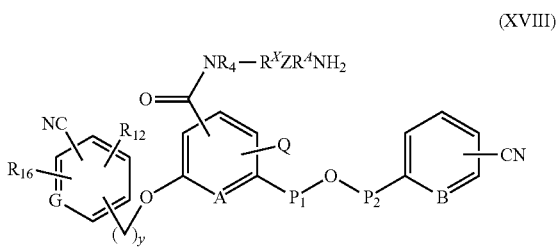

(XVIII)

and following then the last steps of Scheme 1 or 2 to obtain the final product.

Compounds of formula (I), wherein $R_2$ is $C_{1-7}$ alkyl, amino $C_{1-7}$ alkyl, carboxy $C_{1-7}$ alkyl, $C_{1-7}$ alkoxycarbonyl $C_{1-7}$ alkyl, $C_{1-7}$ alkylamino, carboxy $C_{1-7}$ alkylamino, or $R^D C(NIZ_{17})NH_2$, may be prepared starting from a compound of formula (XIX),

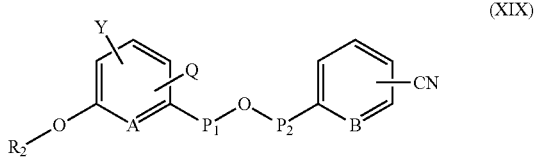

(XIX)

wherein $R_2$ is $C_{1-7}$ alkyl, amino $C_{1-7}$ alkyl, carboxy $C_{1-7}$ alkyl, $C_{1-7}$ alkoxycarbonyl $C_{1-7}$ alkyl, $C_{1-7}$ alkylamino, carboxy $C_{1-7}$ alkylamino, or $R^D C(NR_{17})NH_2$, and Y is —$NH_2$, or —COOH, and following the general procedures of any of Schemes 1 to 9 to obtain the final product.

Compounds of formula (I), wherein $R_2$ is a group of formula (III) and $R_{11}$ is hydrogen, halogen, amino, carboxy, amino $C_{1-7}$ alkyl, $C_{1-7}$ alkoxycarbonyl, halogen $C_{1-7}$ alkoxy, —NHCOR$^G$NH$_2$, R$^J$NHCOOR$^U$ or —CONR$_{19}$R$_{20}$ may be prepared starting from a compound of formula (XX),

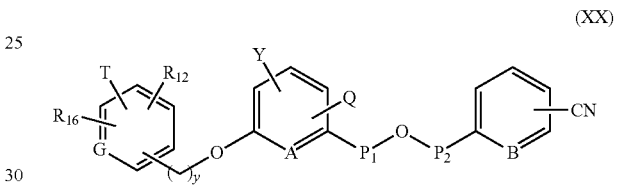

(XX)

wherein T is hydrogen, halogen, amino, carboxy, amino $C_{1-7}$ alkyl, $C_{1-7}$ alkoxy-carbonyl, halogen $C_{1-7}$ alkoxy, —NH-COR$^G$NH$_2$, R$^J$NHCOOR$^U$ or —CONR$_{19}$R$_{20}$, and Y is —$NH_2$, or —COOH, and following the general procedures of any of Schemes 1 to 9 to obtain the final product.

Compounds of formula (I), wherein $R_3$ is amino $C_{1-7}$ alkyl or both $R_3$ and Rn are amino $C_{1-7}$ alkyl, can be prepared by treating the nitrile compound of formula (V), (X), (XI), (XII), (XV), (XVI), (XVII), (XVIII) or (XX) with Raney nickel and $NH_3$-methanol on hydrogen gas pressure.

Compounds of formula (IV) which may be used as intermediates can be prepared according to Scheme 10 in a reaction between halide and alcohol. A halide (or alcohol) of formula (XXI), wherein $M_1$ and $M_2$ is halogen or a hydroxyl group, is treated with an alcohol (or halide) of formula (XXII), wherein $L_1$ is halogen or a hydroxyl group, in the presence of a base such as potassium carbonate, sodium hydride, cesium carbonate and the like in suitable solvent, such as DMF, THF and the like, at temperatures ranging from about 0° C. to 45° C. to obtain a halide (or alcohol) compound of formula (XXIII).

The halide (or alcohol) compound of formula (XXIII) is reacted with an alcohol (or halide) compound of formula (XXIV), wherein $T_1$ is halogen or a hydroxyl group, in the presence of a base and suitable solvent at temperatures ranging from about 40° C. to 85° C. to obtain the nitro compound of formula (XXV). Reduction of the nitro group can be carried out using a reducing agent such as zinc or palladium/carbon under hydrogen pressure along with solvents such as acetic acid/methanol/ethanol at temperatures ranging from about 0° C. to 80° C.

SCHEME 10.

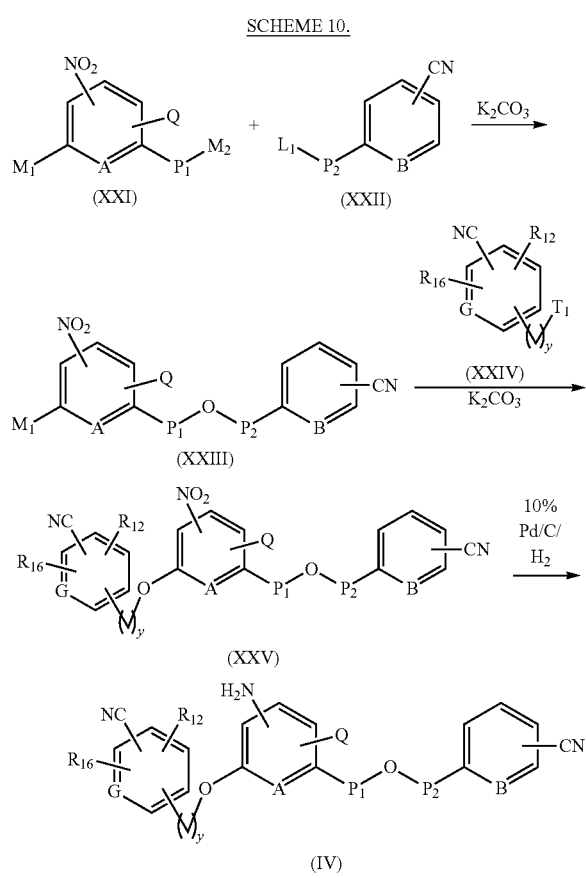

Compounds (IX) which may be used as intermediates can be prepared in a similar manner using a reaction between halide and alcohol according to Scheme 11, wherein $M_1$, $M_2$, $L_1$ and $T_1$ mean halogen or a hydroxyl group. Hydrolysis of ester group of the compound of formula (XXVIII) can be carried out using a base such as lithium hydroxide, sodium hydroxide and the like in solvent such as THF-water mixture at temperatures ranging from about 0° C. to 25° C.

SCHEME 11.

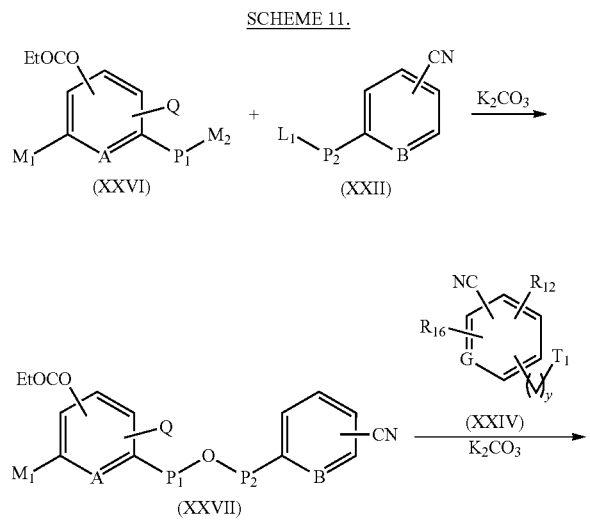

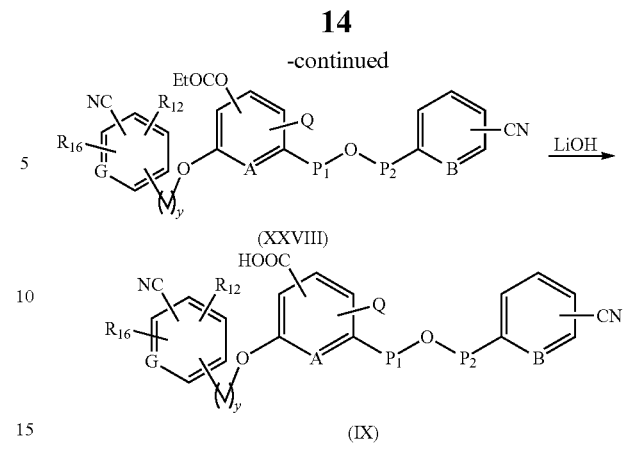

Compounds of formula (XIX) which may be used as intermediates can be prepared using a reaction between halide and alcohol according to Scheme 12, wherein $M_2$ and $L_1$ mean halogen or a hydroxyl group, $Y_1$ means —$NO_2$, —$NH_2$, —COOEt or —COOH group, $R_2$ is $C_{1-7}$ alkyl, amino $C_{1-7}$ alkyl, carboxy $C_{1-7}$ alkyl, $C_{1-7}$alkoxycarbonyl $C_{1-7}$ alkyl, $C_{1-7}$ alkylamino, carboxy $C_{1-7}$ alkylamino, $R^D C(NR_{17})NH_2$, and Y means —$NH_2$ or —COOH group.

SCHEME 12.

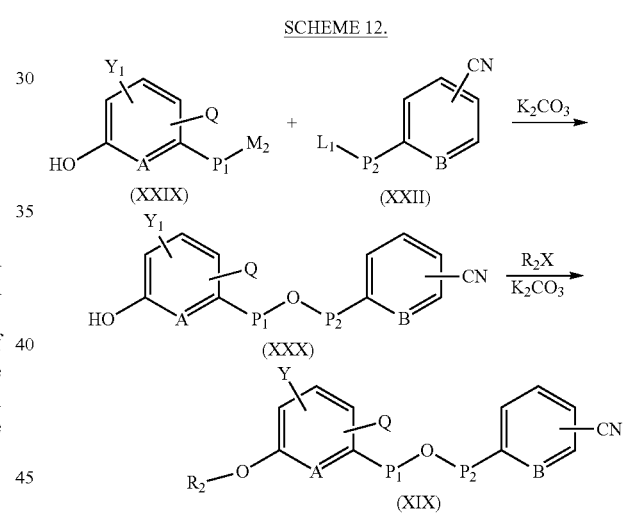

Compounds of formula (I) wherein $R_{10}$, $R_{14}$ and/or $R_{15}$ is halogen, halogen $C_{1-7}$ alkyl or —$C(NR_{17})NH_2$ can be prepared according to the above Schemes starting from compound (XXII) that contain 1 to 3 further nitrile, halogen and/or halogen $C_{1-7}$ alkyl substituents in the ring portion.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The terms employed herein have the following meanings:

The term "halo" or "halogen", as employed herein as such or as part of another group, refers to chlorine, bromine, fluorine or iodine.

The term "$C_{1-7}$ alkyl", as employed herein as such or as part of another group, refers to a straight, branched or cyclized, saturated or unsaturated, chain radical having 1 to 7 carbon atoms. Representative examples of $C_{1-7}$ alkyl include, but are not limited to, methyl, ethyl, ethenyl, n-propyl, isopropyl, propenyl, n-butyl, isobutyl, sec-butyl, tert-butyl, n-pentyl, isopentyl, neopentyl, n-hexyl, cyclopentyl, cyclohexyl and the like. "$C_{1-3}$ alkyl" is an embodiment of "$C_{1-7}$ alkyl" having 1 to 3 carbon atoms.

The term "$C_{2-7}$ alkenyl", as employed herein as such or as part of another group, refers to a straight, branched or cyclized chain radical having 2 to 7 carbon atoms, and containing one or several double bonds.

The term "hydroxy", as employed herein as such or as part of another group, refers to an —OH group. The term "cyano", as employed herein as such or as part of another group, refers to a —CN group. The term "amino", as employed herein as such or as part of another group, refers to a —$NH_2$ group. The term "carboxy", as employed herein as such or as part of another group, refers to —COOH group. The term "carbonyl", as employed herein as such or as part of another group, refers to a carbon atom double-bonded to an oxygen atom (C=O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy, tert-butoxy, and the like.

The term "hydroxyl $C_{1-7}$ alkyl", as employed herein, refers to at least one hydroxy group, as defined herein, appended to the parent molecular moiety through a $C_{1-7}$ alkyl group, as defined herein. Representative examples of hydroxyl $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl, 1-methyl-1-hydroxypropyl, and the like.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl, 3-bromopropyl, and the like.

The term "cyano $C_{1-7}$ alkyl", as employed herein, refers to a cyano group, as defined herein, appended to the parent molecular moiety through a $C_{1-7}$ alkyl group, as defined herein. Representative examples of cyano $C_{1-7}$ alkyl include, but are not limited to, cyanomethyl, 1-cyanoethyl, 1-cyanopropyl, 2-cyanopropyl, and the like.

The term "carboxy $C_{1-7}$ alkyl", as employed herein as such or as part of another group, refers to a carboxy group, as defined herein, appended to the parent molecular moiety through a $C_{1-7}$ alkyl group, as defined herein.

The term "halogen $C_{1-7}$ alkoxy", as employed herein, refers to at least one halogen, as defined herein, appended to the parent molecular moiety through a $C_{1-7}$ alkoxy group, as defined herein.

The term "$C_{1-7}$ alkoxycarbonyl", as employed herein as such or as part of another group, refers to a $C_{1-7}$ alkoxy group, as defined herein, appended to the parent molecular moiety through a carbonyl group, as defined herein.

The term "aminocarbonyl", as employed herein as such or as part of another group, refers to an amino group, as defined herein, appended to the parent molecular moiety through a carbonyl group, as defined herein.

The term "amino $C_{1-7}$ alkyl", as employed herein, refers to at least one amino group, as defined herein, appended to the parent molecular moiety through a $C_{1-7}$ alkyl group, as defined herein. Representative examples of amino $C_{1-7}$ alkyl include, but are not limited to, aminomethyl, 2-aminoethyl, 1-aminoethyl, 2,2-diaminoethyl, 3-aminopropyl, 2-aminopropyl, 4-aminobutyl, 1-methyl-1-aminoethyl, and the like.

The term "$C_{1-7}$ alkylamino", as employed herein as such or as part of another group, refers to at least one $C_{1-7}$ alkyl group, as defined herein, appended to the parent molecular moiety through an amino group, as defined herein. Representative examples of $C_{1-7}$ alkylamino include, but are not limited to methylamino, ethylamino, propylamino, butylamino, dimethylamino, diethylamino, N-ethyl-N-methylamino, and the like.

The term "carboxy $C_{1-7}$ alkylamino", as employed herein as such or as part of another group, refers to at least one carboxy group, as defined herein, appended to the parent molecular moiety through an $C_{1-7}$ alkylamino group, as defined herein The term "$C_{1-7}$ alkoxy $C_{1-7}$ alkyl", as employed herein, refers to at least one $C_{1-7}$ alkoxy group, as defined herein, appended to the parent molecular moiety through an $C_{1-7}$ alkyl group, as defined herein.

The term "$C_{1-7}$ alkoxycarbonyl $C_{1-7}$ alkyl", as employed herein, refers to at least one $C_{1-7}$ alkoxycarbonyl group, as defined herein, appended to the parent molecular moiety through an $C_{1-7}$ alkyl group, as defined herein.

The term "substituted" as used herein in connection with various residues refers to halogen substituents, such as fluorine, chlorine, bromine, iodine, or $C_{1-7}$ alkyl, halo $C_{1-7}$ alkyl, hydroxy, amino, $C_{1-7}$ alkoxy, $C_{2-7}$ acyl $C_{1-7}$ alkylamino, amino $C_{1-7}$ alkyl, nitro, cyano, or thiol substituents.

The "substituted" groups may contain 1 to 3, preferably 1 or 2, most preferably 1 of the above mentioned substituents.

The definition of formula (I) above is inclusive of all the possible stereoisomers of the compounds, including geometric isomers, e.g. Z and E isomers (cis and trans isomers), and optical isomers, e.g. diastereomers and enantiomers, and all prodrug esters, e.g. phosphate esters and carbonate esters, and isotopes. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

Compounds of the invention may be administered to a patient in therapeutically effective amounts which range usually from about 0.1 to about 1000 mg per day depending on the age, weight, ethnic group, condition of the patient, condition to be treated, administration route and the protease inhibitor used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

The present invention will be explained in more detail by the following experiments and examples. The experiments and examples are meant only for illustrating purposes and do not limit the scope of the invention defined in claims.

EXPERIMENTS

1. Inhibition of Matriptase and Other Proteases

Methods

Purified recombinant matriptase was used in a fluorescence-based screening assay using Gln-Ala-Arg peptide as a substrate. In this assay the cleavage of AMC from Boc-Gln-Ala-Arg-7-amido-4 methylcoumarin hydrochloride (Boc-Gln-Ala-Arg-AMC) (Sigma, USA) was monitored by measuring the increase in fluorescence intensity of AMC released upon proteolytic cleavage at 480 nm (kex=360 nm). Similarly, enzymatic assays in fluorimetric or colorimetric format for uPA, Factor Xa, thrombin, plasmin and trypsin (Sigma, USA) were established using substrates pyroGlu-Gly-Arg-pNA.HCl, Boc-Gln-Ala-Arg-AMC, $CH_3OCO$-D-CHA-Gly-Arg-PNA.AcoH, Pyro Glu-Phe-Lys—pNA.HCl and Boc-Gln-Ala-Arg-AMC, respectively.

Results

Enzymatic activity and selectivity of selected compounds of the invention on different proteases is presented in Table 1. The compounds of the invention were found to be potent and selective matriptase inhibitors.

TABLE 1

Inhibition of matriptase and other proteases

| | | Selectivity Screening (% Inhibition at 5 μM) | | | | |
|---|---|---|---|---|---|---|
| Compound | Matriptase Inhibition $IC_{50}$ (μM) | uPA Inhibition (%) | Factor Xa Inhibition (%) | Thrombin Inhibition (%) | Plasmin Inhibition (%) | Trypsin Inhibition (%) |
| Example 13 | 0.02 | 13 | 84 | 28 | 33 | 92 |
| Example 27 | 0.017 | 14 | 83 | 41 | 33 | 61 |
| Example 58 | 0.035 | 7 | 73 | 70 | 42 | 46 |
| Example 57 | 0.029 | 10 | 94 | 57 | 50 | 74 |
| Example 31 | 0.088 | 5 | 94 | 61 | 40 | 85 |
| Example 43 | 0.016 | 7 | 76 | 45 | 33 | 63 |
| Example 42 | 0.010 | 11 | 93 | 36 | 30 | ND |
| Example 47 | 0.038 | −1 | 71 | 3 | 18 | 36 |
| Example 45 | 0.048 | 6 | 47 | −12 | 21 | 35 |
| Example 77 | 0.005 | 11 | 96 | 76 | 22 | 69 |
| Example 65 | 0.0168 | 4 | 63 | 27 | 5 | 23 |
| Example 66 | 0.0161 | 3 | 43 | 21 | 5 | 26 |
| Example 51 | 0.379 | 23 | 52 | 41 | 25 | 53 |
| Example 69 | 0.0189 | 9 | 81 | 26 | 22 | 37 |
| Example 74 | 0.0132 | 11 | 86 | 33 | 10 | 28 |
| Example 35 | 0.31270 | 10 | 69 | 67 | 69 | 84 |
| Example 37 | 0.47943 | 13 | 67 | 74 | 65 | 84 |
| Example 84 | 0.06343 | 5 | 36 | 10 | 37 | |
| Example 103 | 0.002 | 25 | 92 | 44 | 58 | 92 |
| Example 108 | 0.004 | 23 | 81 | 49 | 61 | 76 |
| Example 111 | 0.029 | 17 | 74 | 44 | 46 | 63 |
| Example 119 | 0.007 | 14 | 97 | 47 | 30 | 77 |

2. Cytotoxicity and Inhibition of Migration and Invasion

Methods

Cytotoxicity of the compounds was tested in cell lines or primary cells using Calcein AM assay. This assay measures cell viability by quantitation of cleaved fluorescent product of a cell permeable substrate that is retained in the cytoplasm of cells with uncompromised cytoplasmic membrane integrity. The cells were seeded into 96-well plate and allowed to adhere for a day followed by addition of compound at several different concentrations. After four days of incubation with the compound, media was removed from the cells followed by addition of PBS and addition of Calcein AM reagent at 1 μM final concentration. The cells were then allowed to incubate at 37° C. for half an hour followed by reading on the fluorimeter. Percent viability was calculated based on fluorescence value obtained at 485/520 nm with cut off at 495 nm. In the cytotoxicty assays, none of the compounds tested showed any effect up to 10 μM when tested on the prostate cancer cell lines DU145 and LnCap.

Migration assays were performed to determine the effect of matriptase inhibitors on cell motility. Cells were seeded with 10 μM test compound into transwell chambers and allowed to migrate for 24 hours using a combination of 10% FBS and 5 μg/ml fibronectin as chemoattractant.

Cell invasion assays were done for quantitating the degree to which invasive cells penetrate a barrier essentially as in migration assay but with the use of matrigel consisting of basement membrane components in the transwell inserts and incubating for 48 hours. The barrier used was matrigel. This was followed by fixing and staining of the transwell insert with 0.5% crystal violet in 25% methanol in order to visualize cells migrated.

Soft agar colony formation assays were performed to measure the long-term survival and anchorage-independent growth capacity of tumor cells. DU145 cells were seeded in 0.7% nutrient agar with the test compound on an underlay of 1.4% nutrient agar in a six well plate. On the day following cell seeding, liquid cell culture medium containing the compound was added to the well to prevent the agar from drying out and was changed regularly till the completion of the experiment. The cells were allowed to form colonies for a period of about three weeks following which the colonies were stained with 0.005% solution of crystal violet in 25% methanol. The colonies were counted under a dissecting microscope.

Results

Effects of selected compounds on cytotoxicity, migration and invasion of DU145 cells are presented in Table 2.

TABLE 2

Effect of selected compounds on DU145 cells

| Compound | Matriptase $IC_{50}$ (μM) | Cell survival at 10 μM (%) | Inhibition of migration at 10 μM (%) | Inhibition of invasion at 10 μM (%) |
|---|---|---|---|---|
| Example 27 | 0.017 | 100 | 88 | 79 |
| Example 58 | 0.035 | 100 | 63 | 91 |
| Example 47 | 0.038 | 100 | 39 | 63 |
| Example 65 | 0.016 | 96 | 7 | 88 |
| Example 66 | 0.016 | 87 | 88 | 95 |
| Example 51 | 0.122 | 93 | −4 | 61 |
| Example 74 | 0.013 | 95 | 18 | 45 |
| Example 35 | 0.312 | 78 | 18 | 75 |
| Example 84 | 0.063 | 100 | 80 | 92 |
| Example 87 | 0.158 | 113 | 47 | 88 |

$EC_{50}$ values for inhibition of soft agar colony formation of DU145 cells by selected compounds are presented in Table 3.

TABLE 3

EC$_{50}$ values for inhibition of soft agar colony formation of DU145 cells

| Compound | EC$_{50}$ (µM) |
|---|---|
| Example 13 | 0.5 |
| Example 58 | 0.1 |
| Example 27 | 0.2 |
| Example 51 | 0.7 |
| Example 47 | 0.9 |

3. Efficacy in In-Vivo Tumor Models

Methods

In order to determine the in vivo efficacy, xenograft models were established by injecting 5×10$^6$ DU145 cells with matrigel or 5×10$^6$ PC3 cells without matrigel subcutaneously. Once the tumors reached palpable size (~80 mm3), compound of Example 27 was administered in a vehicle comprising of 2% ethanol, 10% hydroxyl cyclodextrin in 0.9% saline. The compound of Example 27 was dosed subcutaneously to animals with DU145 tumors at 1.5, 5 and 15 mg/kg for 15 days. In the PC3 xenograft study, compound of Example 27 was administered at 0.5, 1.5, 5.0 and 15.0 mg/kg daily.

Results

In DU145 xenograft study the compound of Example 27 caused a significant reduction in tumor volume as shown in Table 4.

TABLE 4

Tumor growth inhibition in DU145 model upon treatment with the compound of Example 27 (for 15 days)

| Compound of Example 27 | Tumor growth inhibition (%) |
|---|---|
| 1.5 mg/kg | 61.2 |
| 5 mg/kg | 84.5 |
| 15 mg/kg | 75 |

In the PC3 xenograft study, the compound of Example 27 caused significant and dose-dependent inhibition of tumor growth as shown in Table 5.

TABLE 5

Tumor growth inhibition in PC3 model upon treatment with the compound of Example 27 (for 21 days)

| Compound of Example 27 | Tumor growth inhibition (%) |
|---|---|
| 0.5 mg/kg | 14 |
| 1.5 mg/kg | 44 |
| 5 mg/kg | 65 |
| 15 mg/kg | 62 |

4. Maximum Tolerated Dose (MTD)

An MTD study was performed for the compound of Example 27. The objective of the study was to establish the maximum dose that does not induce drug related lethality and/or body weight loss of more than 20% of baseline weight during the study period of 14 days. The compound was administered at 1, 3, 10 and 30 mg/kg once daily in male athymic mice via subcutaneous route in 5 mice each. Dosing at the tested doses did not show any mortality. Body weight reduction was less than 2% and no gross changes in clinical signs were seen indicating doses up to 30 mg/kg are well tolerated.

The preparation of the compounds of the invention is illustrated by the following Examples.

EXAMPLES

LCMS data has been recorded in +ve mode unless otherwise mentioned.

Example 1

2,6-Bis-(4-carbamimidoyl-phenoxy)-3-(4-fluorobenzene-sulphonamido)-pyridine a) 2,6-Bis-(4-cyano phenoxy)-3-nitro pyridine Potassium carbonate (2.09 g, 15.1 mmol) was added to a stirred solution of 2,6-Dichloro-3-nitro pyridine (1.0 g, 5.3 mmol), dissolved in 10 ml of DMF, at a temperature of 5° C. The flask was stirred for 10 min at the same temperature. 4-Cyano phenol (1.26 g, 10.6 mmol), dissolved in 5 ml of DMF was added dropwise to the reaction mixture over a period of 10 min and the flask was heated to 80° C. for 10-12 h. The reaction mixture was poured into ice-cold water and the product was extracted with 250 ml of ethyl acetate. Ethyl acetate layer was washed with water and brine solution. The organic layer was dried over anhydrous sodium sulphate and concentrated under reduced pressure to afford 1.35 g of the required 2,6-Bis-(4-cyano phenoxy)-3-nitro pyridine which was used in the next step without further purification. $^1$H NMR (DMSO-d$_6$): δ 7.06 (1H, d), 7.32 (4H, dd), 7.82 (411, t), 8.74 (1H, d).

b) 3-Amino-2,6-bis(4-cyano phenoxy)pyridine

10% Pd/carbon (0.24 g) was added under hydrogen atmosphere (balloon pressure) to a stirred solution of 2,6-Bis(4-Cyano phenoxy)-3-nitro pyridine (1.20 g, 3.35 mmol) in 20 ml of methanol:ethyl acetate (1:1) at ambient temperature and the reaction mixture was stirred for 1 h. The reaction mixture was filtered through celite, washed with 20 ml of ethyl acetate and concentrated under reduced pressure. Water was added to the residual mixture and it was extracted with ethyl acetate. Ethyl acetate layer was washed with water followed by brine. The organic layer was dried over sodium sulphate to afford 0.95 g of the title product which was used for the next step without further purification. $^1$H NMR (DMSO-d$_6$): δ 5.32 (2H, brs), 6.82 (1H, d), 7.15 (1H, d), 7.22 (2H, d), 7.34 (2H, d), 7.80 (4H, m).

c) 2,6-Bis-(4-cyano-phenoxy)-3-(4-fluorobenzene-sulphonamido)-pyridine

4-Fluoro benzene sulfonyl chloride (0.15 g, 0.77 mmol), dissolved in 2 ml of tetrahydrofuran (THF), was added to a stirred solution of 3-amino-2,6-bis(4-cyano phenoxy)pyridine (0.25 g, 0.77 mmol), triethylamine (0.155 g, 1.54 mmol) and N,N-diisopropylethylamine (0.1 g, 0.77 mmol), in 10 ml of THF, in an inert atmosphere and stirred at RT for 12 h. The reaction mixture was concentrated and dissolved in 100 ml of ethyl acetate, washed with 1 N HCl followed by saturated brine solution and dried over anhydrous sodium sulphate. The organic phase was concentrated and the crude product was purified by column chromatography to afford 0.3 g of the required compound. $^1$H NMR (DMSO-d$_6$): δ 6.94 (1H, d), 7.12 (2H, m), 7.25 (1H, d), 7.35 (4H, d), 7.56 (4H, m), 7.80 (4H, m), 8.04 (4H, m).

d) 2,6-Bis-(4-ethoxycarbonimidoyl-phenoxy)-3-(4-fluorobenzene-sulphonamido)-pyridine 2,6-Bis-(4-cyano-phenoxy)-3-(4-fluorobenzene-sulphonamido)-pyridine 0.3 g (0.61 mmol) was added to 70 ml of ethanol (saturated with HCl gas at −25° C.) and the reaction mixture was kept in a tight vessel at room temperature overnight. The reaction mixture was concentrated under reduced pressure to afford 0.46 g of the crude product which was taken for the next step without purification. Percentage purity: 51.1%, (M+1)=578.1+1.

e) 2,6-Bis-(4-carbamimidoyl-phenoxy)-3-(4-fluorobenzene-sulphonamido)-pyridine 0.46 g (0.79 mmol) of 2,6-Bis-(4-ethoxycarbonimidoyl-phenoxy)-3-(4-fluoro-benzene-sulphonamido)-pyridine was added to 70 ml of ammoniated ethanol (ethanol saturated with NH$_3$ gas at −50° C.). The reaction mixture was kept in tight vessel (sealed tube) at room temperature for 48 hrs. The reaction mixture was cooled in dry ice and concentrated under reduced pressure to afford a crude product which was purified by reverse-phase preparative HPLC to afford 0.15 g of the required product. Percentage purity (HPLC): 98.16%, (LCMS): 95.66%. $^1$H NMR (DMSO-d$_6$): δ 6.9 (1H, d), 7.0 (2H, d), 7.3 (4H, m), 7.8 (6H, m), 9.25 (7H, m), 10.3 (1H, s).

Example 2

2,6-Bis-(4-carbamimidoyl phenoxy)-3-(2-naphthyl sulphonamido)-pyridine

Intermediates (a) and (b) are the same as in Example 1.

c) 2,6-Bis-(4-cyano-phenoxy)-3-(2-naphthyl-sulphonamido)-pyridine

2-Naphthyl sulfonyl chloride (0.17 g, 0.76 mmol) was added to a stirred solution of 3-amino-2,6-bis(4-cyano phenoxy)pyridine (0.25 g, 0.76 mmol) along with other reagents as mentioned in Example 1(c) to afford 0.27 g of the required product. $^1$H NMR (DMSO-d$_6$): δ 5.38 (1H, brs), 6.82 (1H, d), 7.12 (1H, d), 7.22 (2H, d), 7.35 (2H, dd), 7.44 (1H, d), 7.80 (7H, m), 7.95 (2H, m), 8.15 (2H, d), 8.56 (1H, s).

d) 2,6-Bis-(4-(N-hydroxycarbamimidoyl)-phenoxy)-3-(2-naphthyl-sulphonamido)-pyridine N,N-Diisopropylethylamine (DIPEA) 0.36 ml (2.08 mmol) followed by 144 mg (2.08 mmol) of hydroxylamine hydrochloride was added to a stirred solution of 2,6-bis-(4-cyano-phenoxy)-3-(2-naphthyl-sulphonamido)-pyridine 0.27 g (0.52 mmol) in 10 ml of ethanol and the flask was heated at 100° C. for 8 h. The reaction mixture was concentrated under reduced pressure to afford 0.35 g (57.5%) of the product which was used for the next step without further purification. M$^+$=584.1+1 (actual mass: 584.1).

e) 2,6-Bis-(4-(N-acetylhydroxycarbamimidoyl)-phenoxy)-3-(2-naphthyl-sulphon-amido)-pyridine Acetic anhydride (0.12 ml, 1.25 mmol) was added dropwise to a solution of 2,6-bis-(4-(N-hydroxycarbamimidoyl)-phenoxy)-3-(2-naphthyl-sulphonamido)-pyridine (0.35 g, 0.59 mmol) in 5 ml of acetic acid at room temperature. The reaction mixture was stirred at room temperature for 2 h. The reaction mixture was concentrated under reduced pressure to afford 0.3 g (51.0%) of the crude product which was used for the next step without further purification. M$^+$=LCMS (+ve mode) 668.1+1.

f) 2,6-Bis-(4-carbamimidoyl-phenoxy)-3-(2-naphthyl-sulphonamido)-pyridine

10% Pd/C (0.1 g) was added under an atmosphere of nitrogen gas to 2,6-bis-(4-(N-acetylhydroxycarbamimidoyl)-phenoxy)-3-(4-fluorobenzene-sulphonamido)-pyridine 0.3 g (0.44 mmol) dissolved in 50 ml methanol. 30 mg of 10% Pd/C was added under nitrogen atmosphere and the reaction mixture was stirred under hydrogen pressure (balloon) at room temperature for 3 h. The reaction mixture was passed through celite, washed with methanol and concentrated under reduced pressure. The concentrate was purified using reverse-phase preparative HPLC column to afford 0.06 g. of the required product. Percentage purity (HPLC): 85.01%, (LCMS): 82.73%. $^1$H NMR (DMSO-d$_6$): 6.75 (2H, d), 6.9 (1H, d), 7.3 (2H, d), 7.5 (2H, d), 7.65 (2H, m), 7.8 (3H, d), 8.0 (4H, m), 8.35 (1H, s), 9.03 (4H, d), 9.2 (4H, s), 10.2 (1H, s).

Example 3

2,6-Bis-(4-carbamimidoyl-phenoxy)-3-(8-quinoline-sulphonamido)-pyridine

Intermediates (a) and (b) are the same as in Example 1.

c) 2,6-Bis-(4-cyano phenoxy)-3-(8-quinoline-sulphonamido)-pyridine

8-Quinoline sulfonyl chloride (0.172 g, 0.76 mmol) was added to a stirred solution of 3-amino-2,6-bis(4-cyano phenoxy)pyridine (0.25 g, 0.76 mmol). Using other reagents and reaction conditions as mentioned in Example 1(c) afforded 0.4 g of the required product. $^1$H NMR (DMSO-d$_6$): δ 6.92 (1H, d), 7.11 (1H, d), 7.18 (2H, d), 7.25 (1H, d), 7.51 (2H, d), 7.56 (1H, dd), 7.66 (1H, t), 7.74 (2H, d), 7.80 (2H, m), 7.98 (1H, d), 8.20 (2H, m), 8.38 (1H, d).

d) 2,6-Bis-(4-(N-hydroxycarbamimidoyl)-phenoxy)-3-(8-quinoline-sulphonamido)-pyridine 2,6-Bis-(4-cyano phenoxy)-3-(8-quinoline-sulphonamido)-pyridine 0.4 g (0.77 mmol), DIPEA 0.53 ml (3.08 mmol) and 214 mg (3.08 mmol) of hydroxylamine hydrochloride were used to synthesize 2,6-bis-(4-(N-hydroxycarbamimidoyl)-phenoxy)-3-(8-quinoline-sulphonamido)-pyridine using the procedure of Example 2(d) to afford 0.4 g of the required product. Percentage purity: 94.4%, (M+1)=585.1+1.

e) 2,6-Bis-(4-(N-acetylhydroxycarbamimidoyl)-phenoxy)-3-(8-quinoline-sulphonamido)-pyridine 2,6-Bis-(4-(N-hydroxycarbamimidoyl)-phenoxy)-3-(8-quinoline-sulphonamido)-pyridine 0.4 g (0.68 mmol) was acetylated with 0.14 g (1.36 mmol) of acetic anhydride using the procedure of Example 2(e) to afford 0.4 g of the required product. Percentage purity: 38.6%, (M+1)=669.1+1.

f) 2,6-Bis-(4-carbamimidoyl-phenoxy)-3-(8-quinoline-sulphonamido)-pyridine 2,6-Bis-(4-(N-acetylhydroxycarbamimidoyl)-phenoxy)-3-(8-quinoline-sulphonamido)-pyridine 0.4 g (0.59 mmol)

was reduced using the procedure of Example 2(f) to afford 0.2 g of required product. Percentage purity (HPLC): 95.88%, (LCMS): 97.3%. NMR (DMSO-d$_6$): δ 6.5 (2H, d), 6.85 (1H, d), 7.25 (2H, d), 7.55 (3H, m), 7.7 (1H, m), 7.8 (2H, d), 8.0 (1H, d), 8.25 (2H, t), 8.4 (1H, d), 8.98 (1H, d), 9.1 (4H, d), 9.2 (4H, d), 9.65 (1H, brs).

Example 4

2,6-Bis-(4-carbamimidoyl-phenoxy)-3-(3,5-difluoro-benzene-sulphonamido)-pyridine Intermediates (a) and (b) are the same as in Example 1.

c) N-[2,6-Bis-(4-cyano-phenoxy)-pyridin-3-yl]-3,5-difluoro-benzenesulfonamide 3,5-difluorobenzene sulfonyl chloride (0.5 g, 2.35 mmol) was added to a stirred solution of 3-amino-2,6-bis(4-cyano phenoxy)pyridine (0.77 g, 2.35 mmol) using the reagents and reaction conditions described in Example 1(c) to afford 0.9 g of the required product. $^1$H NMR (DMSO-d$_6$): δ 6.82 (1H, d), 6.95 (1H, d), 7.11 (2H, d), 7.24 (3H, m), 7.34 (2H, d), 7.80 (7H, m).

d) 2,6-Bis-(4-(N-hydroxycarbamimidoyl)-phenoxy)-3-(3,5-difluoro-benzene-sulphonamido)-pyridine N-[2,6-Bis-(4-cyano-phenoxy)-pyridin-3-yl]-3,5-difluoro-benzenesulfonamide 0.9 g (1.78 mmol), DIPEA 1.24 ml (7.12 mmol) and 0.494 g (7.12 mmol) of hydroxylamine hydrochloride were used as described in Example 2(d) to afford 0.8 g of the required product. Percentage purity: 62.1%, (M+1)=570.0+1.

e) 2,6-Bis-(4-(N-acetylhydroxycarbamimidoyl)-phenoxy)-3-(3,5-difluoro-benzene-sulphonamido)-pyridine 2,6-Bis-(4-(N-hydroxycarbamimidoyl)-phenoxy)-3-(3,5-difluoro-benzene-sulphon-amido)-pyridine, 0.8 g (1.40 mmol), was acetylated with 0.29 g (3.1 mmol) of acetic anhydride using the procedure of Example 2(e) to afford 0.8 g of the required product. Percentage purity: 47.3%. (M+1)=654.1+1.

f) 2,6-Bis-(4-carbamimidoyl-phenoxy)-3-(3,5-difluoro-benzene-sulphonamido)-pyridine 2,6-Bis-(4-(N-acetylhydroxycarbamimidoyl)-phenoxy)-3-(3,5-difluoro-benzene-sulphonamido)-pyridine, 0.8 g (1.22 mmol), was reduced using the procedure of Example 2(f) to afford 0.2 g of required product. Percentage purity (HPLC): 88.35%, (LCMS): 93.37%. $^1$H NMR (DMSO-d$_6$): δ 6.6 (3H, m), 6.9 (1H, d), 7.05 (2H, d), 7.35 (2H, d), 7.5 (3H, m), 7.8 (2H, m), 7.9 (1H, d), 9.1 (3H, s), 9.25 (3H, s), 10.5 (1H, s).

Example 5

2-(1-{2,6-Bis-[4-carbamimidoyl-phenoxy]-pyridine-3-carbonyl}-piperidin-4-yl)-ethylamine a) 2,6-Bis(4-Cyano Phenoxy)-nicotinic Acid Ethyl Ester Potassium carbonate 1.58 g (11.5 mmol) was added to a stirred solution of 2,6-dichloro-nicotinic acid ethyl ester 1.0 g (4.6 mmol) in 5 ml of DMF and stirred for 10 min. 4-Hydroxy-benzonitrile 1.36 g (11.5 mmol), dissolved in 5 ml of DMF, was added dropwise to the stirred DMF solution and the flask was stirred at 80° C. for 4 h. The reaction mixture was poured into ice-cold water and the result was partitioned using ethyl acetate. The organic phase was washed with 1 M of Na$_2$CO$_3$ and saturated brine solution, dried over sodium sulphate and concentrated. The oily residue was purified by column chromatography using hexane-ethyl acetate (10:2) to afford 1.6 g of the required product. Percentage purity: 84.8%, (M+1)=385.1. $^1$H NMR (DMSO-d$_6$): 1.36 (3H, t), 4.22 (214, q), 6.78 (1H, d), 7.06 (4H, d), 7.58 (4H, d), 8.21 (1H, d).

b) 2,6-Bis(4-cyano Phenoxy)-nicotinic Acid 0.2 g (8.4 mmol) of lithium hydroxide was added to a stirred solution of 2,6-bis(4-cyano phenoxy)-nicotinic acid ethyl ester, 1.6 g (4.15 mmol), in a mixture of 5 ml of water and 2.5 ml of THF (2:1) at 5° C. and the contents were stirred for 3 h at RT. The reaction mixture was washed with diethylether. 6 N HCl was added to aqueous layer with stirring until the solution attained a pH of 2. The white precipitate obtained was collected, washed with water and dried under reduced pressure to afford 1.1 g of the required product. Percentage purity (LCMS): 83.2%, (M+1)=357.0+1. $^1$H NMR (DMSO-d$_6$): δ 6.98 (1H, d), 7.26 (4H, d), 7.80 (4H, d), 13.22 (1H, brs).

c) (2-{1-[2,6-Bis-(4-cyano-phenoxy)-pyridine-3-carbonyl]-piperidin-4-yl}-ethyl)-carbamic Acid Tert-butyl Ester A solution of 2,6-Bis-(4-cyano phenoxy)-nicotinic acid, 0.335 g (0.94 mmol), in 5 ml of DMF was added dropwise to the stirred suspension of 0.489 g (0.94 mmol) of benzotriazol-1-yl-oxytripyrrolidinophosphonium hexafluorophosphate (PyBop) in 5 ml of DMF and followed by N,N-diisopropyl-ethylamine 0.242 g (1.88 mmol) while the temperature was maintained below 5° C. during the addition. The mixture was stirred for 10 min and a solution of (2-piperidin-4-yl-ethyl)-carbamic acid tert-butyl ester (0.214 g, 0.94 mmol) in 2 ml of DMF was added. The mixture was stirred overnight at RT. The solvent was concentrated under reduced pressure and the residue was dissolved in a mixture of water (150 ml) and ethyl acetate (150 ml). The pH was adjusted to 2-3 with 6 N HCl and the phases were separated. The aqueous phase was extracted with ethyl acetate. The combined organic phase was washed with 10% solution of potassium hydrogen sulphate followed by saturated sodium bicarbonate solutiona and saturated brine solution, and dried over sodium sulphate and concentrated. The crude oily residue was purified by column chromatography using hexane-ethyl acetate (10:2) to afford 0.4 g of the required product. Percentage purity: 36.3%, (M+1)=567.2. $^1$H NMR (DMSO-d$_6$): δ 1.35 (3H, m), 1.38 (9H, s), 1.65 (2H, m), 2.71 (2H, m), 2.95 (4H, m), 3.75 (2H, m), 6.80 (1H, t), 6.95 (1H, d), 7.32 (4H, d), 7.68 (1H, m), 7.85 (4H, d).

d) 2-(1-{2,6-Bis-[4-ethoxycarbonimidoyl-phenoxy]-pyridine-3-carbonyl}-piperidin-4-yl)-ethylamine Using (2-{1-[2,6-bis-(4-cyano-phenoxy)-pyridine-3-carbonyl]-piperidin-4-yl}-ethyl)-carbamic acid tert-butyl ester (0.4 g, 0.7 mmol) and following the procedure of Example 1(d) afforded 0.4 g of the required product. Percentage purity (LCMS): 30.7% (M+1)=559.2.

e) 2-(1-{2,6-Bis-[4-carbamimidoyl-phenoxy]-pyridine-3-carbonyl}-piperidin-4-yl)-ethylamine Using (2-(1-{2,6-bis-[4-ethoxycarbonimidoyl-phenoxy]-pyridine-3-carbonyl]-piperidin-4-yl)-ethylamine (0.4 g, 0.71 mmol) and following the procedure of Example 1(e) 0.05 g of the required product was obtained. Percentage purity (HPLC): 93.52%, (LCMS): 96.46%. $^1$H NMR (DMSO-$d_6$): δ 1.5 (2H, m), 1.65 (2H, m), 1.85 (2H, m), 2.8 (3H, m), 3.1 (1H, m), 3.7 (2H, m), 4.5 (1H, d), 6.9 (1H, d), 7.2 (1H, s), 7.4 (4H, t), 7.9 (5H, brs), 8.05 (1H, brs), 9.3 (6H, s).

Example 6

N-(4-Amino-cyclohexyl)-2,6-bis-(4-carbamimidoyl-phenoxy)-nicotinamide

Intermediates (a) and (b) are the same as in Example 5.

c) (4-{[2,6-Bis-(4-cyano-phenoxy)pyridine-3-carbonyl]amino}-cyclohexyl)-carbamic Acid Tert-butyl Ester Following the procedure of Example 5(c) 2,6-bis(4-cyano phenoxy)-nicotinic acid 0.335 g (0.94 mmol) and (4-amino-cyclohexyl)-carbamic acid tert-butyl ester (0.2 g, 0.94 mmol) were used to afford 0.35 g of the required product. Percentage purity (LCMS): 86.8%, (M+1)=553.6 (with BOC). $^1$H NMR (DMSO-$d_6$): δ 1.25 (4H, m), 1.38 (9H, s), 1.82 (4H, m), 3.18 (1H, m), 3.64 (1H, m), 6.74 (1H, d), 6.95 (1H, d), 7.28 (4H, dd), 7.82 (4H, dd), 8.08 (1H, d), 8.21 (1H, d).

d) 4-({2,6-Bis-[4-ethoxycarbonimidoyl-phenoxy]-pyridine-3-carbonyl}-amino)-cyclohexylamine (4-{[2,6-Bis-(4-cyano-phenoxy)pyridine-3-carbonyl]amino}-cyclohexyl)carbamic acid tert-butyl ester (0.35 g, 0.63 mmol) was used and the procedure of Example 1(d) was followed to afford 0.3 g of the required product. Percentage purity (LCMS): 40.2%, (M+1)=545.2.

e) N-(4-Amino-cyclohexyl)-2,6-bis-(4-carbamimidoyl-phenoxy)-nicotinamide 4-({2,6-Bis-[4-ethoxycarbonimidoyl-phenoxy]-pyridine-3-carbonyl}-amino)-cyclohexylamine (0.3 g, 0.55 mmol) was used the procedure of Example 1(e) was followed to afford 0.05 g of the required product. Percentage purity (HPLC): 97.07%, (LCMS): 81.64%. $^1$H NMR (DMSO-$d_6$): δ 1.4 (4H, m), 1.95 (4H, m), 3.0 (1H, m), 3.7 (1H, m), 6.9 (1H, d), 7.0 (2H, d), 7.3 (4H, m), 7.8 (6H, m), 9.25 (7H, m), 10.3 (1H, s).

Example 7

3-{[2,6-Bis-(4-carbamimidoyl-phenoxy)-pyridine-3-carbonyl]-amino}-propyl-amine Intermediates (a) and (b) are the same as in Example 5.

c) (3-{[2,6-Bis-(4-cyano-phenoxy)-pyridine-3-carbonyl]-amino}-propyl)-carbamic Acid Tert-butyl Ester Following the procedure of Example 5(c) 2,6-bis(4-Cyano phenoxy)-nicotinic acid 0.335 g (0.94 mmol) and (3-amino-propyl)-carbamic acid tert-butyl ester (0.163 g, 0.94 mmol) were used to afford 0.3 g of the required product. Percentage purity (LCMS): 78.7%, (M+1)=513.5+1.

d) 3-{[2,6-Bis-(4-ethoxycarbonimidoyl-phenoxy)-pyridine-3-carbonyl]-amino}-propylamine (3-{[2,6-Bis-(4-cyano-phenoxy)-pyridine-3-carbonyl]amino}-propyl)-carbamic acid tert-butyl ester (0.3 g, 0.58 mmol) was used following the procedure of Example 1(d) to afford 0.3 g of the required product. Percentage purity (LCMS): 38.6%, (M+1)=505.2.

e) 3-{[2,6-Bis-(4-carbamimidoyl-phenoxy)-pyridine-3-carbonyl]-amino}-propylamine 3-{[2,6-Bis-(4-ethoxycarbonimidoyl-phenoxy)-pyridine-3-carbonyl]-amino}-propylamine (0.3 g, 0.59 mmol) was used following the procedure of Example 1(e) to afford 0.12 g of the required product. Percentage purity (HPLC): 92.98%, (LCMS): 97.61%. $^1$H NMR (DMSO-$d_6$): δ 1.8 (2H, m), 2.85 (2H, m), 3.45 (2H, m), 6.9 (1H, d), 7.0 (1H, s), 7.2 (1H, d), 7.3 (4H, m), 7.85 (6H, d), 8.3 (1H, d), 8.55 (1H, brs), 9.3 (7H, brs).

Example 8

3-{[2,6-Bis-(4-carbamimidoyl-phenoxy)pyridine-3-carbonyl]-amino}propionic Acid Intermediates (a) and (b) are the same as in Example 5.

c) 3-{[2,6-Bis-(4-cyano-phenoxy)-pyridine-3-carbonyl]-amino}-propionicacid Ethyl Ester Following the procedure of Example 5(c) 2,6-bis(4-Cyano phenoxy)-nicotinic acid 0.5 g (1.42 mmol) and 3-amino-propionic acid ethyl ester (0.166 g, 1.42 mmol) were used to afford 0.5 g of the required product. Percentage purity (LCMS): 30.7%, (M+1)=456.1.

d) 3-{[2,6-Bis-(4-cyano-phenoxy)-pyridine-3-carbonyl]-amino}-propionic Acid

3-{[2,6-Bis-(4-cyano-phenoxy)-pyridine-3-carbonyl]-amino}-propionic acid ethyl ester (0.5 g, 1.09 mmol) was deesterified using the procedure of Example 5(b) to afford 0.35 g of the required product. Percentage purity (LCMS): 71.6%, (M+1)=428.4.

e) 3-{[2,6-Bis-(4-ethoxycarbonimidoyl-phenoxy)pyridine-3-carbonyl]amino}-propionic Acid 3-{[2,6-Bis-(4-cyano-phenoxy)-pyridine-3-carbonyl]-amino}-propionic acid (0.35 g, 0.81 mmol) was used and the procedure of Example 1(d) was followed to afford 0.3 g of the required product. Percentage purity (LCMS): 38.6%, (M+1)=520.1+2.

f) 3-{[2,6-Bis-(4-carbamimidoyl-phenoxy)pyridine-3-carbonyl]amino}propionic Acid 3-{[2,6-Bis-(4-ethoxycarbonimidoyl-phenoxy)pyridine-3-carbonyl]amino}-propionic acid (0.3 g, 0.57 mmol) was used and the procedure of Example 1(e) was followed to afford 0.15 g of the required product. Percentage purity (HPLC): 95.73%, (LCMS): 97.10%. NMR (DMSO-$d_6$): δ 2.3

(1H, m), 3.5 (1H, m), 6.9 (1H, d), 7.04 (1H, s), 7.22 (1H, s), 7.4 (3H, m), 7.88 (2H, d), 8.36 (1H, d), 8.52 (1H, m), 9.3 (4H, d).

Example 9

3-{4-[2,6-Bis-(4-carbamimidoyl-phenoxy)-pyridine-3-carbonyl]-piperazin-1-yl}-3-oxo-propylamine Intermediates (a) and (b) are the same as in Example 5.

c) 4-[2,6-Bis-(4-cyano-phenoxy)pyridine-3-carbonyl]-piperazine-1-carboxylic Acid tert-butyl Ester Following the procedure of Example 5(c) 2,6-bis(4-cyano phenoxy)-nicotinic acid 1.25 g (3.5 mmol) and piperazine-1-carboxylic acid tert-butyl ester (0.65 g, 3.5 mmol) were used to afford 1.2 g of the required product. Percentage purity (LCMS): 95.6%, (M+1)=525.2 (with BOC). $^1$H NMR (DMSO-$d_6$): δ 1.40 (9H, s), 3.30 (2H, m), 3.42 (4H, m), 3.61 (2H, m), 6.98 (1H, d), 7.35 (4H, m), 7.82 (4H, dd), 8.02 (2H, d).

d) 4-[2,6-Bis-(4-cyano phenoxy)pyridine-3-carbonyl]piperazine

4-[2,6-Bis-(4-cyano-phenoxy)pyridine-3-carbonyl]-piperazine-1-carboxylic acid tert-butyl ester 1.2 g (2.28 mmol) was dissolved in 5 ml of DCM at 5° C. under inert atmosphere. 0.7 ml of TFA was added over a 10 min period, while the temperature was maintained at 5° C. Stirring was continued for 1 h at RT and reaction progress was monitored by TLC. The reaction mixture was concentrated under reduced pressure and the residual crude product was purified by column chromatography using chloroform: ethylacetate (8:2) as eluant to afford 0.9 g of the required product. Percentage purity (LCMS): 88.2%, (M+1): 425.1. $^1$H NMR (DMSO-$d_6$): δ 3.15 (2H, m), 3.22 (2H, m), 3.64 (2H, m), 3.85 (2H, m), 7.00 (1H, d), 7.34 (4H, t), 7.82 (4H, t), 8.08 (1H, d), 9.02 (1H, brs).

e) (3-{4-[2,6-bis-(4-cyano-phenoxy)pyridine-3-carbonyl]piperazin-1-yl}-3-oxo propyl)carbamic Acid Tert-butyl Ester A solution of 3-tert-butoxycarbonylamino-propionic acid, 0.177 g (0.94 mmol), in 3 ml of DMF was added dropwise to a stirred suspension of 0.72 g (3.76 mmol) of 1-ethyl-3-(3-dimethylaminopropyl) carbodiimide hydrochloride (EDC) and hydroxybenzotriazole (HOBT) 0.508 g (3.76 mmol) in 5 ml of DMF at RT. That was followed by the addition of N,N-diisopropylethylamine (DIPEA) 0.242 g (1.88 mmol) while the temperature was maintained below 5. The mixture was stirred for 10 min and a solution of 4-[2,6-Bis-(4-cyano phenoxy)pyridine-3-carbonyl]piperazine (0.4 g, 0.94 mmol) in DMF (10 ml) was added followed by stirring overnight at RT. The reaction mixture was concentrated under reduced pressure and partitioned between water (150 ml) and ethyl acetate (150 ml) after the pH was adjusted to 2-3 with 6 N HCl. The organic phase was washed with 1 M $Na_2CO_3$ and saturated brine solution, dried over sodium sulphate and concentrated. The crude oily residue was purified by column chromatography using hexane-ethyl acetate (10:2) to afford 0.45 g of the required product. Percentage purity (LCMS): 10.3%. (M+1)=596.2 (with BOC).

f) 3-(4-{2,6-bis-(4-ethoxy-carbonimidoylphenoxy) pyridine-3-carbonyl}-piperazin-1-yl)-3-oxo Propylamine (3-{4-[2,6-bis-(4-cyano-phenoxy)pyridine-3-carbonyl] piperazin-1-yl}-3-oxo propyl)carbamic acid tert-butyl ester (0.45 g, 0.75 mmol) was used and the procedure of Example 1(d) was followed to afford 0.3 g of the required product. Percentage purity (LCMS): 32.8%, (M+1)=496.1.

g) 3-{4-[2,6-Bis-(4-carbamimidoyl-phenoxy)-pyridine-3-carbonyl]-piperazin-1-yl}-3-oxo-propylamine 3-(4-{2,6-bis-(4-ethoxy-carbonimidoylphenoxy)pyridine-3-carbonyl}-piperazin-1-yl)-3-oxo propylamine (0.3 g, 0.60 mmol) was used and the procedure of Example 1(e) was followed to afford 0.12 g of the required product. Percentage purity (HPLC): 73.56%, (LCMS): 97.21%. $^1$H NMR (DMSO-$d_6$): δ 1.8 (2H, m), 2.8 (2H, m), 3.4 (3H, m), 6.9 (1H, d), 7.04 (1H, s), 7.20 (1H, s), 7.4 (5H, m), 7.88 (7H, m), 8.32 (1H, d), 8.54 (1H, brs), 9.34 (6H, s).

Example 10

3-(4-{[2,6-Bis-(4-carbamimidoyl-phenoxy)pyridine-3-carbonyl]-amino}-piperidinyl)-3-oxo propylamine Intermediates (a) and (b) are the same as in Example 5.

c) 4-{[2,6-Bis-(4-cyano-phenoxy)pyridine-3-carbonyl]amino}piperidine-1-carboxylic Acid Tert-butyl Ester Following the procedure of Example 5(c) 2,6-bis(4-cyano phenoxy)-nicotinic acid 1.5 g (4.20 mmol) and 4-amino-piperidine-1-carboxylic acid tert-butyl ester (0.84 g, 4.20 mmol) were used to afford 1.7 g of the required product. Percentage purity (LCMS): 74.6%, (M+1)=539.2 (with BOC).

d) 2,6-Bis-(4-cyano phenoxy)-N-piperidine-4-yl nicotinamide

Following the procedure of Example 9(d) 4-{[2,6-Bis-(4-cyano-phenoxy)pyridine-3-carbonyl]amino}piperidine-1-carboxylic acid tert-butyl ester (1.7 g, 3.15 mmol) were used to afford 1.3 g of the required product. Percentage purity (LCMS): 97.9%, (M+1)=439.1+1.

e) [3-(4-{[2,6-bis-(4-cyano phenoxy)pyridine-3-carbonyl]amino}piperidine-1-yl)-3-oxo Propyl]carbamic Acid Tert-Butyl Ester 3-tert-Butoxycarbonylamino-propionic acid (0.177 g, 0.91 mmol) and 2,6-bis-(4-cyano phenoxy)-N-piperidine-4-yl nicotinamide (0.4 g, 0.91 mmol) and other reagents as described in Example 9(e) were used to afford 0.45 g of the required product. Percentage purity (LCMS): 82.8%, (M+1)= 610.1+1.

f) {3-[4-({2,6-bis-(4-(N-hydroxycarbamimidoyl)-phenoxy)-pyridine-3-carbonyl}-amino)-piperidin-1-yl]-3-oxo Propyl}-carbamic Acid Tert-butyl Ester

[3-(4-{[2,6-bis-(4-cyanophenoxy)pyridine-3-carbonyl] amino}piperidine-1-yl)-3-oxo propyl]carbamic acid tert-butyl ester (0.45 g, 0.73 mmol), hydroxylamine hydrochloride (0.202 g, 2.92 mmol) and DIPEA (0.377 g, 2.92 mmol) were used and the procedure of Example 2(d) was followed to afford 0.4 g of the required product. Percentage purity (LCMS): 68.6%, (M+1)=676.3.

g) {3-[4-({2,6-bis-(4-(N-acetylhydroxycarbamimidoyl)-phenoxy)-pyridine-3-carbonyl}amino)-piperidin-1-yl]-3-oxo propyl}-carbamic Acid Tert-butyl Ester {3-[4-({2,6-bis-(4-(N-hydroxycarbamimidoyl)-phenoxy)-pyridine-3-carbonyl}-amino)-piperidin-1-yl]-3-oxo propyl}-carbamic acid tert-butyl ester 0.4 g (0.59 mmol) was acetylated with 0.123 g (1.2 mmol) of acetic anhydride. The procedure of Example 2(e) was followed to afford 0.45 g of the required product. Percentage purity (LCMS): 40.0%, (M+1)=660.2+1 (de-boc).

h) [3-(4-{[2,6-Bis-(4-carbamimidoyl-phenoxy)pyridine-3-carbonyl]-amino}-piperidinyl)-3-oxo Propyl] carbamic Acid Tert-butyl Ester {3-[4-({2,6-bis-(4-(N-acetylhydroxycarbamimidoyl)-phenoxy)-pyridine-3-carbonyl}amino)-piperidin-1-yl]-3-oxo propyl}-carbamic acid tert-butyl ester 0.45 g (0.59 mmol) was reduced by using the procedure of Example 2(f) to afford 0.2 g of the required product. Percentage purity (LCMS): 58.5%. (M+1)=644.3+1.

i) 3-(4-{[2,6-Bis-(4-carbamimidoyl-phenoxy)pyridine-3-carbonyl]-amino}-piperidinyl)-3-oxo Propylamine The -Boc group was removed from [3-(4-{[2,6-Bis-(4-carbamimidoyl-phenoxy)-pyridine-3-carbonyl]-amino}-piperidinyl)-3-oxo propyl]carbamic acid tert-butyl ester 0.2 g (0.31 mmol) using the procedure of Example 9(d) to afford 0.055 g of the required product. Percentage purity (HPLC): 95.77%, (LCMS): 88.95%. $^1$H NMR (DMSO-d$_6$): δ 1.4 (3H, m), 1.9 (2H, m), 2.6 (1H, m), 3.0 (2H, m), 3.2 (1H, m), 3.7 (2H, d), 4.2 (2H, d), 6.9 (1H, d), 7.05 (1H, s), 7.2 (1H, s), 7.4 (3H, m), 7.9 (5H, s), 8.3 (2H, dd), 9.35 d).

Example 11

N-[1-(3-amino-propyl)piperidin-4-yl]-2,6-bis-(4-carbamimidoyl-phenoxy)-nicotinamide Intermediates (a) to (d) are the same as in Example 10.

e) [3-(4-{[2,6-bis-(4-cyano-phenoxy)pyridine-3-carbonyl]amino}piperidine-1-yl) propyl]carbamic Acid Tert-butyl Ester 0.117 g (0.85 mmol) of K$_2$CO$_3$ and N,N-diisopropylethylamine 0.072 g (0.56 mmol) followed by 0.201 g (0.85 mmol) of (3-bromo-propyl)-carbamic acid tert-butyl ester, dissolved in 5 ml of DMF, were added to a stirred solution of 0.373 g (0.85 mmol) of 2,6-bis-(4-cyano phenoxy)-N-piperidine-4-yl nicotinamide, dissolved in 5 ml of DMF over a period of 15 min at 20° C. Reaction mixture was allowed to attain RT and heated to 45° C. for 2 h. The reaction mixture was concentrated under reduced pressure to remove the solvent. The residue was partitioned between water (150 ml) and ethyl acetate (150 ml). The organic phase was washed with 1 M Na$_2$CO$_3$ and saturated brine solution, and dried over sodium sulphate. The solution was concentrated and the oily residue was purified by column chromatography using hexane-ethyl acetate (10:2) to afford 0.45 g of the required product. Percentage purity (LCMS): 72.5%, (M+1)=596.2+1.

f) 3-(4-[{2,6-bis-(4-ethoxycarbonimidoyl-phenoxy)pyridine-3-carbonyl}amino]-piperidin-1-yl)propylamine

[3-(4-{[2,6-bis-(4-cyano-phenoxy)pyridine-3-carbonyl]amino}piperidine-1-yl) propyl]carbamic acid tert-butyl ester (0.45 g, 0.75 mmol) was used and the procedure of Example 1(d) was followed to afford 0.3 g of the required product. Percentage purity (LCMS): 55.6%, (M+1)=496.2+1.

g) N-[1-(3-amino-propyl)piperidin-4-yl]-2,6-bis-(4-carbamimidoyl-phenoxy)-nicotinamide 3-(4-[{2,6-bis-(4-ethoxycarbonimidoyl-phenoxy)pyridine-3-carbonyl}amino]-piperidin-1-yl) propylamine (0.3 g, 0.60 mmol) was used by following the procedure of Example 1(e) to afford 0.12 g of the required product. Percentage purity (HPLC): 92.11%, (LCMS): 90.51%. $^1$H NMR (DMSO-d$_6$): δ 1.8 (2H, m), 2.0 (5H, m), 2.9 (2H, m), 3.15 (4H, m), 4.0 (2H, m), 6.9 (1H, d), 7.35 (3H, d), 7.85 (3H, m), 8.0 (3H, brs), 8.2 (1H, d), 8.5 (1H, d), 9.3 (7H, d), 10.1 (1H, brs).

Example 12

(2-{1-[2,6-Bis-(4-carbamimidoyl-phenoxy)-pyridine-4-carbonyl]-piperidin-4-yl}-ethylamine a) 2,6-bis(4-Cyano phenoxy)-isonicotinic Acid Ethyl Ester

Potassium carbonate 3.17 g (23.0 mmol) was added to 2,6-dichloro-isonicotinic acid ethyl ester 1.0 g (4.6 mmol), dissolved in 5 ml of DMF, and stirred for 10 min. This was followed by the dropwise addition of 4-hydroxy-benzonitirle 1.64 g (13.8 mmol), dissolved in 5 ml of DMF, followed by stirring at 100° C. for 3 h. The reaction mixture was poured into ice-cold water and extracted with ethyl acetate. The organic phase was washed with 1 M Na$_2$CO$_3$ and saturated brine solution, dried over sodium sulphate and concentrated. The crude oily residue was purified by column chromatography using hexane-ethyl acetate (10:2) to afford 0.4 g of the required product. Percentage purity (LCMS): 87.4%. (M+1)= 385.1+1. $^1$H NMR (DMSO-d$_6$): δ 1.42 (3H, t), 4.44 (2H, q), 7.16 (4H, d), 7.27 (2H, d), 7.64 (4H, d).

b) 2,6-bis(4-Cyano Phenoxy)-isonicotinic Acid 0.4 g (1.03 mmol) of 2,6-bis(4-Cyano phenoxy)-isonicotinic acid ethyl ester was hydrolysed by using the procedure of Example 5(b) to afford 0.3 g of the required product. $^1$H NMR (DMSO-d$_6$): δ 7.22 (2H, s), 7.38 (4H, d), 7.82 (4H, d).

c) (2-{1-[2,6-Bis-(4-cyano-phenoxy)-pyridine-4-carbonyl]piperidine-4-yl}ethyl)-carbamic Acid Tert-butyl Esters 2,6-bis(4-Cyano phenoxy)-isonicotinic acid (0.3 g, 0.84 mmol) and (2-piperidin-4-yl-ethyl)-carbamic acid tert-butyl ester (0.191 g, 0.84 mmol) were coupled using the procedure of Example 5(c) to afford 0.4 g. of the required product. Percentage purity (LCMS): 79.0%, (M+1)=567.2 (with -BOC). $^1$H NMR (DMSO-d$_6$): δ 1.15 (2H, m), 1.38 (9H, s), 1.62 (2H, m), 1.75 (1H, m), 2.74 (1H, m), 2.88 (3H, m), 3.55 (1H, m), 4.42 (1H, m), 6.80 (1H, m), 6.89 (2H, s), 7.35 (4H, d), 7.84 (4H, d).

d) (2-{1-[2,6-Bis-(4-(N-hydroxy-carbamimidoyl)-phenoxy)-pyridine-4-carbonyl]-piperidine-4-yl}ethyl)carbamic Acid Tert-butyl Esters (2-{1-[2,6-Bis-(4-cyano-phenoxy)-pyridine-4-carbonyl] piperidine-4-yl}ethyl)-carbamic acid tert-butyl esters (0.4 g, 0.70 mmol), hydroxylamine hydrochloride (0.194 g, 2.8 mmol) and DIPEA (0.36 g, 2.8 mmol) were used and the procedure of Example 2(d) was followed to afford 0.3 g of the required product. Percentage purity (LCMS): 59.2%, (M+1)=633.3+1.

e) (2-{1-[2,6-Bis-(4-(N-acetylhydroxy-carbamimidoyl)-phenoxy)-pyridine-4-carbonyl]-piperidine-4-yl}ethyl)carbamic Acid Tert-butyl Esters (2-{1-[2,6-Bis-(4-(N-hydroxy-carbamimidoyl)-phenoxy)-pyridine-4-carbonyl]-piperidine-4-yl}ethyl)carbamic acid tert-butyl esters 0.3 g (0.473 mmol) was acetylated with 0.095 g (0.95 mmol) of acetic anhydride using the procedure of Example 2(e) to afford 0.3 g of the required product. Percentage purity (LCMS): 56.2%, (M+1)=717.3+1.

f) (2-{1-[2,6-Bis-(4-carbamimidoyl-phenoxy)-pyridine-4-carbonyl]-piperidine-4-yl}ethyl)carbamic Acid Tert-butyl Esters (2-{1-[2,6-Bis-(4-(N-acetylhydroxy-carbamimidoyl)-phenoxy)-pyridine-4-carbonyl]-piperidine-4-yl}ethyl) carbamic acid tert-butyl esters 0.3 g (0.41 mmol) was reduced using the procedure of Example 2(f) to afford 0.17 g of required product. Percentage purity (LCMS): 59.3%, (M+1)=601.3.

g) 2-{1-[2,6-Bis-(4-carbamimidoyl-phenoxy)-pyridine-4-carbonyl]-piperidine-4-yl}ethylamine The -Boc group was removed from (2-{1-[2,6-Bis-(4-carbamimidoyl-phenoxy)-pyridine-4-carbonyl]-piperidine-4-yl}ethyl)carbamic acid tert-butyl esters 0.17 g (0.31 mmol) using the procedure of Example 9(d) to afford 50 mg of the required product. Percentage purity (HPLC): 95.99%, (LCMS): 98.52%. $^1$H NMR (DMSO-$d_6$): 8· 1.1 (2H, m), 1.5 (2H, m), 1.6 (2H, m), 1.75 (1H, m), 2.7 (1H, m), 2.85 (2H, m), 3.05 (1H, m), 3.55 (1H, m), 4.4 (1H, m), 6.9 (1H, s), 7.4 (4H, d), 7.75 (3H, brs), 7.85 (4H, d), 9.3 (8H, s).

Example 13

N-(4-Amino-cyclohexyl)-2,6-bis-(4-carbamimidoyl-phenoxy)-isonicotinamide

Intermediates (a) and (b) are the same as in Example 12.

c) (4-{[2,6-Bis-(4-cyano-phenoxy)-pyridine-4-carbonyl]amino}-cyclohexyl)-carbamic Acid Tert-butyl Esters 2,6-bis(4-Cyano phenoxy)-isonicotinic acid (0.428 g, 1.2 mmol) and (4-amino-cyclohexyl)-carbamic acid tert-butyl ester (0.282 g, 1.32 mmol) were coupled using the procedure of Example 5(c) to afford 0.51 g of the required product. Percentage purity (LCMS–ve mode): (M−1)=553.2. $^1$H NMR (DMSO-$d_6$): δ 1.25 (4H, m), 1.40 (9H, s), 1.84 (4H, m), 2.74 (1H, s), 2.80 (1H, m), 3.22 (2H, m), 3.72 (1H, m), 6.78 (1H, d), 7.28 (1H, s), 7.35 (3H, d), 7.85 (4H, d), 7.95 (1H, s), 8.60 (1H, brs).

d) (4-{[2,6-Bis-(4-(N-hydroxy-carbamimidoyl)-phenoxy)-pyridine-4-carbonyl]-amino}cyclohexyl)carbamic Acid Tert-butyl Esters (4-{[2,6-Bis-(4-cyano-phenoxy)-pyridine-4-carbonyl] amino}-cyclohexyl)-carbamic acid tert-butyl esters (0.276 g, 0.70 mmol), hydroxylamine hydrochloride (0.208 g, 3.0 mmol) and DIPEA (0.387 g, 3.0 mmol) were used and the procedure of Example 2(d) was followed to afford 0.7 g of the required product. Percentage purity (LCMS): 47.3%, (M+1)= 619.2.

e) (4-{[2,6-Bis-(4-(N-acetylhydroxy-carbamimidoyl)-phenoxy)-pyridine-4-carbonyl]-amino}cyclohexyl)carbamic Acid Tert-butyl Esters (4-{[2,6-Bis-(4-(N-hydroxy-carbamimidoyl)-phenoxy)-pyridine-4-carbonyl]-amino}cyclohexyl)carbamic acid tert-butyl esters 0.6 g (0.96 mmol) was acetylated with 0.2 g (2.0 mmol) of acetic anhydride using the procedure of Example 2(e) to afford 0.65 g of the required product. Percentage purity (LCMS): 59.4%, (M+1)=703.2+1.

f) (4-{[2,6-Bis(4-carbamimidoyl-phenoxy)-pyridine-4-carbonyl]amino}cyclo-hexyl)-carbamic Acid Tert-butyl Esters (4-{[2,6-Bis-(4-(N-acetylhydroxy-carbamimidoyl)-phenoxy)-pyridine-4-carbonyl]-amino}cyclohexyl)carbamic acid tert-butyl esters 0.65 g (0.92 mmol) was reduced by using the procedure of Example 2(f) to afford 0.56 g of required product. Percentage purity (LCMS): 60.2%, (M+1)= 587.2+1.

g) N-(4-Amino-cyclohexyl)-2,6-bis-(4-carbamimidoyl-phenoxy)-isonicotinamide

The -Boc group was removed from (4-{[2,6-bis(4-carbamimidoyl-phenoxy)-pyridine-4-carbonyl]amino}cyclohexyl)-carbamic acid tert-butyl esters 0.55 g (0.93 mmol) using the procedure of Example 9(d) to afford 0.26 mg of the required product. Percentage purity (HPLC): 94.36%, (LCMS): 96.21%. $^1$H NMR (DMSO-$d_6$): δ 1.4 (3H, m), 2.0 (4H, m), 3.0 (2H, m), 3.75 (1H, m), 7.26 (2H, s), 7.4 (3H, d), 7.86 (3H, d), 8.0 (3H, brs), 8.72 (1H, m), 9.30 (61-1, d).

Example 14

N-(4-aminocyclohexyl)-2,6-bis[4-(N-hydroxy-carbamimidoyl)-phenoxy]-isonicotinamide Intermediates (a) to (d) are the same as in Example 13.

e) N-(4-aminocyclohexyl)-2,6-bis[4-(N-hydroxycarbamimidoyl)phenoxy]-isonicotinamide The -Boc group was removed from (4-{[2,6-Bis-(4-(N-hydroxy-carbamimidoyl)-phenoxy)-pyridine-4-carbonyl] amino}cyclohexyl)carbamic acid tert-butyl esters 0.25 g (0.41 mmol) using the procedure of Example 9(d) to afford 0.115 g of the required product. The crude product was purified by reverse-phase preparative HPLC to afford 0.115 g of the required product. Percentage purity (HPLC): 97.73%, (LCMS): 94.78%. $^1$H NMR (DMSO-$d_6$): δ 1.4 (4H, m), 1.9 (4H, m), 3.0 (1H, m), 3.75 (1H, m), 7.20 (2H, s), 7.36 (4H, d), 7.76 (4H, d), 7.9 (31-1, brs), 8.5 (2H, m), 8.68 (1H, d), 11.0 (2H, s).

Example 15

N-[1-(4-amino butyryl)piperidin-4-yl]-2,6-bis[4-carbamimidoylphenoxy]-isonicotinamide

Intermediates (a) and (b) are the same as in Example 12.

c) 4-{[2,6-Bis-(4-cyano-phenoxy)-pyridine-4-carbonyl]amino}-piperidine-1-carboxylic Acid Tert-butyl Ester 2,6-bis(4-Cyano phenoxy)-isonicotinic acid (0.220 g, 0.61 mmol) and 4-amino-piperidine-1-carboxylic acid tert-butyl ester (0.142 g, 0.71 mmol) were coupled using the procedure of Example 5(c) to afford 0.295 g of the required product. Percentage purity (LCMS): 59.4%, (M+1)=439.2+1 (with BOC). $^1$H NMR (DMSO-$d_6$): δ 1.40 (9H, s), 1.81 (4H, m), 2.86 (4H, m), 3.82 (1H, m), 7.26 (2H, s), 7.34 (4H, d), 7.85 (4H, d), 8.64 (1H, d).

d) 2,6-Bis(4-cyano phenoxy)-N-piperidin-4-yl-isonicotinamide

The -Boc group was removed from 4-{[2,6-Bis-(4-cyano-phenoxy)-pyridine-4-carbonyl]amino}-piperidine-1-carboxylic acid tert-butyl ester 0.29 g (0.53 mmol) using the procedure of Example 9(d) to afford 0.2 g of the required product. Percentage purity (LCMS): 88.3%, (M+1)=439.2+1. $^1$H NMR (DMSO-$d_6$): δ 1.62 (2H, m), 2.00 (3H, m), 3.02 (2H, m), 4.05 (2H, m), 7.30 (6H, m), 7.85 (4H, d), 8.32 (2H, brs), 8.88 (1H, d).

e) [3-(4-{[2,6-Bis(4-cyano-phenoxy)-pyridine-4-carbonyl]amino}piperidin-1-yl)-propyl]carbamic Acid Tert-butyl Ester 2,6-Bis(4-cyano phenoxy)-N-piperidin-4-yl-isonicotinamide 0.16 g (0.364 mmol), (3-bromo-propyl)-carbamic acid tert-butyl ester 0.12 g (0.50 mmol) and potassium carbonate 0.175 g (1.26 mmol) were used and the procedure of Example 11(e) was followed to afford 0.175 g of the required product. Percentage purity (LCMS): 80.4%, (M+1)=596.2+1. NMR (DMSO-$d_6$): δ 1.40 (9H, s), 1.88 (9H, m), 2.95 (4H, m), 3.85 (2H, m), 6.86 (2H, brs), 7.26 (2H, s), 7.34 (4H, d), 7.85 (4H, d), 8.15 (2H, brs), 9.02 (1H, brs).

f) [3-(4-{[2,6-Bis(4-(N-hydroxy-carbamimidoyl)-phenoxy)-pyridine-4-carbonyl]-amino}-piperidin-1-yl)-propyl]carbamic Acid Tert-butyl Ester

[3-(4-{[2,6-Bis(4-cyano-phenoxy)-pyridine-4-carbonyl] amino}piperidin-1-yl)-propyl]carbamic acid tert-butyl ester (0.17 g, 0.28 mmol), hydroxylamine hydrochloride (87.5 mg, 1.26 mmol) and DIPEA (162.8 mg, 1.26 mmol) were used and the procedure Example 2(d) was followed to afford 0.13 g of the required product. Percentage purity (LCMS): 42.4%, (M+1)=662.3+1.

g) [3-(4-{[2,6-Bis(4-(N-acetylhydroxy-carbamimidoyl)-phenoxy)-pyridine-4-carbonyl]amino}-piperidin-1-yl)-propyl]carbamic Acid tert-butyl Ester

[3-(4-{[2,6-Bis(4-(N-hydroxy-carbamimidoyl)-phenoxy)-pyridine-4-carbonyl]-amino}-piperidin-1-yl)-propyl] carbamic acid tert-butyl ester 0.13 g (0.19 mmol) was acetylated using 45 mg (0.4 mmol) of acetic anhydride following the procedure of Example 2(e) to afford 0.12 g of the required product. Percentage purity (LCMS): 66.9%, (M+1)=746.3+1.

h) [3-(4-{[2,6-Bis(4-carbamimidoyl-phenoxy)-pyridine-4-carbonyl]amino}-piperidin-1-yl)propyl]carbamic Acid Tert-butyl Ester

[3-(4-{[2,6-Bis(4-(N-acetylhydroxy-carbamimidoyl)-phenoxy)-pyridine-4-carbonyl]amino}-piperidin-1-yl)-propyl]carbamic acid tert-butyl ester 0.13 g (0.17 mmol) was reduced using the procedure of Example 2(f) to afford 0.115 g of the required product. Percentage purity (LCMS): 81.1%, (M+1)=630.3+1.

i) N-[1-(4-amino butyryl)piperidin-4-yl]-2,6-bis[4-carbamimidoyl phenoxy]-isonicotinamide The -Boc group was removed from [3-(4-{[2,6-bis(4-carbamimidoyl-phenoxy)-pyridine-4-carbonyl]amino}-piperidin-1-yl)propyl]carbamic acid tert-butyl ester 0.115 g (0.18 mmol) using the procedure of Example 9(d) to afford 28 mg of the required product. Percentage purity (HPLC): 97.58%, (LCMS): 96.9%. $^1$H NMR (DMSO-$d_6$): δ 1.8 (2H, m), 2.0 (5H, m), 2.9 (2H, m), 3.15 (4H, m), 3.55 (1H, m), 4.1 (1H, m), 7.3 (2H, s), 7.4 (4H, d), 7.85 (6H, m), 8.9 (1H, d), 9.3 (6H, s), 10.05 (1H, brs).

Example 16

4-{4-[4-(2-aminoethyl)piperidine-1-carbonyl]-6-isopropoxypyridine-2-yloxy}-benzamidine a) 2-Hydroxy-6-isopropoxy-isonicotinic Acid isopropyl Ester 2,6-Dihydroxyisonicatonic acid (2.0 g, 12.9 mmol) was dissolved in 20 ml of propane-2-ol at 0° C. 2 ml of concentrated sulfuric acid was added to the stirred solution of dihydroxy acid at 0° C. over a period of 10 min and then the contents of the flask were refluxed overnight at 100° C. The solvent was removed under reduced pressure and the crude residual mixture was dissolved in 250 ml of ethylacetate and washed with water. The organic phase was dried over anhydrous sodium sulphate, concentrated under reduced pressure and subjected to column chromatography, using chloroform: ethylacetate (8:2) as eluant to afford 0.5 g of required product. $^1$H NMR (CDCl$_3$): δ 1.2 (6H, d), 1.35 (6H, d), 4.8 (1H, m), 5.25 (1H, m), 6.85 (1H, s), 6.95 (1H, s), 10.52 (1H, brs).

b) 2-(4-Cyano-phenoxy)-6-isopropoxy-isonicotinic Acid Isopropyl Ester

2-Hydroxy-6-isopropoxy-isonicotinic acid isopropyl ester (0.5 g, 2.09 mmol) and 0.577 g (4.18 mmol) potassium carbonate was dissolved in 5 ml of dry DMF. 0.25 g (2.09 mmol) of 4-fluorobenzonitrile, dissolved in 5 ml of DMF, was added to the stirred solution of hydroxynicotinate over a period of 15 min and then the contents of the reaction flask were stirred overnight at 100° C. Reaction mixture was concentrated and the residue was dissolved in 100 ml of ethylacetate and washed with water. Ethyl acetate layer was dried over anhydrous sodium sulphate and concentrated under reduced pressure to afford 0.3 g of required product which was used for the next step without further purification. $^1$H NMR (CDCl$_3$): δ 1.2 (6H, d), 1.35 (6H, d), 4.8 (1H, m), 5.25 (1H, m), 7.2 (3H, m), 7.7 (3H, m).

c) 2-(4-cyano phenoxy)-6-isopropoxy Isonicotinic Acid 2-(4-cyano phenoxy)-6-isopropoxy isonicotinic acid isopropyl ester (0.3 g, 0.88 mmol) was deesterified using the procedure of Example 5(b) to afford 0.20 g of the required product. Percentage purity (LCMS): 96.71%. $^1$H NMR (DMSO-$d_6$): δ 1.2 (6H, d), 4.8 (1H, m), 6.85 (1H, s), 6.9 (1H, s), 7.4 (2H, d), 7.98 (2H, m), 14.0 (1H, brs).

d) (2-{1-[2-(4-cyano-phenoxy)-6-isopropoxy-pyridine-4-carbonyl]piperidin-4-yl}ethyl)-carbamic Acid Tert-Butyl Ester 2-(4-cyano phenoxy)-6-isopropoxy isonicotinic acid (0.20 g, 0.67 mmol) and (2-piperidin-4-yl-ethyl)-carbamic acid tert-butyl ester (0.16 g, 0.7 mmol) were coupled using the procedure of Example 5(c) to afford 0.12 g of the required product. $^1$H NMR (DMSO-$d_6$): δ 1.12 (2H, m), 1.15 (6H, d), 1.4 (9H, s), 1.6 (2H, m), 1.75 (1H, m), 2.7 (1H, m), 2.98 (3H, m), 3.5 (1H, m), 4.45 (1H, m), 4.8 (1H, m), 6.48 (1H, s), 6.58 (1H, s), 6.8 (1H, brs), 7.38 (2H, d), 7.9 (2H, d).

e) 4-{4-[4-(2-Amino-ethyl)-piperidine-1-carbonyl]-6-isopropoxy-pyridin-2-yloxy}-benzimidic Acid Ethyl Ester (2-{1-[2-(4-cyano-phenoxy)-6-isopropoxy-pyridine-4-carbonyl]piperidin-4-yl}ethyl)-carbamic acid tert-butyl ester (0.12 g, 0.23 mmol) was used and the procedure of Example 1(d) was followed to afford 0.11 g of the required product. Percentage purity (LCMS): 51.13%.

f) 4-{4-[4-(2-amino-ethyl)piperidine-1-carbonyl]-6-isopropoxy-pyridine-2-yloxy}-benzamidine 4-{4-[4-(2-Amino-ethyl)-piperidine-1-carbonyl]-6-isopropoxy-pyridin-2-yloxy}-benzimidic acid ethyl ester (0.11 g, 0.24 mmol) was used and the procedure of Example 1(e) was followed to afford 50 mg of the required product. Percentage purity (HPLC): 99.46%, (LCMS): 97.7%. $^1$H NMR (DMSO-$d_6$): δ 1.15 (6H, s), 1.5 (2H, m), 1.6 (2H, m), 1.75 (1H, m), 2.7 (1H, m), 2.85 (2H, m), 3.0 (1H, m), 3.2 (2H, s), 4.45 (1H, m), 4.85 (1H, m), 6.5 (1H, s), 6.6 (1H, s), 7.4 (2H, d), 7.75 (31-1, brs), 7.9 (2H, d), 9.25 (2H, m), 9.35 (2H, s).

Example 17

4-[5-[4-(2-aminoethyl)-piperidine-1-carbonyl]-6-(4-trifluoromethoxy-phenoxy)-pyridine-2-yloxy]benzamidine a) 2-Chloro-6-(4-cyano phenoxy)nicotinic Acid Ethyl Ester 96.7 mg (0.7 mmol) of potassium carbonate was added to a stirred solution of 2,6-dichloro nicotinic acid ethyl ester 0.15 g (0.7 mmol) in 10 ml of N,N-dimethyl-formamide (DMF) cooled to 5° C. This was followed by dropwise addition (over a period of 10 min) of 4-cyano phenol 80 mg (0.68 mmol) dissolved in 2 ml of DMF. The reaction mixture was allowed to stir at RT for 2 h, concentrated under reduced pressure and the residue was dissolved in 100 ml of ethylacetate. The organic layer was washed with water and dried over anhydrous sodium sulphate and concentrated under reduced pressure. The crude product was purified by column chromatography using hexane:ethylacetate (8:2) as eluants to afford 0.13 g of the required product. $^1$H NMR (DMSO-$d_6$): δ 1.3 (3H, t), 4.3 (2H, q), 7.26 (1H, s), 7.38 (1H, s), 7.48 (2H, d), 7.96 (2H, d).

b) 6-(4-cyano phenoxy)-2-(4-trifluoromethoxy Phenoxy)nicotinic Acid Ethyl Ester Potassium carbonate (60 mg, 0.43 mmol) was added to a stirred and cooled (0° C.) solution of 2-chloro-6-(4-cyano phenoxy)nicotinic acid ethyl ester 0.13 g (0.43 mmol) in 10 ml DMF and stirred for 10 min at the same temperature. This was followed by the addition of 76.5 mg (0.43 mmol) of 4-trifluoromethoxy phenol, dissolved in 2 ml of DMF, over a period of 10 min. After the addition was completed, the contents were allowed to stir at RT. This was followed by heating for 3 h at 80° C. The reaction mixture was concentrated under reduced pressure, poured into ice-cold water and dissolved in 50 ml of ethyl acetate. Organic layer was then washed with brine solution followed by water and the crude product was purified by column chromatography using hexane:ethyl acetate (8:2) to afford 0.18 g of the required product. Percentage purity: LCMS–ve mode): 20.12%.

c) 6-(4-Cyano phenoxy)-2-(4-trifluoromethoxy Phenoxy)nicotinic Acid 6-(4-cyano phenoxy)-2-(4-trifluoromethoxy phenoxy)nicotinic acid ethyl ester (0.18 g, 0.40 mmol) was deesterified by using the procedure of Example 5(b) to afford 0.15 g of the required product. Percentage purity: LCMS (–ve mode): 41.96%.

d) (2-{1-[6-(4-cyano phenoxy)-2-(4-trifluoromethoxy phenoxy)pyridine-3-carbonyl]piperidin-4-yl}ethyl)carbamic Acid Tert-butyl Ester 6-(4-Cyano phenoxy)-2-(4-trifluoromethoxy phenoxy)nicotinic acid (0.15 g, 0.36 mmol) and (2-piperidin-4-yl-ethyl)-carbamic acid tert-butyl ester (0.082 g, 0.36 mmol) were coupled using the procedure of Example 5(c) to afford 0.15 g of the required product. Percentage purity (LCMS): 43.23%.

e) 4-[5-[4-(2-Aminoethyl)piperidine-1-carbonyl]-6-(4-trifluoromethoxy-phenoxy)pyridine-2-yloxy]benzimidic Acid Ethyl Ester (2-{1-[6-(4-cyano phenoxy)-2-(4-trifluoromethoxy phenoxy)pyridine-3-carbonyl]-piperidin-4-yl}ethypcarbamic acid tert-butyl ester (0.15 g, 0.24 mmol) was used and the procedure of Example 1(d) was followed to afford 0.20 g of the required product. Percentage purity: LCMS (+ve mode): 35.2%.

f) 4-[5-[4-(2-aminoethyp-piperidine-1-carbonyl]-6-(4-trifluoromethoxy-phenoxy)-pyridine-2-yloxy]benzamidine 4-[5-[4-(2-Aminoethyl)piperidine-1-carbonyl]-6-(4-trifluoromethoxy-phenoxy)-pyridine-2-yloxy]benzimidic acid ethyl ester (0.20 g, 0.34 mmol) was used and the procedure of Example 1(e) was followed to afford 0.1 g of the required product. Percentage purity (HPLC): 89.68%, (LCMS): 74.9%. NMR (DMSO-$d_6$): δ 1.05 (1H, m), 1.25 (1H, m), 1.65 (5H, m), 2.8 (4H, m), 3.2 (1H, m), 4.5 (1H, m), 6.85 (1H, d), 7.25 (2H, s), 7.35 (4H, m), 7.85 (4H, m), 7.9 (1H, m), 9.2 (2H, s), 9.3 (2H, s).

Example 18

4-[5-[4-(2-amino-ethyl)piperidine-1-carbonyl]-6-(4-fluoro-phenoxy)pyridine-2-yloxy]-benzamidine

Intermediate (a) is the same as in Example 17.

b) 6-(4-Cyano phenoxy)-2-(4-fluoro phenoxy)nicotinic Acid Ethyl Ester

2-Chloro-6-(4-cyano phenoxy)nicotinic acid ethyl ester (0.25 g, 0.81 mmol) and 4-fluorophenol (0.09 g, 0.81 mmol) were coupled using the procedure of Example 17(b) to afford 0.23 g of the required product. Percentage purity (LCMS): 61.86%.

c) 6-(4-cyano phenoxy)-2-(4-fluoro phenoxy)nicotinic Acid 6-(4-Cyano phenoxy)-2-(4-fluoro phenoxy)nicotinic acid ethyl ester (0.23 g, 0.60 mmol) was deesterified using the procedure of Example 5(b) to afford 0.2 g of the required product. Percentage purity: LCMS (−ve mode): 57.29%.

d) (2-{1-[6-(4-cyano phenoxy)-2-(4-fluoro phenoxy)pyridine-3-carbonyl]piperidin-4-yl}ethyl)carbamic Acid Tert-butyl Ester 6-(4-cyano phenoxy)-2-(4-fluoro phenoxy)nicotinic acid (0.2 g, 0.57 mmol) and (2-piperidin-4-yl-ethyl)-carbamic acid tert-butyl ester (0.13 g, 0.57 mmol) were coupled using the procedure of Example 5(c) to afford 0.25 g of the required product. Percentage purity: LCMS (−ve mode): 67.5%.

e) 4-[5-[4-(2-Amino-ethyl)-piperidine-1-carbonyl]-6-(4-fluoro-phenoxy)-pyridin-2-yloxy]-benzimidic Acid Ethyl Ester (2-{1-[6-(4-cyanophenoxy)-2-(4-fluorophenoxy)pyridine-3-carbonyl]piperidin-4-yl}ethyl)carbamic acid tert-butyl ester (0.25 g, 0.44 mmol) was used and the procedure of Example 1(d) was followed to afford 0.28 g of the required product. Percentage purity (LCMS): 51.02%.

f) 4-[5-[4-(2-amino ethyl)piperidine-1-carbonyl]-6-(4-fluoro phenoxy)pyridine-2-yloxy]benzamidine 4-[5-[4-(2-Amino-ethyl)-piperidine-1-carbonyl]-6-(4-fluoro-phenoxy)-pyridin-2-yloxy]-benzimidic acid ethyl ester (0.28 g, 0.55 mmol) was used and the procedure of Example 1(e) was followed to afford 0.12 g of the required product. Percentage purity (HPLC): 95.03%, (LCMS): 90.18%. $^1$H NMR (DMSO-$d_6$): δ 1.05 (2H, m), 1.25 (1H, s), 1.5 (2H, m), 1.65 (2H, m), 1.75 (1H, m), 2.8 (2H, m), 3.05 (3H, m), 3.65 (1H, d), 4.5 (1H, d), 6.8 (1H, s), 7.18 (2H, d), 7.36 (2H, d), 7.68 (2H, brs), 7.82 (1H, d), 7.94 (1H, m), 8.98 (1H, s), 9.30 (1H, s).

Example 19

4-[3-[4-(2-amino ethyl)piperidine-1-carbonyl]-6-(4-trifluoromethoxy phenoxy)pyridin-2-yloxy]benzamidine a) 2-Chloro-6-(4-trifluoromethoxy phenoxy)nicotinic Acid Ethyl Ester 2,6-dichloronicotinic acid ethyl ester (0.22 g, 0.1 mmol) and 4-trifluoromethoxy-phenol (0.178 g, 0.1 mmol) were coupled using the procedure of Example 17(a) to afford 0.3 g of the required produCt. Percentage purity (LCMS): 64.0%.

b) 2-(4-cyano phenoxy)-6-(4-trifluoromethoxy phenoxy)nicotinic Acid Ethyl Ester 2-Chloro-6-(4-trifluoromethoxy phenoxy)nicotinic acid ethyl ester (0.3 g, 0.83 mmol) and 4-cyanophenol (98.8 mg, 0.83 mmol) were coupled using the procedure of Example 17(b) to afford 0.23 g of the required product. Percentage purity (LCMS): 82.35%.

c) 2-(4-cyano phenoxy)-6-(4-trifluoromethoxy Phenoxy)nicotinic Acid 2-(4-cyano phenoxy)-6-(4-trifluoromethoxy phenoxy)nicotinic acid ethyl ester (0.23 g, 0.51 mmol) was deesterified using the procedure of Example 5(b) to afford 0.2 g of the required product. Percentage purity: LCMS (−ve mode): 66.14%.

d) (2-{1-[2-(4-cyanophenoxy)-6-(4-trifluoromethoxyphenoxy)pyridine-3-carbonyl]piperidin-4-yl}ethyl) carbamic Acid Tert-butyl Ester 2-(4-cyano phenoxy)-6-(4-trifluoromethoxy phenoxy)nicotinic acid (0.2 g, 0.48 mmol) and (2-Piperidin-4-yl-ethyl)-carbamic acid tert-butyl ester (0.11 g, 0.48 mmol) were coupled using the procedure of Example 5(c) to afford 0.21 g of the required product. Percentage purity (LCMS): 68.11%.

e) 4-[3-[4-(2-Amino-ethyl)piperidine-1-carbonyl]-6-(4-trifluoromethoxy-phenoxy)-pyridine-2-yloxy] benzimidic Acid Ethyl Ester (2-{1-[2-(4-cyanophenoxy)-6-(4-trifluoromethoxyphenoxy)pyridine-3-carbonyl]piperidin-4-yl}ethyl)carbamic acid tert-butyl ester (0.2 g, 0.319 mmol) was used and the procedure of Example 1(d) was followed to afford 0.25 g of the required product. Percentage purity (LCMS): 52.44%.

f) 4-[3-[4-(2-Amino-ethyl)piperidine-1-carbonyl]-6-(4-trifluoromethoxy-phenoxy)-pyridine-2-yloxy] benzamidine 4-[3-[4-(2-Amino-ethyl)piperidine-1-carbonyl]-6-(4-trifluoromethoxy-phenoxy)-pyridine-2-yloxy]benzimidic acid ethyl ester (0.25 g, 0.43 mmol) was used and the procedure of Example 1(e) was followed to afford 0.050 g of the required product. Percentage purity (HPLC): 94.13%, (LCMS): 91.76%. $^1$H NMR (DMSO-$d_6$): δ 1.5 (2H, m), 1.65 (2H, m), 1.75 (1H, m), 2.3 (1H, m), 2.8 (4H, m), 3.1 (2H, m), 3.65 (1H, d), 4.5 (1H, d), 6.88 (1H, s), 7.26 (2H, m), 7.36 (3H, m), 7.82 (2H, d), 7.94 (2H, brs), 9.14 (2H, s), 9.34 (2H, s).

Example 20

4-[5-[4-(2-amino-ethyl)piperidine-1-carbonyl]-3-fluoro-6-(3-trifluoromethoxy phenoxy)-pyridine-2-yloxy]benzamidine a) 2-chloro-6-(4-cyano phenoxy)-5-fluoro Nicotinic Acid Ethyl Ester 2,6-Dichloro-5-fluoro-nicotinic acid ethyl ester (3.5 g, 15.0 mmol) and 4-cyano-phenol (1.78 g, 15.0 mmol) were coupled using the procedure of Example 17(a) to afford 2.4 g of the required product. $^1$H NMR (DMSO-d$_6$): δ 1.35 (3H, t), 4.4 (2H, q), 7.58 (2H, d), 8.0 (2H, d), 8.4 (1H, d).

b) 6-(4-cyano phenoxy)-5-fluoro-2-(3-trifluoromethoxy phenoxy)nicotinic Acid Ethyl Ester 2-chloro-6-(4-cyano phenoxy)-5-fluoro nicotinic acid ethyl ester (2.4 g, 7.49 mmol) and 3-trifluoromethoxyphenol (1.33 g, 7.49 mmol) were coupled using the procedure of Example 17(b) to afford 1.8 g of the required product. $^1$H NMR (DMSO-d$_6$): δ 1.35 (3H, t), 4.4 (2H, q), 7.22 (2H, d), 7.3 (3H, d), 7.34 (1H, m), 7.54 (2H, d), 8.38 (1H, d).

c) 6-(4-cyano phenoxy)-5-fluoro-2-(3-trifluoromethoxy phenoxy)nicotinic Acid 6-(4-cyano phenoxy)-5-fluoro-2-(3-trifluoromethoxy phenoxy)nicotinic acid ethyl ester (1.8 g, 2.79 mmol) was deesterified using the procedure of Example 5(b) to afford 1.3 g of the required product. $^1$H NMR (DMSO-d$_6$): δ 7.22 (2H, d), 7.3 (4H, m), 7.74 (2H, d), 8.34 (1H, d), 13.2 (1H, brs).

d) (2-{1-[6-(4-cyano phenoxy)-5-fluoro-2-(3-trifluoromethoxy phenoxy)pyridine-3-carbonyl]piperidin-4-yl}ethyl)carbamic Acid Tert-butyl Ester 6-(4-cyano phenoxy)-5-fluoro-2-(3-trifluoromethoxy phenoxy)nicotinic acid (1.3 g, 2.99 mmol) and (2-piperidin-4-yl-ethyl)-carbamic acid tert-butyl ester (0.684 g, 3.0 mmol) were coupled using the procedure of Example 5(c) to afford 1.1 g of the required product. $^1$HNMR (DMSO-d$_6$): δ 1.2 (2H, m), 1.4 (9H, d), 1.5 (2H, m), 1.6 (2H, m), 2.2 (1H, m), 2.35 (1H, m), 3.0 (3H, m), 3.7 (1H, m), 4.45 (1H, m), 6.78 (1H, m), 7.18 (1H, m), 7.26 (2H, m), 7.32 (1H, s), 7.46 (1H, m), 7.76 (1H, m), 7.86 (1H, s), 8.1 (1H, m).

e) 4-[5-[4-(2-Amino ethyl)piperidine-1-carbonyl]-3-fluoro-6-(3-trifluoromethoxy phenoxy)pyridine-2-yloxy]benzimidic Acid Ethyl Ester (2-{1-[6-(4-cyanophenoxy)-5-fluoro-2-(3-trifluoromethoxyphenoxy)pyridine-3-carbonyl]piperidin-4-yl}ethyl)carbamic acid tert-butyl ester (1.1 g, 1.70 mmol) was used and the procedure of Example 1(d) was followed to afford 1.0 g of the required product. Percentage purity (LCMS): 11.21%.

f) 4-[5-[4-(2-Aminoethyl)piperidine-1-carbonyl-3-fluoro-6-(3-trifluoromethoxy phenoxy)pyridine-2-yloxy]benzamidine 4-[3-[4-(2-Amino-ethyl)piperidine-1-carbonyl]-6-(3-trifluoromethyl-phenoxy)-pyridine-2-yloxy]benzimidic acid ethyl ester (1.0 g, 1.69 mmol) was used and the procedure of Example 1(e) was followed to afford 0.250 g of the required product. Percentage purity (HPLC): 98.16%, (LCMS): 90.93%. $^1$H NMR (DMSO-d$_6$): δ 1.5 (3H, m), 1.6 (2H, m), 1.75 (2H, m), 2.0 (1H, m), 2.8 (4H, m), 4.5 (1H, m), 7.1 (2H, m), 7.25 (2H, m), 7.45 (2H, d), 8.0 (3H, m), 8.1 (2H, m), 9.20 (2H, s), 9.35 (2H, s).

Example 21

2,4-Bis-(4-carbamimidoyl-phenoxy)-phenyl-2-naphthalenesulfonamide a) 1,5-Bis-(4-cyano-phenoxy)-2-nitrobenzene 4-cyanophenol 4.5 g (23.0 mmol), dissolved in 5 ml of DMF, was added to a stirred suspension of sodium hydride 0.92 g (23.0 mmol) in 5 ml of DMF cooled to 5° C. The reaction flask was stirred for 10 min at the same temperature and this was followed by dropwise addition (over 15 min) of 2,4-dichloronitrobenzene 2.0 g (10.5 mmol) dissolved in 5 ml of DMF. The reaction mixture was stirred for 6 h at 70° C. The reaction mass was poured into ice-cold water and extracted with 200 ml of ethylacetate. The organic phase was washed with 1 M Na$_2$CO$_3$ and saturated brine solution. The solution was dried over sodium sulphate and concentrated to afford an oily residue, which was purified by column chromatography using chlorofrom-ethyl acetate (10:2) to afford 2.5 g of the required product. $^1$H NMR (DMSO-d$_6$): δ 6.79 (1H, d), 6.93 (1H, d), 7.06 (2H, d), 7.18 (2H, d), 7.75 (4H, d), 8.16 (1H, d).

b) 1,5-Bis-(4-cyano-phenoxy)-2-aminobenzene

Zinc dust, 0.4 g (5.3 mmol) was added portionwise to a reaction flask containing a stirred mixture (10 min) of 1,5-bis-(4-cyano-phenoxy)-2-nitrobenzene 1.5 g (4.2 mmol) and 0.085 g (0.08 mmol) of ammonium chloride dissolved in 25 ml of methanol. The reaction mixture was allowed to stir for 1 h at RT. Reaction mixture was filtered through celite and the filtrate was concentrated to afford a brown viscous residue which was partitioned between ethyl acetate and water. The organic layer was dried over anhydrous sodium sulfate and concentrated to afford an oily residue, which was purified by column chromatography using chloroform-ethyl acetate (10:1) to afford 1.3 g of the required product. $^1$H NMR (DMSO-d$_6$): δ 5.10 (2H, brs), 6.85 (3H, m), 7.06 (4H, m), 7.80 (4H, m).

c) Naphthalene-2-sulfonic acid[2,4-bis-(4-cyano-phenoxy)-phenyl]amide 1,5-Bis-(4-cyano-phenoxy)-2-aminobenzene 0.175 g (0.54 mmol), 2-naphthalene-sulfonyl chloride 0.148 g (0.65 mmol) and N,N-diisopropylethylamine (DIPEA) 0.85 g (0.65 mmol) were dissolved in 5 ml of dry toluene and refluxed for 8 h. The reaction mixture was concentrated under reduced pressure and the residue was partitioned between water and ethyl acetate after the pH was adjusted to 2 with 6 N HCl. The organic phase was washed with 1 M Na$_2$CO$_3$ (5×100 ml) and saturated brine solution. The solution was dried over sodium sulphate and concentrated to afford an oily residue, which was purified by column chromatography using hexane-ethyl acetate (10:2) to afford 0.190 g of the required product. $^1$H NMR (DMSO-d$_6$): δ 6.45 (3H, m), 7.16 (5H, m), 7.42 (6H, m), 7.75 (2H, dd), 8.10 (2H, d), 8.35 (1H, s).

d) Naphthalene-2-sulfonic acid[2,4-bis-(4-ethoxycarbonimidoyl-phenoxy)-phenyl]-amide Using naphthalene-2-sulfonic acid[2,4-bis-(4-cyano-phenoxy)-phenyl]-amide (0.19 g, 0.36 mmol) and following the procedure of Example 1(d) afforded 0.13 g of the required product. Percentage purity (LCMS): 69.6%, (M+1)=(609.1+1).

e) Naphthalene-2-sulfonic acid[2,4-bis-(4-carbamimidoyl-phenoxy)-phenyl]amide

Using naphthalene-2-sulfonic acid[2,4-bis-(4-ethoxycarbonimidoyl-phenyl)-phenyl]-amide (0.13 g, 0.21 mmol) and following the procedure of Example 1(e) 0.033 g of the required product was obtained. Percentage purity (HPLC): 96.91%, (LCMS): 96.74%. $^1$HNMR (DMSO-d$_6$): δ 6.5 (1H, s), 6.7 (3H, m), 6.95 (2H, m), 7.2 (3H, m), 7.3 (1H, s) 7.45

(1H, m), 7.55 (2H, d), 7.7 (2H, m), 7.75 (1H, m), 7.85 (2H, d), 7.95 (2H, m), 8.1 (1H, m), 8.3 (1H, s), 9.0 (3H, m), 9.15 (2H, s), 9.25 (2H.$).

Example 22

4-Fluorobenzene-sulfonic acid[2,4-bis-(4-carbamimidoyl-phenoxy)-phenyl]-amide

Intermediates (a) and (b) are the same as in Example 21.

c) N-[2,4-Bis-(4-cyano-phenoxy)-phenyl]-4-fluorobenzenesulfonamide

4-Fluorobenzene sulfonyl chloride (0.126 g, 0.65 mmol) was added to a stirred solution of 1,5-bis-(4-cyano-phenoxy)-2-aminobenzene (0.175 g, 0.54 mmol) along with other reagents as mentioned in Example 20(c) to afford 0.18 g of the required product. $^1$H NMR (DMSO-$d_6$): δ 6.86 (1H, brs), 6.95 (3H, m), 7.26 (2H, d), 7.34 (1H, d), 7.54 (3H, t), 7.82 (2H, d), 7.95 (2H, d), 7.95 (2H, m).

d) 4-Fluorobenzene-sulfonic Acid[2,4-bis-(4-ethoxycarbonimidoyl-phenoxy)-phenyl]-amide Using N-[2,4-bis-(4-cyano-phenoxy)-phenyl]-4-fluorobenzene sulfonamide (0.18 g, 0.37 mmol) and following the procedure of Example 1(d) afforded 0.16 g of the required product. Percentage purity (LCMS): 62.0%, (M+1)=(577.1+1).

e) 4-Fluorobenzene-sulfonic acid[2,4-bis-(4-carbamimidoyl-phenoxy)-phenyl]-amide Using 4-fluorobenzene-sulfonic acid[2,4-bis-(4-ethoxycarbonimidoyl-phenoxy)-phenyl]-amide (0.16 g, 0.27 mmol) and following the procedure of Example 1(e) 0.033 g of the required product was obtained. Percentage purity (HPLC): 96.54%, (LCMS): 95.4%. $^1$H NMR (DMSO-$d_6$): δ 6.5 (1H, s), 6.75 (1H, s), 6.95 (3H, m), 7.2 (2H, d), 7.3 (2H, d) 7.4 (1H, d), 7.75 (3H, m), 7.85 (2H, d), 8.6 (1H, s), 8.95 (3H, brs), 9.25 (3H, brs), 10.2 (1H, brs).

Example 23

2,4-Bis-(4-carbamimidoyl-phenoxy)-phenyl-1-naphthalenesulfonamide

Intermediates (a) and (b) are the same as in Example 21.

c) Naphthalene-1-sulfonic acid[2,4-bis-(4-cyano-phenoxy)-phenyl]amide

1-Naphthalene sulfonyl chloride (0.148 g, 0.65 mmol) was added to a stirred solution of 1,5-bis-(4-cyano-phenoxy)-2-aminobenzene (0.175 g, 0.54 mmol) along with other reagents as mentioned in Example 20(c) to afford 0.19 g of the required product. $^1$H NMR (DMSO-$d_6$): δ 6.45 (3H, m), 7.16 (5H, m), 7.42 (6H, m), 7.75 (2H, dd), 7.85 (3H, m).

d) 2,4-Bis-(4-ethoxycarbonimidoyl-phenoxy)-phenyl-1-naphthalenesulfonamide

Using naphthalene-1-sulfonic acid[2,4-bis-(4-cyano-phenoxy)-phenyl]amide (0.19 g, 0.36 mmol) and following the procedure of Example 1(d) afforded 0.16 g of the required product. Percentage purity (LCMS): 55.3%, (M+1)=(609.19+1H).

e) 2,4-Bis-(4-carbamimidoyl-phenoxy)-phenyl-1-naphthalenesulfonamide

Using 2,4-bis-(4-ethoxycarbonimidoyl-phenoxy)-phenyl-1-naphthalene sulfonamide (0.16 g, 0.26 mmol) and following the procedure of Example 1(e) 0.035 g. of the required product was obtained. Percentage purity (HPLC): 94.73%, (LCMS): 96.0%. $^1$H NMR (DMSO-$d_6$): δ 6.55 (1H, s), 7.1 (2H, d), 7.3 (2H, m), 7.4 (2H, d), 7.75 (4H, m), 7.9 (4H, m), 8.2 (1H, d), 8.4 (1H, d), 8.5 (2H, brs), 9.1 (4H, d), 9.3 (4H, s).

Example 24

N-(4-Amino-cyclohexyl)-3,5-bis-(5-carbamimidoyl-pyridin-2-yloxy)-benzamide a) 3,5-Bis-(5-cyano-pyridin-2-yloxy)-benzoic Acid Ethyl Ester Potassium carbonate 2.1 g (15.2 mmol) dissolved in DMF solution was added to 3,5-dihydroxy-benzoic acid ethyl ester 1.5 g (8.2 mmol) dissolved in 15 ml of DMF. This was followed by dropwise addition of 6-chloro-nicotinonitrile 2.1 g (15.2 mmol) dissolved in 5 ml of DMF. After complete addition, the reaction mixture was stirred at 60° C. for 8-10 h. The reaction mixture was quenched with ice cold water and extracted with ethyl acetate. The organic layer was washed with water followed by brine, dried over anhydrous sodium sulphate and concentrated to afford a crude solid which was purified by column chromatography using hexane-ethyl acetate (10:2) to afford 2.5 g of the required product. $^1$H NMR (DMSO-$d_6$): δ 1.30 (3H, t), 4.32 (2H, q), 7.35 (2H, d), 7.52 (1H, t), 7.68 (2H, d), 8.39 (2H, d), 8.69 (2H, s).

b) 3,5-Bis-(5-cyano-pyridin-2-yloxy)-benzoic Acid 2.3 g (5.9 mmol) of 3,5-Bis-(5-cyano-pyridin-2-yloxy)-benzoic acid ethyl ester was hydrolysed by using the procedure of Example 5(b) to afford 1.8 g. of the required product. $^1$H NMR (DMSO-$d_6$): δ 7.34 (2H, d), 7.48 (1H, t), 7.61 (2H, d), 8.38 (2H, dd), 8.70 (2H, d), 13.5 (1H, brs).

c) {4-[3,5-Bis-(5-cyano-pyridin-2-yloxy)-benzoylamino]-cyclohexyl}-carbamic Acid Tert-butyl Ester Following the procedure of Example 5(c) 3,5-bis-(5-cyano-pyridin-2-yloxy)-benzoic acid 0.35 g (0.97 mmol) and (4-amino-cyclohexyl)-carbamic acid tert-butyl ester (0.2 g, 0.97 mmol) were used to afford 0.4 g. of the required product. $^1$H NMR (DMSO-$d_6$): δ 1.47 (9H, s), 1.72 (5H, m), 1.82 (3H, m), 3.20 (1H, m), 3.72 (1H, m), 6.74 (1H, m), 7.18 (1H, d), 7.32 (1H, s), 7.50 (1H, brs), 7.59 (1H, s), 8.08 (1H, brs), 8.30 (2H, dd), 8.39 (1H, dd), 8.67 (2H, d).

d) N-(4-Amino-cyclohexyl)-3,5-bis-(5-ethoxycarbonimidoyl-pyridin-2-yloxy)-benzamide Using {4-[3,5-bis-(5-cyano-pyridin-2-yloxy)-benzoylamino]-cyclohexyl}-carbamic acid tert-butyl ester (0.13 g, 0.23 mmol) and following the procedure of Example 1(d) afforded 0.12 g of the required product. Percentage purity (LCMS): 74.6%, (M+1)=546.2.

e) N-(4-Amino-cyclohexyl)-3,5-bis-(5-carbamimidoyl-pyridin-2-yloxy)-benzamide

Using N-(4-amino-cyclohexyl)-3,5-bis-(5-ethoxycarbonimidoyl-pyridin-2-yloxy)-benzamide (0.12 g, 0.21 mmol) and following the procedure of Example 1(e) 0.044 g. of the required product was obtained. Percentage purity (HPLC): 98.4%, (LCMS): 96.7%. $^1$H NMR (DMSO-$d_6$): δ 1.8-2.0 (5H, m), 3.0 (2H, m), 3.7 (3H, m), 7.32 (2H, d), 7.40 (1H, s), 7.62 (2H, d), 7.88 (3H, brs), 8.30 (2H, dd), 8.42 (1H, m), 8.62 (2H, d), 9.24 (4H, s), 9.42 (3H, s).

Example 25

4-amino-1-{4-[3,5-Bis-(5-carbamimidoyl-pyridin-2-yloxy)-benzoyl]-piperazin-1-yl}-butan-1-one Intermediates (a) and (b) are the same as in Example 24.

c) 4-[3,5-Bis-(5-cyano-pyridin-2-yloxy)-benzoyl]-piperazine-1-carboxylic Acid Tert-butyl Ester Following the procedure of Example 5(c) 3,5-bis-(5-cyano-pyridin-2-yloxy)-benzoic acid 0.6 g (1.67 mmol) and piperazine-1-carboxylic acid tert-butyl ester (0.31 g, 1.67 mmol) were used to afford 0.55 g of the required product. $^1$HNMR (DMSO-$d_6$): δ 1.42 (9H, s), 3.45 (6H, m), 3.56 (2H, m), 7.20 (2H, d), 7.27 (1H, t), 7.32 (2H, d), 8.37 (2H, dd), 8.70 (2H, d).

d) 4-[3,5-Bis-(5-cyano-pyridin-2-yloxy)-benzoyl]-piperazine

Using 4-[3,5-bis-(5-cyano-pyridin-2-yloxy)-benzoyl]-piperazine-1-carboxylic acid tert-butyl ester (0.5 g, 0.94 mmol) and following the procedure of Example 9(d) afforded 0.4 g of the required product. $^1$HNMR (DMSO-$d_6$): δ 3.20 (4H, m), 3.46 (4H, m), 5.42 (1H, brs), 7.18 (2H, d), 7.25 (1H, t), 7.31 (2H, d), 8.41 (2H, dd), 8.75 (2H, d).

e) 4-{4-[3,5-Bis-(5-cyano-pyridin-2-yloxy)-benzoyl]-piperazin-1-yl}-4-oxo-butyl)-carbamic Acid Tert-butyl Ester Following the procedure of Example 5(c) 4-[3,5-bis-(5-cyano-pyridin-2-yloxy)-benzoyl]-piperazine 0.4 g (0.93 mmol) and 4-tert-butoxycarbonylamino-butyric acid (0.19 g, 0.93 mmol) were used to afford 0.35 g of the required product. $^1$H NMR (DMSO-$d_6$): δ 1.39 (9H, s), 1.60 (2H, q), 2.32 (3H, m), 2.94 (2H, q), 3.50 (7H, m), 6.80 (1H, brs), 7.15 (1H, d), 7.28 (1H, t), 7.32 (2H, d), 8.37 (2H, dd), 8.72 (2H, d).

f) [4-(4-{3,5-Bis-[5-(N-hydroxycarbamimidoyl)-pyridin-2-yloxy]-benzoyl}-piperazin-1-yl)-4-oxo-butyl]-carbamic Acid Tert-butyl Ester 4-{4-[3,5-Bis-(5-cyano-pyridin-2-yloxy)-benzoyl]-piperazin-1-yl}-4-oxo-butyl)-carbamic acid tert-butyl ester 0.35 g (0.57 mmol), DIPEA 0.3 g (2.28 mmol) and 0.158 g (2.28 mmol) of hydroxylamine hydrochloride were used as described in Example 2(d) to afford 0.25 g of the required product. Percentage purity (LCMS): 86.1%, (M+1)=677.2 (with BOC). $^1$H NMR (DMSO-$d_6$): δ 1.40 (9H, s), 1.62 (2H, q), 2.33 (2H, m), 2.92 (3H, m), 3.18 (1H, m), 3.50 (4H, m), 3.62 (2H, m), 6.16 (3H, brs), 6.82 (2H, t), 7.08 (2H, s), 7.18 (3H, d), 8.14 (2H, dd), 8.48 (2H, s), 9.85 (2H, brs).

g) [4-(4-{3,5-Bis-[5-(N-(acetylhydroxy)-carbamimidoyl)-pyridin-2-yloxy]-benzoyl}-piperazin-1-yl)-4-oxo-butyl]-carbamic Acid Tert-butyl Ester

[4-(4-{3,5-Bis-[5-(N-hydroxycarbamimidoyl)-pyridin-2-yloxy]-benzoyl}-piperazin-1-yl)-4-oxo-butyl]-carbamic acid tert-butyl ester 0.25 g (0.37 mmol) was acetylated with 0.08 g (0.8 mmol) of acetic anhydride using the procedure of Example 2(e) to afford 0.25 g of the required product. Percentage purity (LCMS): 86.1%, (M+1)=761.2 (with BOC). $^1$H NMR (DMSO-$d_6$): δ 1.36 (9H, s), 1.62 (2H, m), 2.14 (6H, s), 2.33 (3H, m), 2.93 (3H, m), 3.55 (6H, brs), 6.82 (1H, brs), 6.95 (4H, brs), 7.18 (5H, m), 8.18 (2H, dd), 8.50 (2H, s).

h) (4-{4-[3,5-Bis-(5-carbamimidoyl-pyridin-2-yloxy)-benzoyl]-piperazin-1-yl}-4-oxo-butyl)-carbamic Acid Tert-butyl Ester

[4-(4-{3,5-Bis-[5-(N-(acetylhydroxy)-carbamimidoyl)-pyridin-2-yloxy]-benzoyl}-piperazin-1-yl)-4-oxo-butyl]-carbamic acid tert-butyl ester 0.25 g (0.32 mmol) was reduced using the procedure of Example 2(f) to afford 0.12 g of the required product. Percentage purity (LCMS): 68.7%, (M+1)= 645.3+1.

i) 4-{4-[3,5-Bis-(5-carbamimidoyl-pyridin-2-yloxy)-benzoyl]-piperazin-1-yl}-4-oxo-butanylamine Using (4-{4-[3,5-bis-(5-carbamimidoyl-pyridin-2-yloxy)-benzoyl]-piperazin-1-yl}-4-oxo-butyl)-carbamic acid tert-butyl ester (0.12 g, 0.18 mmol) and following the procedure of Example 9(d) afforded 0.05 g of the required product. Percentage purity (HPLC): 87.7%, (LCMS): 86.4%. $^1$H NMR (DMSO-$d_6$): δ 1.2 (2H, m), 1.75 (2H, m), 2.8 (2H, m), 3.2 (8H, m), 4.2 (2H, brs), 7.22 (3H, m), 7.36 (2H, m), 7.80 (3H, brs), 8.30 (2H, m), 8.66 (2H, s), 9.22 (3H, s), 9.44 (3H, s).

Example 26

1-[(4-Amino-ethyl)-piperidine-1-carbonyl]-3,5-bis-(4-carbamimidoyl-phenoxy)-benzene a) 3,5-Bis-(4-cyano-phenoxy)-benzoic Acid Ethyl Ester Potassium carbonate 0.611 g (4.4 mmol) was added to a stirred solution of 3,5-dihydroxy-benzoic acid ethyl ester 0.5 g (1.7 mmol) dissolved in 15 ml of DMF and stirred for 10 min. This was followed by dropwise addition of 4-fluorobenzonitrile 0.82 g (6.8 mmol), dissolved in 5 ml of DMF, and the contents of the flask were stirred at 80° C. for 4 h. The reaction mixture was poured into ice-cold water, and extracted with ethyl acetate. The organic phase was washed with $Na_2CO_3$ and saturated brine solution, dried over sodium sulphate and concentrated to afford an oily residue which was purified by column chromatography using hexane-ethyl acetate (10:2) to afford 0.4 g of the required product. The yield was 0.6 g. $^1$H NMR (DMSO-$d_6$): δ 1.30 (3H, t), 4.30 (2H, q), 7.25 (2H, d), 7.32 (1H, t), 7.46 (2H, d), 7.90 (2H, d).

b) 3,5-Bis-(4-cyano-phenoxy)-benzoic Acid 3,5-Bis-(4-cyano-phenoxy)-benzoic acid ethyl ester 0.6 g (1.56 mmol) was hydrolysed by using the procedure of Example 5(b) to afford 0.45 g of required product. $^1$H NMR (DMSO-d$_6$): δ 7.27 (3H, d), 7.40 (2H, d), 7.92 (2H, d), 13.5 (1H, brs).

c) 1-[(4-Boc-Amino-ethyl)-piperidine-1-carbonyl]-3, 5-bis-(4-cyano-phenoxy)-benzene Following the procedure of Example 5(c) 3,5-bis-(4-cyano-phenoxy)-benzoic acid 0.45 g (1.26 mmol) and (2-piperidin-4-yl-ethyl)-carbamic acid tert-butyl ester (0.287 g, 1.26 mmol) were used to afford 0.4 g of the required product. $^1$H NMR (DMSO-d$_6$): 1.05 (2H, m), 1.30 (2H, m), 1.40 (9H, s), 1.45 (4H, m), 2.60 (1H, m), 2.94 (3H, m), 3.54 (1H, m), 4.38 (1H, m), 6.78 (1H, t), 6.75 (2H, d), 7.04 (1H, t), 7.25 (4H, d), 7.88 (2H, d).

d) 1-[(4-Boc-Amino-ethyl)-piperidine-1-carbonyl]-3, 5-bis-[4-(N-hydroxy-carbamimidoyl)-phenoxy]-benzene Following the procedure of Example 2(d) 1-[(4-boc-amino-ethyp-piperidine-1-carbonyl]-3,5-bis-(4-cyano-phenoxy)-benzene 0.4 g (0.7 mmol) and other reagents were used to afford 0.35 g of the required product. Percentage purity (LCMS): 69.2%, (M+1)=632.2+1.

e) 1-[(4-Boc-Amino-ethyl)-piperidine-1-carbonyl]-3, 5-bis-[4-(N-acetyl-hydroxycarbamimidoyl)-phenoxy]-benzene Following the procedure of Example 2(e) 1-[(4-boc-amino-ethyl)-piperidine-1-carbonyl]-3,5-bis-[4-(N-hydroxycarbamimidoyl)-phenoxy]-benzene 0.35 g (0.55 mmol) was used to afford 0.3 g of the required product. Percentage purity (LCMS): 51.0%, (M+1)=716.3 (with BOC).

f) 1-[(4-Boc-Amino-ethyl)-piperidine-1-carbonyl]-3, 5-bis-(4-carbamimidoyl-phenoxy)-benzene 1-[(4-Boc-amino-ethyl)-piperidine-1-carbonyl]-3,5-bis-[4-(N-acetylhydroxy-carbamimidoyl)-phenoxy]-benzene 0.3 g (0.41 mmol) was reduced using the procedure of Example 2(f) to afford 0.2 g of required product. Percentage purity (LCMS): 74.0%, (M+1)=600.3+1.

g) 1-[(4-Amino-ethyl)-piperidine-1-carbonyl]-3,5-bis-(4-carbamimidoyl-phenoxy)-benzene Using 1-[(4-boc-Amino-ethyl)-piperidine-1-carbonyl]-3,5-bis-(4-carbamimidoyl-phenoxy)-benzene (0.2 g, 0.33 mmol) and following the procedure of Example 9(d) afforded 0.06 g of the required product. Percentage purity (HPLC): 97.85%, (LCMS): 94.26%. $^1$H NMR (DMSO-d$_6$): δ 1.05 (2H, m), 1.4-1.8 (5H, m), 2.8 (3H, m), 3.0 (1H, m), 3.4 (1H, m), 4.4 (1H, m), 6.95 (3H, brs), 7.3 (3H, d), 7.9 (6H, d), 9.1-9.6 (7H, d).

Example 27

N-(4-Amino-cyclohexyl)-3,5-bis-(4-carbamimidoyl-phenoxy)-benzamide

Intermediates (a) and (b) are the same as in Example 26.
c) {4-[3,5-Bis-(4-cyano-phenoxy)-benzoylamino]-cyclohexyl}-carbamic Acid Tert-butyl Ester Following the procedure of Example 5(c) 3,5-bis-(4-cyano-phenoxy)-benzoic acid 0.45 g (1.26 mmol) and (4-amino-cyclohexyl)-carbamic acid tert-butyl ester (0.27 g, 1.26 mmol) were used to afford 0.52 g of the required product. $^1$H NMR (DMSO-d$_6$): δ 1.31 (4H, m), 1.45 (9H, s), 1.80 (4H, m), 3.22 (1H, m), 3.68 (1H, m), 6.78 (1H, d, J=7.8 Hz), 7.24 (2H, d, J=9.6 Hz), 7.51 (2H, d, J=2.1 Hz), 7.89 (2H, d, J=8.7 Hz), 8.35 (1H, d, J=7.5 Hz).

d) (4-{3,5-Bis-[4-(N-hydroxycarbamimidoyl)-phenoxy]-benzoylamino}-cyclohexyl)-carbamic Acid Tert-butyl Ester Following the procedure of Example 2(d) {4-[3,5-bis-(4-cyano-phenoxy)-benzoylamino]-cyclohexyl}-carbamic acid tert-butyl ester 0.5 g (9 mmol) and other reagents were used to afford 0.4 g of the required product. Percentage purity (LCMS): 68.0%, (M+1)=618.2+1. $^1$H NMR (DMSO-d$_6$): δ 1.31 (4H, m), 1.45 (9H, s), 1.80 (4H, m), 3.22 (1H, m), 3.68 (1H, m), 6.78 (1H, d, J=7.8 Hz), 7.24 (2H, d, J=9.6 Hz), 7.42 (2H, d, J=2.1 Hz), 7.75 (2H, d, J=8.7 Hz), 7.92 (4H, brs), 8.35 (1H, d, J=7.5 Hz), 11.05 (2H, brs).

e) (4-{3,5-Bis-[4-(N-acetylhydroxycarbamimidoyl)-phenoxy]-benzoylamino}-cyclohexyl)-carbamic Acid Tert-Butyl Ester Following the procedure as in Example 2(e) (4-{3,5-bis-[4-(N-hydroxy-carbamimidoyl)-phenoxy]-benzoylamino}-cyclohexyl)-carbamic acid tert-butyl ester 0.4 g (0.64 mmol) was used to afford 0.45 g of the required product. Percentage purity (LCMS): 89.0%, (M+1)=702.3+1. $^1$H NMR (DMSO-d$_6$): δ 1.28 (4H, m), 1.45 (9H, s), 1.75 (4H, m), 2.62 (6H, s), 3.31 (1H, m), 3.78 (1H, m), 6.81 (1H, d, J=7.8 Hz), 7.04 (2H, d, J=9.2 Hz), 7.31 (2H, d, J=1.9 Hz), 7.58 (2H, d, J=8.6 Hz), 8.30 (5H, brs).

f) {4-[3,5-Bis-(4-carbamimidoyl phenoxy)benzoylamino]cyclohexyl}carbamic Acid Tert-butyl Ester (4-{3,5-Bis-[4-(N-acetylhydroxycarbamimidoyl)-phenoxy]-benzoylamino}-cyclohexyl)-carbamic acid tert-butyl ester 0.45 g (0.64 mmol) was reduced using the procedure of Example 2(f) to afford 0.3 g of required product. Percentage purity (LCMS): 74.0%, (M+1)=586.2+1.

g) N-(4-Amino-cyclohexyl)-3,5-bis-(4-carbamimidoyl-phenoxy)-benzamide

Using {4-[3,5-bis-(4-carbamimidoyl phenoxy)benzoylamino]cyclohexyl}carbamic acid tert-butyl ester (0.3 g, 0.51 mmol) and following the procedure of Example 9(d) afforded 0.06 g of the required product. Percentage purity (HPLC): 87.7%, (LCMS): 94.5%. $^1$H NMR (DMSO-d$_6$): δ 1.44 (4H, m), 1.82 (4H, m), 3.05 (2H, m), 7.15 (1H, m), 7.35 (2H, d, J=9.4 Hz), 7.50 (2H, d, J=2.0 Hz), 7.88 (2H, d, J=8.6 Hz), 8.45 (1H, m), 9.11 (4H, brs), 9.25 (4H, brs).

Example 28

4-{3,5-Bis-[4-(N-hydroxycarbamimidoyl)-phenoxy]-benzoylamino}-cyclohexylamine Intermediates (a) to (d) are the same as in Example 27.

e) 4-{3,5-Bis-[4-(N-hydroxycarbamimidoyl)-phenoxy]-benzoylamino}-cyclohexylamine Using (4-{3,5-bis-[4-(N-hydroxycarbamimidoyl)-phenoxy]-benzoylamino}-cyclohexyl)-carbamic acid tert-butyl ester (0.3 g, 0.48 mmol) and following the procedure of Example 9(d) afforded 0.06 g of the required product. Percentage purity (HPLC): 96.2%, (LCMS): 97.2%. $^1$H NMR (DMSO-$d_6$): δ 1.38 (4H, m), 1.92 (4H, m), 3.02 (2H, m), 3.71 (2H, m), 7.04 (2H, brs), 7.23 (4H, d), 7.44 (2H, s), 7.78 (5H, d), 7.92 (3H, brs), 8.44 (2H, brs), 11.05 (2H, brs).

Example 29

3-{4-[3,5-Bis-(4-carbamimidoyl-phenoxy)-benzoyl]-piperazin-1-yl}-propylamine Intermediates (a) and (b) are the same as in Example 26.

c) 4-[3,5-Bis-(4-cyano-phenoxy)-benzoyl]-piperazine-1-carboxylic Acid Tert-butyl Ester Following the procedure of Example 5(c) 3,5-bis-(4-cyano-phenoxy)-benzoic acid 0.45 g (1.26 mmol) and piperazine-1-carboxylic acid tert-butyl ester (0.23 g, 1.26 mmol) were used to afford 0.5 g of the required product. $^1$H NMR (DMSO-$d_6$): δ 1.40 (9H, sm), 3.35 (6H, m), 3.55 (2H, m) 7.02 (2H, d), 7.08 (1H, t), 7.26 (2H, d), 7.88 (2H, d).

d) 4-[3,5-Bis-(4-cyano-phenoxy)-benzoyl]-piperazine

Following the procedure of Example 9(d) 4-[3,5-bis-(4-cyano-phenoxy)-benzoyl]-piperazine-1-carboxylic acid tert-butyl ester (0.5 g, 0.95 mmol) was used to afford 0.35 g of the required product. $^1$H NMR (DMSO-$d_6$): δ 3.15 (4H, m), 3.45 (4H, m), 7.06 (2H, d), 7.11 (1H, t), 7.26 (4H, d), 7.90 (4H, d), 8.25 (2H, brs).

e) (3-{4-[3,5-Bis-(4-cyano-phenoxy)-benzoyl]-piperazin-1-yl}-propyl)-carbamic Acid Tert-butyl Ester Following the procedure of Example 11(e) 4-[3,5-bis-(4-cyano-phenoxy)-benzoyl]-piperazine 0.35 g (0.82 mmol) and (3-bromo-propyl)-carbamic acid tert-butyl ester (0.195 g, 0.82 mmol) were used to afford 0.35 g of the required product. NMR (DMSO-$d_6$): δ 1.39 (9H, s), 1.52 (2H, m), 2.35 (8H, m), 2.95 (2H, m), 3.56 (2H, brs), 6.79 (1H, m), 6.90 (2H, d), 7.04 (1H, t), 7.25 (4H, d), 7.88 (4H, d).

f) 3-(4-{3,5-Bis-[4-(ethoxycarbonimidoyl)-phenoxy]-benzoyl}-piperazin-1-yl)-propylamine Using (3-{4-[3,5-bis-(4-cyano-phenoxy)-benzoyl]-piperazin-1-yl}-propyl)-carbamic acid tert-butyl ester (0.35 g, 0.60 mmol) and following the procedure of Example 1(d) afforded 0.15 g of the required product. Percentage purity (LCMS): 56.0%, (M+1)=573.3.

g) 3-(4-{3,5-Bis-[4-(carbamimidoyl)-phenoxy]-benzoyl}-piperazin-1-yl)-propylamine Using 3-(4-{3,5-Bis-[4-(ethoxycarbonimidoyl)-phenoxy]-benzoyl}-piperazin-1-yl)-propylamine (0.15 g, 0.26 mmol) and following the procedure of Example 1(e) afforded 0.035 g of the required product. Percentage purity (HPLC): 90.82%, (LCMS): 91.76%. $^1$H NMR (DMSO-$d_6$): δ 1.9 (3H, m), 2.85 (3H, m), 2.8-3.2 (6H, m), 4.4 (2H, m), 7.05 (3H, brs), 7.30 (4H, d), 7.90 (6H, d), 9.1 (3H, brs), 9.30 (4H, s).

Example 30

3-{4-[3,5-Bis-(4-carbamimidoyl-phenoxy)-benzoyl]-piperazin-1-yl}-3-oxo-propylamine Intermediates (a) and (b) are the same as in Example 26.
Intermediates (c) and (d) are the same as in Example 29.

e) (3-{4-[3,5-Bis-(4-cyano-phenoxy)-benzoyl]-piperazin-1-yl}-3-oxo-propyl)-carbamic Acid Tert-butyl Ester 3-tert-Butoxycarbonylamino-propionic acid (0.206 g, 1.09 mmol) and 4-[3,5-bis-(4-cyano-phenoxy)-benzoyl]-piperazine (0.5 g, 1.09 mmol) and other reagents as described in Example 9(e) were used to afford 0.5 g of the required product. $^1$H NMR (DMSO-$d_6$): δ 1.38 (9H, s), 2.45 (2H, m), 3.14 (2H, m), 3.52 (8H, m), 6.71 (1H, brs), 7.01 (2H, s), 7.08 (1H, t), 7.28 (4H, d), 7.89 (4H, d).

f) 3-{4-[3,5-Bis-[4-(ethoxycarbonimidoyl)-phenoxy]-benzoyl]-piperazin-1-yl}-3-oxo-propylamine Using (3-{4-[3,5-bis-(4-cyano-phenoxy)-benzoyl]-piperazin-1-yl}-3-oxo-propyl)-carbamic acid tert-butyl ester (0.5 g, 0.83 mmol) and following the procedure of Example 1(d) afforded 0.25 g of the required product. Percentage purity (LCMS): 33.3%, (M+1)=587.2+1.

g) 3-{4-[3,5-Bis-(4-carbamimidoyl-phenoxy)-benzoyl]-piperazin-1-yl}-3-oxo-propylamine Using 3-{4-[3,5-bis-[4-(ethoxycarbonimidoyl)-phenoxy]-benzoyl]-piperazin-1-yl}-3-oxo-propylamine (0.25 g, 0.42 mmol) and following the procedure of Example 1(e) afforded 0.06 g of the required product. Percentage purity (HPLC): 98.99%, (LCMS): 91.36%. $^1$H NMR (DMSO-$d_6$): δ 2.1 (3H, m), 2.70 (1H, m), 3.0 (1H, m), 3.15 (3H, brs), 3.75 (3H, m), 7.0 (3H, m), 7.30 (4H, d), 7.8 (2H, m), 7.9 (4H, d), 9.1 (2H, brs), 9.30 (5H, s), 9.45 (1H, m).

Example 31

2-{4-[3,5-Bis-(4-carbamimidoyl-phenoxy)-benzoyl]-piperazin-1-yl}-ethylamine Intermediates (a) and (b) are the same as in Example 26.
Intermediates (c) and (d) are the same as in Example 29.

e) (2-{4-[3,5-Bis-(4-cyano-phenoxy)-benzoyl]-piperazin-1-yl}-ethyl)-carbamic Acid Tert-butyl Ester Following the procedure of Example 11(e) 4-[3,5-bis-(4-cyano-phenoxy)-benzoyl]-piperazine 0.35 g (0.82 mmol) and (2-bromo-ethyl)-carbamic acid tert-butyl ester (0.183 g, 0.82 mmol) were used to afford 0.4 g of the required product. $^1$H NMR (DMSO-$d_6$): 1.39 (9H, s), 2.28 (6H, m), 3.04 (2H, m), 3.54 (2H, m), 6.65 (1H, brs), 6.98 (2H, d), 7.05 (1H, t), 7.25 (4H, d), 7.88 (4H, d).

f) 2-{4-[3,5-Bis-[4-(ethoxycarbonimidoyl)-phenoxy]-benzoyl]-piperazin-1-yl}-ethylamine Using (2-{4-[3,5-Bis-(4-cyano-phenoxy)-benzoyl]-piperazin-1-yl}-ethyl)-carbamic acid tert-butyl ester (0.4 g, 0.70 mmol) and following the procedure of Example 1(d) afforded 0.2 g of the required product. Percentage purity (LCMS): 79.3%, (M+1)=559.2+1.

g) 2-{4-[3,5-Bis-(4-carbamimidoyl-phenoxy)-benzoyl]-piperazin-1-yl}-ethylamine Using 2-{4-[3,5-bis-[4-(ethoxycarbonimidoyl)-phenoxy]-benzoyl]-piperazin-1-yl}-ethylamine (0.2 g, 0.35 mmol) and following the procedure of Example 1(e) afforded 0.04 g of the required product. Percentage purity (HPLC): 87.99%, (LCMS): 96.56%. $^1$H NMR (DMSO-$d_6$): δ 1.1 (3H, t), 3.1 (8H, m), 7.0 (3H, s), 7.30 (4H, d), 7.9 (4H, d), 8.2 (2H, brs), 9.30 (8H, s).

Example 32

N-[1-(3-Amino-propyl)-piperidin-4-yl]-3,5-bis-(4-carbamimidoyl-phenoxy)-benzamide Intermediates (a) and (b) are the same as in Example 26.

c) 4-[3,5-Bis-(4-cyano-phenoxy)-benzoylamino]-piperidine-1-carboxylic Acid Tert-butyl Ester Following the procedure of Example 5(c) 3,5-bis-(4-cyano-phenoxy)-benzoic acid 0.45 g (1.26 mmol) and 4-amino-piperidine-1-carboxylic acid tert-butyl ester (0.252 g, 1.26 mmol) were, used to afford 0.5 g of the required product. $^1$H NMR (DMSO-$d_6$): δ 1.40 (9H, s), 1.75 (2H, m), 2.82 (2H, m), 3.18 (2H, d), 3.92 (3H, m), 7.25 (5H, m), 7.54 (2H, d), 7.88 (4H, d), 38 (1H, brs).

d) 3,5-Bis-(4-cyano-phenoxy)-N-piperidin-4-yl-benzamide

Using 4-[3,5-bis-(4-cyano-phenoxy)-benzoylamino]-piperidine-1-carboxylic acid tert-butyl ester (0.5 g, 0.92 mmol) and following the procedure of Example 9(d) afforded 0.35 g of the required product. $^1$H NMR (DMSO-$d_6$): δ 1.60 (2H, m), 1.95 (2H, m), 3.05 (2H, m), 3.34 (2H, m), 4.08 (1H, brs), 7.24 (5H, d), 7.57 (2H, s), 7.90 (4H, d), 8.60 (1H, brs), 8.74 (1H, brs).

e) (3-{4-[3,5-Bis-(4-cyano-phenoxy)-benzoylamino]-piperidin-1-yl}-propyl)-carbamic Acid Tert-butyl Ester Following procedure of Example 11(e) 3,5-bis-(4-cyano-phenoxy)-N-piperidin-4-yl-benzamide 0.35 g (0.79 mmol) and (3-bromo-propyl)-carbamic acid tert-butyl ester (0.188 g, 0.79 mmol) were used to afford 0.4 g of the required product. $^1$H NMR (DMSO-$d_6$): δ 1.38 (9H, s), 1.52 (4H, m), 1.75 (2H, m), 1.90 (2H, m), 2.28 (2H, m), 2.82 (1H, m), 2.92 (2H, m), 3.74 (1H, brs), 3.68 (1H, m), 6.79 (1H, brs), 7.18 (1H, t), 7.26 (4H, d), 7.52 (2H, s), 7.88 (4H, d), 8.38 (1H, d).

f) 3-(4-{3,5-Bis-[4-(ethoxycarbonimidoyl)-phenoxy]-benzoylamino}-piperidin-1-yl)-propylamine Using (3-{4-[3,5-bis-(4-cyano-phenoxy)-benzoylamino]-piperidin-1-yl}-propyl)-carbamic acid tert-butyl ester (0.4 g, 0.67 mmol) and following the procedure of Example 1(d) afforded 0.2 g of the required product. Percentage purity (LCMS): 99.0% (M+1)=587.3+1.

g) 3-{4-[3,5-Bis-(4-carbamimidoyl-phenoxy)-benzoylamino]-piperidin-1-yl}-propylamine Using 3-(4-{3,5-bis-[4-(ethoxycarbonimidoyl)-phenoxy]-benzoylamino}-piperidin-1-yl)-propylamine (0.2 g, 0.34 mmol) and following the procedure of Example 1(e) afforded 0.04 g of the required product. Percentage purity (HPLC): 95.27%, (LCMS): 95.15%. $^1$H NMR (DMSO-$d_6$): δ 1.80 (2H, m), 2.0 (4H, m), 2.85 (2H, m), 3.1 (4H, m), 3.5 (2H, d), 4.0 (1H, m), 7.15 (1H, s), 7.30 (4H, d), 7.5 (2H, s), 7.9 (7H, d), 8.65 (1H, d), 9.25 (8H, d), 10.1 (1H, brs).

Example 33

N-(4-Amino-cyclohexyl)-3,5-bis-(4-aminomethyl-phenoxy)-benzamide

Intermediates (a), (b) and (c) are the same as in Example 26.

d) {4-[3,5-Bis-(4-aminomethyl-phenoxy)-benzoylamino]-cyclohexyl}-carbamic Acid Tert-butyl Ester 0.05 g of Raney nickel was added to 0.3 g (0.54 mmol) of {4-[3,5-bis-(4-cyano-phenoxy)-benzoylamino]-cyclohexyl}-carbamic acid tert-butyl ester stirred with 50 ml of 10% $NH_3$-methanol. The reaction mixture was stirred overnight on hydrogen gas pressure (50 psi) at 50° C. The reaction mixture was filtered through celite and concentrated to afford 0.25 g of the required product which was used for the next step without further purification. Percentage purity (LCMS): 70.8%, (M+1)=560.2+1 e) N-(4-Amino-cyclohexyl)-3,5-bis-(4-aminomethyl-phenoxy)-benzamide

Using {4-[3,5-bis-(4-aminomethyl-phenoxy)-benzoylamino]-cyclohexyl}-carbamic acid tert-butyl ester (0.25 g, 0.44 mmol) and following the procedure of Example 9(d) afforded 0.03 g of the required product. Percentage purity (HPLC): 98.8%, (LCMS): 96.0%. $^1$H NMR (DMSO-$d_6$): δ 1.37 (4H, m), 1.88 (4H, m), 2.96 (1H, m), 3.70 (1H, m), 4.02 (4H, s), 6.76 (1H, s), 7.14 (4H, d), 7.25 (2H, s), 7.51 (4H, d), 7.82 (3H, brs), 8.18 (5H, brs), 8.42 (1H, brs).

Example 34

4-[3,5-Bis-(4-carbamimidoyl-phenoxy)-benzoyl]-piperazine-1-carboxylic Acid Ethyl Ester Intermediates (a) and (b) are the same as in Example 26.

c) 4-[3,5-Bis-(4-cyano-phenoxy)-benzoyl]-piperazine-1-carboxylic acid ethyl ester Following the procedure of Example 5(c) 3,5-bis-(4-cyano-phenoxy)-benzoic acid 0.45 g (1.26 mmol) and piperazine-1-carboxylic acid tert-butyl ester (0.234 g, 1.26 mmol) were used to afford 0.5 g of the required product. $^1$H NMR (DMSO-$d_6$): δ 1.18 (3H, t), 3.52 (8H, m), 4.15 (2H, q), 7.00 (2H, s), 7.07 (1H, s), 7.28 (2H, d), 7.88 (2H, d).

d) 4-{3,5-Bis-[4-(N-hydroxycarbamimidoyl)-phenoxy]-benzoyl}-piperazine-1-carboxylic Acid Ethyl Ester Following the procedure of Example 2(d) 4-[3,5-bis-(4-cyano-phenoxy)-benzoyl]-piperazine-1-carboxylic acid ethyl ester 0.5 g (1.0 mmol) and other reagents were used to afford 0.4 g of the required product. Percentage purity (LCMS): 51.8%, (M+1)=562.2+1.

e) 4-{3,5-Bis-[4-(N-acetylhydroxycarbamimidoyl)-phenoxy]-benzoyl}-piperazine-1-carboxylic Acid Ethyl Ester Following the procedure of Example 2(e) 4-{3,5-bis-[4-(N-hydroxy-carbamimidoyl)-phenoxy]-benzoyl}-piperazine-1-carboxylic acid ethyl ester 0.4 g (0.71 mmol) was used to afford 0.4 g of the required product. Percentage purity (LCMS): 67.6%, (M+1)=646.2+1.

f) 4-{3,5-Bis-[4-carbamimidoyl-phenoxy]-benzoyl}-piperazine-1-carboxylic Acid Ethyl Ester 4-{3,5-Bis-[4-(N-acetylhydroxycarbamimidoyl)-phenoxy]-benzoyl}-piperazine-1-carboxylic acid ethyl ester 0.4 g (0.61 mmol) was reduced by using the procedure of Example 2(f) to afford 0.15 g of required product. Percentage purity (HPLC): 94.1%, (LCMS): 92.83%. $^1$H NMR (DMSO-$d_6$): δ 1.2 (3H, t), 3.4 (8H, m), 4.05 (2H, q), 6.95 (2H, s), 7.35 (4H, d), 7.9 (4H, d), 9.06 (3H, brs), 9.3 (4H, s).

Example 35

1-[3,5-Bis-(4-carbanimidoyl-phenoxy)-benzoyl]-nonahydro-quinoline

Intermediates (a) and (b) are the same as in Example 26.

c) 1-[3,5-Bis-(4-cyano-phenoxy)-benzoyl]-nonahydro-quinoline

Following the procedure of Example 5(c) 3,5-bis-(4-cyano-phenoxy)-benzoic acid 0.45 g (1.26 mmol) and decahydro-quinoline (0.175 g, 1.26 mmol) were used to afford 0.5 g of the required product. $^1$H NMR (DMSO-$d_6$): δ 1.40 (6H, m), 1.62 (5H, m), 1.82 (1H, m), 3.10 (1H, m), 3.20 (1H, m), 3.91 (1H, m), 4.12 (1H, m), 6.88 (1H, s), 6.95 (1H, s), 7.02 (1H, t), 7.28 (2H, d), 7.88 (2H, d).

d) 1-[3,5-Bis-((N-hydroxycarbamimidoyl)-phenoxy)-benzoyl]-nonahydro-quinoline Following the procedure of Example 2(d) 1-[3,5-bis-(4-cyano-phenoxy)-benzoyl]-nonahydro-quinoline 0.5 g (1.04 mmol) and other reagents were used to afford 0.52 g of the required product. Percentage purity (LCMS): 41.7%, (M+1)= 543.2+1.

e) 1-[3,5-BisAN-acetylhydroxycarbamimidoyl)-phenoxy)-benzoyl]-nonahydro-quinoline Following the procedure of Example 2(e) 1-[3,5-bis-((N-hydroxycarbamimidoyl)-phenoxy)-benzoyl]-nonahydro-quinoline 0.5 g (0.91 mmol) was used to afford 0.45 g of the required product. Percentage purity (LCMS): 63.0%, (M+1)= 627.2+1.

f) 1-[3,5-Bis-(4-carbanimidoyl-phenoxy)-benzoyl]-nonahydro-quinoline

1-[3,5-Bis-((N-acetylhydroxycarbamimidoyl)-phenoxy)-benzoyl]-nonahydro-quinoline, 0.45 g (0.71 mmol) was reduced using the procedure of Example 2(f) to afford 0.2 g of required product. Percentage purity (HPLC): 95.37%, (LCMS): 93.43%. $^1$H NMR (DMSO-$d_6$): δ 1.7 (1H, m), 1.85 (1H, m), 3.20 (2H, m), 3.9 (1H, m), 4.05 (1H, m), 6.84 (1H, brs), 6.9 (1H, brs), 7.0 (1H, s), 7.54 (4H, d), 7.88 (4H, d), 9.12 (4H, s), 9.28 (4H, s).

Example 36

3,5-Bis-(4-carbamimidoyl-phenoxy)-N,N-diisobutyl-benzamide

Intermediates (a) and (b) are the same as in Example 26.

c) 3,5-Bis-(4-cyano-phenoxy)-N,N-diisobutyl-benzamide

Following the procedure of Example 5(c) 3,5-bis-(4-cyano-phenoxy)-benzoic acid 0.8 g (2.24 mmol) and diisobutyl-amine (0.29 g, 2.24 mmol) were used to afford 0.74 g of the required product. $^1$H NMR (DMSO-$d_6$): δ 0.72 (6H, d), 0.88 (6H, d), 1.82 (1H, m), 2.00 (1H, m), 3.06 (2H, d), 3.24 (2H, d), 6.98 (2H, d), 7.04 (1H, t), 7.22 (4H, d), 7.89 (4H, d).

d) 3,5-Bis-[4-(ethoxycarbonimidoyl)-phenoxy]-N,N-diisobutyl-benzamide

Using 3,5-bis-(4-cyano-phenoxy)-N,N-diisobutyl-benzamide (0.74 g, 1.58 mmol) and following the procedure of Example 1(d) afforded 0.8 g of the required product. Percentage purity (LCMS): 52.8%, (M+1)=559.3+1.

e) 3,5-Bis-(4-carbamimidoyl-phenoxy)-N,N-diisobutyl-benzamide

Using 3,5-bis-[4-(ethoxycarbonimidoyl)-phenoxy]-N,N-diisobutyl-benzamide (0.8 g, 0.1.42 mmol) and following the procedure of Example 1(e) afforded 0.36 g of the required product. Percentage purity (HPLC): 97.51%, (LCMS): 97.48%. $^1$H NMR (DMSO-$d_6$): δ 0.7 (6H, s), 0.80 (6H, s), 1.8 (1H, m), 2.0 (1H, m), 3.1 (2H, d), 3.2 (2H, d), 6.9 (2H, d), 7.0 (1H, s), 7.3 (4H, d), 7.88 (4H, d), 9.12 (4H, s), 9.28 (4H, s).

Example 37

2-[3,5-Bis-(4-cyano-phenoxy)-benzoyl]-nonahydro-isoquinoline

Intermediates (a) and (b) are the same as in Example 26.

c) 2-[3,5-Bis-(4-cyano-phenoxy)-benzoyl]-nonahydro-isoquinoline

Following the procedure of Example 5(c) 3,5-bis-(4-cyano-phenoxy)-benzoic acid 1.2 g (3.36 mmol) and decahydro-isoquinoline (0.467 g, 3.36 mmol) were used to afford 1.25 g of the required product. $^1$H NMR (DMSO-$d_6$): δ 1.30 (5H, m), 1.62 (5H, m), 1.85 (1H, m), 3.05 (1H, m), 3.18 (1H, m), 3.51 (1H, m), 3.90 (1H, m), 4.12 (1H, m), 6.86 (1H, s), 6.95 (1H, s), 7.04 (1H, t), 7.26 (2H, d), 7.86 (2H, d).

d) 2-[3,5-Bis-(4-(N-hydroxycarbamimidoyl)-phenoxy)-benzoyl]-nonahydro-isoquinoline Following the procedure of Example 2(d) 2-[3,5-bis-(4-cyano-phenoxy)-benzoyl]-nonahydro-isoquinoline 1.25 g (2.61 mmol) and other reagents were used to afford 1.3 g of the required product. Percentage purity (LCMS): 80.0%, (M+1)=543.2+1.

e) 1-[3,5-Bis-(4-(N-acetylhydroxycarbamimidoyl)-phenoxy)-benzoyl]-nonahydro-isoquinoline Following the procedure of Example 2(e) 2-[3,5-bis-(4-(N-hydroxycarbamimidoyl)-phenoxy)-benzoyl]-nonahydro-isoquinoline 1.3 g (2.39 mmol) was acetylated to afford 1.2 g of the required product. Percentage purity (LCMS): 70.0%, (M+1)=627.2+1.

f) 2-[3,5-Bis-(4-carbanimidoyl-phenoxy)-benzoyl]-nonahydro-isoquinoline

2-[3,5-Bis-(4-(N-acetylhydroxycarbamimidoyl)-phenoxy)-benzoyl]-nonahydro-isoquinoline, 1.2 g (1.91 mmol) was reduced using the procedure of Example 2(f) to afford 0.4 g of required product. Percentage purity (HPLC): 95.37%, (LCMS): 93.43%. $^1$H NMR (DMSO-d$_6$): δ 1.7 (1H, m), 1.85 (1H, m), 3.20 (2H, m), 3.9 (1H, m), 4.05 (1H, m), 6.84 (1H, brs), 6.9 (1H, brs), 7.0 (1H, s), 7.54 (4H, d), 7.88 (4H, d), 9.12 (4H, s), 9.28 (4H, s).

Example 38

3,5-Bis-(4-carbamimidoyl-phenoxy)-N,N-diethyl-benzamide

Intermediates (a) and (b) are same as in Example 26.

c)
3,5-Bis-(4-cyano-phenoxy)-N,N-diethyl-benzamide

Following the procedure of Example 5(c) 3,5-bis-(4-cyano-phenoxy)-benzoic acid 1.2 g (3.36 mmol) and diethylamine (0.245 g, 3.36 mmol) were used to afford 1.0 g of the required product. $^1$H NMR (DMSO-d$_6$): δ 1.15 (6H, m), 3.22 (2H, m), 3.40 (2H, m), 6.94 (2H, d), 7.05 (1H, t), 7.25 (2H, d), 7.88 (2H, d).

d) N,N-Diethyl-3,5-bis-[4-(N-hydroxycarbamimidoyl)-phenoxy]-benzamide

Following the procedure of Example 2(d) N,N-diethyl-3,5-bis-[4-(N-hydroxy-carbamimidoyl)-phenoxy]-benzamide 1.0 g (2.43 mmol) and other reagents were used to afford 1.1 g of the required product. Percentage purity (LCMS): 80.0%, (M+1)=477.2+1.

e) N,N-Diethyl-3,5-bis-[4-(N-acetylhydroxycarbamimidoyl)-phenoxy]-benzamide

Following the procedure of Example 2(e) N,N-diethyl-3,5-bis-[4-(N-hydroxy-carbamimidoyl)-phenoxy]-benzamide 1.1 g (2.3 mmol) was acetylated to afford 1.0 g of the required product. Percentage purity (LCMS): 77.0%, (M+1)=561.2+1.

f) 3,5-Bis-(4-carbonimidoyl-phenoxy)-N,N-diethyl-benzamide

N,N-Diethyl-3,5-bis-[4-(N-acetylhydroxycarbamimidoyl)-phenoxy]-benzamide, 1.0 g (1.78 mmol) was reduced using the procedure of Example 2(f) to afford 0.35 g of required product. Percentage purity (HPLC): 95.41%, (LCMS): 93.34%. $^1$H NMR (DMSO-d$_6$): δ 1.02 (6H, s), 3.2 (2H, m), 3.4 (2H, m), 6.9 (2H, d), 7.0 (1H, s), 7.3 (4H, d), 7.88 (4H, d), 9.24 (3H, s), 9.30 (3H, s).

Example 39

N-(3-Amino-propyl)-3,5-bis-(4-carbamimidoyl-phenoxy)-N-cyclopropyl-benzamide

Intermediates (a) and (b) are the same as in Example 26.

c) (3-{[3,5-Bis-(4-cyano-phenoxy)-benzoyl]-cyclopropyl-amino}-propyl)-carbamic Acid Tert-butyl Ester Following the procedure of Example 5(c) 3,5-bis-(4-cyano-phenoxy)-benzoic acid 1.2 g (3.36 mmol) and (3-cyclopropylamino-propyl)-carbamic acid tert-butyl ester (0.72 g, 3.36 mmol) were used to afford 1.5 g of the required product. $^1$H NMR (DMSO-d$_6$): δ 0.48 (1H, m), 0.65 (2H, m), 1.38 (9H, s), 1.42 (2H, m), 1.68 (2H, m), 2.95 (2H, m), 3.22 (2H, m), 6.80 (1H, brs), 6.95 (1H, s), 7.08 (2H, m), 7.25 (4H, m), 7.88 (4H, m).

d) [3-({3,5-Bis-[4-(N-hydroxycarb amimidoyl)-phenoxy]-benzoyl}-cyclopropyl-amino)-propyl]-carbamic Acid Tert-butyl Ester Following the procedure of Example 2(d) (3-{[3,5-bis-(4-cyano-phenoxy)-benzoyl]-cyclopropyl-amino}-propyl)-carbamic acid tert-butyl ester 1.5 g (2.71 mmol) and other reagents were used to afford 1.3 g of the required product. Percentage purity (LCMS): 42.8.0%, (M+1)=618.2 (with BOC).

e) [3-({3,5-Bis-[4-(N-acetylhydroxycarbamimidoyl)-phenoxy]-benzoyl}-cyclopropyl-amino)-propyl]-carbamic Acid Tert-butyl Ester Following the procedure of Example 2(e) [3-({3,5-bis-[4-(N-hydroxy-carbamimidoyl)-phenoxy]-benzoyl}-cyclopropyl-amino)-propyl]-carbamic acid tert-butyl ester 1.3 g (2.1 mmol) was acetylated to afford 1.25 g of the required product. Percentage purity (LCMS): 83.0%, (M+1)=702.3.

f) [3-({3,5-Bis-[4-(carbamimidoyl)-phenoxy]-benzoyl}-cyclopropyl-amino)-propyl]-carbamic Acid Tert-butyl Ester

[3-({3,5-Bis-[4-(N-acetylhydroxycarbamimidoyl)-phenoxy]-benzoyl}-cyclopropyl-amino)-propyl]-carbamic acid tert-butyl ester, 1.25 g (1.77 mmol) was reduced using the procedure of Example 2(f) to afford 0.85 g of the required product. Percentage purity (LCMS): 72.0%, (M+1)=486.3+1 (de-Boc mass; −100).

g) 3,5-Bis-(4-carbamimidoyl-phenoxy)-cyclohexa-1,5-dienecarboxylic Acid (3-amino-propyl)-cyclopropyl-amide Using [3-({3,5-bis-[4-(carbamimidoyl)-phenoxy]-benzoyl}-cyclopropyl-amino)-propyl]-carbamic acid tert-butyl ester (0.85 g, 1.44 mmol) and following the procedure of Example 9(d) afforded 0.2 g of the required product. Percentage purity (HPLC): 96.18%, (LCMS): 94.22%. $^1$H NMR (DMSO-d$_6$): δ 0.50 (2H, m), 0.65 (2H, m), 1.88 (2H, m), 2.85

(3H, m), 3.49 (2H, m), 7.02 (1H, t), 7.14 (2H, s), 7.25 (4H, d), 7.80 (2H, brs), 7.88 (4H, d), 9.22 (3H, s), 9.28 (3H, s).

Example 40

[3,5-Bis-(4-carbamimidoyl-phenoxy)-benzoyl]-3,4-dihydro-1H-quinoline

Intermediates (a) and (b) are the same as in Example 26.

c) [3,5-Bis-(cyano-phenoxy)-benzoyl]-3,4-dihydro-1H-quinoline

Following the procedure of Example 5(c) 3,5-bis-(4-cyano-phenoxy)-benzoic acid 1.2 g (3.36 mmol) and 1,2,3,4-tetrahydro-quinoline (0.44 g, 3.36 mmol) were used to afford 1.3 g of the required product. $^1$H NMR (DMSO-$d_6$): δ 1.92 (2H, t), 2.54 (2H, m) 3.75 (2H, t), 6.92 (2H, d), 7.08 (7H, m), 7.82 (4H, d).

d) [3,5-Bis-[4-(N-hydroxycarbamimidoyl)-phenoxy]-benzoyl]-3,4-Dihydro-1H-quinoline Following the procedure of Example 2(d) [3,5-bis-(4-cyano-phenoxy)-benzoyl]-3,4-dihydro-1H-quinoline 1.3 g (2.75 mmol) and other reagents were used to afford 1.25 g of the required product. Percentage purity (LCMS): 66.1%, (M+1)=537.2.2+1.

e) [3,5-Bis-[4-(N-acetylhydroxycarbamimidoyl)-phenoxy]-benzoyl]-3,4-Dihydro-1H-quinoline Following the procedure of Example 2(e) [3,5-bis-[4-(N-hydroxycarbamimidoyl)-phenoxy]-benzoyl]-3,4-Dihydro-1H-quinoline 1.25 g (2.32 mmol) was acetylated to afford 1.2 g of the required product. Percentage purity (LCMS): 65.5%, (M+1)=621.2+1.

f) [3,5-Bis-(4-carbamimidoyl-phenoxy)-benzoyl]-3,4-Dihydro-1H-quinoline

[3,5-Bis-[4-(N-acetylhydroxycarbamimidoyl)-phenoxy]-benzoyl]-3,4-dihydro-lfl-quinoline, 1.2 g (1.93 mmol) was reduced using the procedure of Example 2(f) to afford 0.75 g of required product. Percentage purity (HPLC): 99.56%, (LCMS): 96.29%. $^1$H NMR (DMSO-$d_6$): δ 1.92 (2H, q), 2.74 (2H, t), 3.75 (2H, t), 6.85 (1H, brs), 6.90 (2H, d), 6.98 (1H, t), 7.15 (7H, m), 7.84 (4H, d), 9.14 (4H, s), 9.26 (4H, s).

Example 41

[3,4-Dihydro-1H-isoquinoline-2-carbonyl]-3,5-Bis-(4-carbamimidoyl-phenoxy)-benzene Intermediates (a) and (b) are the same as in Example 26.

c) [3,4-Dihydro-1H-isoquinoline-2-carbonyl]-3,5-Bis-(4-cyano-phenoxy)-benzene

Following the procedure of Example 5(c) 3,5-bis-(4-cyano-phenoxy)-benzoic acid 0.8 g (2.24 mmol) and 1,2,3,4-tetrahydro-isoquinoline (0.3 g, 2.26 mmol) were used to afford 0.9 g of the required product. $^1$H NMR (DMSO-$d_6$): δ 2.82 (2H, m), 3.58 (1H, m), 3.80 (1H, m), 4.08 (1H, m), 4.74 (1H, m), 7.10 (3H, m), 7.20 (4H, m), 7.28 (4H, d), 7.90 (2H, d).

d) [3,4-Dihydro-1H-isoquinoline-2-carbonyl]-3,5-Bis-(4-(N-hydroxy-carbamimidoyl)-phenoxy)-benzene Following the procedure of Example 2(d) [3,4-dihydro-1H-isoquinoline-2-carbonyl]-3,5-Bis-(4-cyano-phenoxy)-benzene 0.9 g (1.9 mmol) and other reagents were used to afford 0.85 g of the required product. Percentage purity (LCMS): 38.9%, (M+1)=537.0+1.

e) [3,4-Dihydro-1H-isoquinoline-2-carbonyl]-3,5-Bis-(4-(N-acetylhydroxy-carbamimidoyl)-phenoxy)-benzene Following the procedure of Example 2(e) [3,4-dihydro-1H-isoquinoline-2-carbonyl]-3,5-Bis-(4-(N-hydroxycarbamimidoyl)-phenoxy)-benzene 0.85 g (1.58 mmol) was acetylated to afford 0.8 g of the required product. Percentage purity (LCMS): 58.1%, (M+1)=621.2+1.

f) [3,4-Dihydro-1H-isoquinoline-2-carbonyl]-3,5-Bis-(4-carbamimidoyl-phenoxy)-benzene

[3,4-Dihydro-1H-isoquinoline-2-carbonyl]-3,5-bis-(4-(N-acetylhydroxy-carbamimidoyl)-phenoxy)-benzene, 0.8 g (1.28 mmol) was reduced using the procedure of Example 2(f) to afford 0.15 g of required product. Percentage purity (HPLC): 93.50%, (LCMS): 94.20%. $^1$H NMR (DMSO-$d_6$): δ 2.80 (2H, m), 3.60 (1H, m), 3.80 (1H, m), 4.67 (2H, m), 6.98 (2H, m), 7.05 (1H, s), 7.18 (4H, m), 7.35 (4H, d), 7.90 (4H, d), 9.10 (4H, brs), 9.28 (3H, brs).

Example 42

N-(4-Amino cyclohexyl)-3-(3-carbamimidoyl benzyloxy)-5-(4-carbamimidoyl phenoxy)benzamide a) 3-(4-Cyano phenoxy)-5-hydroxy Benzoic Acid Ethyl Ester Potassium carbonate 6.7 g (48.5 mmol) followed by 4-fluoro benzonitrile 3.3 g (27.2 mmol) in 10 ml of DMF was added to a solution of 3,5-dihydroxy benzoic acid ethyl ester 5 g (27.4 mmol) in 20 ml of DMF at 20° C. The reaction mixture was allowed to attain RT and was then heated to 45° C. for 10 h. The reaction mixture was quenched with ice cold water and extracted with ethyl acetate. The organic layer was washed with water followed by brine, dried over anhydrous sodium sulphate and concentrated. The crude compound was purified by column chromatography using hexane-ethyl acetate (10:2) to afford 1.15 g of the required product. $^1$H NMR (DMSO-$d_6$): δ 1.3 (3H, t), 4.3 (2H, q), 6.76 (1H, s), 7.02 (1H, s), 7.36 (2H, d), 7.24 (1H, s), 7.88 (2H, d), 10.3 (1H, s).

b) 3-(3-Cyano benzyloxy)-5-(4-cyano phenoxy)benzoic Acid Ethyl Ester

Potassium carbonate $K_2CO_3$ 0.44 g (3.18 mmol) followed by 3-cyano benzylbromide 0.31 g (1.58 mmol) in 2 ml of DMF were added to a solution of 3-(4-cyano phenoxy)-5-hydroxy benzoic acid ethyl ester 0.45 g (1.58 mmol) in 7 ml of DMF at 20° C. The reaction mixture was allowed to attain RT and stirred overnight. The reaction mixture was quenched with ice cold water, extracted with ethyl acetate. The organic layer was washed with water followed by brine, dried over anhydrous sodium sulphate and concentrated to afford 0.51 g of a thick oily liquid. $^1$H NMR (CDCl$_3$): δ 1.3 (3H, t), 4.3 (2H, q), 5.25 (2H, s), 6.88 (1H, s), 7.02 (2H, d), 7.34 (1H, s), 7.5 (2H, m), 7.66 (4H, m), 7.78 (1H, s).

c) 3-(3-Cyano benzyloxy)-5-(4-cyano phenoxy)benzoic Acid 1.6 g (4.01 mmol) of 3-(3-cyano benzyloxy)-5-(4-cyano phenoxy)benzoic acid ethyl ester was hydrolysed using the procedure of Example 5(b) to afford 1.2 g of the required product. $^1$H NMR (DMSO-$d_6$): δ 5.25 (2H, s), 7.16 (4H, m), 7.44 (1H, s), 7.64 (1H, m), 7.9 (5H, m), 13.4 (1H, brs).

d) {4-[3-(3-Cyano benzyloxy)-5-(4-cyano phenoxy) benzoyl Amino]cyclohexyl}-carbamic Acid Tert-butyl Ester Following the procedure of Example 5(c) 3-(3-cyano benzyloxy)-5-(4-cyano phenoxy)benzoic acid 0.46 g (1.24 mmol) and (4-amino-cyclohexyl)-carbamic acid tert-butyl ester (0.265 g, 1.24 mmol) were used to afford 0.52 g of the required product. $^1$H NMR (DMSO-$d_6$): δ 1.25 (4H, m), 1.40 (9H, s), 1.8 (4H, m), 3.2 (1H, m), 3.7 (1H, m), 5.25 (2H, s), 6.74 (1H, d), 7.02 (1H, s), 7.32 (2H, d), 7.22 (1H, s), 7.44 (1H, s), 7.64 (1H, m), 7.84 (4H, m), 7.95 (1H, s), 8.3 (1H, d).

e) 4-[3-(3-ethoxycarbonimidoyl-benzyloxy)-5-(4-ethoxycarbonimidoyl-phenoxy)benzoyl Amino]cyclohexylamine Using {4-[3-(3-cyano benzyloxy)-5-(4-cyano phenoxy) benzoyl amino]cyclohexyl}-carbamic acid tert-butyl ester (0.5 g, 0.88 mmol) and following the procedure of Example 1(d) afforded 0.3 g of the required product. Percentage purity (LCMS): 64.2%, (M+1)=558.2+1.

f) N-(4-Amino cyclohexyl)-3-(3-carbamimidoyl benzyloxy)-5-(4-carbamimidoyl-phenoxy)benzamide Using 4-[3-(3-ethoxycarbonimidoyl-benzyloxy)-5-(4-ethoxycarbonimidoyl phenoxy)benzoyl amino]cyclohexylamine (0.3 g, 0.53 mmol) and following the procedure as in Example 1(e) afforded 0.16 g of the required product. Percentage purity (HPLC): 96.67%, (LCMS): 99.51%. $^1$H NMR (DMSO-$d_6$): δ 1.4 (4H, m), 1.9 (4H, m), 3.0 (1H, m), 3.70 (1H, m), 5.30 (2H, s), 7.0 (1H, s), 7.2 (3H, d), 7.45 (1H, s), 7.70 (1H, m), 7.8-8.0 (7H, m), 8.4 (1H, d), 9.25 (4H, d), 9.4 (4H, d).

Example 43

N-(4-Aminocyclohexyl)-3-(4-carbamimidoyl benzyloxy)-5-(4-carbamimidoyl phenoxy)benzamide Intermediate (a) is the same as in Example 42.

b) 3-(4-Cyano benzyloxy)-5-(4-cyano phenoxy)benzoic Acid Ethyl Ester

Using 0.66 g (2.3 mmol) of 3-(4-cyano phenoxy)-5-hydroxy benzoic acid ethyl ester and 4-cyanobenzylbromide (0.45 g, 2.3 mmol) and following the procedure of Example 42(b) afforded 0.72 g of the required product. $^1$H NMR (DMSO-$d_6$): δ 1.3 (3H, t), 4.3 (2H, q), 5.35 (2H, s), 7.16 (4H, m), 7.44 (1H, s), 7.66 (2H, d), 7.88 (4H, d).

c) 3-(4-Cyano benzyloxy)-5-(4-cyano Phenoxy)benzoic Acid 0.72 g (1.8 mmol) of 3-(4-cyano benzyloxy)-5-(4-cyano phenoxy)benzoic acid ethyl ester was hydrolysed using the procedure of Example 5(b) to afford 0.55 g of the required product. $^1$H NMR (DMSO-$d_6$): δ 5.25 (2H, s), 7.10 (1H, m), 7.18 (3H, m), 7.42 (1H, s), 7.66 (2H, s), 7.88 (4H, d).

d) {4-[3-(4-Cyano benzyloxy)-5-(4-cyano Phenoxy) benzoyl Amino]cyclohexyl}carbamic Acid Tert-butyl Ester Following the procedure of Example 5(c) 3-(4-cyano benzyloxy)-5-(4-cyano phenoxy)benzoic acid 0.55 g (1.48 mmol) and (4-amino-cyclohexyl)-carbamic acid tert-butyl ester (0.316 g, 1.48 mmol) were used to afford 0.75 g of the required product. $^1$H NMR (DMSO-$d_6$): δ 1.25 (4H, m), 1.40 (9H, s), 1.8 (4H, m), 3.2 (1H, m), 3.7 (1H, m), 5.3 (2H, s), 6.74 (1H, d), 7.02 (1H, s), 7.1 (2H, s), 7.22 (1H, s), 7.44 (1H, s), 7.66 (2H, d), 7.88 (4H, m), 8.28 (1H, d).

e) 4-[3-(4-ethoxycarbonimidoyl-benzyloxy)-5-(4-ethoxycarbonimidoyl-phenoxy)-benzoyl Amino] cyclohexylamine Using {4-[3-(4-cyano benzyloxy)-5-(4-cyano phenoxy) benzoyl amino]-cyclohexyl}carbamic acid tert-butyl ester (0.75 g, 1.32 mmol) and following the procedure of Example 1(d) afforded 0.35 g of the required product. Percentage purity (LCMS): 33.7%, (M+1)=558.2+1.

f) N-(4-Amino-cyclohexyl)-3-(4-carbamimidoyl-benzyloxy)-5-(4-carbamimidoyl-phenoxy)benzamide Using 4-[3-(4-ethoxycarbonimidoyl-benzyloxy)-5-(4-ethoxy carbonimidoyl-phenoxy)-benzoylamino]cyclohexylamine (0.35 g, 0.62 mmol) and following the procedure of Example 1(e) afforded 0.12 g of the required product. Percentage purity (HPLC): 91.03%, (LCMS): 96.32%. $^1$H NMR (DMSO-$d_6$): δ 1.4 (4H, m), 1.9 (4H, m), 3.0 (1H, m), 3.70 (1H, m), 5.30 (2H, s), 7.0 (1H, s), 7.2 (3H, d), 7.45 (1H, s), 7.70 (2H, d), 7.9 (6H, m), 8.4 (1H, m), 9.3 (7H, t).

Example 44

N-(4-Amino-cyclohexyl)-3-[4-(N-hydroxycarbamimidoyl)-benzyloxy]-5-[4-(N-hydroxycarbamimidoyl)-phenoxy]-benzamide Intermediates (a) to (d) are the same as in Example 43.

e) (4-{3-[4-(N-Hydroxycarbamimidoyl)-benzyloxy]-5-[4-(N-hydroxy-carbamimidoyl)-phenoxy]-benzoylamino}-cyclohexyl)-carbamic Acid Tert-butyl Ester Following the procedure of Example 2(d) {4-[3-(4-cyano benzyloxy)-5-(4-cyano phenoxy)benzoyl amino] cyclohexyl}carbamic acid tert-butyl ester 0.65 g (1.14 mmol) and other reagents were used to afford 0.52 g of the required product. Percentage purity (LCMS): 48.2%, (M+1)=632.3+1.

f) N-(4-Amino-cyclohexyl)-3-[4-(N-hydroxycarbamimidoyl)-benzyloxy]-5-[4-(N-hydroxycarbamimidoyl)-phenoxy]-benzamide Using (4-{3-[4-(N-hydroxycarbamimidoyl)-benzyloxy]-5-[4-(N-hydroxy-carbamimidoyl)-phenoxy]-benzoylamino}-cyclohexyl)-carbamic acid tert-butyl ester (0.5 g, 0.8 mmol) and following the procedure of Example 9(d) afforded 0.28 g of the required product. Percentage purity (HPLC): 96.4%, (LCMS): 96.7%. ¹H NMR (DMSO-d₆): δ 1.48 (4H, m), 1.98 (4H, m), 3.04 (1H, m), 3.76 (1H, m), 5.42 (2H, s), 7.05 (1H, s), 7.24 (3H, m), 7.48 (2H, m), 7.70 (2H, d), 7.81 (4H, d), 7.91 (3H, brs), 8.42 (1H, d), 8.72 (2H, brs), 11.04 (2H, brs).

Example 45

N-(4-Aminocyclohexyl)-3-(4-aminomethyl benzyloxy)-5-(4-carbamimidoyl phenoxy)benzamide Intermediate (a) is the same as in Example 42.

b) 3-(4-(tert-Butoxycarbonyl Aminomethyl)benzyloxy)-5-(4-cyano phenoxy)benzoic Acid Ethyl Ester Using 0.85 g (3.0 mmol) of 3-(4-cyano phenoxy)-5-hydroxy benzoic acid ethyl ester and (4-bromomethyl-benzyl)-carbamic acid tert-butyl ester (0.9 g, 3.0 mmol) and following the procedure of Example 42(b) afforded 1.32 g of the required product. ¹H NMR (CDCl₃): δ 1.3 (3H, t), 1.4 (9H, s), 4.15 (2H, d), 4.3 (2H, q), 5.25 (2H, s), 7.18 (4H, m), 7.26 (2H, d), 7.4 (4H, m), 7.88 (2H, d).

c) 3-(4-(tert-Butoxycarbonyl Aminomethyl)benzyloxy)-5-(4-cyano Phenoxy)benzoic Acid 1.3 g (2.58 mmol) of 3-(4-(tert-butoxycarbonyl aminomethyl)benzyloxy)-5-(4-cyano phenoxy)benzoic acid ethyl ester was hydrolysed using the procedure of Example 5(b) to afford 1.1 g. of the required product. ¹H NMR (DMSO-d₆): δ 1.4 (9H, s), 4.15 (2H, d), 5.2 (2H, s), 7.08 (1H, m), 7.16 (3H, m), 7.26 (2H, d), 7.88 (2H, d), 13.2 (1H, brs)

d) {4-[3-(4-(tert-Butoxycarbonyl Aminomethyl)benzyloxy)-5-(4-cyano phenoxy)benzoyl Amino] cyclohexyl}carbamic Acid Tert-butyl Ester Following the procedure of Example 5(c) 3-(4-(tert-butoxycarbonyl aminomethyl)benzyloxy)-5-(4-cyano phenoxy)benzoic acid 1.1 g (2.31 mmol) and (4-amino-cyclohexyl)-carbamic acid tert-butyl ester (0.494 g, 2.31 mmol) were used to afford 1.24 g of the required product. ¹H NMR (DMSO-d₆): δ 1.2 (4H, m), 1.4 (18H, s), 1.8 (4H, m), 3.2 (1H, m), 3.7 (1H, m), 4.1 (2H, d), 5.15 (2H, s), 6.74 (1H, d), 6.88 (1H, s), 7.12 (2H, d), 7.18 (1H, s), 7.26 (2H, d), 7.4 (4H, d), 7.86 (2H, d), 8.26 (1H, d).

e) 4-[3-(4-Amino cyclohexylcarbamoyl)-5-(4-aminomethyl benzyloxy)phenoxy]benzimidic Acid Ethyl Ester Using {4-[3-(4-(tert-butoxycarbonyl aminomethyl)benzyloxy)-5-(4-cyano phenoxy)benzoyl amino] cyclohexyl}carbamic acid tert-butyl ester (1.2 g, 1.78 mmol) and following the procedure of Example 1(d) afforded 0.5 g of the required product. Percentage purity (LCMS): 52.0%, (M+1)=516.2±1.

f) N-(4-Aminocyclohexyl)-3-(4-aminomethylbenzyloxy)-5-(4-carbamimidoyl-phenoxy)benzamide Using 4-[3-(4-aminocyclohexylcarbamoyl)-5-(4-aminomethyl benzyloxy)phenoxy]benzimidic acid ethyl ester (0.5 g, 0.96 mmol) and following the procedure of Example 1(e) afforded 0.15 g of the required product. Percentage purity (HPLC): 96.46%, (LCMS): 98.41%. NMR (DMSO-d₆): δ 1.4 (4H, m), 1.85 (2H, m), 1.95 (2H, m), 3.0 (1H, m), 4.1 (3H, s), 5.20 (2H, s), 7.0 (1H, s), 7.2 (3H, m), 7.5 (5H, m), 7.85 (4H, m), 8.25 (2H, brs), 8.4 (1H, d), 9.2 (4H, s).

Example 46

N-(4-Amino-cyclohexyl)-3-(4-aminomethyl-benzyloxy)-5-[4-(N-hydroxy-carbamimidoyl)-phenoxy]-benzamide Intermediates (a) to (d) are the same as in Example 45.

e) (4-{3-[4-(tert-Butoxycarbonylamino-methyl)-benzyloxy]-5-[4-(N-hydroxy-carbamimidoyl)-phenoxy]-benzoylamino}-cyclohexyl)-carbamic Acid Tert-butyl Ester Following the procedure of Example 2(d) {4-[3-(4-(tert-butoxycarbonylamino-methyl)benzyloxy)-5-(4-cyanophenoxy)benzoylamino]cyclohexyl}carbamic acid tert-butyl ester 0.6 g (0.89 mmol) and other reagents were used to afford 0.55 g of the required product. Percentage purity (LCMS): 38.9%, (M+1)=703.3+1.

g) N-(4-Amino-cyclohexyl)-3-(4-aminomethyl-benzyloxy)-5-[4-(N-hydroxy-carbamimidoyl)-phenoxy]-benzamide Using (4-{3-[4-(tert-butoxycarbonylamino-methyl)-benzyloxy]-5-[4-(N-hydroxy-carbamimidoyl)-phenoxy]-benzoylamino}-cyclohexyl)-carbamic acid tert-butyl ester (0.55 g, 0.78 mmol) and following the procedure of Example 9(d) afforded 0.15 g of the required product. Percentage purity (HPLC): 96.9%, (LCMS): 92.4%. ¹H NMR (DMSO-d₆): δ 1.40 (4H, m), 1.90 (4H, m), 3.00 (1H, m), 3.71 (1H, m), 4.15 (2H, s), 5.18 (2H, s), 6.98 (1H, s), 7.16 (3H, m), 7.40 (1H, s), 7.50 (4H, m), 7.76 (2H, d), 7.90 (3H, brs), 8.30 (4H, brs), 8.65 (1H, brs), 11.25 (1H, brs).

Example 47

N-(4-Aminocyclohexyl)-3-(3-aminomethyl benzyloxy)-5-(4-carbamimidoyl phenoxy)benzamide Intermediate (a) is the same as in Example 42.

b) 3-(3-(tert-Butoxycarbonyl Aminomethyl)benzyloxy)-5-(4-cyano Phenoxy)benzoic Acid Ethyl Ester Using 1.4 g (4.94 mmol) of 3-(4-cyano phenoxy)-5-hydroxy benzoic acid ethyl ester and (3-bromomethyl-benzyl)-carbamic acid tert-butyl ester (1.48 g, 4.94 mmol) and following the procedure of Example 42(b) afforded 1.9 g of the required product. NMR (DMSO-d₆): δ 1.3 (3H, t), 1.4 (9H, s), 4.15 (2H, d), 4.35 (2H, q), 5.25 (2H, s), 7.18 (5H, m), 7.32 (3H, m), 7.44 (2H, s), 7.88 (2H, d).

c) 3-(3-(tert-Butoxycarbonyl Aminomethyl)benzyloxy)-5-(4-cyano Phenoxy)benzoic Acid 1.9 g (3.78 mmol) of 3-(3-(tert-butoxycarbonyl aminomethyl)benzyloxy)-5-(4-cyano phenoxy)benzoic acid ethyl ester was hydrolysed using the procedure of Example 5(b) to afford 1.35 g of the required product. ¹H NMR (DMSO-d₆): δ 1.4 (9H, s), 4.05 (2H, s), 5.2 (2H, s), 7.1 (5H, m), 7.3 (5H, m), 7.9 (2H, m), 13.2 (1H, brs)

d) {4-[3-(3-(tert-Butoxycarbonylaminomethyl)benzyloxy)-5-(4-cyano phenoxy)-benzoyl Amino]cyclohexyl}carbamic Acid Tert-butyl Ester Following the procedure of Example 5(c) 3-(3-(tert-butoxycarbonyl aminomethyl)benzyloxy)-5-(4-cyano phenoxy)benzoic acid 0.65 g (1.36 mmol) and (4-amino-cyclohexyl)-carbamic acid tert-butyl ester (0.29 g, 1.36 mmol) were used to afford 0.7 g of the required product. $^1$H NMR (DMSO-d$_6$): δ 1.2 (4H, m), 1.4 (18H, s), 1.8 (4H, m), 3.2 (1H, m), 3.7 (1H, m), 4.1 (2H, d), 5.15 (2H, s), 6.74 (1H, d), 6.9 (1H, s), 7.10 (2H, d), 7.2 (2H, m), 7.35 (3H, m), 7.45 (2H, m), 7.86 (2H, d), 8.26 (1H, d).

e) 4-[3-(4-Aminocyclohexylcarbamoyl)-5-(3-aminomethyl benzyloxy)phenoxy]benzimidic Acid Ethyl Ester Using {4-[3-(3-(tert-butoxycarbonyl aminomethyl)benzyloxy)-5-(4-cyano phenoxy)benzoyl amino]cyclohexyl}carbamic acid tert-butyl ester (0.7 g, 1.04 mmol) and following the procedure of Example 1(d) afforded 0.3 g of the required product. Percentage purity (LCMS): 98.0%, (M+1)=703.3+1.

f) N-(4-Amino cyclohexyl)-3-(3-aminomethyl benzyloxy)-5-(4-carbamimidoyl phenoxy)benzamide Using 4-[3-(4-aminocyclohexylcarbamoyl)-5-(3-aminomethyl benzyloxy)phenoxy]benzimidic acid ethyl ester (0.3 g, 0.58 mmol) and following the procedure of Example 1(e) afforded 0.12 g of the required product. Percentage purity (HPLC): 97.76%, (LCMS): 92.64%. $^1$H NMR (DMSO-d$_6$): δ 1.35 (4H, m), 1.9 (4H, m), 3.0 (2H, m), 4.1 (2H, d), 5.20 (2H, s), 7.0 (1H, s), 7.2 (3H, m), 7.45 (3H, m), 7.55 (1H, s), 7.85 (4H, m), 8.2 (2H, brs), 8.35 (1H, d), 9.0 (2H, s), 9.25 (2H, s).

Example 48

N-(4-Amino-cyclohexyl)-3-(3-aminomethyl-benzyloxy)-5-[4-(N-hydroxy-carbamimidoyl)-phenoxy]-benzamide Intermediates (a) to (d) are the same as in Example 47.

e) (4-{3-[3-(tert-Butoxycarbonylamino-methyl)-benzyloxy]-5-[4-(N-hydroxy-carbamimidoyl)-phenoxy]-benzoylamino}-cyclohexyl)-carbamic Acid Tert-butyl Ester Following the procedure of Example 2(d) {4-[3-(3-(tert-butoxycarbonylamino-methyl)benzyloxy)-5-(4-cyanophenoxy)benzoylamino}cyclohexyl]carbamic acid tert-butyl ester 0.65 g (0.97 mmol) and other reagents were used to afford 0.6 g of the required product. Percentage purity (LCMS): 38.9%, (M+1)=503.3+1 (de-Boc; 2×100).

f) N-(4-Amino-cyclohexyl)-3-(3-aminomethyl-benzyloxy)-5-[4-(N-hydroxy-carbamimidoyl)-phenoxy]-benzamide Using (4-{3-[3-(tert-butoxycarbonylamino-methyl)-benzyloxy]-5-[4-(N-hydroxy-carbamimidoyl)-phenoxy]-benzoylamino}-cyclohexyl)-carbamic acid tert-butyl ester (0.6 g, 0.85 mmol) and following the procedure of Example 9(d) afforded 0.2 g of the required product. Percentage purity (HPLC): 98.8%, (LCMS): 94.1%. $^1$H NMR (DMSO-d$_6$): δ 1.4 (4H, m), 1.82 (4H, m), 3.03 (1H, m), 3.65 (1H, m), 4.10 (3H, brs), 5.18 (2H, s), 6.98 (1H, s), 7.18 (3H, d), 7.4 (1H, s), 7.46 (3H, m), 7.55 (1H, s), 7.76 (2H, d), 7.88 (3H, brs), 8.25 (3H, brs), 8.38 (1H, d), 11.10 (1H, brs).

Example 49

N-(4-Amino cyclohexyl)-3-(3-bromo benzyloxy)-5-(4-carbamimidoyl Phenoxy)benzamide Intermediate (a) is the same as in Example 42.

b) 3-(4-Cyano phenoxy)-5-hydroxy Benzoic Acid 1.2 g (4.23 mmol) of 3-(4-cyano phenoxy)-5-hydroxy benzoic acid ethyl ester was hydrolysed using the procedure of Example 5(b) to afford 0.95 g of the required product. $^1$H NMR (DMSO-d$_6$): δ 6.75 (1H, s), 7.0 (1H, s), 7.15 (2H, d), 7.25 (1H, s), 7.85 (2H, d), 10.2 (1H, s), 13.2 (1H, brs).

c) {4-[3-(4-Cyanophenoxy)-5-hydroxybenzoylamino]cyclohexyl}carbamic Acid Tert-butyl Ester Following the procedure of Example 5(c) 3-(4-cyano phenoxy)-5-hydroxy benzoic acid 0.9 g (3.52 mmol) and (4-amino-cyclohexyl)-carbamic acid tert-butyl ester (0.75 g, 3.52 mmol) were used to afford 0.6 g of the required product. $^1$H NMR (DMSO-d$_6$): 1.35 (4H, m), 1.4 (9H, s), 1.8 (4H, m), 3.15 (1H, m), 3.7 (1H, m), 6.62 (1H, s), 6.76 (1H, d), 7.04 (1H, s), 7.16 (3H, m), 7.86 (2H, m), 8.2 (1H, d), 10.0 (1H, s).

d) {4-[3-(3-bromo-benzyloxy)-5-(4-cyano-phenoxy)benzoylamino}-cyclohexyl]-carbamic Acid Tert-butyl Ester Using 0.6 g (1.32 mmol) of {4-[3-(4-cyanophenoxy)-5-hydroxybenzoylamino]cyclohexyl}carbamic acid tert-butyl ester and 1-bromo-3-bromomethyl-benzene (0.33 g, 1.32 mmol) and following the procedure of Example 42(b) afforded 0.7 g of the required product. $^1$H NMR (DMSO-d$_6$): δ 1.25 (4H, m), 1.4 (9H, s), 1.8 (4H, m), 3.2 (1H, m), 3.7 (1H, m), 5.2 (2H, s), 6.76 (1H, d), 7.0 (1H, s), 7.12 (2H, d), 7.2 (1H, s), 7.44 (3H, m), 7.56 (1H, d), 7.68 (1H, s), 7.84 (2H, d), 8.3 (1H, d).

e) 4-[3-(4-amino-cyclohexyl-carbamoyl)-5-(3-bromobenzyloxy)phenoxy]-benzimidic Acid Ethyl Ester Using {4-[3-(3-bromo-benzyloxy)-5-(4-cyano-phenoxy)benzoylamino]-cyclohexyl}-carbamic acid tert-butyl ester (0.7 g, 1.12 mmol) and following the procedure of Example 1(d) afforded 0.35 g of the required product. Percentage purity (LCMS): 59.0%, (M+1)=503.3+1.

f) N-(4-Amino cyclohexyl)-3-(3-bromo benzyloxy)-5-(4-carbamimidoyl Phenoxy)benzamide Using 4-[3-(4-amino-cyclohexyl-carbamoyl)-5-(3-bromobenzyloxy)phenoxy]-benzimidic acid ethyl ester (0.35 g, 0.61 mmol) and following the procedure of Example 1(e) afforded 0.15 g of the required product. Percentage purity (HPLC): 98.8%, (LCMS): 96.6%. $^1$H NMR (DMSO-d$_6$): δ 1.40 (4H, m), 1.92 (4H, m), 3.02 (1H, m), 3.71 (1H, m), 5.20 (2H, s), 7.02 (1H, s), 7.14 (1H, s), 7.21 (2H, d), 7.42 (3H, m), 7.58 (1H, d), 7.68 (1H, s), 7.88 (4H, d), 8.35 (1H, d), 9.12 (2H, brs), 9.26 (2H, brs).

Example 50

N-(4-Amino-cyclohexyl)-3-(3-bromo-benzyloxy)-5-[4-(N-hydroxy-carbamimidoyl)-phenoxy]-benzamide Intermediates (a) to (d) are the same as in Example 49.

e) (4-{3-(3-Bromo-benzyloxy)-5-[4-(N-hydroxycarbamimidoyl)-phenoxy]-benzoylamino}-cyclohexyl)-carbamic Acid Tert-butyl Ester Following the procedure of Example 2(d) {4-[3-(3-bromo-benzyloxy)-5-(4-cyano-phenoxy)benzoylamino]-cyclohexyl}-carbamic acid tert-butyl ester 0.58 g (0.93 mmol) and other reagents were used to afford 0.6 g of the required product. Percentage purity (LCMS): 48.2%, (M+1)=653.2+1.

f) N-(4-Amino-cyclohexyl)-3-(3-bromo-benzyloxy)-5-[4-(N-hydroxy-carbamimidoyl)-phenoxy]-benzamide Using (4-{3-(3-bromo-benzyloxy)-5-[4-(N-hydroxycarbamimidoyl)-phenoxy]-benzoylamino}-cyclohexyl)-carbamic acid tert-butyl ester (0.6 g, 0.91 mmol) and following the procedure of Example 9(d) afforded 0.35 g of the required product. Percentage purity (HPLC): 98.4%, (LCMS): 97.2%. $^1$H NMR (DMSO-$d_6$): δ 1.40 (4H, m), 1.90 (4H, m), 3.00 (1H, m), 3.70 (1H, m), 5.18 (2H, s), 6.98 (1H, m), 7.11 (1H, s), 7.18 (2H, d), 7.42 (3H, m), 7.52 (1H, d), 7.68 (1H, s), 7.78 (2H, d), 7.90 (3H, brs), 8.36 (1H, d), 8.85 (1H, brs), 11.15 (1H, brs).

Example 51

N-(4-Amino cyclohexyl)-3-(4-bromo benzyloxy)-5-(4-carbamimidoyl phenoxy)benzamide Intermediates (a)-(c) are the same as in Example 49.

d) {4-[3-(4-bromo-benzyloxy)-5-(4-cyano-phenoxy)benzoylamino]cyclohexyl}-carbamic Acid Tert-butyl Ester Using 1.3 g (2.88 mmol) of {4-[3-(4-cyanophenoxy)-5-hydroxybenzoylamino]cyclohexyl}carbamic acid tert-butyl ester and 1-bromo-4-bromomethyl-benzene (0.72 g, 2.88 mmol) and following the procedure of Example 42(b) afforded 1.5 g of the required product. $^1$H NMR (DMSO-$d_6$): δ 1.20 (4H, m), 1.4 (9H, s), 1.8 (4H, m), 3.2 (1H, m), 3.7 (1H, m), 5.2 (2H, s), 6.78 (1H, d), 6.88 (1H, s), 7.12 (2H, d), 7.2 (1H, s), 7.4 (3H, s), 7.6 (2H, d), 7.86 (2H, d), 8.28 (1H, d).

e) 4-[3-(4-amino-cyclohexylcarbamoyl)-5-(4-bromo benzyloxy)phenoxy]-benzimidic Acid Ethyl Ester Using {4-[3-(4-bromo-benzyloxy)-5-(4-cyano-phenoxy)benzoylamino]cyclohexyl}-carbamic acid tert-butyl ester (0.85 g, 1.36 mmol) and following the procedure of Example 1(d) afforded 0.7 g of the required product. Percentage purity (LCMS): 68.08%, (M+1)=565.1+1.

f) N-(4-Amino-cyclohexyl)-3-(4-bromo benzyloxy)-5-(4-carbamimidoyl Phenoxy)benzamide Using 4-[3-(4-amino-cyclohexylcarbamoyl)-5-(4-bromo benzyloxy)phenoxy]-benzimidic acid ethyl ester (0.7 g, 1.23 mmol) and following the procedure of Example 1(e) afforded 0.32 g of the required product. Percentage purity (HPLC): 98.39%, (LCMS): 99.72%. $^1$H NMR (DMSO-$d_6$): δ 1.40 (4H, m), 1.85 (2H, m), 1.95 (2H, m), 3.0 (1H, m), 3.70 (1H, m), 5.20 (2H, s), 7.0 (1H, s), 7.2 (3H, s), 7.45 (3H, d), 7.6 (2H, d), 7.9 (5H, m), 8.36 (1H, d), 9.26 (4H, d).

Example 52

N-(4-Amino-cyclohexyl)-3-(4-bromo-benzyloxy)-5-[4-(N-hydroxy-carbamimidoyl)-phenoxy]-benzamide Intermediates (a) to (d) are the same as in Example 51.

e) (4-{3-(4-Bromo-benzyloxy)-5-[4-(N-hydroxycarbamimidoyl)-phenoxy]-benzoylamino}-cyclohexyl)-carbamic Acid Tert-butyl Ester Following the procedure of Example 2(d) {4-[3-(4-bromo-benzyloxy)-5-(4-cyano-(phenoxy)benzoylamino]cyclohexyl}-carbamic acid tert-butyl ester 0.6 g (0.96 mmol) and other reagents were used to afford 0.45 g of the required product. Percentage purity (LCMS): 38.9%, (M+1)=652.2+1.

f) N-(4-Amino-cyclohexyl)-3-(4-bromo-benzyloxy)-5-[4-(N-hydroxy-carbamimidoyl)-phenoxy]-benzamide Using (4-{3-(4-bromo-benzyloxy)-5-[4-(N-hydroxycarbamimidoyl)-phenoxy]-benzoylamino}-cyclohexyl)-carbamic acid tert-butyl ester (0.45 g, 0.68 mmol) and following the procedure of Example 9(d) afforded 0.21 g of the required product. Percentage purity (HPLC): 97.9%, (LCMS): 98.5%. $^1$H NMR (DMSO-$d_6$): δ 1.40 (4H, m), 1.92 (4H, m), 3.00 (1H, m), 3.70 (1H, m), 5.18 (2H, s), 6.96 (1H, m), 7.18 (3H, m), 7.42 (3H, d), 7.61 (2H, d), 7.76 (2H, d), 7.90 (3H, brs), 8.36 (1H, d), 8.85 (2H, brs), 11.14 (1H, brs).

Example 53

N-(4-Amino cyclohexyl)-3-(6-bromo pyridine-3-ylmethoxy)-5-(4-carbamimidoyl phenoxy)benzamide Intermediates (a)-(c) are the same as in Example 49.

d) {4-[3-(6-bromopyridine-3-ylmethoxy)-5-(4-cyanophenoxy)benzoylamino]-cyclohexyl}carbamic Acid Tert-butyl Ester Using 1.4 g (3.1 mmol) of {4-[3-(4-cyano-phenoxy)-5-hydroxy-benzoylamino]-cyclohexyl}-carbamic acid tert-butyl ester and 2-bromo-5-bromomethyl-pyridine (0.77 g, 3.1 mmol) and following the procedure of Example 42(b) afforded 1.5 g of the required product. $^1$H NMR (DMSO-$d_6$): δ 1.20 (4H, m), 1.40 (9H, s), 1.80 (4H, m), 3.2 (1H, m), 3.70 (1H, m), 5.25 (2H, s), 6.75 (1H, d), 7.0 (1H, s), 7.15 (2H, d), 7.22 (1H, s), 7.45 (1H, s), 7.7 (1H, d), 7.85 (3H, m), 8.3 (1H, d), 8.5 (1H, s).

e) 4-[3-(4-aminocyclohexylcarbamoyl)-5-(6-bromopyridine-3-ylmethoxy)phenoxy]benzimidic Acid Ethyl Ester Using {4-[3-(6-bromopyridine-3-ylmethoxy)-5-(4-cyanophenoxy)benzoyl amino]-cyclohexyl}carbamic acid tert-butyl ester (0.9 g, 1.44 mmol) and following the procedure of Example 1(d) afforded 0.54 g of the required product. Percentage purity (LCMS): 68.08% (M+1)=566.1+1.

f) N-(4-Amino cyclohexyl)-3-(6-bromo pyridine-3-ylmethoxy)-5-(4-carbamimidoyl phenoxy)benzamide Using 4-[3-(4-amino-cyclohexylcarbamoyl)-5-(4-bromo benzyloxy)phenoxy]-benzimidic acid ethyl ester (0.54 g, 0.95 mmol) and following the procedure of Example 1(e) afforded 0.14 g of the required product. Percentage purity (HPLC): 95.76%, (LCMS): 99.15%. $^1$H NMR (DMSO-$d_6$): δ 1.40 (4H, m), 1.9 (4H, m), 3.0 (1H, m), 3.70 (1H, m), 5.2 (2H, s), 7.0 (1H, s), 7.2 (3H, m), 7.4 (1H, s), 7.7 (1H, d), 7.9 (5H, m), 8.4 (1H, d), 8.5 (1H, d), 9.2 (2H, s), 9.3 (2H, s).

Example 54

N-(4-Amino cyclohexyl)-3-(6-amino pyridin-3-ylmethoxy)-5-(4-carbamimidoyl phenoxy)benzamide Intermediates (a)-(c) are the same as in Example 49.

d) {5-[3-(4-tert-Butoxycarbonylamino-cyclohexylcarbamoyl)-5-(4-cyano-phenoxy)-phenoxymethyl]-pyridin-2-yl}-carbamic Acid Tert-Butyl Ester Using 1.2 g (2.65 mmol) of {4-[3-(4-cyano-phenoxy)-5-hydroxy-benzoylamino]-cyclohexyl}-carbamic acid tert-butyl ester and (5-bromomethyl-pyridin-2-yl)-carbamic acid tert-butyl ester (0.76 g, 2.65 mmol) and following the procedure of Example 42(b) afforded 1.42 g of the required product. $^1$HNMR (DMSO-$d_6$): δ 1.25 (4H, m), 1.4 (27H, s), 1.8 (4H, m), 3.20 (1H, m), 3.75 m), 5.25 (2H, s), 6.75 (1H, d), 7.05 (1H, s), 7.15 (2H, d), 7.2 (1H, s), 7.45 (2H, m), 7.85 (2H, d), 7.95 (1H, d), 8.25 (1H, d), 8.5 (1H, s).

e) 4-[3-(4-Amino-cyclohexylcarbamoyl)-5-(6-amino-pyridin-3-ylmethoxy)-phenoxy]-benzimidic Acid Ethyl Ester Using {5-[3-(4-tert-butoxycarbonylamino-cyclohexylcarbamoyl)-5-(4-cyano-phenoxy)-phenoxymethyl]-pyridin-2-yl}-carbamic acid tert-butyl ester (1.4 g, 2.12 mmol) and following the procedure of Example 1(d) afforded 0.64 g of the required product. Percentage purity (LCMS): 83.8%, (M+1)=566.1+1.

f) N-(4-Amino cyclohexyl)-3-(6-amino pyridine-3-ylmethoxy)-5-(4-carbamimidoyl Phenoxy)benzamide Using 4-[3-(4-amino-cyclohexylcarbamoyl)-5-(6-amino-pyridin-3-ylmethoxy)-phenoxy]-benzimidic acid ethyl ester (0.64 g, 1.27 mmol) and following the procedure of Example 1(e) afforded 0.14 g of the required product. Percentage purity (HPLC): 96.58%, (LCMS): 94.17%. $^1$H NMR (DMSO-$d_6$): δ 1.4 (4H, m), 1.9 (4H, m), 3.0 (1H, m), 3.7 (1H, m), 5.05 (2H, s), 7.0 (2H, m), 7.2 (2H, d), 7.4 (1H, s), 7.86 (5H, m), 8.0 (1H, d), 8.1 (2H, s), 8.36 (1H, d), 9.08 (2H, s), 9.26 (2H, s).

Example 55

4-[3-(4-Aminocyclohexylcarbamoyl)-5-(4-carbamimidoylphenoxy)phenoxy-methyl]-benzoic Acid Ethyl Ester Intermediates (a)-(c) are the same as in Example 49.

d) 4-[3-(4-tert-Butoxycarbonylaminocyclohexylcarbamoyl)-5-(4-cyanophenoxy)-phenoxy Methyl] benzoic Acid Ethyl Ester Using 1.2 g (2.65 mmol) of {4-[3-(4-cyano-phenoxy)-5-hydroxy-benzoylamino]-cyclohexyl}-carbamic acid tert-butyl ester and 4-bromomethyl-benzoic acid ethyl ester (0.644 g, 2.65 mmol) and following the procedure of Example 42(b) afforded 1.32 g of the required product. Percentage purity (LCMS): 84.4%, (M+1)=613.2+1.

e) 4-[3-(4-Amino cyclohexyl carbamoyl)-5-(4-ethoxycarbonimidoyl phenoxy)phenoxymethyl]benzoic Acid Ethyl Ester Using 4-[3-(4-tert-butoxycarbonylaminocyclohexylcarbamoyl)-5-(4-cyano-phenoxy)-phenoxy methyl]benzoic acid ethyl ester (1.32 g, 2.12 mmol) and following the procedure of Example 1(d) afforded 0.54 g of the required product. Percentage purity (LCMS): 68.7%, (M+1)=559.2+1.

f) 4-[3-(4-Aminocyclohexylcarbamoyl)-5-(4-carbamimidoylphenoxy)phenoxy-methyl]-benzoic Acid Ethyl Ester Using 4-[3-(4-amino cyclohexyl carbamoyl)-5-(4-ethoxycarbonimidoyl phenoxy)phenoxymethyl]benzoic acid ethyl ester (0.54 g, 0.96 mmol) and following the procedure of Example 1(e) afforded 0.23 g of the required product. Percentage purity (HPLC): 97.37%, (LCMS): 97.15%. NMR (DMSO-$d_6$): δ 1.35 (3H, t), 1.4 (4H, m), 1.95 (4H, m), 3.0 (1H, m), 3.7 (1H, m), 4.35 (2H, q), 5.3 (2H, s) 7.0 (1H, s), 7.2 (3H, m), 7.42 (1H, s), 7.60 (2H, d), 7.82 (4H, m), 8.0 (2H, d), 8.38 (1H, d), 9.08 (2H, s), 9.26 (2H, s).

Example 56

4-{3-[4-(2-amino ethyl)piperidine-1-carbonyl]-5-phenethyloxy phenoxy}-benzamidine Intermediate (a) is the same as in Example 42.

b) 3-(4-Cyano phenoxy)-5-phenethyloxy Benzoic Acid Ethyl Ester

Using 1.0 g (3.53 mmol) of 3-(4-cyano phenoxy)-5-hydroxy benzoic acid ethyl ester and (2-bromo-ethyl)-benzene (0.65 g, 3.53 mmol) and following the procedure of Example 42(b) afforded 0.95 g of the required product. $^1$H NMR (CDCl$_3$): δ 1.35 (3H, t), 3.1 (2H, t), 4.2 (2H, t), 4.35 (2H, q), 6.78 (1H, t), 7.0 (2H, s), 7.22 (1H, m) 7.32 (5H, m), 7.42 (1H, m), 7.62 (2H, s).

c) 3-(4-Cyano phenoxy)-5-phenethyloxy Benzoic Acid 0.95 g (2.45 mmol) of 3-(4-cyano phenoxy)-5-phenethyloxy benzoic acid ethyl ester was hydrolysed using the procedure of Example 5(b) to afford 0.6 g. of the required product. $^1$H NMR (DMSO-$d_6$): δ 3.02 (2H, t), 4.26 (2H, t), 7.0 (1H, t), 7.18 (3H, m), 7.24 (1H, m) 7.32 (5H, m), 7.88 (2H, s), 13.4 (1H, brs).

d) (2-{1-[3-(4-cyanophenoxy)-5-phenethyloxybenzoyl]piperidin-4-yl}ethyl)-carbamic Acid Tert-butyl Ester Following the procedure of Example 5(c) 3-(4-cyano phenoxy)-5-phenethyloxy benzoic acid 0.6 g (1.66 mmol) and (2-piperidin-4-yl-ethyl)-carbamic acid tert-butyl ester (0.378 g, 1.66 mmol) were used to afford 0.55 g of the required product. $^1$H NMR (DMSO-d$_6$): δ 1.05 (3H, m), 1.4 (9H, s), 1.55 (2H, m), 1.7 (1H, m), 2.1 (5H, s), 3.0 (5H, m), 4.2 (2H, t), 4.4 (1H, m), 6.62 (1H, s), 6.78 (2H, s), 7.14 (2H, d), 7.24 (1H, m), 7.3 (4H, d), 7.88 (2H, d).

e) 4-{3-[4-(2-aminoethyl)piperidine-1-carbonyl]-5-phenethyloxyphenoxy}-benzimidic Acid Ethyl Ester Using (2-{1-[3-(4-cyanophenoxy)-5-phenethyloxybenzoyl]piperidin-4-yl}ethyl)-carbamic acid tert-butyl ester (0.55 g, 0.96 mmol) and following the procedure of Example 1(d) afforded 0.28 g of the required product. Percentage purity (LCMS): 56.4%, (M+1)=515.2+1 f) 4-{3-[4-(2-aminoethyl)piperidine-1-carbonyl]-5-phenethyloxyphenoxy}-benzamidine Using 4-{3-[4-(2-aminoethyl)piperidine-1-carbonyl]-5-phenethyloxy phenoxy}-benzimidic acid ethyl ester (0.28 g, 0.54 mmol) and following the procedure of Example 1(e) afforded 0.06 g of the required product. Percentage purity (HPLC): 87.23%, (LCMS): 76.08%. $^1$H NMR (DMSO-d$_6$): δ 1.10 (3H, t), 1.50 (2H, m), 1.60 (2H, m), 1.75 (1H, m), 2.70 (1H, m), 2.85 (2H, m), 3.05 (3H, m), 3.6 (1H, m), 4.25 (2H, t), 4.45 (1H, m), 6.6 (s), 6.8 (2H, m), 7.25 (2H, m), 7.35 (3H, s), 7.7 (2H, brs), 7.9 (2H, s), 9.05 (2H, s), 9.25 (2H, s).

Example 57

2-{1-[3-(3-Carbamimidoyl-benzyloxy)-5-(4-carbamimidoyl-phenoxy)-benzoyl]-piperidin-4-yl}-ethylamine Intermediates (a)-(c) are the same as in Example 42.

d) (2-{1-[3-(3-cyanobenzyloxy)-5-(4-cyanophenoxy)benzoyl]piperidin-4-yl}ethyl)-carbamic Acid Tert-butyl Ester Following the procedure of Example 5(c) 3-(3-cyano-benzyloxy)-5-(4-cyano-phenoxy)-benzoic acid 0.75 g (2.02 mmol) and (2-piperidin-4-yl-ethyl)-carbamic acid tert-butyl ester (0.46 g, 2.02 mmol) were used to afford 0.7 g of the required product. Percentage purity (LCMS): 62.3%, (M+1)= 480.2+1 (de-Boc mass, –100).

e) 2-{1-[3-(3-ethoxycarbonimidoyl-benzyloxy)-5-(4-ethoxycarbonimidoyl-phenoxy)benzoyl]piperidin-4-yl}ethylamine Using (2-{1-[3-(3-cyanobenzyloxy)-5-(4-cyanophenoxy) benzoyl]piperidin-4-yl}ethyl)-carbamic acid tert-butyl ester (0.7 g, 1.2 mmol) and following the procedure of Example 1(d) afforded 0.43 g of the required product. Percentage purity (LCMS): 49.2%, (M+1)=572.3+1.

f) 2-{1-[3-(3-carbamimidoyl-benzyloxy)-5-(4-carbamimidoyl-phenoxy)-benzoyl]-piperidin-4-yl}ethylamine Using 2-{1-[3-(3-ethoxycarbonimidoyl-benzyloxy)-5-(4-ethoxy carbonimidoyl-phenoxy)benzoyl]piperidin-4-yl}ethylamine (0.43 g, 0.54 mmol) and following the procedure of Example 1(e) afforded 0.16 g of the required product. Percentage purity (HPLC): 98.59%, (LCMS): 98.49%. $^1$H NMR (DMSO-d$_6$): δ 1.10 (2H, m), 1.50 (2H, m), 1.60 (2H, m), 1.75 (1H, m), 2.80 (3H, m), 3.0 (2H, m), 4.45 (1H, m), 5.2 (2H, s), 6.65 (1H, s), 6.9 (2H, s), 7.25 (2H, s), 7.65 (1H, m), 7.7-7.85 (5H, m), 7.9 (3H, s), 9.1 (2H, s), 9.25 (3H, d), 9.4 (2H, s).

Example 58

2-{1-[3-(4-carbamimidoyl-benzyloxy)-5-(4-carbamimidoyl-phenoxy)benzoyl]-piperidin-4-yl}ethylamine Intermediates (a)-(c) are the same as in Example 43.

d) (2-{1-[3-(4-cyanobenzyloxy)-5-(4-cyanophenoxy)benzoyl]piperidin-4-yl}ethyl)-carbamic Acid Tert-butyl Ester Following the procedure of Example 5(c) 3-(4-cyano-benzyloxy)-5-(4-cyano-phenoxy)-benzoic acid 0.8 g (2.16 mmol) and (2-piperidin-4-yl-ethyl)-carbamic acid tert-butyl ester (0.49 g, 2.16 mmol) were used to afford 0.92 g of the required product. $^1$H NMR (DMSO-d$_6$): δ 1.10 (2H, m), 1.30 (2H, m), 1.4 (9H, s), 1.50 (2H, m), 1.75 (1H, m), 2.70 (1H, m), 2.8 (3H, m), 3.5 (1H, m), 4.4 (1H, m), 5.2 (2H, s), 6.65 (1H, s), 6.78 (1H, m), 6.88 (2H, m), 7.16 (2H, s), 7.64 (2H, d), 7.88 (4H, m).

e) 2-{1-[3-(4-ethoxycarbonimidoyl-benzyloxy)-5-(4-ethoxycarbonimidoyl-phenoxy)benzoyl]piperidin-4-yl}ethylamine Using (2-{1-[3-(4-cyanobenzyloxy)-5-(4-cyanophenoxy) benzoyl]piperidin-4-yl}ethyl)-carbamic acid tert-butyl ester (0.92 g, 1.58 mmol) and following the procedure of Example 1(d) afforded 0.54 g of the required product. Percentage purity (LCMS): 3.0.4%, (M+1)=572.3+1.

f) 2-{1-[3-(4-carbamimidoyl-benzyloxy)-5-(4-carbamimidoyl-phenoxy)benzoyl]-piperidin-4-yl}ethylamine Using 2-{1-[3-(4-ethoxycarbonimidoyl-benzyloxy)-5-(4-ethoxy carbonimidoyl-phenoxy)benzoyl]piperidin-4-yl}ethylamine (0.54 g, 0.94 mmol) and following the procedure of Example 1(e) afforded 0.32 g of the required product. Percentage purity (HPLC): 98.97%, (LCMS): 93.02%. $^1$H NMR (DMSO-d$_6$): δ 1.10 (2H, m), 1.50 (2H, m), 1.60 (2H, m), 1.75 (1H, m), 2.85 (4H, m), 3.0 (1H, m), 4.45 (1H, m), 5.3 (2H, s), 6.65 (1H, s), 6.9 (2H, s), 7.2 (2H, d), 7.7 (2H, d), 7.8 (2H, brs), 7.9 (4H, t), 9.3 (6H, t).

Example 59

4-[3-(4-aminomethyl benzyloxy)-5-(4-carbamimidoyl phenoxy)benzoyl]-piperazine-1-carboxylic Acid Ethyl Ester Intermediate (a) is the same as in Example 42.
Intermediates (b) and (c) are the same as in Example 45.

d) 4-[3-[4-(tert-butoxycarbonylaminomethyl)benzyloxy]-5-(4-cyanophenoxy)-benzoyl]piperazine-1-carboxylic Acid Ethyl Ester Following the procedure of Example 5(c) 3-(4-(tert-butoxycarbonyl aminomethyl)benzyloxy)-5-(4-cyano phenoxy)benzoic acid 0.85 g (1.79 mmol) and piperazine-1-carboxylic acid ethyl ester (0.283 g, 1.79 mmol) were used to afford 0.91 g of the required product. $^1$H NMR (DMSO-d$_6$): δ 1.20 (3H, t), 1.40 (9H, s), 3.3 (2H, m), 3.6 (6H, m), 4.05 (2H, q), 4.15 (2H, d), 5.1 (2H, s), 6.7 (1H, s), 6.9 (2H, s), 7.18 (2H, d), 7.26 (2H, d), 7.4 (3H, d), 7.86 (2H, d), 7.86 (2H, s).

e) 4-[3-(4-aminomethyl benzyloxy)-5-(4-ethoxy carbonimidoyl phenoxy)benzoyl]piperazine-1-carboxylic Acid Ethyl Ester Using 4-[3-[4-(tert-butoxycarbonylaminomethyl)benzyloxy]-5-(4-cyanophenoxy)-benzoyl]piperazine-1-carboxylic acid ethyl ester (0.91 g, 1.48 mmol) and following the procedure of Example 1(d) afforded 0.34 g of the required product. Percentage purity (LCMS): 73.3%, (M+1)=560.2+1.

f) 4-[3-(4-Aminomethylbenzyloxy)-5-(4-carbamimidoylphenoxy)benzoyl]-piperazine-1-carboxylic Acid Ethyl Ester Using 4-[3-(4-aminomethyl benzyloxy)-5-(4-ethoxy carbonimidoyl phenoxy)-benzoyl]piperazine-1-carboxylic acid ethyl ester (0.34 g, 0.6 mmol) and following the procedure of Example 1(e) afforded 0.15 g of the required product. Percentage purity (HPLC): 93.79%, (LCMS): 95.27%. $^1$H NMR (DMSO-d$_6$): δ 1.2 (3H, t), 3.4 (2H, m), 3.6 (2H, m), 3.75 (6H, m), 4.1 (2H, q), 5.2 (2H, s), 6.66 (1H, s), 6.9 (2H, s), 7.22 (2H, d), 7.5 (3H, s), 7.88 (2H, d), 8.2 (2H, brs), 9.06 (2H, s), 9.25 (2H, s).

Example 60

4-[3-(4-Carbamimidoylphenoxy)-5-(4-ethoxycarbonylbenzyloxy)-benzoyl]-piperazine-1-carboxylic Acid Ethyl Ester Intermediates (a) and (b) are the same as in Example 49.

c) 4-[3-(4-Cyano phenoxy)-5-hydroxy benzoyl]piperazine-1-carboxylic Acid Ethyl Ester Following the procedure of Example 5(c) 3-(4-cyano phenoxy)-5-hydroxy benzoic acid 0.9 g (3.52 mmol) and piperazine-1-carboxylic acid ethyl ester (0.556 g, 3.52 mmol) were used to afford 0.52 g of the required product. Percentage purity (LCMS): 90.2%, (M+1)=395.1+1.

d) 4-[3-(4-Cyanophenoxy)-5-(4-ethoxycarbonylbenzyloxy)-benzoyl]piperazine-1-carboxylic Acid Ethyl Ester Using 0.52 g (1.31 mmol) of 4-[3-(4-cyano phenoxy)-5-hydroxy benzoyl]-piperazine-1-carboxylic acid ethyl ester and 4-bromomethyl-benzoic acid ethyl ester (0.318 g, 1.31 mmol) and following the procedure of Example 42(b) afforded 0.61 g of the required product. Percentage purity (LCMS): 60.0% (M+1)=557.2+1.

e) 4-[3-(4-Ethoxycarbonimidoyl Phenoxy)-5-(4-ethoxycarbonyl Benzyloxy)-benzoyl]piperazine-1-carboxylic Acid Ethyl Ester Using 4-[3-(4-cyanophenoxy)-5-(4-ethoxycarbonyl-benzyloxy)-benzoyl]piperazine-1-carboxylic acid ethyl ester (0.6 g, 1.07 mmol) and following the procedure of Example 1(d) afforded 0.32 g of the required product. Percentage purity (LCMS): 42.2%, (M+1)=603.2+1.

f) 4-[3-(4-Carbamimidoylphenoxy)-5-(4-ethoxycarbonylbenzyloxy)-benzoyl]-piperazine-1-carboxylic Acid Ethyl Ester Using 4-[3-(4-ethoxycarbonimidoyl phenoxy)-5-(4-ethoxycarbonyl benzyloxy)-benzoyl]piperazine-1-carboxylic acid ethyl ester (0.32 g, 0.53 mmol) and following the procedure of Example 1(e) afforded 0.15 g of the required product. Percentage purity (HPLC): 94.77%, (LCMS): 99.8%. $^1$H NMR (DMSO-d$_6$): δ 1.2 (3H, t), 1.35 (3H, t), 3.3 (2H, m), 3.4 (2H, m), 3.6 (4H, m), 4.1 (2H, q), 4.4 (2H, q), 5.3 (2H, s), 6.7 (1H, s), 6.9 (2H, d), 7.25 (2H, d), 7.6 (2H, d), 7.85 (2H, d), 8.0 (2H, d), 9.0 (2H, s), 9.25 (2H, s).

Example 61

4-[3-(4-Bromo benzyloxy)-5-(4-carbamimidoyl phenoxy)benzoyl]piperazine-1-carboxylic Acid Ethyl Ester Intermediates (a)-(c) are the same as in Example 60.

d) 4-[3-(4-Bromo benzyloxy)-5-(4-cyano phenoxy) benzoyl]piperazine-1-carboxylic Acid Ethyl Ester Using 0.75 g (1.89 mmol) of 4-[3-(4-cyano phenoxy)-5-hydroxy benzoyl]-piperazine-1-carboxylic acid ethyl ester and 1-bromo-4-bromomethyl-benzene (0.472 g, 1.89 mmol) and following the procedure of Example 42(b) afforded 0.85 g of the required product. Percentage purity (LCMS): 75.2%, (M+1)=563.1+1.

e) 4-[3-(4-Bromobenzyloxy)-5-(4-ethoxycarbonimidoylphenoxy)benzoyl]-piperazine-1-carboxylic Acid Ethyl Ester Using 4-[3-(4-bromobenzyloxy)-5-(4-cyano phenoxy) benzoyl]piperazine-1-carboxylic acid ethyl ester (0.85 g, 1.5 mmol) and following the procedure of Example 1(d) afforded 0.37 g of the required product. Percentage purity (LCMS): 43.1%, (M+1)=609.1+1.

f) 4-[3-(4-Bromo Benzyloxy)-5-(4-carbamimidoyl phenoxy)benzoyl]piperazine-1-carboxylic Acid Ethyl Ester Using 4-[3-(4-bromobenzyloxy)-5-(4-ethoxycarbonimidoylphenoxy)benzoyl]-piperazine-1-carboxylic acid ethyl ester (0.37 g, 0.6 mmol) and following the procedure of Example 1(e) afforded 0.15 g of the required product. Percentage purity (HPLC): 98.96%, (LCMS): 91.78%. $^1$H NMR (DMSO-d$_6$): δ 1.2 (3H, t), 3.35 (6H, m), 3.6 (2H, m), 3.6 (4H, m), 4.1 (2H, q), 5.2 (2H, s), 6.68 (1H, s), 6.7 (2H, m), 7.24 (2H, d), 7.4 (2H, d), 7.6 (2H, d), 7.86 (2H, d), 8.9 (2H, s), 9.25 (2H, s).

Example 62

3-(3-Amino benzyloxy)-N-(4-amino cyclohexyl)-5-(4-carbamimidoyl Phenoxy)benzamide Intermediate (a) is the same as in Example 42.

b) 3-(4-Cyano phenoxy)-5-(3-nitro benzyloxy)benzoic Acid Ethyl Ester

Using 1.2 g (4.23 mmol) of 3-(4-cyano phenoxy)-5-hydroxy benzoic acid ethyl ester and 1-bromomethyl-3-nitrobenzene (0.913 g, 4.23 mmol) and following the procedure of Example 42(b) afforded 1.43 g of the required product. $^1$H NMR (DMSO-d$_6$): δ 1.3 (3H, t), 4.3 (2H, q), 5.4 (2H, s), 7.2 (4H, m), 7.45 (1H, s), 7.72 (1H, t), 7.9 (3H, m), 8.25 (1H, d), 8.35 (1H, s).

c) 3-(4-Cyano phenoxy)-5-(3-nitro benzyloxy)benzoic Acid 1.43 g (3.41 mmol) of 3-(4-cyano phenoxy)-5-(3-nitro benzyloxy)benzoic acid ethyl ester was hydrolysed using the procedure of Example 5(b) to afford 1.1 g of the required product. $^1$H NMR (DMSO-d$_6$): δ 5.4 (2H, s), 7.16 (4H, d), 7.45 (1H, s), 7.5 (1H, t), 7.9 (3H, d), 8.22 (1H, d), 8.34 (1H, s), 13.4 (1H, brs)

d) {4-[3-(4-cyanophenoxy)-5-(3-nitrobenzyloxy) benzoylamino]cyclohexyl}-carbamic Acid Tert-butyl Ester Following the procedure of Example 5(c) 3-(4-cyano phenoxy)-5-(3-nitro benzyloxy)benzoic acid 1.1 g (2.81 mmol) and (4-amino-cyclohexyl)-carbamic acid tert-butyl ester (0.6 g, 2.81 mmol) were used to afford 1.2 g of the required product. $^1$H NMR (DMSO-d$_6$): δ 1.2 (4H, m), 1.4 (9H, s), 1.8 (4H, m), 3.2 (1H, m), 3.7 (1H, m), 5.35 (2H, s), 6.78 (1H, d), 7.04 (1H, s), 7.12 (2H, d), 7.22 (1H, s), 7.46 (1H, s), 7.72 (1H, t), 7.9 (3H, d), 8.2 (1H, d), 8.34 (2H, m).

e) {4-[3-(3-amino benzyloxy)-5-(4-cyano phenoxy) benzoylamino]cyclohexyl}carbamic Acid Tert-butyl Ester 1.2 g (2.04 mmol) of {4-[3-(4-cyano phenoxy)-5-(3-nitro benzyloxy)benzoyl amino]cyclohexyl}carbamic acid tert-butyl ester, dissolved in 10 ml of THF, 0.455 g (8.16 mmol) of iron powder and 0.436 g (8.16 mmol) of NH$_4$Cl solution (5 ml water) were mixed. The resulting reaction mixture was refluxed overnight. After completion of reaction, the reaction mixture was filtered through celite, and the filtrate was concentrated under reduced pressure. 100 ml water was added to the concentrated mixture and the mixture was extracted with 100 ml of ethyl acetate. The organic layer was washed with water followed by saturated brine, dried over anhydrous sodium sulphate and concentrated to afford crude compound which was purified by column chromatography using hexane-ethylacetate (10:2) to afford 0.75 g of the required product. $^1$H NMR (DMSO-d$_6$): δ 1.25 (4H, m), 1.4 (9H, s), 1.8 (4H, m), 3.2 (1H, m), 3.7 (1H, m), 5.0 (2H, s), 5.15 (2H, s), 6.5 (2H, m), 6.62 (1H, s), 6.78 (1H, d), 6.94 (1H, s), 7.0 (1H, t), 7.12 (3H, m), 7.4 (1H, s), 7.82 (2H, d), 8.26 (1H, d).

f) 4-[3-(3-amino benzyloxy)-5-(4-aminocyclohexyl carbamoyl)phenoxy]benzimidic Acid Ethyl Ester Using {4-[3-(3-aminobenzyloxy)-5-(4-cyano phenoxy) benzoylamino]cyclohexyl}carbamic acid tert-butyl ester (0.65 g, 1.16 mmol) and following the procedure of Example 1(d) afforded 0.23 g of the required product. Percentage purity (LCMS): 98.0%, (M+1)=502.2+1.

g) 3-(3-Aminobenzyloxy)-N-(4-aminocyclohexyl)-5-(4-carbamimidoylphenoxy)benzamide Using 4-[3-(3-amino benzyloxy)-5-(4-aminocyclohexyl carbamoyl)phenoxy]benzimidic acid ethyl ester (0.23 g, 0.45 mmol) and following the procedure of Example 1(e) afforded 0.04 g of the required product. Percentage purity (HPLC): 97.77%, (LCMS): 94.67%. $^1$H NMR (DMSO-d$_6$): δ 1.40 (4H, m), 1.9 (4H, m), 3.0 (1H, m), 3.7 (1H, m), 5.10 (2H, s), 6.85 (3H, m), 6.95 (1H, s), 7.20 (4H, m), 7.40 (1H, s), 7.85 (5H, s), 8.35 (1H, d), 9.1 (2H, brs), 9.25 (2H, s).

Example 63

N-(4-Amino Cyclohexyl)-3-[3-(3-amino propionylamino)benzyloxy]-5-(4-carbamimidoyl Phenoxy) benzamide Intermediates (a)-(e) are the same as in Example 62.

f) {4-[3-[3-(3-tert-butoxycarbonylaminopropionylamino) benzyloxy]-5-(4-cyano phenoxy)-benzoyl Amino] cyclohexyl}carbamic Acid Tert-butyl Ester 3-tert-Butoxycarbonylamino-propionic acid (0.206 g, 1.09 mmol) and {4-[3-(3-amino benzyloxy)-5-(4-cyano phenoxy) benzoylamino]cyclohexyl}carbamic acid tert-butyl ester (0.6 g, 1.09 mmol) and other reagents as described in Example 9(e) were used to afford 0.45 g of the required product. $^1$H NMR (DMSO-d$_6$): δ 1.25 (4H, m), 1.4 (18H, s), 1.8 (4H, m), 2.45 (2H, m), 3.1 (3H, m), 3.7 (2H, m), 5.15 (2H, s), 6.74 (1H, d), 6.88 (1H, m), 6.98 1H, s), 7.12 (3H, d), 7.2 (1H, s), 7.3 (1H, t), 7.42 (1H, s), 7.54 (1H, d), 7.72 (1H, s), 7.86 (2H, d), 8.26 (1H, d).

g) 4-{3-(4-Amino cyclohexyl carbamoyl)-5-[3-(3-amino propionylamino)benzyloxy] phenoxy}benzimidic Acid Ethyl Ester Using {4-[3-[3-(3-tert-butoxycarbonylaminopropionylamino)benzyloxy]-5-(4-cyano phenoxy)-benzoyl amino] cyclohexyl}carbamic acid tert-butyl ester (0.45 g, 0.61 mmol) and following the procedure of Example 1(d) afforded 0.15 g of the required product. Percentage purity (LCMS): 51.2%, (M+1)=573.3+1.

h) N-(4-Aminocyclohexyl)-3-[3-(3-aminopropionylamino)benzyloxy]-5-(4-carbamimidoyl phenoxy) benzamide Using 4-{3-(4-amino cyclohexyl carbamoyl)-5-[3-(3-amino propionylamino)-benzyloxy]phenoxy}benzimidic acid ethyl ester (0.15 g, 0.26 mmol) and following the procedure of Example 1(e) afforded 0.03 g of the required product. Percentage purity (HPLC): 91.6%, (LCMS): 92.3%. $^1$H NMR (DMSO-d$_6$): δ 1.40 (4H, m), 1.92 (4H, m), 2.72 (2H, t), 3.0 (1H, m), 3.10 (2H, q), 3.72 (1H, m), 5.14 (2H, s), 6.98 (1H, s), 7.14 (1H, s), 7.20 (2H, d), 7.35 (1H, t), 7.40 (1H, s), 7.72 (1H, s), 7.81 (3H, brs), 7.88 (6H, d), 8.35 (1H, d), 9.14 (2H, brs), 9.25 (2H, s), 10.24 (1H, brs).

Example 64

N-(4-Aminocyclohexyl)-3-(4-carbamimidoylphenoxy)-5-(3-carbamimidoyl-propoxy)benzamide Intermediates (a)-(c) are the same as in Example 49.

d) {4-[3-(4-cyanophenoxy)-5-(3-cyano propoxy) benzoylamino]cyclohexyl}-carbamic Acid Tert-butyl Ester Using 0.75 g (1.66 mmol) of {4-[3-(4-cyanophenoxy)-5-hydroxybenzoylamino]cyclohexyl}carbamic acid tert-butyl ester and 4-bromo-butyronitrile (0.245 g, 1.66 mmol) and following the procedure of Example 42(b) afforded 0.82 g of the required product. $^1$H NMR (DMSO-d$_6$): δ 1.20 (3H, m), 1.4 (9H, s), 1.8 (4H, m), 2.05 (3H, m), 2.65 (2H, m), 3.2 (1H, m), 3.7 (1H, m), 4.1 (2H, m), 6.76 (1H, d), 6.92 (1H, s), 7.14 (2H, d), 7.2 (1H, s), 7.34 (1H, s), 7.86 (2H, d), 8.28 (1H, d)

e) 4-[3-(4-Aminocyclohexylcarbamoyl)-5-(3-ethoxy-carbonimidoylpropoxy)phenoxy]benzimidic Acid Ethyl Ester Using {4-[3-(4-cyanophenoxy)-5-(3-cyano propoxy)benzoylamino]cyclohexyl}-carbamic acid tert-butyl ester (0.82 g, 1.58 mmol) and following the procedure of Example 1(d) afforded 0.43 g of the required product. Percentage purity (LCMS): 62.1%, (M+1)=510.2+1.

f) N-(4-Aminocyclohexyl)-3-(4-carbarnimidoylphenoxy)-5-(3-carbamimidoyl propoxy)benzamide Using 4-[3-(4-aminocyclohexylcarbamoyl)-5-(3-ethoxy-carbonimidoyl propoxy)-phenoxy]benzimidic acid ethyl ester (0.43 g, 0.84 mmol) and following the procedure of Example 1(e) afforded 0.14 g of the required product. Percentage purity (HPLC): 98.11%, (LCMS): 99.32%. NMR (DMSO-d$_6$): δ 1.40 (4H, m), 1.9 (4H, m), 2.1 (2H, m), 2.6 (2H, m), 3.0 (2H, m), 4.1 (2H, m), 6.90 (1H, s), 7.20 (3H, m), 7.35 (1H, s), 7.85 (5H, s), 8.35 (1H, d), 8.7 (2H, brs), 8.95 (2H, s), 9.1 (2H, brs), 9.25 (2H, s).

Example 65

N-(4-Aminocyclohexyl)-3-(4-carbamimidoylbutoxy)-5-(4-carbamimidoyl-phenoxy)-benzamide Intermediates (a)-(c) are the same as in Example 49.

d) {4-[3-(4-cyanobutoxy)-5-(4-cyanophenoxy)benzoylamino]cyclohexyl}-carbamic Acid Tert-butyl Ester Using 0.85 g (1.88 mmol) of {4-[3-(4-cyanophenoxy)-5-hydroxybenzoylamino]cyclohexyl}carbamic acid tert-butyl ester and 5-bromo-pentanenitrile (0.304 g, 1.88 mmol) and following the procedure of Example 42(b) afforded 1.0 g of the required product. $^1$H NMR (DMSO-d$_6$): δ 1.25 (3H, m), 1.4 (9H, s), 18 (7H, m), 2.6 (3H, m), 3.2 (1H, m), 3.7 (1H, m), 4.2 (2H, m), 6.76 (1H, d), 6.92 (1H, s), 7.14 (3H, m), 7.34 (1H, s), 7.88 (2H, d), 8.28 (1H, d).

e) 4-[3-(4-Amino-cyclohexylcarbamoyl)-5-(4-ethoxycarbonimidoyl-butoxy)-phenoxy]-benzimidic Acid Ethyl Ester Using {4-[3-(4-cyanobutoxy)-5-(4-cyanophenoxy)benzoylamino]cyclohexyl}-carbamic acid tert-butyl ester (1.0 g, 1.87 mmol) and following the procedure of Example 1(d) afforded 0.52 g of the required product. Percentage purity (LCMS): 64.4%, (M+1)=524.3+1 f) N-(4-Aminocyclohexyl)-3-(4-carbamimidoylbutoxy)-5-(4-carbamimidoyl phenoxy)benzamide Using 4-[3-(4-amino-cyclohexylcarbamoyl)-5-(4-ethoxycarbonimidoyl-butoxy)-phenoxy]-benzimidic acid ethyl ester (0.52 g, 0.99 mmol) and following the procedure of Example 1(e) afforded 0.23 g of the required product. Percentage purity (HPLC): 97.4%, (LCMS): 92.3%. $^1$H NMR (DMSO-d$_6$): δ 1.41 (4H, m), 1.72 (4H, m), 1.85 (2H, m), 1.95 (2H, m), 2.44 (2H, t), 3.00 (1H, m), 3.82 (1H, m), 4.08 (2H, m), 6.89 (1H, s), 7.12 (1H, s), 7.20 (2H, d), 7.32 (1H, s), 7.86 (4H, d), 8.34 (1H, d), 8.68 (2H, brs), 8.92 (2H, brs), 9.14 (2H, brs), 9.26 (2H, brs).

Example 66

N-(4-Aminocyclohexyl)-3-(5-carbamimidoylpentyloxy)-5-(4-carbamimidoyl-phenoxy)-benzamide Intermediates (a)-(c) are the same as in Example 49.

d) {4-[3-(5-cyanopentyloxy)-5-(4-cyanophenoxy) benzoylamino]cyclohexyl}-carbamic Acid Tert-butyl Ester Using 0.85 g (1.88 mmol) of {4-[3-(4-cyanophenoxy)-5-hydroxybenzoylamino]cyclohexyl}carbamic acid tert-butyl ester and 6-bromo-hexanenitrile (0.33 g, 1.88 mmol) and following the procedure of Example 42(b) afforded 1.15 g of the required product. $^1$H NMR (DMSO-d$_6$): δ 1.25 (3H, m), 1.4 (9H, s), 1.6 (4H, m), 1.8 (6H, m), 3.2 (1H, m), 3.7 (1H, m), 4.05 (2H, m), 6.75 (1H, d), 6.90 (1H, s), 7.14 (3H, m), 7.34 (1H, s), 7.88 (2H, d), 8.28 (1H, d).

e) 4-[3-(4-Amino-cyclohexylcarbamoyl)-5-(5-ethoxycarbonimidoyl-pentyloxy)-phenoxy]-benzimidic Acid Ethyl Ester Using {4-[3-(5-cyanopentyloxy)-5-(4-cyanophenoxy) benzoylamino]cyclohexyl}-carbamic acid tert-butyl ester (1.15 g, 2.1 mmol) and following the procedure of Example 1(d) afforded 0.61 g of the required product. Percentage purity (LCMS): 70.5%, (M+1)=538.3+1.

f) N-(4-Amino cyclohexyl)-3-(5-carbamimidoyl pentyloxy)-5-(4-carbamimidoyl phenoxy)benzamide Using 4-[3-(4-amino-cyclohexylcarbamoyl)-5-(5-ethoxycarbonimidoyl-pentyloxy)-phenoxy]-benzimidic acid ethyl ester (0.61 g, 1.13 mmol) and following the procedure of Example 1(e) afforded 0.25 g of the required product. Percentage purity (HPLC): 98.2%, (LCMS): 90.6%. $^1$H NMR (DMSO-d$_6$): δ 1.42 (4H, m), 1.72 (4H, m), 1.86 (2H, m), 1.98 (2H, m), 2.42 (2H, t), 3.00 (1H, m), 3.72 (1H, m), 4.06 (2H, t), 6.89 (1H, s), 7.12 (1H, s), 7.20 (2H, d), 7.32 (1H, s), 7.88 (4H, d), 8.32 (1H, d), 8.68 (2H, brs), 8.90 (2H, brs), 9.14 (2H, brs), 9.26 (2H, brs).

Example 67

5-[3-(4-Aminocyclohexylcarbamoyl)-5-(4-carbamimidoylphenoxy)phenoxy]-pentanoic Acid Ethyl Ester Intermediates (a)-(c) are the same as in Example 49.

d) 5-[3-(4-tert-Butoxycarbonylaminocyclohexylcarbamoyl)-5-(4-cyano phenoxy)phenoxy]pentanoic Acid Ethyl Ester Using 0.63 g (1.39 mmol) of {4-[3-(4-cyanophenoxy)-5-hydroxybenzoylamino]cyclohexyl}carbamic acid tert-butyl ester and 5-bromo-pentanoic acid ethyl ester (0.29 g, 1.39 mmol) and following the procedure of Example 42(b) afforded 0.71 g of the required product. $^1$H NMR (DMSO-$d_6$): δ 1.2 (4H, m), 1.25 (2H, m), 1.4 (9H, s), 1.75 (9H, m), 2.35 (2H, m) 3.2 (1H, m), 3.7 (1H, m), 4.05 (4H, m), 6.75 (1H, d), 6.9 (1H, s), 7.15 (3H, d), 7.35 (1H, s), 7.85 (2H, d), 8.25 (1H, d).

e) 5-[3-(4-amino cyclohexylcarbamoyl)-5-(4-ethoxy-carbonimidoyl phenoxy)phenoxy]pentanoic Acid Ethyl Ester Using 5-[3-(4-tert-butoxycarbonylaminocyclohexylcarbamoyl)-5-(4-cyano-phenoxy)phenoxy]pentanoic acid ethyl ester (0.71 g, 1.22 mmol) and following the procedure of Example 1(d) afforded 0.36 g of the required product. Percentage purity (LCMS): 90.9%, (M+1)=525.2+1.

f) 5-[3-(4-Aminocyclohexylcarbamoyl)-5-(4-carbamimidoylphenoxy)phenoxy]-pentanoic Acid Ethyl Ester Using 5-[3-(4-amino cyclohexylcarbamoyl)-5-(4-ethoxycarbonimidoyl phenoxy)phenoxy]pentanoic acid ethyl ester (0.36 g, 0.68 mmol) and following the procedure of Example 1(e) afforded 0.18 g of the required product. Percentage purity (HPLC): 96.9%, (LCMS): 95.1%. $^1$H NMR (DMSO-$d_6$): δ 1.18 (31-1, t), 1.40 (4H, m), 1.72 (4H, m), 1.92 (4H, m), 2.38 (2H, t), 3.02 (1H, m), 3.72 (1H, m), 4.05 (4H, m), 6.88 (1H, s), 7.12 (1H, s), 7.21 (2H, d), 7.30 (1H, s), 7.88 (4H, d), 8.34 (1H, d), 9.14 (2H, brs), 9.26 (2H, brs).

Example 68

6-[3-(4-Aminocyclohexylcarbamoyl)-5-(4-carbamimidoylphenoxy)phenoxy]-hexanoic Acid Ethyl Ester Intermediate (a)-(c) are the same as in Example 49.

d) 6-[3-(4-tert-Butoxycarbonylaminocyclohexylcarbamoyl)-5-(4-cyanophenoxy)-phenoxy]hexanoic Acid Ethyl Ester Using 0.84 g (1.86 mmol) of {4-[3-(4-cyanophenoxy)-5-hydroxybenzoylamino]cyclohexyl}carbamic acid tert-butyl ester and 6-bromo-hexaanoic acid ethyl ester (0.41 g, 1.86 mmol) and following the procedure of Example 42(b) afforded 0.95 g of the required product. $^1$H NMR (DMSO-$d_6$): δ 1.15 (3H, t), 1.25 (2H, m), 1.4 (9H, s), 1.45 (3H, m), 1.6 (2H, m) 1.7 (2H, m), 1.8 (4H, m), 2.3 (2H, t), 3.2 (1H, m), 3.7 (1H, m), 4.05 (4H, m), 6.72 (1H, d), 6.88 (1H, s), 7.12 (3H, m), 7.3 (1H, s), 7.84 (2H, d), 8.24 (1H, d).

e) 6-[3-(4-amino cyclohexylcarbamoyl)-5-(4-ethoxycarbonimidoyl phenoxy)phenoxy]hexanoic Acid Ethyl Ester Using 6-[3-(4-tert-butoxycarbonylaminocyclohexylcarbamoyl)-5-(4-cyano-phenoxy)-phenoxy]hexanoic acid ethyl ester (0.95 g, 1.6 mmol) and following the procedure of Example 1(d) afforded 0.45 g of the required product. Percentage purity (LCMS): 90.08%, (M+1)=539.3+1.

f) 6-[3-(4-Aminocyclohexylcarbamoyl)-5-(4-carbamimidoylphenoxy)phenoxy]-hexanoic Acid Ethyl Ester Using 6-[3-(4-amino cyclohexylcarbamoyl)-5-(4-ethoxycarbonimidoyl phenoxy)phenoxy]hexanoic acid ethyl ester (0.45 g, 0.83 mmol) and following the procedure of Example 1(e) afforded 0.17 g of the required product. Percentage purity (HPLC): 95.7%, (LCMS): 95.0%. $^1$H NMR (DMSO-$d_6$): δ 1.18 (3H, t), 1.42 (6H, m), 1.60 (2H, m), 1.74 (2H, m), 1.78 (2H, brs), 1.98 (2H, brs), 2.32 (2H, t), 3.02 (1H, m), 3.70 (1H, m), 4.06 (4H, m), 6.90 (1H, s), 7.12 (1H, s), 7.22 (2H, d), 7.32 (1H, s), 7.88 (4H, d), 8.35 (1H, d), 9.14 (2H, brs), 9.28 (2H, brs).

Example 69

N-(4-Amino cyclohexyl)-3-(4-carbamimidoyl-2-chloro phenoxy)-5-(4-carbamimidoyl phenoxy)benzamide Intermediate (a) is the same as in Example 42.

b) 3-(2-Chloro-4-cyano phenoxy)-5-(4-cyano phenoxy)benzoic Acid Ethyl Ester

To 1.2 g (4.23 mmol) of 3-(4-cyano-phenoxy)-5-hydroxybenzoic acid ethyl ester, dissolved in 10 ml of DMF, potassium carbonate 1.17 g (8.46 mmol) was added and stirred for 30 min at RT. 1.31 g (8.46 mmol) of 3-chloro-4-fluoro-benzonitrile, dissolved in 5 ml of DMF, was added dropwise to the reaction mixture during 15 min and final contents were stirred at 80° C. overnight. The reaction mixture was concentrated, residue was dissolved in 200 ml of ethyl acetate and partitioned with water. The organic layer was washed with brine followed by of water. Organic layer was dried over anhydrous sodium sulphate and concentrated under reduced pressure. The crude product was subjected to column chromatography, using silica-gel and eluted with hexane:ethyl acetate (8:2) to afford 1.4 g of pure product. $^1$H NMR (DMSO-$d_6$): δ 1.3 (3H, t), 4.3 (2H, q), 7.2-7.36 (4H, m), 7.44 (2H, dd), 7.88 (3H, m), 8.26 (1H, d).

c) 3-(2-Chloro-4-cyano phenoxy)-5-(4-cyano Phenoxy)benzoic Acid 3-(2-Chloro-4-cyano phenoxy)-5-(4-cyano phenoxy)benzoic acid ethyl ester, 1.4 g (3.34 mmol), was hydrolysed using the procedure of Example 5(b) to afford 1.05 g of required product. $^1$H NMR (DMSO-$d_6$): δ 7.2-7.42 (6H, m), 7.88 (3H, m) 8.26 (1H, s), 13.8 (1H, brs).

d) {4-[3-(2-Chloro-4-cyanophenoxy)-5-(4-cyano Phenoxy)benzoylamino]cyclohexyl}carbamic Acid Tert-butyl Ester Following the procedure of Example 5(c) 3-(2-chloro-4-cyano phenoxy)-5-(4-cyano phenoxy)benzoic acid 1.0 g (2.55 mmol) and (4-amino-cyclohexyl)-carbamic acid tert-butyl ester (0.54 g, 2.55 mmol) were used to afford 1.2 g of the required product. $^1$H NMR (DMSO-$d_6$): δ 1.24 (4H, m), 1.38 (9H, s), 1.8 (4H, m), 3.2 (1H, m), 3.68 (1H, m), 6.76 (1H, d), 7.22 (4H, m), 7.5 (2H, s), 7.88 (3H, m), 8.26 (1H, d), 8.38 (1H, d).

e) 4-[3-(4-Aminocyclohexylcarbamoyl)-5-(4-ethoxy-carbonimidoylphenoxy)-phenoxy]-3-chloro Benzimidic Acid Ethyl Ester Using {4-[3-(2-chloro-4-cyanophenoxy)-5-(4-cyano phenoxy)benzoyl amino]-cyclohexyl}carbamic acid tert-butyl ester (1.2 g, 2.04 mmol) and following the procedure of Example 1(d) afforded 0.64 g of the required product. Percentage purity (LCMS): 44.3%, (M+1)=539.3+1.

f) N-(4-Aminocyclohexyl)-3-(4-carbamimidoyl-2-chlorophenoxy)-5-(4-carbamimidoyl Phenoxy)benzamide Using 4-[3-(4-aminocyclohexylcarbamoyl)-5-(4-ethoxy-carbonimidoyl phenoxy)-phenoxy]-3-chloro benzimidic acid ethyl ester (0.64 g, 1.1 mmol) and following the procedure of Example 1(e) afforded 0.16 g of the required product. Percentage purity (HPLC): 99.16%, (LCMS): 92.13%. $^1$H NMR (DMSO-$d_6$): δ 1.4 (4H, m), 1.9 (4H, m), 3.0 (1H, s), 3.7 (1H, m) 7.16 (1H, s), 7.32 (3H, m), 7.48 (2H, s), 7.82 (1H, dd), 7.9 (4H, m), 8.14 (1H, d), 8.46 (1H, d), 9.2 (2H, s), 9.3 (2H, s), 9.38 (3H, s).

Example 70

4-[3-[4-(2-Amino ethyl)piperidine-1-carbonyl]-5-(3-amino Propoxy)phenoxy]benzamidine Intermediate (a) is the same as in Example 42.

b) 3-(3-tert-Butoxycarbonylamino propoxy)-5-(4-cyano Phenoxy)benzoic Acid Ethyl Ester Following the procedure of Example 69(b) 3-(4-cyano-phenoxy)-5-hydroxy-benzoic acid ethyl ester 0.9 g (3.17 mmol) and (3-bromo-propyl)-carbamic acid tert-butyl ester (1.5 g, 6.34 mmol) were used to afford 0.95 g of the required product. $^1$H NMR (DMSO-$d_6$): δ 2.05 (4H, m), 3.35 (2H, m), 3.90 (3H, s), 4.08 (2H, t), 4.72 (1H, brs), 6.78 (1H, t), 7.02 (2H, d), 7.28 (1H, s), 7.41 (1H, s), 7.62 (2H, d), 8.05 (1H, brs).

c) 3-(3-tert-Butoxycarbonylamino propoxy)-5-(4-cyano phenoxy)benzoic Acid 3-(3-tert-Butoxycarbonylamino propoxy)-5-(4-cyano phenoxy)benzoic acid ethyl ester, 0.95 g (2.15 mmol) was hydrolysed by using the procedure of Example 5(b) to afford 0.7 g of required product. $^1$H NMR (DMSO-$d_6$): δ 1.85 (2H, t), 3.12 (2H, m), 4.02 (2H, t), 6.85 (1H, s), 6.95 (1H, s), 7.15 (3H, m), 7.32 (1H, s), 7.85 (2H, d), 13.22 (1H, brs).

d) {3-[3-[4-(2-tert-Butoxycarbonylaminoethyl)piperidine-1-carbonyl]-5-(4-cyano phenoxy)phenoxy]propyl}carbamic Acid Tert-butyl Ester Following the procedure of Example 5(c) 3-(3-tert-butoxycarbonylamino propoxy)-5-(4-cyano phenoxy)benzoic acid 0.7 g (1.69 mmol) and (4-amino-cyclohexyl)-carbamic acid tert-butyl ester (0.38 g, 1.69 mmol) were used to afford 0.72 g of the required product. Percentage purity (LCMS): 47.0%, (M+1)=422.3+1 (de bisboc mass −200).

e) 4-[3-[4-(2-amino ethyl)piperidine-1-carbonyl]-5-(3-amino Propoxy)phenoxy]benzimidic Acid Ethyl Ester Using {3-[3-[4-(2-tert-butoxycarbonylaminoethyl)piperidine-1-carbonyl]-5-(4-cyano phenoxy)phenoxy] propyl}carbamic acid tert-butyl ester (0.72 g, 1.15 mmol) and following the procedure of Example 1(d) afforded 0.25 g of the required product. Percentage purity (LCMS): 63.9%, (M+1)=468.2+1.

f) 4-[3-[4-(2-Amino ethyl)piperidine-1-carbonyl]-5-(3-amino Propoxy)phenoxy]benzamidine Using 4-[3-[4-(2-amino ethyl)piperidine-1-carbonyl]-5-(3-amino propoxy)phenoxy]benzimidic acid ethyl ester (0.25 g, 0.53 mmol) and following the procedure of Example 1(e) afforded 0.065 g of the required product. Percentage purity (HPLC): 97.13%, (LCMS): 89.6%. $^1$H NMR (DMSO-$d_6$): δ 1.10 (2H, m), 1.50 (2H, m), 1.60-1.80 (3H, m), 2.0 (2H, m), 2.70 (1H, m), 2.8 (2H, m), 3.0 (3H, m), 4.1 (2H, t), 4.5 (1H, s), 6.60 (1H, s), 6.8 (2H, s), 7.20 (2H, d), 7.80 (3H, brs), 7.9 (4H, d), 9.3 (3H, s).

Example 71

N-(4-Aminocyclohexyl)-3-(6-aminopyridine-3-yloxy)-5-(4-carbamimidoyl-phenoxy)-benzamide Intermediates (a)-(c) are the same as in Example 49.

d) {4-[3-(4-Cyanophenoxy)-5-(6-nitropyridine-3-yloxy)benzoylamino]-cyclo-hexyl}carbamic Acid Tert-butyl Ester Following the procedure of Example 69(b) {4-[3-(4-cyanophenoxy)-5-hydroxy-benzoylamino] cyclohexyl}carbamic acid tert-butyl ester 1.2 g (2.65 mmol) and 5-chloro-2-nitro-pyridine (0.84 g, 5.31 mmol) were used to afford 1.2 g of the required product. $^1$H NMR (DMSO-$d_6$): δ 1.28 (3H, m), 1.4 (10H, s), 1.8 (5H, m), 3.20 (1H, m), 3.7 (1H, m), 6.75 (1H, d), 7.25 (2H, d), 7.35 (1H, d), 7.5 (2H, s), 7.8 (1H, dd), 7.9 (2H, d), 8.35 (2H, d), 8.5 (1H, s).

e) {4-[3-(6-Aminopyridine-3-yloxy)-5-(4-cyanophenoxy)benzoylamino]-cyclohexyl}carbamic Acid Tert-butyl Ester Following the procedure of Example 62(e) {4-[3-(4-cyanophenoxy)-5-(6-nitro-pyridine-3-yloxy)benzoylamino]-cyclohexyl}carbamic acid tert-butyl ester 1.2 g (2.09 mmol) was used to afford 0.45 g of the required product. $^1$H NMR (DMSO-$d_6$): δ 1.28 (4H, m), 1.4 (10H, s), 1.8 (4H, m), 3.20 (1H, m), 3.7 (1H, m), 5.9 (2H, s), 6.5 (1H, d), 6.75 (1H, d), 6.85 (2H, s), 7.15 (3H, d), 7.3 (3H, m), 7.85 (3H, d), 8.3 (1H, m).

f) 4-[3-(4-Amino cyclohexylcarbamoyl)-5-(6-amino Pyridine-3-yloxy)phenoxy]benzimidic Acid Ethyl Ester Using {4-[3-(6-aminopyridine-3-yloxy)-5-(4-cyanophenoxy)benzoyl amino]-cyclohexyl}carbamic acid tert-butyl ester (0.45 g, 0.82 mmol) and following the procedure of Example 1(d) afforded 0.21 g of the required product. Percentage purity (LCMS): 93.0%, (M+1)=489.2+1.

g) N-(4-Amino cyclohexyl)-3-(6-amino pyridine-3-yloxy)-5-(4-carbamimidoyl phenoxy)benzamide Using 4-[3-(4-amino cyclohexylcarbamoyl)-5-(6-amino pyridine-3-yloxy)-phenoxy]benzimidic acid ethyl ester (0.21 g, 0.42 mmol) and following the procedure of Example 1(e)

afforded 0.065 g of the required product. Percentage purity (HPLC): 95.3%, (LCMS): 90.3%. ¹H NMR (DMSO-d$_6$): δ 1.39 (4H, m), 1.9 (4H, m), 3.0 (1H, m), 3.70 (1H, m), 6.88 (1H, d), 7.02 (1H, s), 7.24 (2H, d), 7.36 (2H, d), 7.72 (1H, d), 7.86 (5H, d), 7.96 (1H, s), 8.42 (1H, d), 9.23 (4H, d).

Example 72

N-(4-Aminocyclohexyl)-3-(4-aminophenoxy)-5-(4-carbamimidoylphenoxy)-benzamide

Intermediates (a)-(c) are the same as in Example 49.

d) {4-[3-(4-Cyanophenoxy)-5-(4-nitro phenoxy) benzoylamino]cyclohexyl}-carbamic Acid Tert-butyl Ester Following the procedure of Example 69(b) {4-[3-(4-cyanophenoxy)-5-hydroxy-benzoylamino] cyclohexyl}carbamic acid tert-butyl ester 1.1 g (2.43 mmol) and 1-chloro-4-nitro-benzene (0.765 g, 4.86 mmol) were used to afford 0.94 g of the required product. NMR (DMSO-d$_6$): δ 1.2 (4H, m), 1.40 (9H, s), 1.8 (4H, m), 3.2 (1H, m), 3.7 (1H, m), 6.7 (1H, d), 7.25 (5H, m), 7.55 (2H, m), 7.8 (2H, d), 8.3 (2H, d), 8.4 (1H, d).

e) {4-[3-(4-Aminophenoxy)-5-(4-cyanophenoxy) benzoylamino]cyclohexyl}-carbamic Acid Tert-butyl Ester Following the procedure of Example 62(e) {4-[3-(4-cyanophenoxy)-5-(4-nitro phenoxy)benzoylamino] cyclohexyl}carbamic acid tert-butyl ester 0.94 g (1.64 mmol) was used to afford 0.39 g of the required product. NMR (DMSO-d$_6$): δ 1.2 (4H, m), 1.40 (9H, s), 1.8 (4H, m), 3.2 (1H, m), 3.7 (1H, m), 5.1 (2H, s), 6.6 (2H, d), 6.76 (2H, m), 6.82 (2H, d), 7.14 (2H, d), 7.26 (2H, s), 7.86 (2H, d), 8.28 (1H, d).

f) 4-[3-(4-Aminocyclohexylcarbamoyl)-5-(4-aminophenoxy)phenyl]-benzimidic Acid Ethyl Ester Using {4-[3-(4-aminophenoxy)-5-(4-cyanophenoxy)benzoylamino]cyclohexyl}-carbamic acid tert-butyl ester (0.39 g, 0.71 mmol) and following the procedure of Example 1(d) afforded 0.16 g of the required product. Percentage purity (LCMS): 80.0%, (M+1)=488.2+1 g) N-(4-Aminocyclohexyl)-3-(4-aminophenoxy)-5-(4-carbamimidoylphenoxy)-benzamide Using 4-[3-(4-aminocyclohexylcarbamoyl)-5-(4-aminophenoxy)phenyl]-benzimidic acid ethyl ester (0.16 g, 0.32 mmol) and following the procedure of Example 1(e) afforded 0.05 g of the required product. Percentage purity (HPLC): 97.05%, (LCMS): 96.25%. ¹H NMR (DMSO-d$_6$): δ 1.40 (4H, m), 1.9 (4H, m), 3.0 (1H, m), 3.70 (1H, m), 6.85 (1H, s), 7.0 (4H, s), 7.3 (4H, d), 7.85 (5H, d), 8.4 (1H, d), 9.2 (2H, s), 9.3 (2H, d).

Example 73

N-(4-Aminocyclohexyl)-3-[4-(3-aminopropionylamino)phenoxy]-5-(4-carbamimidoyl phenoxy)benzamide Intermediates (a)-(e) are the same as in Example 72.

f) {4-[3-[4-(3-tert-Butoxycarbonyl Amino Propionylamino)phenoxy]-5-(4-cyano phenoxy)benzoylamino]cyclohexyl}carbamic Acid Tert-butyl Ester 3-tert-Butoxycarbonylamino-propionic acid (0.31 g, 1.63 mmol) and {4-[3-(4-aminophenoxy)-5-(4-cyanophenoxy) benzoylamino]cyclohexyl}-carbamic acid tert-butyl ester (0.884 g, 1.63 mmol) and other reagents as described in Example 9(e) were used to afford 0.75 g. of the required product. NMR (DMSO-d$_6$): δ 1.25 (4H, m), 1.4 (18H, s), 1.8 (4H, m), 2.4 (2H, m), 3.2 (3H, m), 3.7 (1H, m), 6.72 (1H, d), 6.88 (2H, m), 7.06 (2H, d), 7.16 (2H, d), 7.32 (2H, s), 7.64 (2H, d), 7.86 (2H, d), 8.3 (1H, d).

g) 4-{3-(4-Amino cyclohexylcarbamoyl)-5-[4-(3-amino propionylamino)phenoxy] phenoxy}benzimidic Acid Ethyl Ester Using {4-[3-[4-(3-tert-butoxycarbonyl Amino propionylamino)phenoxy]-5-(4-cyano phenoxy)benzoylamino] cyclohexyl}carbamic acid tert-butyl ester (0.75 g, 1.05 mmol) and following the procedure of Example 1(d) afforded 0.34 g of the required product. Percentage purity (LCMS): 85.9%, (M+1)=559.2+1.

h) N-(4-Aminocyclohexyl)-3-[4-(3-aminopropionylamino)phenoxy]-5-(4-carbamimidoyl Phenoxy) benzamide Using 4-{3-(4-aminocyclohexylcarbamoyl)-5-[4-(3-amino propionyl amino) phenoxy]phenoxy}benzimidic acid ethyl ester (0.34 g, 0.60 mmol) and following the procedure of Example 1(e) afforded 0.14 g of the required product. Percentage purity (HPLC): 96.79%, (LCMS): 92.82%. NMR (DMSO-d$_6$): δ 1.35 (4H, m), 1.9 (4H, m), 2.7 (2H, t), 2.95 (2H, m), 3.1 (2H, m), 6.9 (1H, s), 7.1 (2H, d), 7.3 (4H, d), 7.65 (2H, d), 7.85 (8H, m), 8.4 (1H, d), 9.1 (2H, s), 9.25 (2H, s), 10.35 (1H, s).

Example 74

N-(4-Aminocyclohexyl)-3-(4-carbamimidoyl-3-methylphenoxy)-5-(4-carbamimidoyl phenoxy)benzamide Intermediates (a)-(c) are the same as in Example 49.

d) {4-[3-(4-Cyano-3-methyl phenoxy)-5-(4-cyano phenoxy)benzoylamino]cyclohexyl}carbamic Acid Tert-butylester Following the procedure of Example 69(b) {4-[3-(4-cyanophenoxy)-5-hydroxy-benzoylamino] cyclohexyl}carbamic acid tert-butyl ester 0.85 g (1.88 mmol) and 4-fluoro-2-methyl-benzonitrile (0.508 g, 3.76 mmol) were used to afford 0.76 g of the required product. ¹H NMR (DMSO-d$_6$): δ 1.20 (4H, m), 1.4 (9H, s), 1.8 (4H, m), 2.45 (3H, s), 3.15 (1H, m), 3.7 (1H, m), 6.72 (1H, d), 7.02 (1H, d), 7.2 (4H, m), 7.5 (2H, s), 7.8 (1H, d), 7.88 (2H, d), 8.34 (1H, d).

e) (4-{3-[4-(N-Hydroxycarbamimidoyl)-3-methylphenoxy]-5-[4N-hydroxy-carbamimidoyl)phenoxy]benzoylamino}cyclohexyl)carbamic Acid Tert-butylester Following the procedure of Example 2(d) {4-[3-(4-cyano-3-methyl phenoxy)-5-(4-cyano phenoxy)benzoylamino]

cyclohexyl}carbamic acid tert-butylester 0.76 g (1.34 mmol) and other apropriate reagents were used to afford 0.64 g of the required product. Percentage purity (LCMS): 44.5%, (M+1)=632.3+1.

f) (4-{3-[4-(N-Acetylhydroxycarbamimidoyl)-3-methylphenoxy]-5-[4-(N-hydroxy-carbamimidoyl)phenoxy]benzoylamino}cyclohexyl)carbamic Acid Tert-butylester Following the procedure of Example 2(e) (4-{3-[4-(N-hydroxycarbamimidoyl)-3-methylphenoxy]-5-[4-(N-hydroxy-carbamimidoyl)phenoxy]benzoylamino}cyclohexyl) carbamic acid tert-butylester 0.64 g (1.01 mmol) was used to afford 0.52 g of the required product. Percentage purity (LCMS): 49.7%, (M+1)=716.3.

g) {4-[3-(4-Carbamimidoyl-3-methylphenoxy)-5-(4-carbamimidoylphenoxy)-benzoylamino]cyclohexyl}carbamic Acid Tert-butylester (4-{3-[4-(N-Acetylhydroxycarbamimidoyl)-3-methylphenoxy]-5-[4-(N-acetyl-hydroxy-carbamimidoyl)phenoxy]benzoylamino}cyclohexyl) carbamic acid tert-butylester 0.52 g (0.72 mmol) was reduced using the procedure of Example 2(f) to afford 0.25 g of required product. Percentage purity (LCMS): 44.5%, (M+1)=600.3+1.

h) N-(4-Aminocyclohexyl)-3-(4-carbamimidoyl-3-methylphenoxy)-5-(4-carbamimidoyl Phenoxy)benzamide Using {4-[3-(4-carbamimidoyl-3-methylphenoxy)-5-(4-carbamimidoylphenoxy)-benzoylamino]cyclohexyl}carbamic acid tert-butylester (0.25 g, 0.41 mmol) and following the procedure of Example 9(d) afforded 0.05 g of the required product. Percentage purity (HPLC): 97.87%, (LCMS): 97.27%. $^1$H NMR (DMSO-d$_6$): δ 1.4 (4H, m), 1.85 (2H, m), 1.95 (2H, m), 2.4 (3H, s), 3.0 (1H, s), 3.7 (1H, m) 7.0 (1H, s), 7.1 (1H, d), 7.18 (1H, s), 7.28 (2H, d), 7.46 (2H, s), 7.54 (1H, s), 7.88 (5H, m), 8.44 (1H, d), 9.14 (2H, s), 9.28 (6H, s).

Example 75

N-(4-Amino cyclohexyl)-3,5-bis-(4-carbamimidoyl Benzyloxy)benzamide a) 3,5-Bis(4-cyano Phenoxy)benzoic Acid Ethyl Ester

To a solution of 3,5-dihydroxy benzoic acid ethyl ester 1.2 g (6.58 mmol), dissolved in 10 ml DMF, was added K$_2$CO$_3$ 3.63 g (26.32 mmol) followed by 4-bromomethyl-benzonitrile 5.16 g (26.32 mmol) in 5 ml of DMF at 20° C. The reaction mixture was allowed to attain RT and then heated to 35° C. for 8 h. The solvent was removed under reduced pressure and the residue was dissolved in 200 ml of ethyl acetate. The organic layer was washed with brine and water. Organic phase was dried over anhydrous sodium sulphate and solvent was removed under reduced pressure. The crude product was subjected to column chromatography and eluted using hexane:ethyl acetate (8:2) to afford 2.1 g of purified product. $^1$H NMR (DMSO-d$_6$): 1.3 (3H, t), 4.3 (2H, q), 5.3 (4H, s), 7.0 (1H, s), 7.18 (2H, s), 7.64 (4H, d), 7.86 (4H, d).

b) 3,5-Bis(4-cyano Phenoxy)benzoic Acid 2.1 g (5.46 mmol) of 3,5-bis(4-cyano phenoxy)benzoic acid ethyl ester was hydrolysed using the procedure of Example 5(b) to afford 1.65 g of the required product. $^1$H NMR (DMSO-d$_6$): 5.2 (4H, s), 6.8 (1H, s), 7.18 (2H, s), 7.64 (4H, d), 7.86 (4H, d).

c) {4-[3,5-Bis(4-cyano benzyloxy)benzoylamino]cyclohexyl}carbamic Acid Tert-butyl Ester 3,5-Bis(4-cyano phenoxy)benzoic acid (0.75 g, 2.1 mmol) and (4-amino-cyclo-hexyl)-carbamic acid tert-butyl ester (0.45 g, 2.1 mmol) and other reagents as described in Example 9(e) were used to afford 0.82 g. of the required product. $^1$H NMR (DMSO-d$_6$): δ 1.25 (4H, m), 1.4 (9H, s), 1.8 (4H, m), 3.70 (2H, m), 5.25 (4H, s), 6.72 (1H, m), 6.84 (1H, s), 7.12 (2H, s), 7.64 (4H, d), 7.86 (4H, d), 8.18 (1H, m).

d) N-(4-Aminocyclohexyl)-3,5-bis-(4-ethoxycarbonimidoyl Benzyloxy)benzamide Using {4-[3,5-Bis(4-cyanobenzyloxy)benzoylamino]cyclohexyl}carbamic acid tert-butyl ester (0.82 g, 1.41 mmol) and following the procedure of Example 1(d) afforded 0.32 g of the required product. Percentage purity (LCMS): 49.4%, (M+1)=572.3+1.

e) N-(4-Amino cyclohexyl)-3,5-bis-(4-carbamimidoyl Benzyloxy)benzamide

Using N-(4-aminocyclohexyl)-3,5-bis-(4-ethoxycarbonimidoyl benzyloxy)-benzamide (0.32 g, 0.55 mmol) and following the procedure of Example 1(e) afforded 0.07 g of the required product. Percentage purity (HPLC): 98.01%, (LCMS): 99.73%. $^1$H NMR (DMSO-d$_6$): δ 1.4 (4H, m), 1.8 (2H, m), 2.0 (2H, m), 3.0 (1H, m), 3.70 (1H, m), 5.3 (4H, s), 6.9 (1H, s), 7.15 (2H, d), 7.7 (4H, d), 7.85 (4H, s), 7.9 (3H, m), 8.3 (1H, m), 9.3 (8H, s).

Example 76

2-{1-[3,5-Bis-(4-carbamimidoyl-benzyloxy)-benzoyl]-piperidin-4-yl}-ethylamine Intermediates (a) and (b) are the same as in Example 75.

c) (2-{1-[3,5-Bis-(4-cyano benzyloxy)benzoyl]piperidine-4-yl}ethyl)carbamic Acid tert-butyl Ester 3,5-Bis(4-cyano phenoxy)benzoic acid (0.64 g, 1.79 mmol) and (2-piperidin-4-yl-ethyl)-carbamic acid tert-butyl ester (0.408 g, 1.79 mmol) and other reagents as described in Example 9(e) were used to afford 0.72 g of the required product. Percentage purity (LCMS): 88.39,%. $^1$H NMR (DMSO-d$_6$): δ 1.3 (2H, m), 1.35 (9H, m), 1.5 (3H, m), 1.7 (1H, m), 2.98 (2H, m), 3.45 (2H, m), 5.25 (4H, s), 6.58 (2H, s), 6.76 (2H, m), 7.65 (4H, d), 7.88 (4H, d).

d) 2-{1-[3,5-Bis-(4-ethoxycarbonimidoylbenzyloxy)benzoyl]piperidine-4-yl}-ethylamine Using (2-{1-[3,5-bis-(4-cyano benzyloxy)benzoyl]piperidine-4-yl}ethyl)carbamic acid tert-butyl ester (0.72 g, 1.21 mmol) and following the procedure of Example 1(d) afforded 0.34 g of the required product. Percentage purity (LCMS): 49.9%, (M+1)=586.3+1.

e) 2-{1-[3,5-Bis-(4-ethoxycarbamimidoylbenzyloxy)benzoyl]piperidine-4-yl}-ethylamine Using 2-{1-[3,5-bis-(4-ethoxycarbonimidoylbenzyloxy)benzoyl]piperidine-4-yl}-ethylamine (0.34 g, 0.58 mmol)

and following the procedure of Example 1(e) afforded 0.17 g of the required product. Percentage purity (HPLC): 96.25%, (LCMS): 97.96%. $^1$H NMR (DMSO-d$_6$): δ 1.05 (2H, m), 1.50-1.8 (5H, m), 2.8 (4H, m), 3.5 (1H, m), 4.4 (1H, m), 5.25 (4H, s), 6.60 (2H, s), 6.8 (1H, brs), 7.65 (4H, d), 7.85 (6H, d), 9.4 (7H, s).

Example 77

N-(4-Amino cyclohexyl)-3,5-bis-(3-carbamimidoyl Benzyloxy)benzamide a) 3,5-Bis(3-cyano phenoxy)benzoic Acid Ethyl Ester 3,5-Dihydroxy benzoic acid ethyl ester (1.45 g, 7.95 mmol) and 3-bromomethyl-benzonitrile (6.23 g, 31.8 mmol) and other reagents as described in Example 75(a) were used to afford 2.3 g of the required product. $^1$H NMR (DMSO-d$_6$): 1.15 (3H, t), 4.15 (2H, q), 5.3 (4H, s), 7.0 (1H, s), 7.18 (2H, s), 7.64 (4H, d), 7.86 (4H, d).

b) 3,5-Bis(3-cyano Phenoxy)benzoic Acid 2.3 g (5.98 mmol) of 3,5-bis(3-cyano phenoxy)benzoic acid ethyl ester was hydrolysed using the procedure of Example 5(b) to afford 1.85 g. of the required product. $^1$H NMR (DMSO-d$_6$): 6.86 (1H, s), 7.2 (214, d), 7.62 (2H, s), 7.82 (4H, m), 7.94 (2H, s).

c) {4-[3,5-Bis(3-cyano benzyloxy)benzoylamino]cyclohexyl}carbamic Acid Tert-butyl Ester 3,5-Bis(3-cyano phenoxy)benzoic acid (1.2 g, 3.36 mmol) and (4-amino-cyclo-hexyl)-carbamic acid tert-butyl ester (0.72 g, 3.36 mmol) and other reagents as described in Example 9(e) were used to afford 1.33 g of the required product. $^1$H NMR (DMSO-d$_6$): δ 1.25 (4H, m), 1.4 (9H, s), 1.8 (4H, m), 3.20 (1H, m), 3.70 (1H, m), 5.25 (4H, s), 6.74 (1H, m), 6.86 (1H, s), 7.16 (2H, s), 7.64 (211, t), 7.82 (4H, t), 7.94 (2H, s), 8.22 (1H, d)

d) 4-[3,5-Bis(3-ethoxycarbonimidoyl benzyloxy)benzoylamino]cyclohexylamine

Using {4-[3,5-bis(3-cyano benzyloxy)benzoylamino]cyclohexyl}carbamic acid tert-butyl ester (1.33 g, 2.3 mmol) and following the procedure of Example 1(d) afforded 0.91 g of the required product. Percentage purity (LCMS): 14.8%, (M+1)=572.3+1.

e) N-(4-Amino cyclohexyl)-3,5-bis-(3-carbamimidoyl Benzyloxy)benzamide

Using 4-[3,5-Bis(3-ethoxycarbonimidoyl benzyloxy)benzoylamino]cyclohexyl-amine (0.91 g, 1.58 mmol) and following the procedure of Example 1(e) afforded 0.16 g of the required product. Percentage purity (HPLC): 98.81%, (LCMS) 97.40%. NMR (DMSO-d$_6$): δ 1.4 (4H, m), 1.9 (4H, m), 3.0 (1H, m), 3.70 (1H, m), 5.25 (4H, s), 6.9 (1H, s), 7.15 (2H, d), 7.7 (2H, t), 7.80 (4H, t), 7.9 (5H, s), 8.3 (1H, m), 9.4 (8H, s).

Example 78

2-{1-[3,5-Bis-(3-carbamimidoyl-benzyloxy)-benzoyl]-piperidin-4-yl}-ethyl-amine

Intermediates (a) and (b) are the same as in Example 77.

c) (2-{1-[3,5-Bis-(3-cyano benzyloxy)benzoyl]piperidine-4-yl}ethyl)carbamic Acid Tert-butyl Ester 3,5-Bis(3-cyano phenoxy)benzoic acid (0.6 g, 1.68 mmol) and (2-piperidin-4-yl-ethyl)-carbamic acid tert-butyl ester (0.383 g, 1.68 mmol) and other reagents as described in Example 9(e) were used to afford 0.65 g of the required product. $^1$H NMR (DMSO-d$_6$): δ 1.25 (2H, m), 1.4 (9H, s), 1.5 (3H, m), 1.7 (2H, m), 2.7 (2H, m), 2.9 (3H, m), 4.4 (1H, m), 5.25 (4H, s), 6.6 (2H, s), 6.80 (2H, brs), 7.62 (2H, t), 7.82 (4H, m), 7.94 (2H, s).

d) 2-{1-[3,5-Bis-(3-ethoxycarbonimidoyl-benzyloxy)-benzoyl]-piperidin-4-yl}-ethylamine Using (2-{1-[3,5-bis-(3-cyano benzyloxy)benzoyl]piperidine-4-yl}ethyl)carbamic acid tert-butyl ester (0.65 g, 1.09 mmol) and following the procedure of Example 1(d) afforded 0.43 g of the required product. Percentage purity (LCMS): 36.1%, (M+1) 586.3+1.

e) 2-{1-[3,5-Bis-(3-carbamimidoyl-benzyloxy)-benzoyl]piperidin-4-yl}-ethylamine Using 2-{1-[3,5-bis-(3-ethoxycarbonimidoyl-benzyloxy)-benzoyl]-piperidin-4-yl}-ethylamine (0.43 g, 0.73 mmol) and following the procedure of Example 1(e) afforded 0.081 g of the required product. Percentage purity (HPLC): 97.84%, (LCMS): 98.96%. $^1$H NMR (DMSO-d$_6$): δ 1.0 (2H, m), 1.50-1.6 (4H, m), 1.75 (1H, m), 2.7 (1H, m), 2.8-3.0 (4H, m), 4.45 (1H, m), 5.4 (4H, s), 6.6 (2H, s), 6.8 (1H, brs), 7.65 (2H, m), 7.75 (6H, brs), 7.9 (2H, s), 9.45 (8H, s).

Example 79

N-(4-Amino cyclohexyl)-2,4-bis-(4-carbamimidoyl Benzyloxy)benzamide a) [4-(2,4-Dihydroxy benzoylamino)cyclohexyl]carbamic Acid Tert-butyl Ester 2,4-Dihydroxy benzoic acid (1.6 g, 10.38 mmol) and (4-amino-cyclohexyl)-carbamic acid tert-butyl ester (2.22 g, 10.38 mmol) and other reagents as described in Example 9(e) were used to afford 0.95 g of the required product. $^1$H NMR (DMSO-d$_6$): δ 1.20 (4H, m), 1.4 (9H, m), 2.1 (4H, m), 3.2 (1H, m), 3.7 (1H, m), 6.2 (2H, d), 6.74 (1H, s), 7.7 (1H, s), 8.26 (1H, s), 10.0 (1H, brs), 13.0 (1H, brs).

b) {4-[2,4-Bis-(4-cyano benzyloxy)benzoylamino]cyclohexyl}carbamic Acid Tert-butyl Ester

[4-(2,4-Dihydroxy benzoylamino)cyclohexyl]carbamic acid tert-butyl ester (0.95 g, 2.71 mmol) and 4-bromomethyl-benzonitrile (2.12 g, 10.84 mmol) and other reagents as described in Example 75(a) were used to afford 1.2 g of the required product. $^1$H NMR (DMSO-d$_6$): δ 1.20 (5H, m), 1.4

(9H, m), 1.75 (4H, m), 3.6 (1H, m), 5.3 (4H, s), 6.7 (1H, s), 6.85 (1H, s), 7.35 (2H, d), 7.5 (1H, s), 7.75 (4H, d), 7.9 (4H, s).

c) 4-[2,4-Bis-(4-ethoxycarbonimidoyl-benzyloxy) benzoylamino]-cyclohexyl-amine

Using {4-[2,4-bis-(4-cyanobenzyloxy)benzoylamino] cyclohexyl}carbamic acid tert-butyl ester (1.2 g, 2.06 mmol) and following the procedure of Example 1(d) afforded 0.61 g of the required product. Percentage purity (LCMS): 56.9%, (M+1)=572.3+1.

d) 4-[2,4-Bis-(4-carbamimidoyl-benzyloxy)benzoylamino]-cyclohexyl-amine

Using 4-[2,4-bis-(4-ethoxycarbonimidoyl-benzyloxy) benzoylamino]-cyclohexyl-amine (0.61 g, 1.06 mmol) and following the procedure of Example 1(e) afforded 0.24 g of the required product. Percentage purity (HPLC): 97.52%, (LCMS): 96.14%. $^1$H NMR (DMSO-$d_6$): δ 1.10 (2H, m), 1.35 (2H, m), 2.85 (4H, m), 2.9 (1H, m), 3.6 (1H, m), 5.3 (4H, d), 6.75 (1H, d), 6.9 (1H, s), 7.7 (3H, m), 7.75-8.0 (8H, m), 8.35 (1H, d), 8.7 (2H, brs), 8.95 (2H, s), 9.1 (2H, brs), 9.2-9.5 (7H, s).

Example 80

2-{1-[2,4-Bis-(4-carbamimidoyl-benzyloxy)-benzoyl]-piperidin-4-yl}-ethyl-amine a) {2-[1-(2,4-Dihydroxy Benzoyl)piperidin-4-yl]ethyl}carbamic Acid Tert-butyl Ester 2,4-Dihydroxy benzoic acid (1.25 g, 8.11 mmol) and (2-piperidin-4-yl-ethyl)-carbamic acid tert-butyl ester (1.85 g, 8.11 mmol) and other reagents as described in Example 9(e) were used to afford 1.13 g of the required product. $^1$H NMR (DMSO-$d_6$): δ 1.05 (2H, m), 1.25 (2H, m), 1.4 (9H, s), 1.65 (2H, m), 2.75 (2H, m), 2.95 (2H, m), 3.15 (1H, m), 4.0 (2H, m), 6.24 (2H, m), 6.78 (1H, m), 6.9 (1H, d), 9.6 (2H, brs).

b) (2-{1-[2,4-Bis-(4-cyano-benzyloxy)benzoyl]piperidin-4-yl}ethyl)carbamic Acid Tert-butyl Ester {2-[1-(2,4-Dihydroxy benzoyl)piperidin-4-yl] ethyl}carbamic acid tert-butyl ester (1.13 g, 3.1 mmol) and 4-bromomethyl-benzonitrile (2.43 g, 12.4 mmol) and other reagents as described in Example 75(a) were used to afford 1.3 g of the required product. $^1$H NMR (DMSO-$d_6$): δ 1.35 (8H, s), 2.1 (4H, s), 2.9 (3H, m), 4.55 (4H, d), 5.25 (3H, s), 5.5 (2H, t), 6.8 (1H, m), 7.3 (1H, d), 7.4 (1H, d), 7.5 (4H, d), 7.66 (1H, d), 7.8 (3H, m), 7.86 (2H, m).

c) 2-{1-[2,4-Bis-(4-ethoxycarbonimidoyl-benzyloxy)-benzoyl]-piperidin-4-yl}-ethylamine Using (2-{1-[2,4-bis-(4-cyano-benzyloxy)benzoyl]piperidin-4-yl}ethyl) carbamic acid tert-butyl ester (1.3 g, 2.18 mmol) and following the procedure of Example 1(d) afforded 0.52 g of the required product. Percentage purity (LCMS): 71.2%, (M+1)=586.3+1.

d) 2-{1-[2,4-Bis-(4-carbamimidoyl-benzyloxy)-benzoyl]-piperidin-4-yl}-ethyl-amine Using 2-{1-[2,4-bis-(4-ethoxycarbonimidoyl-benzyloxy)-benzoyl]-piperidin-4-yl}-ethylamine (0.52 g, 0.88 mmol) and following the procedure of Example 1(e) afforded 0.19 g of the required product. Percentage purity (HPLC): 90.96%, (LCMS): 98.53%. $^1$H NMR (DMSO-$d_6$): δ 1.0 (1H, m), 1.30 (1H, m), 1.5 (3H, m), 1.7 (1H, m), 2.7 (4H, m), 2.9 (1H, m), 3.4 (1H, m), 4.5 (1H, m), 5.30 (4H, d), 6.65 (1H, d), 6.8 (1H, s), 7.15 (1H, m), 7.7 (7H, m), 7.85 (4H, d) 9.2 (4H, s), 9.35 (4H, s).

Example 81

N-(4-Amino cyclohexyl)-2,4-bis(3-carbamimidoyl Benzyloxy)benzamide

Intermediate (a) is the same as in Example 79(a).

b) {4-[2,4-Bis-(3-cyano benzyloxy)benzoylamino]cyclohexyl}carbamic Acid Tert-butyl Ester

[4-(2,4-Dihydroxy benzoylamino)cyclohexyl]carbamic acid tert-butyl ester (0.85 g, 2.42 mmol) and 3-bromomethyl-benzonitrile (1.89 g, 9.68 mmol) and other reagents as described in Example 75(a) were used to afford 0.75 g of the required product. $^1$H NMR (DMSO-$d_6$): δ 1.4 (9H, s), 1.75 (4H, m), 3.15 (1H, m), 3.65 (2H, m), 4.55 (1H, m), 5.25 (4H, s), 6.72 (2H, m), 6.9 (1H, s), 7.7 (6H, m), 7.85 (4H, m), 7.94 (1H, s), 8.04 (1H, s).

c) 4-[2,4-Bis-(3-ethoxycarbonimidoyl-benzyloxy) benzoylamino]-cyclohexyl-amine

Using {4-[2,4-bis-(3-cyanobenzyloxy)benzoylamino] cyclohexyl}carbamic acid tert-butyl ester (0.75 g, 1.29 mmol) and following the procedure of Example 1(d) afforded 0.32 g of the required product. Percentage purity (LCMS): 90.7%, (M+1)=572.3+1.

d) 4-[2,4-Bis-(3-carbamimidoyl-benzyloxy)benzoylamino]-cyclohexyl-amine

Using 4-[2,4-bis-(3-ethoxycarbonimidoyl-benzyloxy) benzoylamino]-cyclohexyl-amine (0.32 g, 0.55 mmol) and following the procedure of Example 1(e) afforded 0.08 g of the required product. Percentage purity (HPLC): 95.22%, (LCMS): 93.7%. $^1$H NMR (DMSO-$d_6$): δ 1.2 (2H, m), 1.40 (2H, m), 1.9 (4H, m), 2.95 (1H, m), 3.7 (1H, m), 5.35 (4H, d), 6.75 (1H, d), 6.9 (1H, s), 7.7 (5H, m), 7.85 (7H, m), 9.1-9.4 (8H, s).

Example 82

2-{1-[2,4-Bis-(3-carbamimidoyl-benzyloxy)-benzoyl]-piperidin-4-yl}-ethylamine

Intermediate (a) is the same as in Example 80(a).

b) (2-{1-[2,4-Bis(3-cyano benzyloxy)benzoyl]piperidin-4-yl}ethyl)carbamic Acid Tert-butyl Ester {2-[1-(2,4-Dihydroxy benzoyl)piperidin-4-yl] ethyl}carbamic acid tert-butyl ester (1.05 g, 2.88 mmol) and 3-bromomethyl-benzonitrile (2.25 g, 11.5 mmol) and other reagents as described in Example 75(a) were used to afford 1.15 g of the required product. $^1$H NMR (DMSO-$d_6$): δ 1.4 (9H, s), 2.1 (2H, d), 2.6 (1H, m), 2.95 (4H, m), 3.45 (1H, m), 4.5 (2H, m), 5.2 (4H, s), 6.7 (2H, d), 6.84 (1H, d), 7.14 (1H, dd), 7.52 (1H, m), 7.62 (3H, d), 7.7 (2H, d), 7.8 (5H, m), 7.95 (1H, s).

c) 2-{1-[2,4-Bis-(3-ethoxycarbonimidoyl-benzyloxy)-benzoyl]-piperidin-4-yl}-ethylamine Using (2-{1-[2,4-Bis(3-cyanobenzyloxy)benzoyl]piperidin-4-yl}ethyl)carbamic acid tert-butyl ester (1.15 g, 1.93 mmol) and following the procedure of Example 1(d) afforded 0.41 g of the required product. Percentage purity (LCMS): 62.5%, (M+1)=586.3+1.

d) 2-{1-[2,4-Bis-(3-carbamimidoyl-benzyloxy)-benzoyl]-piperidin-4-yl}-ethyl-amine Using 2-{1-[2,4-bis-(3-ethoxycarbonimidoyl-benzyloxy)-benzoyl]-piperidin-4-yl}-ethylamine (0.41 g, 0.69 mmol) and following the procedure of Example 1(e) afforded 0.16 g of the required product. Percentage purity (HPLC): 91.53%, (LCMS) 95.59%. $^1$H NMR (DMSO-d$_6$): δ 0.9 (2H, m), 1.25 (2H, m), 1.5 (3H, m), 1.75 (1H, m), 2.8 (3H, m), 2.9 (1H, m), 3.4 (2H, m), 4.5 (1H, m), 5.25 (3H, d), 6.55 (1H, s), 6.7 (1H, d), 6.9 (1H, d), 7.3 (1H, m), 7.8 (8H, m) 7.9 (1H, s), 9.25 (314, d), 9.4 (3H, s).

Example 83

4-[3-(4-Aminomethyl phenoxy)-5-(4-carbamimidoyl phenoxy)benzoyl]-1-carboxylic Acid Ethyl Ester Intermediates (a)-(c) are the same as in Example 62.

d) 4-[3-(4-Aminomethyl phenoxy)-5-hydroxy benzoyl]piperazine-1-carboxylic Acid Ethyl Ester Raney nickel (0.1 g, 1.7 mmols) was added to a stirred solution of 4-[3-(4-cyano phenoxy)-5-hydroxy benzoyl]piperazine-1-carboxylic acid ethyl ester (0.5 g, 1.26 mmols) dissolved in methanolic ammonia (50 ml) and the reaction mixture was heated to 50° C. in Paar apparatus under 50 Psi hydrogen gas pressure for 3 h. The reaction mixture was cooled and filtered through celite pad. The filtrate was concentrated to afford 0.4 g of the required product which was used for the next step without further purification. Percentage purity (LCMS): 74.3%, (M+1)=399.1+1.

e) 4-[3-(4-(tert-Butoxycarbonylaminomethyp-phenoxy)-5-hydroxybenzoyl]-piperazine-1-carboxylic Acid Ethyl Ester (Boc)$_2$O (0.24 g, 1.1 mmols) was added slowly with stirring to 4-[3-(4-aminomethyl phenoxy)-5-hydroxy benzoyl]piperazine-1-carboxylic acid ethyl ester (0.4 g, 1.0 mmols) in 1,4-dioxane and water (1:1) and stirring was continued for 3 h at RT. The reaction mixture was quenched with ice cold water and extracted with ethyl acetate. The organic layer was washed with water followed by brine and dried over anhydrous sodium sulphate and concentrated to afford 0.3 g of the required product. $^1$H NMR (DMSO-d$_6$): δ 1.20 (3H, t), 1.4 (9H, s), 3.5 (8H, ms), 4.2 (4H, m), 6.38 (2H, d), 6.48 (1H, s), 7.02 (2H, d), 7.28 (2H, d), 7.4 (1H, m), 9.8 (1H, s).

f) 4-[3-[4-(tert-Butoxycarbonylaminomethyl)-phenoxy]-5-(4-cyano-phenoxy)-benzoyl]piperazine-1-carboxylic acid ethyl ester Using 0.3 g (0.6 mmol) of 4-[3-(4-cyano phenoxy)-5-hydroxy benzoyl]piperazine-1-carboxylic acid ethyl ester and 4-fluorobenzonitrile (0.19 g, 1.5 mmol) and following the procedure of Example 42(b) afforded 0.38 g of the required product. $^1$H NMR (DMSO-d$_6$): δ 1.2 (3H, t), 1.4 (9H, s), 3.3 (2H, m), 3.4 (4H, m), 3.55 (2H, m), 4.05 (2H, q), 4.15 (m), 6.84 (3H, m), 7.1 (2H, d), 7.26 (4H, d), 7.4 (1H, m), 7.88 (2H, s).

g) 4-[3-(4-Aminomethyl phenoxy)-5-(4-ethoxycarbonimidoyl phenoxy)benzoyl]piperazine-1-carboxylic Acid Ethyl Ester Using 4-[3-[4-(tert-butoxycarbonylaminomethyl)-phenoxy]-5-(4-cyano-phenoxy)-benzoyl]piperazine-1-carboxylic acid ethyl ester (0.38 g, 0.63 mmol) and following the procedure of Example 1(d) afforded 0.17 g of the required product. Percentage purity (LCMS): 81.7%, (M+1)=546.2+1.

h) 4-[3-(4-Aminomethylphenoxy)-5-(4-carbamimidoyl phenoxy)benzoyl]-piperazine-1-carboxylic Acid Ethyl Ester Using 4-[3-(4-aminomethyl phenoxy)-5-(4-ethoxycarbonimidoyl phenoxy)-benzoyl]piperazine-1-carboxylic acid ethyl ester (0.17 g, 0.31 mmol) and following the procedure of Example 1(e) afforded 0.07 g of the required product. Percentage purity (HPLC): 97.62%, (LCMS): 94.31%. $^1$H NMR (DMSO-d$_6$): δ 1.2 (31-1, t), 3.35 m), 3.55 (2H, m), 3.9 (6H, m), 4.1 (2H, q), 6.8 (1H, s), 6.85 (2H, m), 7.20 (2H, d), 7.3 (2H, d), 7.5 (2H, d), 7.9 (2H, d), 8.2 (3H, brs), 9.1 (2H, s), 9.3 (2H, s).

Example 84

N-(4-Amino cyclohexyl)-3-(4-aminomethyl phenoxy)-5-(4-carbamimidoyl phenoxy)benzamide Intermediates (a)-(c) are the same as in Example 49.

d) {4-[3-[4-Aminomethylphenoxy]-5-hydroxybenzoylamino]cyclohexyl}carbamic Acid Tert-butyl Ester Using {4-[3-(4-cyano-phenoxy)-5-hydroxy-benzoylamino]-cyclohexyl}-carbamic acid tert-butyl ester (2.0 g, 4.43 mmol) and following the procedure of Example 83(d) afforded 1.5 g of the required product. $^1$H NMR (DMSO-d$_6$): δ 1.2 (4H, m), 1.4 (9H, s), 1.8 (4H, m), 3.2 (1H, m), 3.7 (3H, m), 6.48 (1H, s), 6.78 (1H, d), 6.9 (1H, s), 7.0 (2H, m), 7.38 (1H, m), 8.18 (1H, d).

e) {4-[3-[4-tert-Butoxycarbonylaminomethylphenoxy]-5-hydroxybenzoylamino]-cyclohexyl}carbamic Acid Tert-butyl Ester Using 1.5 g (3.29 mmol) of {4-[3-[4-aminomethylphenoxy]-5-hydroxybenzoyl-amino]cyclohexyl}carbamic acid tert-butyl ester and boc-anhydride (0.787 g, 3.61 mmol) and following the procedure of Example 83(e) afforded 1.4 g of the required product. $^1$H NMR (DMSO-d$_6$): δ 1.2 (3H, m), 1.4 (18H, s), 1.8 (4H, m), 3.2 (2H, m), 3.7 (1H, m), 4.15 (2H, d), 6.45 (1H, s), 6.7 (1H, d), 6.9 (1H, s), 7.0 (3H, d), 7.25 (2H, d), 7.4 (1H, brs), 8.15 (1H, d), 9.8 (1H, s).

f) {4-[3-[4-(tert-Butoxycarbonylamino methyl)phenoxy]-5-(4-cyano phenoxy)benzoylamino] cyclohexyl}carbamic Acid Tert-butyl Ester Using 1.4 g (2.51 mmol) of {4-[3-[4-tert-Butoxycarbonylaminomethylphenoxy]-5-hydroxybenzoylamino]- cyclohexyl}carbamic acid tert-butyl ester and 4-fluoro-benzonitrile (0.76 g, 6.27 mmol) and following the procedure of Example 42(b) afforded 1.53 g of the required product. $^1$H NMR (DMSO-d$_6$): δ 1.3 (4H, m), 1.4 (18H, s), 1.8 (4H, m), 3.2 (1H, m), 3.7 (1H, m), 4.15 (2H, d), 6.72 (1H, d), 7.20 (1H, s), 7.06 (2H, d), 7.18 (2H, d), 7.28 (2H, d), 7.38 (3H, d), 7.86 (2H, s), 8.3 (1H, d).

g) 4-[3-(4-Amino-cyclohexylcarbamoyl)-5-(4-aminomethyl-phenoxy)-phenoxy]-benzimidic Acid Ethyl Ester Using {4-[3-[4-(tert-butoxycarbonylamino methyl)phenoxy]-5-(4-cyano phenoxy)benzoylamino]cyclohexyl}carbamic acid tert-butyl ester (1.53 g, 2.32 mmol) and following the procedure of Example 1(d) afforded 1.15 g of the required product. Percentage purity (LCMS): 33.53%, (M+1)=502.2+1.

h) N-(4-Aminocyclohexyl)-3-(4-aminomethylphenoxy)-5-(4-carbamimidoyl Phenoxy)benzamide Using 4-[3-(4-amino-cyclohexylcarbamoyl)-5-(4-aminomethyl-phenoxy)-phenoxy]-benzimidic acid ethyl ester (1.15 g, 2.28 mmol) and following the procedure of Example 1(e) afforded 0.75 g of the required product. Percentage purity (HPLC): 96.64%, (LCMS): 96.88%. $^1$H NMR (DMSO-d$_6$): δ 1.45 (4H, t), 1.90 (4H, m), 3.0 (1H, m), 3.7 (1H, m), 4.05 (2H, d), 6.9 (1H, s), 7.18 (2H, d), 7.26 (2H, d), 7.38 (2H, s), 7.52 (2H, d), 7.88 (4H, d), 8.22 (2H, brs), 8.42 (1H, d), 9.2 (2H, brs), 9.3 (2H, s).

Example 85

(4-{3-(4-Amino-cyclohexylcarbamoyl)-5-[4-(N-hydroxycarbamimidoyl)-phenoxy]-phenoxy}-benzyl)-carbamic Acid Ethyl Ester Intermediates (a) to (d) are the same as in Example 84.

e) (4-{3-[4-(Ethoxycarbonylamino-methyl)-phenoxy]-5-hydroxy-benzoylamino}-cyclohexyl)-carbamic acid tert-butyl ester To 1.0 g (2.19 mmol) of {4-[3-(4-aminomethyl-phenoxy)-5-hydroxy-benzoyl-amino]-cyclohexyl}-carbamic acid tert-butyl ester, dissolved in 5 ml of THF, 0.13 g (5.47 mmol) of sodium hydride was added at 0° C. and the mixture was stirred for 15 min at same temperature. 0.26 g (2.40 mmol) of ethylchloroformate, dissolved in 2 ml of THF, was added dropwise to the stirred solution during 10 min and then the reaction mixture was stirred at RT for 6 h. After reaction completion, solvent was removed under reduced pressure and the obtained residue was dissolved in 200 ml of ethyl acetate. Organic layer was washed with (3×100 ml) of brine followed by water (2×100 ml). Organic phase was dried over anhydrous sodium sulphate and concentrated under reduced pressure to afford 0.56 g of required product which was used for the next step witout further purification. Percentage purity (LCMS): 59.7%, (M+1)=527.2+1.

f) (4-{3-(4-Cyano-phenoxy)-5-[4-(ethoxycarbonylamino-methyl)-phenoxy]-benzoylamino}-cyclohexyl)-carbamic Acid Tert-butyl Ester Using 0.56 g (1.06 mmol) of (4-{3-[4-(Ethoxycarbonylamino-methyl)-phenoxy]-5-hydroxy-benzoylamino}-cyclohexyl)-carbamic acid tert-butyl ester and 4-fluoro-benzonitrile (0.32 g, 2.65 mmol) and following the procedure of Example 42(b) afforded 0.61 g of the required product. Percentage purity (LCMS): 45.2%, (M+1)=628.3+1.

g) (4-{3-[4-(Ethoxycarbonylamino-methyl)-phenoxy]-5-[4-(N-hydroxy carbamimidoyl)-phenoxy]-benzoylamino}-cyclohexyl)-carbamic Acid Tert-butyl Ester Following the procedure of Example 2(d) (4-{3-(4-cyano-phenoxy)-5-[4-(ethoxy-carbonylamino-methyl)-phenoxy]-benzoylamino}-cyclohexyl)-carbamic acid tert-butyl ester 0.61 g (0.97 mmol) and other reagents were used to afford 0.68 g of the required product. Percentage purity (LCMS): 38.9%, (M+1)=661.3+1.

h) (4-{3-(4-Amino-cyclohexylcarbamoyl)-5-[4-(N-hydroxycarbamimidoyl)-phenoxy]-phenoxy}-benzyl)-carbamic Acid Ethyl Ester Using (4-{3-[4-(ethoxycarbonylamino-methyl)-phenoxy]-5-[4-(N-hydroxy carbamimidoyl)-phenoxy]-benzoylamino}-cyclohexyl)-carbamic acid tert-butyl ester (0.68 g, 1.02 mmol) and following the procedure of Example 9(d) afforded 0.28 g of the required product. Percentage purity (HPLC): 97.5%, (LCMS): 96.6%. $^1$H NMR (DMSO-d$_6$): δ 1.24 (3H, t), 1.38 (4H, m), 1.92 (4H, m), 3.0 (1H, m), 3.8 (1H, m), 4.00 (2H, q), 4.20 (2H, d), 6.88 (1H, s), 7.06 (2H, d), 7.22 (2H, d), 7.32 (4H, m), 7.65 (2H, m), 7.78 (5H, m), 8.18 (1H, d), 11.0 (1H, brs).

Example 86

4-[3-(4-Aminomethylphenoxy)-5-(octahydroquinoline-1-carbonyl)-phenoxy]-benzmidine Intermediates (a) and (b) are the same as in Example 49.

c) 4-[3-Hydroxy-5-(octahydro quinoline-1-carbonyl)phenoxy]benzonitrile 3-(4-Cyano-phenoxy)-5-hydroxy-benzoic acid (1.5 g, 5.87 mmol) and decahydro-quinoline (0.89 g, 6.45 mmol) and other reagents as described in Example 9(e) were used to afford 1.6 g of the required product. NMR (DMSO-d$_6$): δ 1.35 (6H, m), 1.80 (7H, m), 3.0 (1H, m), 3.6 (1H, m), 4.5 (1H, m), 6.44 (1H, s), 6.54 (2H, m), 7.16 (2H, d), 7.88 (2H, d), 10.1 (1H, brs).

d) [3-(4-amino methyl phenoxy)-5-hydroxy phenyl]-(octahydro quinolin-1-yl)methanone Using 4-[3-hydroxy-5-(octahydro quinoline-1-carbonyl) phenoxy]benzonitrile (1.6 g, 4.27 mmol) and following the procedure of Example 83(d) afforded 1.2 g of the required product. Percentage purity (LCMS): 94.5%, (M+1)=661.3+1.

e) {4-[3-hydroxy-5-(octahydro quinoline-1-carbonyl)phenoxy]benzyl}carbamic Acid Tert-butyl Ester Using 1.2 g (3.17 mmol) of [3-(4-amino methyl phenoxy)-5-hydroxy phenyl]-(octahydro quinolin-1-yl)methanone and boc-anhydride (0.76 g, 3.48 mmol) and following the procedure of Example 83(e) afforded 1.34 g of the required product. ¹H NMR (DMSO-d₆): δ 1.30 (8H, m), 1.40 (9H, s), 1.55 (2H, m), 1.75 (4H, m), 3.0 (1H, m), 3.55 (1H, m), 4.1 (2H, d), 6.24 (1H, s), 6.42 (2H, s), 7.0 (2H, d), 7.26 (2H, d), 7.4 (1H, t), 9.8 (1H, s).

f) {4-[3-(4-Cyanophenoxy)-5-(octahydroquinoline-1-carbonyl)phenoxy]benzyl}-carbamic Acid Tert-butyl Ester Using 1.34 g (2.79 mmol) of {4-[3-hydroxy-5-(octahydroquinoline-1-carbonyl)phenoxy]benzyl}carbamic acid tert-butyl ester and 4-fluorobenzonitrile (0.84 g, 6.97 mmol) and following the procedure of Example 42(b) afforded 1.6 g of the required product. ¹H NMR (DMSO-d₆): δ 1.30 (8H, m), 1.40 (9H, s), 1.8 (8H, m), 4.1 (2H, d), 6.68 (1H, s), 6.82 (2H, s), 7.08 (2H, d), 7.22 (2H, d), 7.28 (2H, d), 7.4 (1H, t), 7.88 (2H, d).

g) {4-[3-[4-(N-Hydroxycarbamimidoyl)phenoxy]-5-(octahydroquinoline-1-carbonyl)-phenoxy]benzyl}carbamic Acid Tert-butyl Ester Following the procedure of Example 2(d) {4-[3-(4-cyanophenoxy)-5-(octahydro-quinoline-1-carbonyl)phenoxy]benzyl}-carbamic acid tert-butyl ester 1.6 g (2.76 mmol) and other reagents were used to afford 1.43 g of the required product. Percentage purity (LCMS): 54.6%, (M+1)=612.3+1.

h) {4-[3-[4-(N-acetylhydroxycarbamimidoyl)phenoxy]-5-(octahydro quinoline-1-carbonyl)phenoxy]benzyl}carbamic Acid Tert-butyl Ester {4-[3-[4-(N-Hydroxycarbamimidoyl)phenoxy]-5-(octahydroquinoline-1-carbonyl)-phenoxyl]benzyl}carbamic acid tert-butyl ester, 1.4 g (2.28 mmol) was acetylated with 0.26 g (2.5 mmol) of acetic anhydride using the procedure of Example 2(e) to afford 1.04 g of the required product. Percentage purity (LCMS): 36.1%, (M+1)=654.3+1.

i) 4-[3-(4-Aminomethylphenoxy)-5-(octahydroquinoline-1-carbonyl)phenoxy]benzmidine 1.0 g (1.52 mmol) of {4-[3-[4-(N-acetylhydroxycarbamimidoyl)phenoxy]-5-(octahydro quinoline-1-carbonyl)phenoxy]benzyl}carbamic acid tert-butyl ester was reduced using the procedure of Example 2(f) to afford 0.43 g of the required product. Percentage purity (HPLC): 83.4%, (LCMS): 96.26%. ¹H NMR (DMSO-d₆): δ 1.3 (5H, m), 1.55 (2H, m), 1.75 (5H, m), 2.7 (1H, m), 3.05 (1H, m), 4.0 (2H, d), 4.25 (1H, m), 4.45 (1H, m), 6.75 (4H, m), 7.2 (2H, d), 7.3 (2H, d), 7.55 (2H, d), 7.9 (2H, d), 8.4 (3H, brs), 9.1 (2H, s), 9.4 (2H, s)

Example 87

N-(4-Amino-cyclohexyl)-3-(4-aminomethyl-phenoxy)-5-(4-carbamimidoyl-2,6-difluoro-phenoxy)-benzamide Intermediates (a) and (e) are the same as in Example 84.

f) {4-[3-[4-(tert-Butoxycarbonylamino-methyl)-phenoxy]-5-(4-cyano-2,6-difluoro-phenoxy)-benzoylamino]-cyclohexyl}-carbamic Acid Tert-butyl Ester Using 0.5 g (0.89 mmol) of {4-[3-[4-tert-Butoxycarbonylaminomethylphenoxy]-5-hydroxybenzoylamino]-cyclohexyl}carbamic acid tert-butyl ester and 3,4,5-trifluorobenzonitrile (0.34 g, 2.22 mmol) and following the procedure of Example 42(b) afforded 0.4 g of the required product. ¹H NMR (DMSO-d₆): δ 1.25 (4H, m), 1.38 (18H, d), 1.78 (4H, m), 3.18 (1H, m), 3.64 (1H, m), 4.12 (2H, d), 6.74 (1H, d), 6.90 (1H, s), 7.02 (2H, d), 7.20 (2H, d), 7.28 (2H, d), 7.40 (1H, m), 8.08 (2H, d), 8.32 (1H, d).

g) (4-{3-[4-(tert-Butoxycarbonylamino-methyl)-phenoxy]-5-[2,6-difluoro-4-(N-hydroxycarbamimidoyl)-phenoxy]-benzoylamino}-cyclohexyl)-carbamic Acid Tert-butyl Ester Using {4-[3-[4-(tert-Butoxycarbonylamino-methyl)-phenoxy]-5-(4-cyano-2,6-difluoro-phenoxy)-benzoylamino]-cyclohexyl}-carbamic acid tert-butyl ester (0.4 g, 0.57 mmol) and following the procedure of Example 2(d) afforded 0.45 g of the required product. Percentage purity (LCMS): 83.53%, (M+1)=525.2+1 (de-bis BOC product mass).

h) (4-{3-[4-(tert-Butoxycarbonylamino-methyl)-phenoxy]-5-[2,6-difluoro-4-(N-acetylhydroxycarbamimidoyl)-phenoxy]-benzoylamino}-cyclohexyl)-carbamic Acid tert-butyl Ester Using (4-{3-[4-(tert-Butoxycarbonylamino-methyl)-phenoxy]-5-[2,6-difluoro-4-(N-hydroxycarbamimidoyl)-phenoxy]-benzoylamino}-cyclohexyl)-carbamic acid tert-butyl ester (0.45 g, 0.62 mmol) and following the procedure of Example 2(e) afforded 0.5 g of the required product. Percentage purity (LCMS): 81.00%, (M+1)=667.2+1 (de-BOC product mass).

i) {4-[3-[4-(tert-Butoxycarbonylamino-methyp-phenoxy]-5-(4-carbamimidoyl-2,6-difluoro-phenoxy)-benzoylamino]-cyclohexyl}-carbamic Acid Tert-butyl Ester (4-{3-[4-(tert-Butoxycarbonylamino-methyp-phenoxy]-5-[2,6-difluoro-4-(N-acetylhydroxycarbamimidoyl)-phenoxy]-benzoylamino}-cyclohexyl)-carbamic acid tert-butyl ester 0.5 g (0.65 mmol) was reduced using the procedure of Example 2(f) to afford 0.3 g of the required product. Percentage purity (LCMS): 85.0%, (M+1)=709.3+1.

j) N-(4-Amino-cyclohexyl)-3-(4-aminomethyl-phenoxy)-5-(4-carbamimidoyl-2,6-difluoro-phenoxy)-benzamide Using {4-[3-[4-(tert-Butoxycarbonylamino-methyl)-phenoxy]-5-(4-carbamimidoyl-2,6-difluoro-phenoxy)-benzoylamino]-cyclohexyl}-carbamic acid tert-butyl ester (0.3 g, 0.42 mmol) and following the procedure of Example 9(d) afforded 0.15 g of the required product. Percentage purity (HPLC): 97.83%, (LCMS): 92.22%. ¹H NMR (DMSO-d₆): δ 1.44 (4H, m), 1.88 (4H, m), 3.02 (1H, m), 3.48 (1H, m), 4.05 (2H, d), 6.92 (1H, s), 7.14 (2H, d), 7.25 (2H, d), 7.50 (2H, d), 7.90 (5H, m), 8.25 (3H, brs), 8.44 (1H, d), 9.52 (4H, d).

Example 88

N-(4-Amino-cyclohexyl)-3-(4-aminomethyl-phenoxy)-5-(4-carbamimidoyl-2-trifluoromethyl-phenoxy)-benzamide Intermediates (a) and (e) are the same as in Example 84.

g) {4-[3-[4-(tert-Butoxycarbonylamino-methyl)-phenoxy]-5-(4-cyano-2-trifluoromethyl-phenoxy)-benzoylamino]-cyclohexyl}-carbamic Acid Tert-butyl Ester Using 0.46 g (0.82 mmol) of {4-[3-[4-tert-butoxycarbonylaminomethylphenoxy]-5-hydroxybenzoylamino]-cyclohexyl}carbamic acid tert-butyl ester and 4-fluoro-3-trifluoromethylbenzonitrile (0.313 g, 1.65 mmol) and following the procedure of Example 42(b) afforded 0.3 g of the required product. NMR (DMSO-$d_6$): δ 1.25 (4H, m), 1.38 (18H, d), 1.8 (4H, m), 3.18 (1H, m), 3.64 (1H, m), 4.12 (2H, d), 6.75 (1H, d), 7.02 (1H, s), 7.08 (2H, d), 7.20 (1H, d), 7.28 (2H, d), 7.41 (3H, m), 8.1 (1H, m), 8.38 (2H, m).

h) (4-{3-[4-(tert-Butoxycarbonylamino-methyl)-phenoxy]-5-[2-trifluoromethyl-4-(N-hydroxycarbamimidoyl)-phenoxy]-benzoylamino}-cyclohexyl)-carbamic Acid Tert-butyl Ester Using {4-[3-[4-(tert-Butoxycarbonylamino-methyl)-phenoxy]-5-(4-cyano-2-tri-fluoromethyl-phenoxy)-benzoylamino]-cyclohexyl}-carbamic acid tert-butyl ester (0.3 g, 0.41 mmol) and following the procedure of Example 2(d) afforded 0.3 g of the required product. Percentage purity (LCMS): 75.8%, (M+1)=557.2+1 (de-bis BOC product mass).

i) (4-{3-[4-(tert-Butoxycarbonylamino-methyl)-phenoxy]-5-[2-trifluoromethyl-4-(N-acetylhydroxycarbamimidoyl)-phenoxy]-benzoylamino}-cyclohexyl)-carbamic Acid Tert-butyl Ester Using (4-{3-[4-(tert-Butoxycarbonylamino-methyl)-phenoxy]-5-[2-trifluoromethyl-4-(N-hydroxycarbamimidoyl)-phenoxy]-benzoylamino}-cyclohexyl)-carbamic acid tert-butyl ester (0.3 g, 0.39 mmol) and following the procedure of Example 2(e) afforded 0.35 g of the required product. Percentage purity (LCMS): 59.00%, (M+1)=699.2+1 (de-BOC product mass).

j) {4-[3-[4-(tert-Butoxycarbonylamino-methyp-phenoxy]-5-(4-carbamimidoyl-2-trifluoromethyl-phenoxy)-benzoylamino]-cyclohexyl}-carbamic Acid Tert-butyl Ester (4-{3-[4-(tert-Butoxycarbonylamino-methyl)-phenoxy]-5-[2-trifluoromethyl-4-(N-acetylhydroxycarbamimidoyl)-phenoxy]-benzoylamino}-cyclohexyl)-carbamic acid tert-butyl ester 0.35 g (0.47 mmol) was reduced using the procedure of Example 2(f) to afford 0.2 g of the required product. Percentage purity (LCMS): 70.0%, (M+1)=741.3+1.

k) N-(4-Amino-cyclohexyl)-3-(4-aminomethyl-phenoxy)-5-(4-carbamimidoyl-2-trifluoromethyl-phenoxy)-benzamide Using {4-[3-[4-(tert-Butoxycarbonylamino-methyl)-phenoxy]-5-(4-carbamimidoyl-2,6-difluoro-phenoxy)-benzoylamino]-cyclohexyl}-carbamic acid tert-butyl ester (0.3 g, 0.42 mmol) and following the procedure of Example 9(d) afforded 0.15 g of the required product. Percentage purity (HPLC): 99.55%, (LCMS): 96.52%. $^1$H NMR (DMSO-$d_6$): δ 1.44 (4H, m), 1.85 (2H, m), 1.95 (2H, m), 3.0 (1H, m), 3.6 (1H, m), 4.05 (2H, d), 7.08 (1H, s), 7.22 (2H, d), 7.30 (1H, d), 7.42 (2H, d), 7.52 (2H, d), 7.88 (3H, brs), 8.08 (1H, d), 8.22 (2H, brs), 8.28 (1H, s), 8.48 (1H, d), 9.45 (4H, d).

Example 89

N-(4-Amino-cyclohexyl)-3-(4-aminomethyl-2,6-difluoro-phenoxy)-5-(4-carbamimidoyl-phenoxy)-benzamide a) 3-(4-Cyano-2,6-difluoro-phenoxy)-5-hydroxy-benzoic Acid Ethyl Ester

Using 1.5 g (9.55 mmol) of 3,4,5-trifluoro-benzonitrile and 3,5-dihydroxy-benzoic acid ethyl ester (1.73 g, 9.55 mmol) and following the procedure of Example 42(a) afforded 1.2 g of the required product. $^1$H NMR (DMSO-$d_6$): δ 1.28 (3H, t), 4.27 (2H, q), 6.67 (1H, t), 6.92 (1H, s), 7.18 (1H, s), 8.08 (2H, d), 10.20 (1H, brs).

b) 3-[4-(tert-Butoxycarbonylamino-methyl)-2,6-difluoro-phenoxy]-5-hydroxy-benzoic Acid Ethyl Ester 0.9 g (2.82 mmol) of 3-(4-cyano-2,6-difluoro-phenoxy)-5-hydroxy-benzoic acid ethyl ester was dissolved in 50 ml of methanol and 1.23 g (5.64 mmol) of di-tert-butyl dicarbonate was slowly added at 0° C. Nickel chloride (60.0 mg, 0.28 mmol) and sodium borohydride (0.75 g, 19.74 mmol) were added at 0° C. at 10 min interval each. After complete addition the reaction mixture was stirred at RT for 30 min. Then 0.3 g (3.22 mmol) of diethylenetriamine was added during 15 min and finally reaction mixture was stirred for 2 h at RT. Reaction progress was monitored by TLC. The reaction mixture was concentrated under reduced pressure and partitioned between water (100 ml) and ethyl acetate (100 ml). The organic phase was washed with 2×100 ml solution of saturated sodium bicarbonate solution and then with 2×100 ml of saturated brine solution, dried over sodium sulphate and concentrated. The crude residue was purified by column chromatography using hexane-ethyl acetate (10:2) to afford 0.5 g of the required product. $^1$H NMR (DMSO-$d_6$): δ 1.25 (3H, t), 1.40 (9H, s), 4.18 (2H, d), 4.28 (214, q) 6.60 (1H, s), 6.84 (1H, s), 7.10 (1H, s), 7.18 (2H, d), 7.54 (1H, t), 10.2 (1H, brs).

c) 3-[4-(tert-Butoxycarbonylamino-methyl)-2,6-difluoro-phenoxy]-5-(4-cyano-phenoxy)-benzoic Acid Ethyl Ester Using 0.5 g (1.18 mmol) of 3-[4-(tert-butoxycarbonylamino-methyl)-2,6-difluoro-phenoxy]-5-hydroxy-benzoic acid ethyl ester and 4-fluorobenzonitrile (0.21 g, 1.77 mmol) and following the procedure of Example 42(b) afforded 0.3 g of the required product. $^1$H NMR (DMSO-$d_6$): δ 1.25 (3H, t), 1.42 (9H, s), 4.2 (2H, d), 4.28 (2H, q), 7.22 (6H, m), 7.32 (1H, s), 7.54 (1H, t), 7.90 (2H, d).

d) 3-[4-(tert-Butoxycarbonylamino-methyl)-2,6-difluoro-phenoxy]-5-(4-cyano-phenoxy)-benzoic Acid 1.1 g (2.09 mmol) of 3-[4-(tert-Butoxycarbonylamino-methyl)-2,6-difluoro-phenoxy]-5-(4-cyano-phenoxy)-benzoic acid ethyl ester was hydrolysed using the procedure of Example 5(b) to afford 0.8 g of the required product. $^1$H NMR (DMSO-$d_6$): δ 1.42 (9H, s), 4.22 (2H, d), 7.25 (7H, m), 7.52 (1H, m), 7.90 (2H, s), 12.4 (1H, brs).

e) {4-[3-[4-(tert-Butoxycarbonylamino-methyl)-2,6-difluoro-phenoxy]-5-(4-cyano-phenoxy)-benzoylamino]-cyclohexyl}-carbamic Acid Tert-butyl Ester 3-[4-(tert-butoxycarbonylamino-methyl)-2,6-difluoro-phenoxy]-5-(4-cyano-phenoxy)-benzoic acid (0.6 g, 1.2 mmol) and (4-amino-cyclohexyl)-carbamic acid tert-butyl ester (0.28 g, 1.3 mmol) and other reagents as described in Example 9(e) were used to afford 0.4 g of the required product. $^1$H NMR (DMSO-$d_6$): δ 1.24 (4H, m), 1.42 (18H, s), 1.8 (4H, m), 3.18 (1H, m), 3.64 (1H, m), 4.20 (2H, d), 6.74 (1H, d), 7.0 (1H, s), 7.16 (4H, m), 7.24 (1H, s), 7.38 (1H, s), 7.54 (1H, t), 7.88 (2H, d), 36 (1H, d).

f) (4-{3-[4-(tert-Butoxycarbonylamino-methyl)-2,6-difluoro-phenoxy]-5-[4-(N-hydroxycarbamimidoyl)-phenoxy]-benzoylamino}-cyclohexyl)-carbamic Acid Tert-butyl Ester Using {4-[3-[4-(tert-Butoxycarbonylamino-methyl)-2,6-difluoro-phenoxy]-5-(4-cyano-phenoxy)-benzoylamino]-cyclohexyl}-carbamic acid tert-butyl ester (0.53 g, 0.76 mmol) and following the procedure of Example 2(d) afforded 0.6 g of the required product. Percentage purity (LCMS): 74.23%, (M+1)=725.3+1.

g) (4-{3-[4-(tert-Butoxycarbonylamino-methyl)-2,6-difluoro-phenoxy]-5-[4-(N-acetylhydroxycarbamimidoyl)-phenoxy]-benzoylamino}-cyclohexyl)-carbamic Acid Tert-butyl Ester Using (4-{3-[4-(tert-Butoxycarbonylamino-methyl)-2,6-difluoro-phenoxy]-5-[4-(N-hydroxycarbamimidoyl)-phenoxy]-benzoylamino}-cyclohexyl)-carbamic acid tert-butyl ester (0.6 g, 0.82 mmol) and following the procedure of Example 2(e) afforded 0.6 g of the required product. Percentage purity (LCMS): 21.0%, (M+1)=667.2+1 (de-BOC product mass).

h) {4-[3-[4-(tert-Butoxycarbonylamino-methyl)-2,6-difluoro-phenoxy]-5-(4-carbamimidoyl-phenoxy)-benzoylamino]-cyclohexyl}-carbamic Acid Tert-butyl Ester (4-{3-[4-(tert-butoxycarbonylamino-methyl)-2,6-difluoro-phenoxy]-5-[4-(N-acetylhydroxycarbamimidoyl)-phenoxy]-benzoylamino}-cyclohexyl)-carbamic acid tert-butyl ester 0.6 g (0.78 mmol) was reduced using the procedure of Example 2(f) to afford 0.35 g of the required product. Percentage purity (LCMS): 75.0%, (M+1)=709.3+1.

i) N-(4-Amino-cyclohexyl)-3-(4-aminomethyl-2,6-difluoro-phenoxy)-5-(4-carbamimidoyl-phenoxy)-benzamide Using {4-[3-[4-(tert-Butoxycarbonylamino-methyl)-2,6-difluoro-phenoxy]-5-(4-carbamimidoyl-phenoxy)-benzoylamino]-cyclohexyl}-carbamic acid tert-butyl ester (0.35 g, 0.49 mmol) and following the procedure of Example 9(d) afforded 0.15 g of the required product. Percentage purity (HPLC): 98.72%, (LCMS): 96.32%. $^1$H NMR (DMSO-$d_6$): δ 1.38 (4H, m), 1.85 (2H, m), 1.95 (2H, m), 2.98 (1H, m), 3.65 (1H, m), 4.14 (2H, d), 6.98 (1H, t), 7.22 (3H, m), 7.38 (1H, s), 7.50 (2H, d), 7.90 (5H, m), 8.45 (3H, m), 9.30 (4H, d).

Example 90

1-[3,5-Bis-(4-carbamimidoyl-phenoxy)-benzoyl]-piperidine-4-carboxylic Acid

Intermediates (a) and (b) are the same as in Example 26.

c) 1-[3,5-Bis-(4-cyano-phenoxy)-benzoyl]-piperidine-4-carboxylic Acid Ethyl Ester Following the procedure of Example 5(c) 3,5-bis-(4-cyano-phenoxy)-benzoic acid 0.6 g (1.68 mmol) and piperidine-4-carboxylic acid ethyl ester (0.31 g, 2.02 mmol) were used to afford 0.54 g of the required product. $^1$H NMR (DMSO-$d_6$): δ 1.18 (3H, t), 1.5 (2H, m), 1.82 (2H, m), 2.6 (1H, m), 2.90 (1H, m), 3.12 (1H, m), 3.52 (1H, m), 4.08 (2H, q), 4.25 (1H, m), 6.96 (2H, d), 7.06 (1H, t), 7.26 (4H, d), 7.88 (4H, d).

d) 1-[3,5-Bis-(4-cyano-phenoxy)-benzoyl]-piperidine-4-carboxylic Acid 0.48 g (0.96 mmol) of 1-[3,5-bis-(4-cyano-phenoxy)-benzoyl]-piperidine-4-carboxylic acid ethyl ester was hydrolysed using the procedure of Example 5(b) to afford 0.4 g of the required product. $^1$H NMR (DMSO-$d_6$): δ 1.28 (2H, m), 1.5 (2H, m), 1.82 (2H, m), 3.10 (1H, m), 3.58 (1H, m), 4.24 (1H, m), 6.98 (1H, d), 7.16 (2H, m), 7.25 (4H, m), 7.88 (4H, m), 12.5 (1H, brs).

e) 1-{3,5-Bis-[4-(N-hydroxycarbamimidoyl)-phenoxy]-benzoyl}-piperidine-4-carboxylic Acid Using 1-[3,5-Bis-(4-cyano-phenoxy)-benzoyl]-piperidine-4-carboxylic acid (0.4 g, 0.85 mmol) and following the procedure of Example 2(d) afforded 0.4 g of the required product. Percentage purity (LCMS): 95.0%, (M+1)=531.0+1.

f) 1-{3,5-Bis-[4-(carbamimidoyl)-phenoxy]-benzoyl}-piperidine-4-carboxylic Acid

1-{3,5-Bis-[4-(N-hydroxycarbamimidoyl)-phenoxy]-benzoyl}-piperidine-4-carboxylic acid 0.4 g (0.74 mmol) was reduced using the procedure of Example 2(f) to afford 0.1 g of the required product. Percentage purity (HPLC): 95.33%, (LCMS): 98.43%. $^1$H NMR (DMSO-$d_6$): δ 1.48 (2H, m), 1.85 (2H, m), 2.92 (1H, m), 3.10 (1H, m), 3.58 (1H, m), 4.25 (2H, m), 6.92 (2H, d), 7.0 (1H, t), 7.32 (4H, d), 7.88 (4H, d), 9.12 (4H, brs), 9.28 (4H, brs).

Example 91

4-{1-[3,5-Bis-(4-carbamimidoyl-phenoxy)-benzoyl]-piperidin-4-yl}-butyric Acid

Intermediates (a) and (b) are the same as in Example 26.

c) 4-{1-[3,5-Bis-(4-cyano-phenoxy)-benzoyl]-piperidin-4-yl}-butyric Acid Ethyl Ester Following the procedure of Example 5(c) 3,5-bis-(4-cyano-phenoxy)-benzoic acid 1.2 g (3.37 mmol) and 4-piperidin-4-yl-butyric acid ethyl ester (0.68 g, 3.7 mmol) were used to afford 0.9 g of the required product. $^1$H NMR (DMSO-$d_6$): δ 1.20 (4H, m), 1.52

(5H, m), 1.70 (1H, m), 2.3 (2H, t), 2.68 (1H, m), 3.6 (3H, s), 4.4 (2H, q), 4.25 (1H, m), 6.95 (2H, d), 7.04 (1H, t), 7.25 (4H, d), 7.88 (4H, d).

d) 4-(1-{3,5-Bis-[4-(N-hydroxycarbamimidoyl)-phenoxy]-benzoyl}-piperidin-4-yl)-butyric Acid Ethyl Ester Using 4-{1-[3,5-Bis-(4-cyano-phenoxy)-benzoyl]-piperidin-4-yl}-butyric acid ethyl ester (1.0 g, 1.91 mmol) and following the procedure of Example 2(d) afforded 1.1 g of the required product. Percentage purity (LCMS): 28.2%, (M+1)= 589.2+1.

e) 4-(1-{3,5-Bis-[4-(N-acetylhydroxycarbamimidoyl)-phenoxy]-benzoyl}-piperidin-4-yl)-butyric Acid Ethyl Ester Using 4-(1-{3,5-bis-[4-(N-hydroxycarbamimidoyl)-phenoxy]-benzoyl}-piperidin-4-yl)-butyric acid ethyl ester (1.0 g, 1.65 mmol) and following the procedure of Example 2(e) afforded 0.6 g of the required product. Percentage purity (LCMS): 38.0%, (M+1)=673.2+1.

f) 4-(1-{3,5-Bis-[4-(carbamimidoyl)-phenoxy]-benzoyl}-piperidin-4-yl)-butyric Acid Ethyl Ester 4-(1-{3,5-Bis-[4-(N-acetylhydroxycarbamimidoyl)-phenoxy]-benzoyl}-piperidin-4-A-butyric acid ethyl ester 0.6 g (0.87 mmol) was reduced using the procedure of Example 2(f) to afford 0.14 g of the required product. Percentage purity (HPLC): 90.04%, (LCMS): 81.94%. $^1$H NMR (DMSO-d$_6$): δ 1.20 (2H, m), 1.52 (4H, m), 1.70 (1H, m), 2.30 (2H, t), 2.7 (2H, m), 3.0 (1H, m), 3.6 (3H, s), 4.4 (2H, m), 6.9 (2H, s), 7.0 (1H, s), 7.32 (4H, d), 7.88 (4H, d), 9.25 (8H, brs).

Example 92

4-[3-(4-Amino-cyclohexylcarbamoyl)-5-(4-carbamimidoyl-phenoxy)-phenoxy]-benzoic Acid Intermediates (a)-(c) are the same as in Example 49.

d) {4-[3-(4-Cyano-phenoxy)-5-(4-formyl-phenoxy)-benzoylamino]-cyclohexyl}-carbamic acid tert-butyl ester Using 3.0 g (6.6 mmol) of {4-[3-(4-cyano-phenoxy)-5-hydroxy-benzoylamino]-cyclohexyl}-carbamic acid tert-butyl ester and 4-fluorobenzaldehyde (1.66 g, 13.3 mmol) and following the procedure of Example 42(b) afforded 2.2 g of the required product. $^1$H NMR (DMSO-d$_6$): δ 1.25 (4H, m), 1.4 (9H, s), 1.8 (4H, m), 3.18 (1H, m), 3.68 (1H, m), 6.75 (1H, d), 7.25 (4H, m), 7.50 (2H, s), 7.82 (2H, d), 7.95 (2H, d), 8.38 (1H, d), 9.94 (1H, s).

e) 4-[3-(4-tert-Butoxycarbonylamino-cyclohexylcarbamoyl)-5-(4-cyano-phenoxy)-phenoxy]-benzoic Acid 0.5 g (0.9 mmol) of {4-[3-(4-cyano-phenoxy)-5-(4-formyl-phenoxy)-benzoyl-amino]-cyclohexyl}-carbamic acid tert-butyl ester was dissolved in 15 ml of THF and 0.43 g (2.7 mmol) of potassium permanganate, dissolved in 8 ml of water, was added to THF solution at 10° C. during 10 min. The reaction mixture stirred over night at RT. Reaction progress was monitored by TLC. Reaction mixture was filtered through celite and washed with THF and thus obtained mother liquor was concentrated under vacuo. Product was crystallized with ethyl acetate to afford 0.25 g of the required product. $^1$H NMR (DMSO-d$_6$): δ 1.25 (4H, m), 1.36 (9H, s), 1.78 (4H, m), 3.18 (1H, m), 3.66 (1H, m), 6.75 (1H, d), 6.94 (3H, m), 7.18 (2H, d), 7.36 (2H, s), 7.86 (4H, d), 8.38 (1H, d).

f) 4-[3-(4-tert-Butoxycarbonylamino-cyclohexylcarbamoyl)-5-(4-cyano-phenoxy)-phenoxy]-benzoic Acid Benzyl Ester 0.6 g (1.05 mmol) of 4-[3-(4-tert-butoxycarbonylamino-cyclohexylcarbamoyl)-5-(4-cyano-phenoxy)-phenoxy]-benzoic acid was dissolved in 5 ml of DMF. At 0° C. 50 mg (0.35 mmol) of potassium carbonate followed by 45 mg (0.26 mmol) benzylbromide were added and the reaction mixture was stirred for 4 h at RT. Reaction progress was monitored by TLC. Upon completion of the reaction the contents were diluted with 50 ml of ice-water and extracted with 3×50 ml of ethyl acetate, dried over anhydrous sodium sulphate and concentrated under vacuo. Thus obtained crude residue was purified by column chromatography using 60-120 mesh silica-gel and eluted with ethylacetate:hexane (1:9) to give 0.38 mg of the required product. $^1$H NMR (DMSO-d$_6$): δ 1.25 (4H, m), 1.4 (9H, s), 1.8 (4H, m), 3.18 (1H, m), 3.66 (1H, m), 5.36 (2H, s), 6.76 (1H, d), 7.22 (5H, m), 7.46 (7H, m), 7.88 (2H, d), 8.05 (2H, d), 8.36 (1H, d).

g) 4-{3-(4-tert-Butoxycarbonylamino-cyclohexylcarbamoyl)-5-[4-(N-hydroxycarbamimidoyl)-phenoxy]phenoxy}-benzoic Acid Benzyl Ester Using 4-[3-(4-tert-Butoxycarbonylamino-cyclohexylcarbamoyl)-5-(4-cyano-phenoxy)-phenoxy]-benzoic acid benzyl ester (0.4 g, 0.61 mmol) and following the procedure of Example 2(d) afforded 0.39 g of the required product. Percentage purity (LCMS): 52.0%, (M+1)=694.3+1.

h) 4-{3-(4-tert-Butoxycarbonylamino-cyclohexylcarbamoyl)-5-[4-(N-acetyl-hydroxycarbamimidoyl)-phenoxy]-phenoxy}-benzoic Acid Benzyl Ester Using 4-{3-(4-tert-Butoxycarbonylamino-cyclohexylcarbamoyl)-5-[4-(N-hydroxycarbamimidoyl)-phenoxy]-phenoxy}-benzoic acid benzyl ester (0.39 g, 0.56 mmol) and following the procedure of Example 2(e) afforded 0.41 g of the required product. Percentage purity (LCMS): 53.0%, (M+1)=680.5+1 (Boc-acid mass).

i) 4-[3-(4-tert-Butoxycarbonylamino-cyclohexylcarbamoyl)-5-(4-carbamimidoyl-phenoxy)-phenoxy]-benzoic Acid 4-{3-(4-tert-butoxycarbonylamino-cyclohexylcarbamoyl)-5-[4-(N-acetylhydroxy-carbamimidoyl)-phenoxy]-phenoxy}-benzoic acid benzyl ester 0.41 g (0.56 mmol) was reduced using the procedure of Example 2(f) to afford 0.13 g of the required product. Percentage purity (LCMS): 74.1%, (M+1)=587.1+1.

j) N-(4-Amino-cyclohexyl)-3,5-bis-(4-carbamimidoyl-phenoxy)-benzamide

Using 4-[3-(4-tert-Butoxycarbonylamino-cyclohexylcarbamoyl)-5-(4-carbamimidoyl-phenoxy)-phenoxy]-benzoic acid (0.13 g, 0.22 mmol) and following the procedure of Example 9(d) afforded 35 mg of the required product. Percentage purity (HPLC): 97.00%, (LCMS): 93.86%. NMR (DMSO-d$_6$): δ 1.40 (4H, m), 1.92 (4H, m), 3.02 (1H, m), 3.70 (1H, m), 7.02 (1H, s), 7.15 (2H, d), 7.35 (2H, d), 7.45 (2H, d), 7.76 (1H, brs), 7.88 (4H, dd), 8.40 (1H, d), 8.88 (2H, brs), 9.25 (2H, brs).

Example 93

4-[3-(4-Amino-cyclohexylcarbamoyl)-5-(4-carbamimidoyl-phenoxy)-phenoxy]-benzoic Acid Ethyl Ester Intermediates (a)-(c) are the same as in Example 49.

d) 4-[3-(4-tert-Butoxycarbonylamino-cyclohexylcarbamoyl)-5-(4-cyano-phenoxy)-phenoxy]-benzoic Acid Ethyl Ester Using 2.0 g (4.4 mmol) of {4-[3-(4-cyano-phenoxy)-5-hydroxy-benzoylamino]-cyclohexyl}-carbamic acid tert-butyl ester and 4-fluoro-benzoic acid ethyl ester (1.2 g, 6.6 mmol) and following the procedure of Example 42(b) afforded 1.8 g of the required product. $^1$H NMR (DMSO-d$_6$): δ 1.35 (4H, m), 1.4 (9H, s), 1.8 (4H, m), 3.2 (1H, m), 3.68 (1H, m), 4.30 (2H, q), 6.75 (1H, d), 7.20 (5H, m), 7.48 (2H, d), 7.88 (2H, d), 8.00 (2H, d), 8.36 (1H, d).

e) 4-[3-(4-Amino-cyclohexylcarbamoyl)-5-(4-ethoxycarbonimidoyl-phenoxy)-phenoxy]-benzoic Acid Ethyl Ester Using 4-[3-(4-tert-Butoxycarbonylamino-cyclohexylcarbamoyl)-5-(4-cyano-phenoxy)-phenoxy]-benzoic acid ethyl ester (0.6 g, 1.0 mmol) and following the procedure of Example 1(d) afforded 0.55 g of the required product. Percentage purity (LCMS): 96.0%, (M+1)=545.4+1.

f) 4-[3-(4-Amino-cyclohexylcarbamoyl)-5-(4-carbamimidoyl-phenoxy)-phenoxy]-benzoic Acid Using 4-[3-(4-Amino-cyclohexylcarbamoyl)-5-(4-ethoxycarbonimidoyl-phenoxy)-phenoxy]-benzoic acid (0.45 g, 0.82 mmol) and following the procedure of Example 1(e) afforded 0.25 g of the required product. Percentage purity (HPLC): 97.88%, (LCMS): 95.45%. $^1$H NMR (DMSO-d$_6$): δ 1.45 (4H, m), 1.95 (4H, m), 3.0 (2H, m), 3.4 (1H, m), 4.34 (2H, m), 7.1 (1H, s), 7.18 (2H, d), 7.3 (2H, d), 7.5 (2H, d) 7.9 (4H, m), 8.0 (2H, d), 8.4 (1H, m), 9.00 (2H, brs), 9.26 (2H, brs).

Example 94

N-(4-Amino-cyclohexyl)-3-(4-carbamimidoyl-phenoxy)-5-(4-carbamoyl-phenoxy)-benzamide Intermediates (a)-(e) are the same as in Example 92.

f) {4-[3-(4-Carbamoyl-phenoxy)-5-(4-cyano-phenoxy)-benzoylamino]-cyclo-hexyl}-carbamic Acid Tert-butyl Ester 0.6 g (1.05 mmol) of 4-[3-(4-tert-butoxycarbonylamino-cyclohexylcarbamoyl)-5-(4-cyano-phenoxy)-phenoxy]-benzoic acid was dissolved in 15 ml of THF. At −10° C. 0.18 ml (1.57 mmol) of N-methylmorpholine was added. The reaction mixture was stirred for 15 min at 0° C. 0.14 ml (1.36 mmol) of tert-butylchloroformate was added and the reaction mixture was stirred for 1 h at RT. Further 6.0 ml of 30% of ammonia solution was added during 10 min at 0° C. and reaction progress was monitored by TLC. Upon completion of the reaction the contents were diluted with 50 ml ethyl acetate. Organic layer was separated and Washed with 3×50 ml saturated sodium bicarbonate solution, dried over anhydrous sodium sulphate and concentrated under reduced pressure to afford 0.4 g of the required product. Percentage purity (LCMS): 60.0%, (M+1)=570.2.

g) 4-[3-(4-Amino-cyclohexylcarbamoyl)-5-(4-carbamoyl-phenoxy)-phenoxy]-benzimidic Acid Ethyl Ester Using {4-[3-(4-carbamoyl-phenoxy)-5-(4-cyano-phenoxy)-benzoylamino]-cyclohexyl}-carbamic acid tert-butyl ester (0.45 g, 0.79 mmol) and following the procedure of Example 1(d) afforded 0.48 g of the required product. Percentage purity (LCMS): 77.0%, (M+1)=516.1+1.

h) N-(4-Amino-cyclohexyl)-3-(4-carbamimidoyl-phenoxy)-5-(4-carbamoyl-phenoxy)-benzamide Using 4-[3-(4-Amino-cyclohexylcarbamoyl)-5-(4-carbamoyl-phenoxy)-phenoxy]-benzimidic acid ethyl ester (0.48 g, 0.93 mmol) and following the procedure of Example 1(e) afforded 0.055 g of the required product. Percentage purity (HPLC): 97.22%, (LCMS): 93.33%. $^1$H NMR (DMSO-d$_6$): δ 1.45 (4H, m), 1.90 (4H, m), 3.0 (1H, m), 3.7 (1H, m), 7.0 (1H, s), 7.15 (2H, d) 7.32 (3H, d), 7.45 (2H, d), 7.88 (6H, m), 8.40 (1H, d), 8.88 (2H, brs), 9.25 (2H, brs).

Example 95

4-[3,5-Bis-(4-carbamimidoyl-phenoxy)-benzoylamino]-cyclohexanecarboxylic Acid Ethyl Ester Intermediates (a) and (b) are the same as in Example 26.

c) 4-[3,5-Bis-(4-cyano-phenoxy)-benzoylamino]-cyclohexanecarboxylic Acid Ethyl Ester Following the procedure of Example 9(e) 3,5-bis-(4-cyano-phenoxy)-benzoic acid 1.0 g (2.6 mmol) and 4-amino-cyclohexanecarboxylic acid ethyl ester (0.48 g, 2.6 mmol) were used to afford 0.5 g of the required product. $^1$H NMR (DMSO-d$_6$): δ 1.34 (5H, m), 1.41 (5H, m), 1.92 (4H, m), 2.1 (1H, t), 3.81 (1H, m), 4.12 (2H, q), 7.04 (4H, dd), 7.51 (2H, s), 7.89 (3H, d), 8.41 (1H, d). Percentage purity (HPLC): 89.3%.

d) 4-{3,5-Bis-[4-(N-hydroxycarbamimidoyl)-phenoxy]-benzoylamino}-cyclo-hexanecarboxylic Acid Ethyl Ester 0.6 g (1.17 mmol) of 4-[3,5-Bis-(4-cyano-phenoxy)-benzoylamino]-cyclohexane-carboxylic acid ethyl ester was dissolved in 30 ml of ethanol and 0.2 ml (9.4 mmol) of 50% aqueous solution of hydroxylamine was added at RT during 5 min. The reaction mixture stirred for 6 h at 80° C. Reaction progress was monitored by TLC. Reaction mixture was cooled to RT and solvent was removed under reduced pressure and thus obtained crude product, yield 0.6 g, was subjected to the next step without further purification. Percentage purity (HPLC): 80%, (LCMS): 83.3%, (M+1)=575.23+1.

e) 4-{3,5-Bis-[4-(N-acetylhydroxycarbamimidoyl)-phenoxy]-benzoylamino}-cyclohexanecarboxylic Acid Ethyl Ester Using 4-{3,5-bis-[4-(N-hydroxycarbamimidoyl)-phenoxy]-benzoylamino}-cyclohexanecarboxylic acid ethyl ester (0.6 g, 1.14 mmol) and following the procedure of Example 2(e) afforded 0.5 g of the required product. Percentage purity (LCMS): 55.3%, (M+1)=659.3+1.

f) 4-[3,5-Bis-(4-carbamimidoyl-phenoxy)-benzoylamino]-cyclohexanecarboxylic Acid Ethyl Ester Using 4-{3,5-bis-[4-(N-acetylhydroxycarbamimidoyl)-phenoxy]-benzoylamino}-cyclohexanecarboxylic acid ethyl ester (0.45 g, 0.68 mmol) and following the procedure of Example 2(f) afforded 0.25 g of the required product. Percentage purity (HPLC): 92.31%, (LCMS): 91.81%. $^1$H NMR (DMSO-$d_6$): δ 1.1 (3H, t), 1.31 (4H, m), 1.90 (4H, m), 2.21 (1H, m), 3.0 (1H, m), 4.12 (2H, q), 7.21 (7H, dd), 7.90 (4H, d), 8.52 (1H, d), 9.21 (8H, d).

Example 96

3,5-Bis-(4-carbamimidoyl-phenoxy)-N-(4-hydroxy-cyclohexyl)-benzamide

Intermediates (a) and (b) are the same as in Example 26.

c) 3,5-Bis-(4-cyano-phenoxy)-N-(4-hydroxy-cyclohexyl)-benzamide

Following the procedure of Example 9(e) 3,5-bis-(4-cyano-phenoxy)-benzoic acid 0.1 g (0.28 mmol) and 4-amino-cyclohexanol (0.046 g, 0.42 mmol) were used to afford 0.05 g of the required product. Percentage purity (LCMS): 92.3%, (M+1)=453.1+1.

d) 3,5-Bis-[4-(N-hydroxycarbamimidoyl)-phenoxy]-N-(4-hydroxy-cyclohexyl)-benzamide Using 3,5-bis-(4-cyano-phenoxy)-N-(4-hydroxy-cyclohexyl)-benzamide (0.5 g, 1.10 mmol) and following the procedure of Example 95(d) afforded 0.45 g of the required product. Percentage purity (LCMS): 81.1%, (M+1)=519.3+1.

e) 3,5-Bis-[4-(N-acetylhydroxycarbamimidoyl)-phenoxy]-N-(4-hydroxy-cyclohexyl)-benzamide Using 3,5-bis-[4-(N-hydroxycarbamimidoyl)-phenoxy]-N-(4-hydroxy-cyclohexyl)-benzamide (0.5 g, 0.96 mmol) and following the procedure of Example 2(e) afforded 0.40 g of the required product. Percentage purity (LCMS): 49.2%, (M+1)=603.3+1.

f) 3,5-Bis-(4-carbamimidoyl-phenoxy)-N-(4-hydroxy-cyclohexyl)-benzamide

Using 3,5-bis-[4-(N-acetylhydroxycarbamimidoyl)-phenoxy]-N-(4-hydroxy-cyclohexyl)-benzamide (0.4 g, 0.66 mmol) and following the procedure of Example 2(f) afforded 0.2 g of the required product. Percentage purity (1-IPLC): 97.19%, (LCMS): 93.81%. $^1$H NMR (DMSO-$d_6$): δ 1.21 (4H, m), 1.89 (4H, m), 3.11 (1H, m), 3.7 (1H, m), 7.11 (1H, t), 7.45 (4H, d), 7.51 (2H, d), 7.88 (4H, d), 8.40 (1H, d), 9.4 (8H, d).

Example 97

N-(4-Amino-cyclohexyl)-3-(4-aminomethyl-phenoxy)-5-(6-amino-pyridin-3-yloxy)-benzamide Intermediates (a) and (e) are the same as in Example 84.

f) (4-{3-(6-Nitro-pyridin-3-yloxy)-5-[4-(tert-butoxycarbonylamino-methyl)-phenoxy]-benzoylamino}-cyclohexyl)-carbamic Acid Tert-butyl Ester Following the procedure of Example 69(b) (4-{3-[4-(tert-Butoxycarbonylamino-methyl)-phenoxy]-5-hydroxy-benzoylamino}-cyclohexyl)-carbamic acid tert-butyl ester 0.4 g (0.72 mmol) and 5-bromo-2-nitro-pyridine (0.17 g, 0.86 mmol) were used to afford 0.3 g of the required product. $^1$H NMR (DMSO-$d_6$): δ 1.31 (18H, d), 1.8 (4H, d), 3.20 (2H, m), 3.8 (2H, m), 4.1 (2H, d), 7.35 (3H, d), 7.4 (3H, m), 7.9 (1H, d), 8.35 (2H, d), 8.5 (1H, s).

g) (4-{3-(6-Amino-pyridin-3-yloxy)-5-[4-(tert-butoxycarbonylamino-methyl)-phenoxy]-benzoylamino}-cyclohexyl)-carbamic Acid Tert-butyl Ester Following the procedure of Example 62(e) (4-{3-(6-Nitro-pyridin-3-yloxy)-5-[4-(tert-butoxycarbonylamino-methyl)-phenoxy]-benzoylamino}-cyclohexyl)-carbamic acid tert-butyl ester 0.3 g (0.44 mmol) was used to afford 0.2 g of the required product. Percentage purity (LCMS): 68.4%, (M+1)= 647.3+1.

h) N-(4-Amino-cyclohexyl)-3-(4-aminomethyl-phenoxy)-5-(6-amino-pyridin-3-yloxy)-benzamide Using (4-{3-(6-Amino-pyridin-3-yloxy)-5-[4-(tert-butoxycarbonylamino-methyl)-phenoxy]-benzoylamino}-cyclohexyl)-carbamic acid tert-butyl ester (0.2 g, 0.30 mmol) and following the procedure of Example 9(d) afforded 0.15 g of the required product. Percentage purity (HPLC): 95.31%, (LCMS): 97.4%. $^1$H NMR (DMSO-$d_6$): 1.28 (4H, m), 1.91 (4H, dd), 2.91 (1H, m), 3.8 (1H, m), 4.1 (2H, d), 6.91 (2H, m), 7.21 (4H, m), 7.51 (2H, d), 7.91 (5H, m), 8.3 (3H, brs), 8.45 (1H, d).

Example 98

4-[3-[4-(2-Amino-ethyl)-piperidine-1-carbonyl]-5-(4-aminomethyl-phenoxy)-phenoxy]-benzamidine Intermediates (a) and (b) are the same as in Example 49.

c) (2-{1-[3-(4-Cyano-phenoxy)-5-hydroxy-benzoyl]-piperidin-4-yl}-ethyl)-carbamic Acid Tert-butyl Ester Following the procedure of Example 9(e) 3-(4-cyano phenoxy)-5-hydroxy benzoic acid 1.6 g (6.3 mmol) and (2-piperidin-4-yl-ethyl)-carbamic acid tert-butyl ester (1.43 g, 6.27 mmol) were used to afford 2.0 g of the required product. Percentage purity (LCMS): 79.6%, (M+1)=465.2+1.

d) [2-(1-{3-[4-(tert-butoxycarbonylamino-methyp-phenoxy]-5-hydroxy-benzoyl]-piperidin-4-yl)-ethyl}-carbamic Acid Tert-butyl Ester Nickelchloride (0.1 g, 0.4 mmols) and Boc-anhydride (1.9 g, 0.8 mmol) were added to a stirred solution of (2-{1-[3-(4-cyano-phenoxy)-5-hydroxy-benzoyl]-piperidin-4-yl}- ethyl)-carbamic acid tert-butyl ester (2.0 g, 4.3 mmol) dissolved in methanol (50 ml) at 0° C. Sodiumborohydride (1.1 g, 30.1 mmol) was added in portions over 30 min at 0° C. The obtained reaction mixture was stirred at RT for 2 h. After reaction completion solvent was evaporated under vacuo. Thus obtained residue was partitioned between ethylacetate (150 ml) and saturated solution of sodiumbicarbonate (75 ml) and stirred to get a clear layer. Organic layer was separated and further washed with saturated aqueous solution of sodiumbicarbonate and dried over anhydrous sodium sulphate. Thus obtained crude product was subjected to column chromatography using silica gel as an absorbent and eluted using ethylacetate:hexane (20:80) mixture to afford 1.2 g of the required product. Percentage purity (LCMS): 68.2%, (M+1)= 569.1+1.

e) (2-{1-[3-[4-(tert-Butoxycarbonylamino-methyl)-phenoxy]-5-(4-cyano-phenoxy)-benzoyl]-piperidin-4-yl}-ethyl)-carbamic Acid Tert-butyl Ester Using 1.2 g (2.1 mmol) of [2-(1-{3-[4-(tert-Butoxycarbonylamino-methyl)-phenoxy]-5-hydroxy-benzoyl}-piperidin-4-yl)-ethyl]carbamic acid tert-butyl ester and 4-fluorobenzonitrile (0.5 g, 4.2 mmol) and following the procedure of Example 42(b) afforded 0.610 g of the required product. Percentage purity (LCMS): 89.1%, (M+1)=670.3+1.

f) [2-(1-{3-[4-(tert-Butoxycarbonylamino-methyl)-phenoxy]-5-[4-(N-hydroxy-carbamimidoyl)-phenoxy]-benzoyl}-piperidin-4-yl)-ethyl]-carbamic Acid Tert-butyl Ester Using (2-{1-[3-[4-(tert-butoxycarbonylamino-methyl)-phenoxy]-5-(4-cyano-phenoxy)-benzoyl]-piperidin-4-yl}-ethyl)-carbamic acid tert-butyl ester (0.8 g, 1.19 mmol) and following the procedure of Example 95(d) afforded 0.76 g of the required product. Percentage purity (LCMS): 69.14%, (M+1)=703.2+1.

g) [2-(1-{3-[4-(tert-Butoxycarbonylamino-methyl)-phenoxy]-5-[4-(N-acetyl-hydroxycarbamimidoyl)-phenoxy]-benzoyl}-piperidin-4-yl)-ethyl]-carbamic Acid Tert-butyl Ester Using [2-(1-{3-[4-(tert-Butoxycarbonylamino-methyl)-phenoxy]-5-[4-(N-hydroxy-carbamimidoyl)-phenoxy]-benzoyl}-piperidin-4-yl)-ethyl]-carbamic acid tert-butyl ester (0.75 g, 1.07 mmol) and following the procedure of Example 2(e) afforded 0.80 g of the required product. Percentage purity (LCMS): 73.97%, (M+1)=745.2+1.

h) (2-{1-[3-[4-(tert-Butoxycarbonylamino-methyl)-phenoxy]-5-(4-carbamimidoyl-phenoxy)-benzoyl]-piperidin-4-yl}-ethyl)-carbamic Acid Tert-butyl Ester

[2-(1-{3-[4-(tert-Butoxycarbonylamino-methyl)-phenoxy]-5-[4-(N-acetyl hydroxycarbamimidoyl)-phenoxy]-benzoyl}-piperidin-4-yl)-ethyl]-carbamic acid tert-butyl ester 0.8 g (1.07 mmol) was reduced using the procedure of Example 2(f) to afford 0.70 g of the required product. Percentage purity (LCMS): 92.8%, (M+1)=687.1+1.

i) 4-[3-[4-(2-Amino-ethyl)-piperidine-1-carbonyl]-5-(4-aminomethyl-phenoxy)-phenoxy]-benzamidine Using (2-{1-[3-[4-(tert-Butoxycarbonylamino-methyp-phenoxy]-5-(4-carbamimidoyl-phenoxy)-benzoyl]-piperidin-4-yl}-ethyl)-carbamic acid tert-butyl ester (0.70 g, 1.02 mmol) and following the procedure of Example 9(d) afforded 0.20 g of the required product. Percentage purity (HPLC): 98.22%, (LCMS): 95.01%. $^1$H NMR (DMSO-d$_6$): δ 1.21 (6H, m), 2.82 (4H, s), 3.02 (2H, m), 3.5 (2H, m), 4.52 (1H, m), 6.81 (3H, d), 7.21 (4H, dd), 7.51 (2H, d), 7.88 (2H, d).

Example 99

N-(4-Amino-cyclohexyl)-3-(4-carbamimidoyl-phenoxy)-5-(4-methylcarbamoyl-phenoxy)-benzamide Intermediates (a)-(e) are the same as in Example 92.

f) {4-[3-(4-Cyano-phenoxy)-5-(4-methylcarbamoyl-phenoxy)-benzoylamino]-cyclohexyl}-carbamic Acid Tert-butyl Ester 0.7 g (1.22 mmol) of 4-[3-(4-tert-butoxycarbonylamino-cyclohexylcarbamoyl)-5-(4-cyano-phenoxy)-phenoxy]-benzoic acid was dissolved in 10 ml of DMF. At 0° C. 0.125 mg (1.83 mmol) of N-methylaminehydrochloride, 0.37 mg (1.96 mmol) of EDC, 0.2 mg (1.47 mmol) of HOBt and 0.49 ml (2.69 mmol) of DIPEA were added and the resulting reaction mixture was stirred overnight at RT. Reaction progress was monitored by TLC. After reaction completion, mixture was diluted with ice-water and thus obtained white solid was filtered off and washed with water and then with hexane. Thus obtained crude product was subjected to coloumn chromatography using silica-gel as an adsorbent and the product was eluted with 50-70% of ethylacetate:hexane mixture to afford 0.45 g of the required product. Percentage purity (LCMS): 91.9%, (M+1)=484.1+1. $^1$H NMR (DMSO-d$_6$): δ 1.21 (4H, d), 1.31 (9H, s), 1.92 (4H, s), 2.81 (3H, d), 3.11 (1H, s), 3.71 (1H, s), 6.81 (1H, s), 7.35 (61-1, d), 7.91 (4H, s), 8.32 (2H, d)

g) {4-[3-[4-(N-Hydroxycarbamimidoyl)-phenoxy]-5-(4-methylcarbamoyl-phenoxy)-benzoylamino]-cyclohexyl}-carbamic Acid Tert-butyl Ester Using {4-[3-(4-Cyano-phenoxy)-5-(4-methylcarbamoyl-phenoxy)-benzoylamino]-cyclohexyl}-carbamic acid tert-butyl ester (0.61 g, 1.04 mmol) and following the procedure of Example 95(d) afforded 0.56 g of the required product. Percentage purity (LCMS): 89.6%, (M+1)=617.1+1.

h) {4-[3-(4-Carbamimidoyl-phenoxy)-5-(4-methyl-carbamoyl-phenoxy)-benzoylamino]-cyclohexyl}-carbamic Acid Tert-butyl Ester Using 4{4-[3-[4-(N-Hydroxycarbamimidoyl)-phenoxy]-5-(4-methylcarbamoyl-phenoxy)-benzoylamino]-cyclohexyl}-carbamic acid tert-butyl ester (0.56 g, 0.90 mmol) and following the procedure of Example 2(e) afforded 0.53 g of the required product. (LCMS): 91.7%, (M+1)=659.1+1.

i) {4-[3-(4-Carbamimidoyl-phenoxy)-5-(4-methyl-carbamoyl-phenoxy)-benzoyl-amino]-cyclohexyl}-carbamic acid tert-butyl ester Using {4-[3-[4-(N-acetylhydroxycarbamimidoyl)-phenoxy]-5-(4-methylcarbamoyl-phenoxy)-benzoylamino]-cyclohexyl}-carbamic acid tert-butyl ester (0.53 g, 0.80 mmol) and following the procedure of Example 2(f) afforded 0.25 g of the required product. (LCMS): 94.5%. (M+1)=601.1+1.

j) N-(4-Amino-cyclohexyl)-3-(4-carbamimidoyl-phenoxy)-5-(4-methylcarbamoyl-phenoxy)-benzamide Using {4-[3-(4-Carbamimidoyl-phenoxy)-5-(4-methyl-carbamoyl-phenoxy)-benzoylamino]-cyclohexyl}-carbamic acid tert-butyl ester (0.50 g, 0.83 mmol) and following the procedure of Example 9(d) afforded 0.40 g of the required product. Percentage purity (HPLC): 98.72%, (LCMS): 97.22%. $^1$H NMR (DMSO-$d_o$): δ 1.31 (4H, m), 1.92 (4H, d), 2.81 (3H, d), 3.02 (1H, brs), 3.62 (1H, brs), 7.22 (7H, m), 7.91 (7H, m) 8.40 (2H, d), 9.12 (4H, d).

Example 100

N-(4-Amino-cyclohexyl)-3-(4-carbamimidoyl-phenoxy)-5-(4-dimethyl-carbamoyl-phenoxy)-benzamide Intermediates (a)-(e) are the same as in Example 92.

f) {4-[3-(4-Cyano-phenoxy)-5-(4-dimethylcarbamoyl-phenoxy)-benzoylamino]-cyclohexyl}-carbamic Acid Tert-butyl Ester Using 4-[3-(4-tert-butoxycarbonylamino-cyclohexylcarbamoyl)-5-(4-cyano-phenoxy)-phenoxy]-benzoic acid (0.7 g, 1.225 mmol) and following the procedure of Example 99(f) afforded 0.51 g of the required product. Percentage purity (LCMS): 93.7%, (M+1)=598.1+1.

g) (4-{3-(4-Dimethylcarbamoyl-phenoxy)-5-[4-(N-hydroxycarbamimidoyl)-phenoxy]-benzoylamino}-cyclohexyl)-carbamic Acid Tert-butyl Ester Using {4-[3-(4-cyano-phenoxy)-5-(4-dimethylcarbamoyl-phenoxy)-benzoylamino}-cyclohexyl]-carbamic acid tert-butyl ester (0.6 g, 1.01 mmol) and following the procedure of Example 95(d) afforded 0.57 g of the required product. Percentage purity (LCMS): 93.2%, (M+1)=631.1+1.

h) (4-{3-(4-Dimethylcarbamoyl-phenoxy)-5-[4-(N-acetylhydroxycarbamimidoyl)-phenoxy]-benzoylamino}-cyclohexyl)-carbamic Acid Tert-butyl Ester Using (4-{3-(4-Dimethylcarbamoyl-phenoxy)-5-[4-(N-hydroxycarbamimidoyl)-phenoxy]-benzoylamino}-cyclohexyl)-carbamic acid tert-butyl ester (0.57 g, 0.91 mmol) and following the procedure of Example 2(e) afforded 0.61 g of the required product. NMR (DMSO-$d_6$): δ 1.31 (9H, s), 1.35 (3H, s), 1.95 (4H, s), 2.91 (1H, s) 3.02 (3H, s), 3.11 (1H, s), 3.2 (3H, s), 3.8 (1H, s), 6.81 (1H, s), 7.22 (3H, d), 7.55 (4H, s), 7.92 (2H, s), 8.20 (1H, s).

i) {4-[3-(4-Carbamimidoyl-phenoxy)-5-(4-dimethyl-carbamoyl-phenoxy)-benzoylamino}-cyclohexyl]-carbamic Acid Tert-butyl Ester Using (4-{3-(4-dimethylcarbamoyl-phenoxy)-5-[4-(N-acetylhydroxy-carbamimidoyl)-phenoxy]-benzoylamino}-cyclohexyl)-carbamic acid tert-butyl ester (0.61 g, 0.91 mmol) and following the procedure of Example 2(f) afforded 0.55 g of the required product. Percentage purity (LCMS): 82.1%, (M+1)=615.1+1.

j) N-(4-amino-cyclohexyl)-3-(4-carbamimidoyl-phenoxy)-5-(4-dimethylcarbamoyl-phenoxy)-benzamide Using {4-[3-(4-carbamimidoyl-phenoxy)-5-(4-dimethyl-carbamoyl-phenoxy)-benzoylamino]-cyclohexyl}-carbamic acid tert-butyl ester (0.55 g, 0.89 mmol) and following the procedure of Example 9(d) afforded 200 mg of the required product. Percentage purity (HPLC): 95.01%, (LCMS): 95.82%. $^1$H NMR (DMSO-$d_6$): δ 1.21 (4H, m), 1.92 (4H, d), 2.91 (7H, s), 3.51 (1H, m), 7.21 (7H, d), 7.32 (2H, d), 7.56 (4H, d), 7.88 (5H, m), 8.45 (1H, m), 9.25 (2H, s), 9.31 (2H, s).

Example 101

N-(4-Amino-cyclohexyl)-3-(4-carbamimidoyl-phenoxy)-5-(4-methoxy-carbamoyl-phenoxy)-benzamide Intermediates (a)-(e) are the same as in Example 92.

f) {4-[3-(4-Cyano-phenoxy)-5-(4-methoxycarbamoyl-phenoxy)-benzoylamino]-cyclohexyl}-carbamic Acid Tert-butyl Ester Using 4-[3-(4-tert-butoxycarbonylamino-cyclohexylcarbamoyl)-5-(4-cyano-phenoxy)-phenoxy]-benzoic acid (0.9 g, 1.6 mmol) and following the procedure of Example 99(f) afforded 0.73 g of the required product. $^1$H NMR (DMSO-$d_6$): δ 1.25 (15H, d), 1.92 (4H, d), 3.78 (4H, s), 6.81 (1H, d), 7.21 (5H, m), 7.51 (2H, d), 7.91 (41-1, dd), 8.30 (1H, d).

g) {4-[3-[4-(N-hydroxycarbamimidoyl)-phenoxy]-5-(4-methoxycarbamoyl-phenoxy)-benzoylamino]-cyclohexyl}-carbamic Acid Tert-butyl Ester Using {4-[3-(4-cyano-phenoxy)-5-(4-methoxycarbamoyl-phenoxy)-benzoylamino]-cyclohexyl}-carbamic acid tert-butyl ester (0.85 g, 0.14 mmol) and following the procedure of Example 95(d) afforded 0.87 g of the required product. Percentage purity (LCMS): 94.4%, (M+1)=633.2+1.

h) ({4-[3-[4-(N-acetylhydroxycarbamimidoyl)-phenoxy]-5-(4-methoxycarbamoyl-phenoxy)-benzoylamino]-cyclohexyl}-carbamic acid tert-butyl ester Using {4-[3-[4-(N-hydroxycarbamimidoyl)-phenoxy]-5-(4-methoxycarbamoyl-phenoxy)-benzoylamino]-cyclohexyl}-carbamic acid tert-butyl ester (0.87 g, 1.4 mmol) and following the procedure of Example 2(e) afforded 0.89 g of the required product. Percentage purity (LCMS): 64.5%, (M+1)=675.1+1.

i) {4-[3-(4-Carbamimidoyl-phenoxy)-5-(4-methoxycarbamoyl-phenoxy)-benzoylamino]-cyclohexyl}-carbamic Acid Tert-butyl Ester Using ({4-[3-[4-(N-acetylhydroxycarbamimidoyl)-phenoxy]-5-(4-methoxy-carbamoyl-phenoxy)-benzoylamino]-cyclohexyl}-carbamic acid tert-butyl ester (0.89 g, 1.3 mmol) and following the procedure of Example 2(f) afforded 0.81 g of the required product. Percentage purity (LCMS): 92.5%, (M+1)=617.1+1.

j) N-(4-amino-cyclohexyl)-3-(4-carbamimidoyl-phenoxy)-5-(4-methoxycarbamoyl-phenoxy)-benzamide Using {4-[3-(4-carbamimidoyl-phenoxy)-5-(4-methoxy-carbamoyl-phenoxy)-benzoylamino]-cyclohexyl}-carbamic acid tert-butyl ester (0.8 g, 1.3 mmol) and following the procedure of Example 9(d) afforded 0.09 mg of the required product. Percentage purity (HPLC): 95.11%, (LCMS): 96.41%. NMR (DMSO-$d_6$): δ 1.24 (4H, m), 1.92 (4H, m), 3.11 (2H, brs), 3.92 (3H, s), 7.22 (5H, m), 7.51 (2H, d), 7.91 (7H, m), 8.22 (1H, d), 9.25 (2H, s), 9.31 (2H, s), 11.91 (1H, brs).

Example 102

N-(4-amino-cyclohexyl)-3-(4-aminomethyl-phenoxy)-5-[4-(N-hydroxy-carbamimidoyl)-phenoxy]-benzamide Intermediates (a)-(f) are the same as in Example 84.

g) (4-{3-[4-(tert-butoxycarbonylamino-methyl)-phenoxy]-5-[4-(N-hydroxy-carbamimidoyl)-phenoxy]-benzoylamino}-cyclohexyl)-carbamic Acid Tert-butyl Ester Using {4-[3-[4-(tert-butoxycarbonylamino methyl)phenoxy]-5-(4-cyano phenoxy)benzoylamino] cyclohexyl}carbamic acid tert-butyl ester (0.3 g, 0.45 mmol) and following the procedure of Example 95(d) afforded 0.35 g of the required product. Percentage purity (LCMS): 64.5%, (M+1)=689.3+1.

h) N-(4-amino-cyclohexyl)-3-(4-aminomethyl-phenoxy)-5-[4-(N-hydroxy-carbamimidoyl)-phenoxy]-benzamide Using 0.3 g (0.43 mmol) of (4-{3-[4-(tert-butoxycarbonylamino-methyp-phenoxy]-5-[4-(N-hydroxycarbamimidoyl)-phenoxy]-benzoylamino}-cyclohexyl)-carbainic acid tert-butyl ester and following the procedure of Example 9(d) afforded 0.15 g of the required product. Percentage purity (HPLC): 98.81%, (LCMS): 95.62%. $^1$H NMR (DMSO-d$_6$): δ 1.2 (4H, m), 1.8 (4H, m), 2.9 (1H, m), 3.8 (1H, m), 4.15 (2H, d), 6.7 (1H, t), 7.3 (6H, m), 7.5 (2H, d), 7.7 (2H, d), 7.9 (3H, d), 8.2 (3H, brs), 8.4 (1H, d), 10.9 (1H, brs).

Example 103

3,5-Bis-(4-carbamimidoyl-phenoxy)-benzoic acid 4-amino-cyclohexyl Ester

Intermediates (a) and (b) are the same as in Example 26.

c) 3,5-Bis-(4-cyano-phenoxy)-benzoic Acid 4-benzyloxycarbonylamino-cyclohexyl Ester Following the procedure of Example 9(e) 3,5-bis-(4-cyano-phenoxy)-benzoic acid 1.0 g (2.8 mmol) and (4-hydroxy-cyclohexyl)-carbamic acid benzyl ester (0.69 g, 2.8 mmol) were used to afford 0.8 g of the required product. $^1$H NMR (DMSO-d$_6$): δ 1.21 (4H, m), 1.32 (4H, m), 3.12 (1H, m), 3.32 (1H, m), 4.51 (2H, s), 5.21 (2H, s), 7.3 (10H, m), 7.89 (2H, d).

d) 3,5-Bis-[4-(N-hydroxycarbamimidoyl)-phenoxy]-benzoic acid 4-benzyloxy-carbonylamino-cyclohexyl Ester Following the procedure of Example 2(d) 3,5-bis-(4-cyano-phenoxy)-benzoic acid 4-benzyloxycarbonylamino-cyclohexyl ester 0.8 g (1.36 mmol) and other reagents were used to afford 0.7 g of the required product. Percentage purity (LCMS): 73.2%, (M+1) 653.2+1.

e) 3,5-Bis-[4-(N-acetylhydroxycarbamimidoyl)-phenoxy]-benzoic Acid 4-benzyloxycarbonylamino-cyclohexyl Ester Following the procedure as in Example 2(e) 3,5-Bis-[4-(N-hydroxycarbamimidoyl)-phenoxy]-benzoic acid 4-benzyloxycarbonylamino-cyclohexyl ester 0.7 g (1.22 mmol) was used to afford 0.7 g of the required product. Percentage purity (LCMS): 63.8%, (M+1) 737.2+1.

f) 3,5-Bis-(4-carbamimidoyl-phenoxy)-benzoic acid 4-amino-cyclohexyl Ester 3,5-Bis-[4-(N-acetylhydroxycarbamimidoyl)-phenoxy]-benzoic acid 4-benzyloxycarbonylamino-cyclohexyl ester 0.7 g (0.9 mmol) was reduced using the procedure of Example 2(f) to afford 0.45 g of the required product. Percentage purity (HPLC): 99.21%, (LCMS): 97.9%. $^1$H NMR (DMSO-d$_6$): δ 1.21 (4H, m), 1.9 (4H, m), 3.1 (1H, m), 3.2 (1H, m), 4.91 (1H, brs), 7.35 (6H, m), 8.01 (7H, m), 9.2 (8H, d).

Example 104

3-(4-Aminomethyl-phenoxy)-5-(4-carbamimidoyl-phenoxy)-benzoic acid 4-amino-cyclohexyl Ester Intermediate (a) is the same as in Example 42.

b) 3-[4-(tert-butoxycarbonylamino-methyl)-phenoxy]-5-hydroxy-benzoic Acid Ethyl Ester Using 1.3 g (4.5 mmol) of 3-(4-cyano-phenoxy)-5-hydroxy-benzoic acid ethyl ester and following the procedure of Example 95(d) afforded 1.1 g of the required product. Percentage purity (LCMS): 48.4%, (M+1) 387.1+1.

c) 3-[4-(tert-butoxycarbonylamino-methyl)-phenoxy]-5-(4-cyano-phenoxy)-benzoic Acid Ethyl Ester Using 3-[4-(tert-butoxycarbonylamino-methyl)-phenoxy]-5-hydroxy-benzoic acid ethyl ester (1.1 g, 2.48 mmol) and following the procedure of Example 42(b) afforded 0.95 g of the required product. $^1$H NMR (DMSO-d$_6$): δ 1.21 (2H, m), 1.32 (9H, s), 3.81 (1H, s), 4.21 (2H, d), 4.35 (2H, m), 7.32 (9H, m), 7.91 (2H, d).

d) 3-[4-(tert-butoxycarbonylamino-methyl)-phenoxy]-5-(4-cyano-phenoxy)-benzoic Acid 0.95 g (2.06 mmol) of 3-[4-(tert-butoxycarbonylamino-methyl)-phenoxy]-5-(4-cyano-phenoxy)-benzoic acid ethyl ester was hydrolysed using the procedure of Example 5(b) to afford 0.85 g of the required product. NMR (DMSO-d$_6$): δ 1.2 (9H, s), 4.1 (3H, s), 7.21 (9H, m) 7.9 (2H, d), 13.4 (1H, brS).

e) 3-[4-(tert-butoxycarbonylamino-methyl)-phenoxy]-5-(4-cyano-phenoxy)-benzoic Acid 4-benzyloxycarbonylamino-cyclohexyl Ester Following the procedure of Example 9(e) 3-[4-(tert-butoxycarbonylamino-methyl)-phenoxy]-5-(4-cyano-phenoxy)-benzoic acid (0.85 g, 1.85 mmol) and (4-hydroxy-cyclohexyl)-carbamic acid benzyl ester (0.50 g, 2.03 mmol)

were used to afford 0.5 g of the required product. Percentage purity (LCMS): 67.0%, (M+1) 691.2+1.

3-[4-(tert-butoxycarbonylamino-methyl)-phenoxy]-5-[4-(N-hydroxy-carbamimidoyl)-phenoxy]-benzoic acid 4-benzyloxycarbonylamino-cyclohexyl ester Using 3-[4-(tert-butoxycarbonylamino-methyl)-phenoxy]-5-(4-cyano-phenoxy)-benzoic acid 4-benzyloxycarbonylamino-cyclohexyl ester (0.6 g, 0.87 mmol) and following the procedure of Example 95(d) afforded 0.6 g of the required product. Percentage purity (LCMS): 69.3%, (M+1)= 724+1.

g) 3-[4-(tert-butoxycarbonylamino-methyl)-phenoxy]-5-[4-(N-acetylhydroxy-carbamimidoyl)-phenoxy]-benzoic Acid 4-benzyloxycarbonylamino-cyclohexyl Ester Using 3-[4-(tert-butoxycarbonylamino-methyl)-phenoxy]-5-[4-(N-hydroxy-carbamimidoyl)-phenoxy]-benzoic acid 4-benzyloxycarbonylamino-cyclohexyl ester (0.6 g, 0.82 mmol) and following the procedure as in Example 2(e) afforded 0.55 g of the required product. Percentage purity (LCMS): 69.1%, (M+1)=766.2+1.

h) 3-[4-(tert-butoxycarbonylamino-methyl)-phenoxy]-5-(4-carbamimidoyl-phenoxy)-benzoic Acid 4-amino-cyclohexyl Ester 3-[4-(tert-butoxycarbonylamino-methyl)-phenoxy]-5-[4-(N-acetylhydroxy-carbamimidoyl)-phenoxy]-benzoic acid 4-benzyloxycarbonylamino-cyclohexyl ester 0.55 g (0.71 mmol) was reduced using the procedure of Example 2(f) to afford 0.5 g of the required product. Percentage purity (LCMS): 54.6%, (M+1)=574.2+1.

i) 3-(4-Aminomethyl-phenoxy)-5-(4-carbamimidoyl-phenoxy)-benzoic Acid 4-amino-cyclohexyl Ester 3-[4-(tert-butoxycarbonylamino-methyl)-phenoxy]-5-(4-carbamimidoyl-phenoxy)-benzoic acid 4-amino-cyclohexyl ester 0.5 g (0.87 mmol) was treated using procedure of Example 9(d) to afford 0.2 g of the required product. Percentage purity (HPLC): 94.21%, (LCMS): 96.9%. NMR (DMSO-$d_6$): δ 1.25 (4H, m), 1.91 (4H, m), 3.1 (1H, m), 4.11 (2H, brs), 4.8 (1H, m), 7.21 (7H, m), 7.9 (4H, m), 8.2 (3H, m), 9.11 (4H, d).

Example 105

[3,5-Bis-(4-carbamimidoyl-phenoxy)-phenyl]-2-naphthylsulphonamide

Intermediates (a) and (b) are the same as in Example 26.

c) [3,5-Bis-(4-cyano-phenoxy)-phenyl]-carbamic Acid Tert-butyl Ester

A mixture of 3,5-bis-(4-cyano-phenoxy)-benzoic acid (2.0 g, 5.6 mmol), diphenylphosphorylazide (1.2 ml, 5.6 mmol) and DIPEA (1 ml, 5.6 mmol) were dissolved in 20 ml of tert-butanol and stirred overnight at 80° C. Reaction mixture was cooled and diluted with 50 ml saturated solution of sodiumhydrogencarbonate and extracted with ethylacetate (3×50 ml). Combined organic layer was washed with 2×50 ml saturated solution of brineand dried over anhydrous sodium sulphate. Solvent was evaporated under vacuo and thus obtained crude product was subjected to column chromatography using silica gel as an absorbent and eluted with 10-20% mixture of ethylacetate and hexane to afford 1.0 g of the required product. Percentage purity (LCMS): 89.6%, (M+1)= 427.1+1.

d) [3,5-Bis-(4-cyano-phenoxy)-phenyl]-amine

Following the procedure of Example 9(d) [3,5-bis-(4-cyano-phenoxy)-phenyl]-carbamic acid tert-butyl ester 1.0 g (2.34 mmol) and other reagents were used to afford 0.7 g of the required product. Percentage purity (LCMS): 95.0%, (M+1)=327.1+1.

e) [3,5-Bis-(4-cyano-phenoxy)-phenyl]-2-naphthyl-sulphonamide

[3,5-Bis-(4-cyano-phenoxy)-phenyl]-amine (0.35 g, 1.07 mmol) and 2-naphthyl-sulphonyl chloride (0.29 g, 1.28 mmol) were dissolved in 10 ml of dichloromethane and cooled to 0° C. Further 0.18 ml (2.14 mmol) of pyridine and 15 mg (0.107 mmol) of DMAP was added to the reaction mixture and allowed to stirred overnight at RT. After completion, reaction mixture was diluted with 50 ml of dichloromethane and washed with 50 ml 1N HCl solution and then with brine. Organic layer was dried over anhydrous sodium sulphate and concentrated under vacuo. Thus obtained crude product was subjected to column chromatography and eluted with ethylacetate and hexane mixture to afford 0.4 g of the required product. Percentage purity (LCMS): 90.4% M+1=517.1+1.

f) [3,5-Bis-(4-(N-hydroxycarbamimidoyl)-phenoxy)-phenyl]-2-naphthyl-sulphonamide Following the procedure of Example 95(d) [3,5-bis-(4-cyano-phenoxy)-phenyl]-2-naphthylsulphonamide 0.45 g (0.83 mmol) was afforded 0.41 g of the required product. Percentage purity (LCMS): 94.3%, (M−1)=583.2-1.

g) [3,5-Bis-(4-(N-acetylhydroxycarbamimidoyl)-phenoxy)-phenyl]-2-naphthyl-sulphonamide

[3,5-Bis-(4-(N-hydroxycarbamimidoyl)-phenoxy)-phenyl]-2-naphthylsulphonamide 0.41 g (0.71 mmol) was acetylated using the procedure of Example 2(e) to afford 0.43 g of the required product. Percentage purity (LCMS): 88.3%, (M+1)=667.2+1.

h) [3,5-Bis-(4-carbamimidoyl-phenoxy)-phenyl]-2-naphthylsulphonamide

[3,5-Bis-(4-(N-acetylhydroxycarbamimidoyl)-phenoxy)-phenyl]-2-naphthyl-sulphonamide 0.43 g (0.644 mmol) was reduced using the procedure of Example 2(f) to afford 0.23 g of the required product. Percentage purity (HPLC): 96.1%, (LCMS): 97.01%. $^1$H NMR (DMSO-$d_6$): δ 6.7 (1H, s), 6.8 (2H, s), 7.15 (4H, d), 8.1 (3H, t), 8.45 (1H, s), 9.2 (6H, brs), 10.8 (1H, brs).

Example 106

[3,5-Bis-(4-carbamimidoyl-phenoxy)-phenyl]-4-fluoro-benzenesulphonamide

Intermediates (a) to (d) are the same as in Example 105.

e) [3,5-Bis-(4-cyano-phenoxy)-phenyl]-4-fluoro-benzenesulphonamide

Following the procedure of Example 105(e) [3,5-bis-(4-cyano-phenoxy)-phenyl]-amine (0.08 g, 0.24 mmols) and 4-fluoro-benzenesulfonyl chloride (0.05 g, 0.27 mmol) were used to afford 0.05 g of the required product. $^1$H NMR (DMSO-$d_6$): δ 6.56 (3H, d), 7.22 (4H, d), 7.51 (2H, d), 7.95 (6H, d).

f) [3,5-Bis-(4-(N-hydroxycarbamimidoyl)-phenoxy)-phenyl]-4-fluoro-benzene-sulphonamide

[3,5-Bis-(4-cyano-phenoxy)-phenyl]-4-fluoro-benzenesulphonamide 0.4 g (0.82 mmol) was subjected to form N-hydroxycarbamimidoyl using the procedure of Example 95(d) to afford 0.4 g of the required product. $^1$H NMR (DMSO-$d_6$): δ 6.56 (3H, d), 7.22 (4H, d), 7.51 (2H, d), 7.95 (6I-1, d), 9.12 (1H, brs).

g) [3,5-Bis-(4-(N-acetylhydroxycarbamimidoyl)-phenoxy)-phenyl]-4-fluoro-benzenesulphonamide

[3,5-Bis-(4-(N-hydroxycarbamimidoyl)-phenoxy)-phenyl]-4-fluoro-benzene-sulphonamide 0.4 g (0.72 mmol) was acetylated using the procedure of Example 2(e) to afford 0.42 g of the required product. Percentage purity (LCMS): 57.3%, (M+1)=635.2+1.

h) [3,5-Bis-(4-carbamimidoyl-phenoxy)-phenyl]-4-Fluoro-benzenesulphonamide

[3,5-Bis-(4-(N-acetylhydroxycarbamimidoyl)-phenoxy)-phenyl]-4-fluoro-benzene-sulphonamide 0.42 g (0.66 mmol) was reduced using the procedure of Example 2(f) to afford 0.15 g of the required product. Percentage purity (HPLC): 95.71%, (LCMS): 94.7%. $^1$H NMR (DMSO-$d_6$): δ 6.71 (3H, d), 7.15 (4H, d), 7.51 (2H, t), 7.91 (6I-1, d), 9.2 (8H, d), 10.9 (1H, s).

Example 107

4-Amino-cyclohexanecarboxylic acid[3,5-bis-(4-carbamimidoyl-phenoxy)-phenyl]-amide Intermediates (a) to (d) are the same as in Example 105.

e) {4-[3,5-Bis-(4-cyano-phenoxy)-phenylcarbamoyl]-cyclohexyl}-carbamic Acid Tert-butyl Ester N-methylmorpholine (0.75 ml, 6.57 mmol) and 2-(1H-7-azabenzotriazol-1-yl)-1,1,3,3-tetramethyl uronium hexafluorophosphate methanaminium (2.35 g, 6.16 mmol) were added to the stirred solution of racemic mixture of 4-tert-butoxycarbonylamino-cyclohexanecarboxylic acid (0.67 g, 2.05 mmol), dissolved in 5.0 ml of DMF. Further 0.50 g (2.05 mmol) of {4-[3,5-bis-(4-cyano-phenoxy)-phenylcarbamoyl]-cyclohexyl}-carbamic acid tert-butyl ester, dissolved in 5 ml of DMF, was added to the reaction mixture at RT and resulting mixture was allowed to stirred overnight at RT. After reaction completion, mixture was poured into ice-water to afford white solid compound which was filtered off and dissolved in ethylacetate and organic layer was washed with 2×50 ml of saturated sodiumhydrogencarbonate and then with water. Organic layer was dried over anhydrous sodium sulphate and concentrated under vacuo to afford the crude product which was subjected to column chromatography using silica gel as an absorbent and eluted with 40-60% ethylacetate:hexane mixture to afford 0.65 g of the required product. NMR (DMSO-$d_6$): δ 1.25 (9H, s), 1.32 (4H, m), 2.31 (4H, m), 3.21 (1H, m), 3.52 (1H, m), 6.12 (1H, s), 7.21 (6H, d), 7.91 (4H, d), 10.01 (1H, s).

f) (4-{3,5-Bis-[4-(N-hydroxycarbamimidoyl)-phenoxy]-phenylcarbamoyl}-cyclohexyl)-carbamic Acid Tert-butyl Ester {4-[3,5-Bis-(4-cyano-phenoxy)-phenylcarbamoyl]-cyclohexyl}-carbamic acid tert-butyl ester 0.8 g (1.44 mmol) was subjected to form N-hydroxycarbamimidoyl using the procedure of Example 95(d) to afford 0.86 g of the required product. Percentage purity (LCMS): 93.4%, (M+1)=618.2+1.

g) (4-{3,5-Bis-[4-(N-acetylhydroxycarbamimidoyl)-phenoxy]-phenylcarbamoyl}-cyclohexyl)-carbamic Acid Tert-butyl Ester (4-{3,5-Bis-[4-(N-hydroxycarbamimidoyl)-phenoxy]-phenylcarbamoyl}-cyclohexyl)-carbamic acid tert-butyl ester 0.86 g (1.39 mmol) was acetylated using the procedure of Example 2(e) to afford 0.89 g of the required product. Percentage purity (LCMS): 88.8%, (M+1)=702.2+1.

h) {4-[3,5-Bis-(4-carbamimidoyl-phenoxy)-phenylcarbamoyl]-cyclohexyl}-carbamic Acid Tert-butyl Ester (4-{3,5-Bis-[4-(N-acetylhydroxycarbamimidoyl)-phenoxy]-phenylcarbamoyl}-cyclohexyl)-carbamic acid tert-butyl ester 0.89 g (1.26 mmol) was reduced using the procedure of Example 2(f) to afford 0.7 g of the required product. (LCMS): 93.3%, (M+1)=586.2+1.

i) 4-Amino-cyclohexanecarboxylic Acid[3,5-bis-(4-carbamimidoyl-phenoxy)-phenyl]-amide {4-[3,5-Bis-(4-carbamimidoyl-phenoxy)-phenylcarbamoyl]-cyclohexyl}-carbamic acid tert-butyl ester 0.7 g (1.19 mmol) was reduced using the procedure of Example 9(d) to afford 0.4 g of the required product. Percentage purity (HPLC): 97.81%, (LCMS): 100%. $^1$H NMR (DMSO-$d_6$): δ 1.31 (4H, m), 1.9 (4H, m), 2.2 (1H, m), 3.2 (1H, m), 6.7 (1H, s), 7.21 (6H, dd), 7.91 (7H, d), 9.31 (8H, s), 10.1 (1H, s).

Example 108

Trans-4-amino-cyclohexanecarboxylic Acid[3,5-bis-(4-carbamimidoyl-phenoxy)-phenyl]-amide Intermediates (a) to (d) are the same as in Example 105.

e) {Trans-4-[3,5-bis-(4-cyano-phenoxy)-phenylcarbamoyl]-cyclohexyl}-carbamic Acid Tert-butyl Ester Following the procedure of Example 107(e) trans-4-tert-butoxycarbonylamino-cyclohexanecarboxylic acid 10.4 g (42.79 mmol) and [3,5-bis-(4-cyano-phenoxy)-phenyl]-amine (14.0 g, 42.79 mmol) were used to afford 12 g of the required product. $^1$H NMR (DMSO-$d_6$): δ 1.2 (4H, m), 1.31

(9H, s), 1.8 (4H, d), 2.21 (1H, t), 3.1 (1H, m), 6.81 (1H, d), 7.04 (1H, s), 7.2 (6H, m) 7.91 (4H, dd), 10.0 (1H, s).

f) (Trans-4-{3,5-bis-[4-(N-hydroxycarbamimidoyl)-phenoxy]-phenylcarbamoyl}-cyclohexyl)-carbamic Acid Tert-butyl Ester {Trans-4-[3,5-bis-(4-cyano-phenoxy)-phenylcarbamoyl]-cyclohexyl}-carbamic acid tert-butyl ester 5.0 g (9.05 mmol) was subjected to form N-hydroxycarbamimidoyl using the procedure of Example 95(d) to afford 5.2 g of the required product. Percentage purity (LCMS): 88.9%, (M+1)=618.2+1.

g) (Trans-4-{3,5-bis-[4-(N-acetylhydroxycarbamimidoyl)-phenoxy]-phenyl-carbamoyl}-cyclohexyl)-carbamic Acid Tert-butyl Ester (Trans-4-{3,5-bis-[4-(N-hydroxycarbamimidoyl)-phenoxy]-phenylcarbamoyl}-cyclohexyl)-carbamic acid tert-butyl ester 5.2 g (8.40 mmol) was acetylated using the procedure of Example 2(e) to afford 5.50 g of the required product. Percentage purity (LCMS): 91.6%, (M+1)=702.1+1.

h) {Trans-4-[3,5-bis-(4-carbarnimidoyl-phenoxy)-phenylcarbamoyl]-cyclohexyl}-carbamic Acid Tert-butyl Ester (Trans-4-{3,5-bis-[4-(N-acetylhydroxycarbamimidoyl)-phenoxy]-phenyl-carbamoyl}-cyclohexyl)-carbamic acid tert-butyl ester 5.5 g (7.831 mmol) was reduced using the procedure of Example 2(f) to afford 4.2 g of the required product. Percentage purity (LCMS): 98.3%, (M+1)=586.1+1.

i) Trans-4-amino-cyclohexanecarboxylic acid[3,5-bis-(4-carbamimidoyl-phenoxy)-phenyl]-amide {Trans-4-[3,5-bis-(4-carbamimidoyl-phenoxy)-phenylcarbamoyl]-cyclohexyl}-carbamic acid tert-butyl ester 3.8 g (6.47 mmol) was reduced using the procedure of Example 9(d) to afford 2.5 g of the required product. Percentage purity (HPLC): 99.1%, (LCMS): 99.9%. $^1$H NMR (DMSO-$d_6$): δ 1.22 (4H, m), 1.9 (4H, m), 2.1 (1H, d), 3.1 (1H, m), 6.7 (1H, s), 7.35 (5H, m), 7.91 (7H, d), 9.25 (8H, d), 10.3 (1H, brs).

Example 109

1-(2-Amino-ethyl)-piperidine-4-carboxylic Acid[3,5-bis-(4-carbamimidoyl-phenoxy)-phenyl]-amide Intermediates (a) to (d) are the same as in Example 105.

e) 4-[3,5-Bis-(4-cyano-phenoxy)-phenylcarbamoyl]-piperidine-1-carboxylic Acid Tert-butyl Ester Following the procedure of Example 9(e) piperidine-1,4-dicarboxylic acid mono-tert-butyl ester 0.7 g (3.05 mmol) and [3,5-bis-(4-cyano-phenoxy)-phenyl]-amine (1.0 g, 3.05 mmol) were used to afford 0.85 g of the required product. $^1$H NMR (DMSO-$d_6$): δ 1.2 (4H, m), 1.31 (9H, s), 1.8 (4H, d), 2.21 (1H, t), 3.1 (1H, m), 6.81 (1H, d), 7.04 (1H, s), 7.2 (6H, m), 7.91 (4H, dd), 10.0 (1H, brs).

f) 4-[3,5-Bis-(4-cyano-phenoxy)-phenylcarbamoyl]-piperidine

Following the procedure of Example 9(d) 4-[3,5-bis-(4-cyano-phenoxy)-phenyl-carbamoyl]-piperidine-1-carboxylic acid tert-butyl ester (0.85 g, 1.579 mmol) was used to afford 0.54 g of the required product. Percentage purity (LCMS): 90.6%, (M+1)=438.1+1.

g) (2-{4-[3,5-Bis-(4-cyano-phenoxy)-phenylcarbamoyl]-piperidin-1-yl}-ethyl)-carbamic Acid Tert-butyl Ester Following the procedure of Example 11(e) 4-[3,5-bis-(4-cyano-phenoxy)-phenyl-carbamoyl]-piperidine (0.8 g, 1.82 mmol) and (2-bromo-ethyl)-carbamic acid tert-butyl ester (0.49 g, 2.19 mmol) were used to afford 0.4 g of the required product. $^1$H NMR (DMSO-$d_6$): δ 1.4 (9H, s), 1.42 (4H, m), 2.31 (3H, m), 1.8 (2H, t), 2.81 (2H, m), 3.15 (1H, m), 3.7 (1H, m), 6.76 (1H, s), 7.26 (6H, m), 7.86 (4H, d).

h) [2-(4-{3,5-Bis-[4-(N-hydroxycarbamimidoyl)-phenoxy]-phenylcarbamoyl}-piperidin-1-yl)-ethyl]-carbamic Acid Tert-butyl Ester (2-{4-[3,5-Bis-(4-cyano-phenoxy)-phenylcarbamoyl]-piperidin-1-yl}-ethyl)-carbamic acid tert-butyl ester 0.4 g (0.687 mmol) was subjected to form N-hydroxycarbamimidoyl using the procedure of Example 95(d) to afford 0.4 g of the required product. Percentage purity (LCMS): 91.1%, (M+1)=647.2+1.

i) [2-(4-{3,5-Bis-[4-(N-acetylhydroxycarbamimidoyl)-phenoxy]-phenyl-carbamoyl}-piperidin-1-yl)-ethyl]-carbamic Acid Tert-butyl Ester

[2-(4-{3,5-Bis-[4-(N-hydroxycarbamimidoyl)-phenoxy]-phenylcarbamoyl}-piperidin-1-yl)-ethyl]-carbamic acid tert-butyl ester 0.4 g (0.618 mmol) was acetylated using the procedure of Example 2(e) to afford 0.45 g of the required product. Percentage purity (LCMS): 61.9%, (M+1)=731.2+1.

j) (2-{4-[3,5-Bis-(4-carbamimidoyl-phenoxy)-phenylcarbamoyl]-piperidin-1-yl}-ethyl)-carbamic Acid Tert-butyl Ester

[2-(4-{3,5-Bis-[4-(N-acetylhydroxycarbamimidoyl)-phenoxy]-phenylcarbamoyl}-piperidin-1-yl)-ethyl]-carbamic acid tert-butyl ester 0.5 g (0.68 mmol) was reduced using the procedure of Example 2(f) to afford 0.4 g of the required product. Percentage purity (LCMS): 100%, (M+1)=615.2+1.

k) 1-(2-Amino-ethyl)-piperidine-4-carboxylic Acid [3,5-bis-(4-carbamimidoyl-phenoxy)-phenyl]-amide (2-{4-[3,5-Bis-(4-carbamimidoyl-phenoxy)-phenylcarbamoyl]-piperidin-1-yl}-ethyl)-carbamic acid tert-butyl ester 0.4 g (0.65 mmol) was reduced using the procedure of Example 9(d) to afford 0.25 g of the required product. Percentage purity (HPLC): 98.91%, (LCMS): 99.6%. $^1$H NMR (DMSO-$d_6$): δ 1.22 (4H, m), 2.1 (4H, m), 2.8 (2H, t), 3.2 (2H, m), 3.5 (1H, m), 6.1 (1H, s), 7.2 (5H, d), 7.9 (4H, d), 8.22 (2H, brs), 9.2 (8H, d), 9.6 (1H, brs), 10.5 (1H, s).

Example 110

1-(3-Amino-propionyl)-piperidine-4-carboxylic acid [3,5-bis-(4-carbamimidoyl-phenoxy)-phenyl]-amide Intermediates (a) to (f) are the same as in Example 109.

g) (3-{4-[3,5-Bis-(4-cyano-phenoxy)-phenylcarbamoyl]-piperidin-1-yl}-3-oxo-propyl)-carbamic Acid Tert-butyl Ester Following the procedure of Example 9(e) 4-[3,5-bis-(4-cyano-phenoxy)-phenyl-carbamoyl]-piperidine 1.0 g (2.28 mmol) and 3-tert-butoxycarbonylamino-propionic acid (0.431 g, 2.28 mmol) were used to afford 0.95 g of the required product. 114 NMR (DMSO-$d_6$): δ 1.4 (9H, s), 1.42 (4H, m), 2.31 (3H, m), 1.8 (2H, t), 2.81 (2H, m), 3.15 (1H, m), 3.7 (1H, m), 6.76 (1H, s), 7.26 (6H, m), 7.86 (4H, d), 10.01 (1H, s).

h) [2-(4-{3,5-Bis-[4-(N-hydroxycarbamimidoyl)-phenoxy]-phenylcarbamoyl}-piperidin-1-yl)-ethyl]-carbamic Acid Tert-butyl Ester (3-{4-[3,5-Bis-(4-cyano-phenoxy)-phenylcarbamoyl]-piperidin-1-yl}-3-oxo-propyl)-carbamic acid tert-butyl ester 1.0 g (1.64 mmol) was subjected to form N-hydroxycarbamimidoyl using the procedure of Example 95(d) to afford 1.0 g of the required product. Percentage purity (LCMS): 98.5%, (M+1)=675.2+1.

i) [2-(4-{3,5-Bis-[4-(N-acetylhydroxycarbamimidoyl)-phenoxy]-phenyl-carbamoyl}-piperidin-1-yl)-ethyl]-carbamic Acid Tert-butyl Ester

[2-(4-{3,5-Bis-[4-(N-hydroxycarbamimidoyl)-phenoxy]-phenylcarbamoyl}-piperidin-1-yl)-ethyl]-carbamic acid tert-butyl ester 1.0 g (1.48 mmol) was acetylated using the procedure of Example 2(e) to afford 0.1 g of the required product. Percentage purity (LCMS): 99.9%, (M+1)=759.2+1.

j) (3-{4-[3,5-Bis-(4-carbamimidoyl-phenoxy)-phenylcarbamoyl]-piperidin-1-yl}-3-oxo-propyl)-carbamic Acid Tert-butyl Ester

[2-(4-{3,5-Bis-[4-(N-acetylhydroxycarbamimidoyl)-phenoxy]-phenylcarbamoyl}-piperidin-1-yl)-ethyl]-carbamic acid tert-butyl ester 1.1 g (1.45 mmol) was reduced using the procedure of Example 2(f) to afford 0.93 g of the required product. Percentage purity (LCMS): 99.9%, (M+1)=643.2+2.

k) 1-(3-Amino-propionyl)-piperidine-4-carboxylic acid[3,5-bis-(4-carbamimidoyl-phenoxy)-phenyl]-amide (3-{4-[3,5-Bis-(4-carbamimidoyl-phenoxy)-phenylcarbamoyl]-piperidin-1-yl}-3-oxo-propyl)-carbamic acid tert-butyl ester 0.93 g (1.44 mmol) was reduced using the procedure of Example 9(d) to afford 0.3 g of the required product. Percentage purity (HPLC): 97.9%, (LCMS): 94.9%. $^1$H NMR (DMSO-$d_6$): δ 1.25 (4H, m), 1.92 (4H, m), 2.5 (2H, m), 3.05 (3H, m), 4.1 (1H, d), 6.7 (1H, s), 7.35 (6H, m), 7.6 (2H, brs), 7.9 (4H, d), 9.2 (7H, d), 10.4 (1H, s).

Example 111

1-(2-Hydroxy-ethyl)-piperidine-4-carboxylic acid[3,5-bis-(4-carbamimidoyl-phenoxy)-phenyl]-amide Intermediates (a) to (f) are the same as in Example 109.

g) 1-(3-Hydroxy-propionyl)-piperidine-4-carboxylic acid[3,5-bis-(4-cyano-phenoxy)-phenyl]-amide Following the procedure of Example 11(e) 4-[3,5-bis-(4-cyano-phenoxy)-phenyl-carbamoyl]-piperidine 1.5 g (3.42 mmol) and 2-bromoethanol (0.647 g, 4.79 mmol) were used to afford 1.1 g of the required product. $^1$H NMR (DMSO-$d_6$): δ 2.11 (4H, m), 2.52 (2H, m), 3.15 (4H, m), 3.21 (1H, m), 3.31 (1H, m), 4.21 (1H, t), 6.76 (1H, s), 7.31 (6H, d), 7.92 (4H, d).

h) 1-(3-Hydroxy-propionyl)-piperidine-4-carboxylic Acid{3,5-bis-[4-(N-hydroxy carbamimidoyl)-phenoxy]-phenyl}-amide 1-(3-Hydroxy-propionyl)-piperidine-4-carboxylic acid[3,5-bis-(4-cyano-phenoxy)-phenyl]-amide 1.1 g (2.28 mmol) was subjected to form N-hydroxycarbamimidoyl using the procedure of Example 95(d) to afford 1.3 g of the required product. Percentage purity (LCMS): 96.7%, (M+1)=548.2+1.

i) 1-(2-Hydroxy-ethyl)-piperidine-4-carboxylic acid [3,5-bis-(4-carbamimidoyl-phenoxy)-phenyl]-amide 1-(3-Hydroxy-propionyl)-piperidine-4-carboxylic acid{3,5-bis-[4-(N-hydroxy-carbamimidoyl)-phenoxy]-phenyl}-amide 1.3 g (2.37 mmol) was reduced using the procedure of Example 2(f) to afford 0.55 g of the required product. Percentage purity (HPLC): 97.18%, (LCMS): 98.8%. $^1$H NMR (DMSO-$d_6$): δ 1.91 (4H, m), 3.2 (6H, m), 3.5 (5H, m), 6.7 (1H, s), 7.35 (6H, d), 7.91 (4H, d), 9.25 (8H, d), 10.5 (1H, s).

Example 112

Cis-4-amino-cyclohexanecarboxylic acid[3,5-bis-(4-carbamimidoyl-phenoxy)-phenyl]-amide Intermediates (a) to (d) are the same as in Example 106.

e) {Cis-4-[3,5-bis-(4-cyano-phenoxy)-phenylcarbamoyl]-cyclohexyl}-carbamic Acid Tert-butyl Ester Following the procedure of Example 9(e) cis-4-tert-butoxycarbonylamino-cyclo-hexanecarboxylic acid 1.0 g (4.15 mmol) and [3,5-bis-(4-cyano-phenoxy)-phenyl]-amine (1.34 g, 4.15 mmol) were used to afford 1.5 g of the required product. $^1$H NMR (DMSO-$d_6$): δ 1.4 (9H, s), 2.3 (4H, m), 2.81 (1H, m), 3.15 (4H, m), 3.5 (1H, m), 6.71 (1H, s), 6.81 (1H, brs), 7.21 (6H, m), 7.92 (4H, d), 10.0 (1H, brs).

f) (cis-4-{3,5-bis-[4-(N-hydroxycarbamimidoyl)-phenoxy]-phenylcarbamoyl}-cyclohexyl)-carbamic Acid Tert-butyl Ester {Cis-4-[3,5-bis-(4-cyano-phenoxy)-phenylcarbamoyl]-cyclohexyl}-carbamic acid tert-butyl ester 1.56 g (2.82 mmol) was subjected to form N-hydroxycarbamimidoyl using the procedure of Example 95(d) to afford 1.5 g of the required product. Percentage purity (LCMS): 99.9%, (M+1)=618.2+1.

g) (Cis-4-{3,5-bis-[4-(N-acetylhydroxycarbamimidoyl)-phenoxy]-phenyl-carbamoyl}-cyclohexyl)-carbamic acid tert-butyl ester (Cis-4-{3,5-bis-[4-(N-hydroxycarbamimidoyl)-phenoxy]-phenylcarbamoyl}-cyclohexyl)-carbamic acid tert-butyl ester 1.5 g (0.82 mmol) was acetylated using the procedure of Example 2(e) to afford 1.4 g of the required product. Percentage purity (LCMS): 68.0%, (M+1)=702.2+1.

h) {Cis-4-[3,5-bis-(4-carbamimidoyl-phenoxy)-phenylcarbamoyl]-cyclohexyl}-carbamic Acid Tert-butyl Ester (Cis-4-{3,5-bis-[4-(N-acetylhydroxycarbamimidoyl)-phenoxy]-phenylcarbamoyl}-cyclohexyl)-carbamic acid tert-butyl ester 1.4 g (2.1 mmol) was reduced using the procedure of Example 2(f) to afford 1.2 g of the required product. Percentage purity (LCMS): 100%, (M+1)=586.2+1.

i) Cis-4-amino-cyclohexanecarboxylic acid[3,5-bis-(4-carbamimidoyl-phenoxy)-phenyl]-amide {Cis-4-[3,5-bis-(4-carbamimidoyl-phenoxy)-phenylcarbamoyl]-cyclohexyl}-carbamic acid tert-butyl ester 1.2 g (2.1 mmol) was reduced using the procedure of Example 9(d) to afford 1.0 g of the required product. Percentage purity (HPLC): 98.7%, (LCMS): 100%. $^1$H NMR (DMSO-$d_6$): δ 1.82 (4H, m), 1.9 (4H, m), 3.11 (1H, m), 3.8 (1H, m), 6.7 (1H, s), 7.21 (6H, d), 7.91 (7H, d), 9.21 (8H, d), 10.1 (1H, s).

Example 113

[3,5-Bis-(4-carbamimidoyl-phenoxy)-phenyl]-amine

Intermediates (a) to (d) are the same as in Example 105.

e) {3,5-Bis-[4-(N-hydroxycarbamimidoyl)-phenoxy]-phenyl}-amine

[3,5-Bis-(4-cyano-phenoxy)-phenyl]-amine 0.3 g (0.917 mmol) was subjected to form N-hydroxycarbamimidoyl using the procedure of Example 95(d) to afford 0.34 g of the required product. Percentage purity (LCMS): 100.0%, (M+1)= 393.1+1.

f) [3,5-Bis-(4-carbamimidoyl-phenoxy)-phenyl]-amine

{3,5-Bis-[4-(N-hydroxycarbamimidoyl)-phenoxy]-phenyl}-amine 0.34 g (0.864 mmol) was reduced using the procedure of Example 2(1) to afford 0.15 g of the required product. Percentage purity (HPLC): 96.6%, (LCMS): 99.5%. NMR (DMSO-$d_6$): 5.9 (1H, t), 6.2 (2H, d), 7.35 (4H, d), 7.9 (4H, d), 9.11 (4H, brs), 9.25 (4H, brs).

Example 114

1-(2-Amino-ethyl)-piperidine-4-carboxylic acid[3,5-bis-(4-carbamimidoyl-phenoxy)-phenyl]-amide Intermediates (a) to (f) are the same as in Example 109.

g) 1-Cyclopropylmethyl-piperidine-4-carboxylic acid[3,5-bis-(4-cyano-phenoxy)-phenyl]-amide Following the procedure of Example 11(e) 4-[3,5-bis-(4-cyano-phenoxy)-phenyl-carbamoyl]-piperidine 1.5 g (3.42 mmol) and bromomethylcyclopropane (0.647 g, 4.79 mmol) were used to afford 1.0 g of the required product. Percentage purity (LCMS): 73.1%, (M+1)=492.1+1.

h) 1-Cyclopropylmethyl-piperidine-4-carboxylic acid{3,5-bis-[4-(N-hydroxy-carbamimidoyl)-phenoxy]-phenyl}-amide 1-Cyclopropylmethyl-piperidine-4-carboxylic acid[3,5-bis-(4-cyano-phenoxy)-phenyl]-amide 1.0 g (2.03 mmol) was subjected to form N-hydroxycarbamimidoyl using the procedure of Example 95(d) to afford 1.1 g of the required product. Percentage purity (LCMS): 100.0%, (M+1)=558.2+1.

i) 1-Cyclopropylmethyl-piperidine-4-carboxylic acid{3,5-bis-[4-(N-acetylhydroxy-carbamimidoyl)-phenoxy]-phenyl}-amide 1-Cyclopropylmethyl-piperidine-4-carboxylic acid{3,5-bis-[4-(N-hydroxy-carbamimidoyl)-phenoxy]-phenyl}-amide 1.1 g (1.97 mmol) was acetylated using the procedure of Example 2(e) to afford 1.6 g of the required product. Percentage purity (LCMS): 57.70%, (M+1)=642.2+1.

j) 1-Cyclopropylmethyl-piperidine-4-carboxylic acid [3,5-bis-(4-carbamimidoyl-phenoxy)-phenyl]-amide 1-Cyclopropylmethyl-piperidine-4-carboxylic acid {3,5-bis-[4-(N-acetylhydroxy-carbamimidoyl)-phenoxy]-phenyl}-amide 1.6 g (2.49 mmol) was reduced using the procedure of Example 2(f) to afford 0.8 g of the required product. Percentage purity (HPLC): 99.01%, (LCMS): 98.9%. $^1$H NMR (DMSO-$d_6$): δ 0.3 (2H, d), 0.6 (2H, d), 1.1 (1H, m), 1.82 (4H, m), 3.05 (4H, m), 3.1 (2H, d), 6.7 (1H, s), 7.2 (5H, d), 7.98 (4H, d), 9.11 (8H, brs), 9.55 (1H, brs), 10.5 (1H, s).

Example 115

N-(4-Amino-cyclohexyl)-3,5-bis-[4-(N-methoxy-carbamimidoyl)-phenoxy]-benzamide Intermediates (a) to (c) are the same as in Example 27.

d) (4-{3,5-Bis-[4-(N-methoxy-carbamimidoyl)-phenoxy]-benzoylamino}-cyclohexyl)-carbamic Acid Tert-butyl Ester Triethylamine (2.5 ml, 1.81 mmol) was added to the suspension of {4-[3,5-bis-(4-cyano-phenoxy)-benzoylamino]-cyclohexyl}-carbamic acid tert-butyl ester (1.0 g, 1.81 mmol) in 15 ml of ethanol at 55° C. O-methyl-hydroxylamine hydrochloride solution (0.91 g in 3 ml of water (30% w/w)) and mercaptoacetic acid (0.51 ml, 7.24 mmol) were added to the reaction mixture at 55° C. under inert nitrogen atmosphere. Reaction mixture was stirred under nitrogen atmosphere at 90° C. for 40 h. After reaction completion, solvent was removed under vacuo and the residue was poured into ice-water to obtain white solid product which was filtered off and washed with water and hexane to afford 0.7 g of the required product. Percentage purity (LCMS): 69.3%, (M+1)=646+1.

e) N-(4-Amino-cyclohexyl)-3,5-bis-[4-(N-methoxy-carbamimidoyl)-phenoxy]-benzamide Using (4-{3,5-bis-[4-(N-methoxy-carbamimidoyl)-phenoxy]-benzoylamino}-cyclohexyl)-carbamic acid tert-butyl ester (0.8 g, 1.23 mmol) and following the procedure of Example 9(d) afforded 0.51 g of the required product. Percentage purity (HPLC): 98.3%, (LCMS) 98.9%. $^1$H NMR (DMSO-$d_6$): δ 1.24 (4H, m), 1.82 (4H, m), 3.05 (1H, m), 3.51 (1H, m), 3.9 (6H, s), 6.9 (1H, t), 7.25 (4H, d), 7.45 (2H, d), 7.88 (4H, d), 7.9 (3H, brs), 8.45 (1H, d).

Example 116

4-Amino-cyclohexanecarboxylic acid[3-(4-aminomethyl-phenoxy)-5-(4-carbamimidoyl-phenoxy)-phenyl]-amide Intermediate (a) to (c) are same as in Example 104.

d) 3-(4-Aminomethyl-phenoxy)-5-(4-cyano-phenoxy)-benzoic Acid Ethyl Ester

Using 10.0 g (20.48 mmol) of 3-[4-(tert-butoxycarbonylamino-methyl)-phenoxy]-5-(4-cyano-phenoxy)-benzoic acid ethyl ester and following the procedure of Example 9(d) afforded 7.4 g of the required product. Percentage purity (LCMS): 82.0%, (M+1)=388.4+1.

e) 3-[4-(Benzyloxycarbonylamino-methyp-phenoxy]-5-(4-cyano-phenoxy)-benzoic Acid Ethyl Ester Mixture of 7.4 g (15.1 mmol) of 3-(4-aminomethyl-phenoxy)-5-(4-cyano-phenoxy)-benzoic acid ethyl ester, benzyl chloro formate (3.8 g, 22.6 mmol) and triethylamine (4.6 g, 45.4 mmol) were stirred overnight at RT. After reaction completion solvent was removed under reduced pressure and thus obtained rsidue was dissolved in ice-water and extrated with 500 ml×2 of ethylacetate. Organic layer was dried over anhydrous sodium sulphate, solvent was removed and thus obtained crude product was purified by column chromatography using silica-gel as an adsorbent and eluted with ethylacetate:hexane (10:90) to afford 8.0 g of the required product. Percentage purity (LCMS): 87.2%, (M+1)=522.5+1.

f) 3-[4-(Benzyloxycarbonylamino-methyl)-phenoxy]-5-(4-cyano-phenoxy)-benzoic Acid 8.0 g (15.32 mmol) of 3-[4-(benzyloxycarbonylamino-methyl)-phenoxy]-5-(4-cyano-phenoxy)-benzoic acid ethyl ester was hydrolysed using the procedure of Example 5(b) to afford 7.0 g of the required product. Percentage purity (LCMS): 91.6%, (M+1)=494.5+1.

g) [3-[4-(Benzyloxycarbonylamino-methyp-phenoxy]-5-(4-cyano-phenoxy)-phenyl]-carbamic Acid Tert-butyl Ester Using 7.0 g (14.1 mmol) of 3-[4-(benzyloxycarbonylamino-methyp-phenoxy]-5-(4-cyano-phenoxy)-benzoic acid and following the procedure of Example 105(c) afforded 3.5 g of the required product. Percentage purity (LCMS): 65.0%, (M+1)=565.6+1.

h) {4-[3-Amino-5-(4-cyano-phenoxy)-phenoxy]-benzyl}-carbamic Acid Benzyl Ester Using 1.0 g (1.76 mmol) of [3-[4-(benzyloxycarbonylamino-methyl)-phenoxy]-5-(4-cyano-phenoxy)-phenyl]-carbamic acid tert-butyl ester and following the procedure of Example 9(d) afforded 0.90 g of the required product. Percentage purity (LCMS): 89.2%, (M+1)=465.5±1.

i) {4-[3-[4-(Benzyloxycarbonylamino-methyp-phenoxy]-5-(4-cyano-phenoxy)-phenylcarbamoyl]-cyclohexyl}-carbamic Acid Tert-butyl Ester Using 0.9 g (1.93 mmol) of {4-[3-amino-5-(4-cyano-phenoxy)-phenoxy]-benzyl}7 carbamic acid benzyl ester and 0.47 g (1.93 mmol) of (4-amino-cyclohexyl)-carbamic acid tert-butyl ester, and following the procedure of Example 9(e) afforded 1.0 g of the required product. Percentage purity (LCMS): 91.0%, (M+1)=690.7±1.

j) (4-{3-[4-(Benzyloxycarbonylamino-methyp-phenoxy]-5-[4-(N-hydroxy-carbamimidoyl)-phenoxy]-phenylcarbamoyl}-cyclohexyl)-carbamic Acid Tert-butyl Ester {4-[3-[4-(Benzyloxycarbonylamino-methyp-phenoxy]-5-(4-cyano-phenoxy)-phenylcarbamoyl]-cyclohexyl}-carbamic acid tert-butyl ester 0.9 g (1.30 mmol) was subjected to form N-hydroxycarbamimidoyl using the procedure of Example 95(d) to afford 1.0 g of the required product. Percentage purity (LCMS): 74.4%, (M+1)=723.8+1.

k) (4-{3-[4-(Benzyloxycarbonylamino-methyp-phenoxy]-5-[4-(N-acetylhydroxy-carbamimidoyl)-phenoxy]-phenylcarbamoyl}-cyclohexyl)-carbamic acid tert-butyl ester (4-{3-[4-(Benzyloxycarbonylamino-methyl)-phenoxy]-5-[4-(N-hydroxy-carbamimidoyl)-phenoxy]-phenylcarbamoyl}-cyclohexyl)-carbamic acid tert-butyl ester 1.0 g (1.38 mmol) was acetylated using the procedure of Example 2(e) to afford 1.10 g of the required product. Percentage purity (LCMS): 78.2%, (M+1)=765.8+1.

l) {4-[3-(4-Aminomethyl-phenoxy)-5-(4-carbamimidoyl-phenoxy)-phenylcarbamoyl]-cyclohexyl}-carbamic Acid Tert-butyl Ester (4-{3-[4-(Benzyloxycarbonylamino-methyl)-phenoxy]-5-[4-(N-acetylhydroxy-carbamimidoyl)-phenoxy]-phenylcarbamoyl}-cyclohexyl)-carbamic acid tert-butyl ester 1.1 g (1.43 mmol) was reduced using the procedure of Example 2(f) to afford 0.8 g of the required product. Percentage purity (LCMS): 54.2%, (M+1)=573.2+1.

l) 4-Amino-cyclohexanecarboxylic acid[3-(4-aminomethyl-phenoxy)-5-(4-carbamimidoyl-phenoxy)-phenyl]-amide {4-[3-(4-Aminomethyl-phenoxy)-5-(4-carbamimidoyl-phenoxy)-phenylcarbamoyl]-cyclohexyl}-carbamic acid tert-butyl ester 0.80 g (1.39 mmol) was treated using the procedure of Example 9(d) to afford 0.50 g of the required product. Percentage purity (HPLC): 98.3%, (LCMS): 100.0%. $^1$H NMR (DMSO-d$_6$): δ 1.44 (4H, m), 1.82 (4H, m), 3.05 (2H, m), 6.51 (1H, s), 7.15 (6H, m), 7.50 (2H, d), 8.02 (5H, d), 8.45 (2H, m), 9.11 (4H, brs), 10.11 (1H, brs).

Example 117

4-Amino-cyclohexanecarboxylic acid[3-(2-amino-1H-1-benzoimidazol-5-yloxy)-5-(4-carbamimidoyl-phenoxy)-phenyl]-amide Intermediates (a) and (b) are the same as in Example 49.

c) [3-(4-Cyano-phenoxy)-5-hydroxy-phenyl]-carbamic Acid Tert-butyl Ester

Using 3-(4-cyano-phenoxy)-5-hydroxy-benzoic acid (1.4 g, 5.4 mmol) and following the procedure of Example 105(c)

afforded 1.0 g of the required product. Percentage purity (LCMS): 86.7%, (M+1)=326.3+1.

d) [3-(4-Cyano-phenoxy)-5-hydroxy-phenyl]-amine

Using [3-(4-cyano-phenoxy)-5-hydroxy-phenyl]-carbamic acid tert-butyl ester (1.0 g, 3.06 mmol) and following the procedure of Example 9(d) afforded 0.67 g of the required product. Percentage purity (LCMS): 92.5%, (M+1)=226.2+1.

e) {Trans-4-[3-(4-cyano-phenoxy)-5-hydroxy-phenylcarbamoyl]-cyclohexyl}-carbamic Acid Tert-butyl Ester Following the procedure of Example 9(e) Trans-4-tert-butoxycarbonylamino-cyclohexanecarboxylic acid 0.72 g (2.96 mmol) and [3-(4-cyano-phenoxy)-5-hydroxy-phenyl]-amine (0.67 g, 2.96 mmol) were used to afford 1.0 g of the required product. Percentage purity (LCMS): 73.5%, (M+1)=451.5+1.

f) {Trans-4-[3-(3-amino-4-nitro-phenoxy)-5-(4-cyano-phenoxy)-phenyl-carbamoyl]-cyclohexyl}-carbamic Acid Tert-butyl Ester Using {trans-4-[3-(4-cyano-phenoxy)-5-hydroxy-phenyl-carbamoyl]-cyclohexyl}-carbamic acid tert-butyl ester (1.5 g, 5.29 mmol) and 5-fluoro-2-nitro-phenylamine (0.91 g, 5.82 mmol) following the procedure of Example 42(b) afforded 1.6 g of the required product $^1$H NMR (DMSO-$d_6$): δ 1.45 (9H, s), 1.8 (4H, m), 2.5 (4H, m), 3.2 (1H, m), 6.48 (2H, m), 6.75 (1H, d), 7.24 (2H, m), 7.51 (4H, m), 7.78 (2H, d), 8.05 (1H, d), 8.38 (1H, d).

g) {Trans-4-[3-(4-cyano-phenoxy)-5-(3,4-diamino-phenoxy)-phenylcarbamoyl]-cyclohexyl}-carbamic Acid Tert-butyl Ester {Trans-4-[3-(3-amino-4-nitro-phenoxy)-5-(4-cyano-phenoxy)-phenyl-carbamoyl]-cyclohexyl]-carbamic acid tert-butyl ester (1.0 g, 1.7 mmol), zinc (1.11 g, 17.02 mmol) and ammoniumchloride (0.91 g, 17.02 mmol) were dissolved in 20 ml of methanol and stirred for 2 h at 60° C. After reaction completion contents were filtered through celite and filetrate was concentrated to afford 0.8 g of the required product. $^1$H NMR (DMSO-$d_6$): δ 1.45 (9H, s), 1.78 (4H, m), 2.45 (4H, m), 3.2 (1H, m), 4.42 (2H, s), 6.45 (2H, m), 6.5 (1H, d), 6.71 (2H, m), 7.15 (2H, d), 7.3 (2H, s), 7.8 (2H, d), 8.28 (1H, d).

h) {Trans-4-[3-(2-amino-1H-benzoimidazol-5-yloxy)-5-(4-cyano-phenoxy)-phenylcarbamoyl]-cyclohexyl}-carbamic Acid Tert-butyl Ester {Trans-4-[3-(4-cyano-phenoxy)-5-(3,4-diamino-phenoxy)-phenylcarbamoyl]-cyclohexyl}-carbamic acid tert-butyl ester (0.9 g, 1.61 mmol) and canogenbromide (0.25 g, 2.42 mmol) were dissolved in 10 ml of ethanol and stirred at 80° C. for 4 h. After reaction completion mixture was cooled to RT and concentrated under vacuo to afford 0.9 g of the required product. $^1$H NMR (DMSO-$d_6$): δ 1.4 (9H, s), 1.8 (4H, m), 2.5 (4H, m), 3.1 (1H, m), 3.8 (1H, m), 6.46 (1H, brs), 6.7 (1H, d), 6.95 (3H, m), 7.17 (5H, m), 7.4 (4H, m), 7.78 (2H, d), 8.4 (1H, d), 8.51 (2H, s), 12.4 (2H, brs).

i) (Trans-4-{3-(2-amino-1H-benzoimidazol-5-yloxy)-5-[4-(N-hydroxy-carbamimidoyl)-phenoxy]-phenylcarbamoyl}-cyclohexyl)-carbamic Acid Tert-butyl Ester {Trans-4-[3-(2-amino-1H-benzoimidazol-5-yloxy)-5-(4-cyano-phenoxy)-phenylcarbamoyl]-cyclohexyl}-carbamic acid tert-butyl ester 0.9 g (1.54 mmol) was subjected to form N-hydroxycarbamimidoyl using the procedure of Example 95(d) to afford 0.85 g of the required product. Percentage purity (LCMS): 100.0%, (M+1)=615.3+1.

j) {Trans-4-[3-(2-Amino-1H-benzoimidazol-5-yloxy)-5-(4-carbamimidoyl-phenoxy)-phenylcarbamoyl]-cyclohexyl}-carbamic Acid Tert-butyl Ester (Trans-4-{3-(2-amino-1H-benzoimidazol-5-yloxy)-5-[4-(N-hydroxy-carbamimidoyl)-phenoxy]-phenylcarbamoyl}-cyclohexyl)-carbamic acid tert-butyl ester 0.85 g (1.38 mmol) was reduced using the procedure of Example 2(f) to afford 0.7 g of the required product. Percentage purity (LCMS): 99.8%, (M+1)=599.2+1.

k) 4-Amino-cyclohexanecarboxylic acid[3-(2-amino-1H-benzoimidazol-5-yloxy)-5-(4-carbamimidoyl-phenoxy)-phenyl]-amide {4-[3-(2-Amino-1H-benzoimidazol-5-yloxy)-5-(4-carbamimidoyl-phenoxy)-phenylcarbamoyl]-cyclohexyl}-carbamic acid tert-butyl ester 0.7 g (0.45 mmol) was treated using the procedure of Example 9(d) to afford 0.23 g of the required product. Percentage purity (HPLC): 96.9%, (LCMS): 100%. $^1$H NMR (DMSO-$d_6$): δ 1.40 (4H, m), 1.82 (4H, m), 3.0 (1H, m), 3.67 (1H, m), 6.92 (2H, m), 7.12 (1H, s), 7.22 (2H, d), 7.38 (3H, m), 7.78 (5H, m), 8.40 (1H, d), 8.62 (2H, s), 9.25 (4H, brs).

Example 118

4-Amino-cyclohexanecarboxylic Acid[3,5-bis-(4-carbamimidoyl-benzyloxy)-phenyl]-amide Intermediates (a) and (b) are the same as in Example 75.

c) [3,5-Bis-(4-cyano-benzyloxy)-phenyl]-carbamic Acid Tert-butyl Ester

Using 3,5-bis-(4-cyano-benzyloxy)-benzoic acid (1.6 g, 4.2 mmol) and following the procedure of Example 105(c) afforded 0.65 g of the required product. $^1$H NMR (DMSO-$d_6$): δ 1.3 (9H, s), 5.2 (4H, s), 6.48 (1H, s), 6.9 (2H, d), 7.72 (2H, m), 7.81 (2H, d), 7.91 (4H, m) 9.52 (1H, s).

d) [3,5-Bis-(4-cyano-benzyloxy)-phenyl]-amine

Using [3,5-Bis-(4-cyano-benzyloxy)-phenyl]-carbamic acid tert-butyl ester (0.6 g, 1.32 mmol) and following the procedure of Example 9(d) afforded 0.37 g of the required product. $^1$H NMR (DMSO-$d_6$): δ 5.2 (4H, s), 6.48 (1H, s), 6.9 (2H, d), 7.72 (2H, m), 7.81 (2H, d), 7.91 (4H, m).

e) {4-[3,5-Bis-(4-cyano-benzyloxy)-phenylcarbamoyl]-cyclohexyl}-carbamic Acid tert-butyl Ester Following the procedure of Example 107(e) trans-4-tert-butoxycarbonylamino-cyclohexanecarboxylic acid 0.255 g (1.04 mmol) and [3,5-Bis-(4-cyano-benzyloxy)-phenyl]- amine (0.37 g, 1.04 mmol) were used to afford 0.39 g of the required product. Percentage purity (LCMS): 94.8%, (M−1)= 580.0-1.

f) (4-{3,5-Bis-[4-(N-hydroxycarbamimidoyl)-benzyloxy]-phenylcarbamoyl}-cyclohexyl)-carbamic Acid Tert-butyl Ester {4-[3,5-Bis-(4-cyano-benzyloxy)-phenylcarbamoyl]-cyclohexyl}-carbamic acid tert-butyl ester 0.39 g (0.672 mmol) was subjected to form N-hydroxycarbamimidoyl using the procedure of Example 95(d) to afford 0.4 g of the required product. Percentage purity (LCMS): 100.0%, (M+1)=646.2+1.

g) {4-[3,5-Bis-(4-carbamimidoyl-benzyloxy)-phenylcarbamoyl]-cyclohexyl}-carbamic Acid Tert-butyl Ester Acetic anhydride (0.36 ml, 3.72 mmol) was added to the solution of (4-{3,5-bis-[4-(N-hydroxycarbamimidoyl)-benzyloxy]-phenylcarbamoyl}-cyclohexyl)-carbamic acid tert-butyl ester (0.40 g, 0.62 mmol) in 10 ml of acetic acid and reaction mixture was stirred for 3 h. After completion of reaction, at RT zinc dust (0.4 g, 6.2 mmol) was added and resulting mixture was stirred over night. Recation mixture was filtered through celite and filtrate was concentrated to dryness. Product was washed with cold diethyl ether and dried to afford 0.52 g of the required product. Percentage purity (LCMS): 100.0%, (M−1)=615.2-1.

h) 4-Amino-cyclohexanecarboxylic acid[3,5-bis-(4-carbamimidoyl-benzyloxy)-phenyl]-amide {4-[3,5-Bis-(4-carbamimidoyl-benzyloxy)-phenylcarbamoyl]-cyclohexyl}-carbamic acid tert-butyl ester 0.52 g (0.846 mmol) was treated using the procedure of Example 9(d) to afford 0.3 g of the required product. Percentage purity (HPLC): 94.49%, (LCMS): 99.4%. $^1$H NMR (DMSO-$d_6$): δ 1.24 (4H, m), 1.41 (4H, m), 2.1 (1H, m), 2.31 (1H, m), 5.2 (4H, s), 6.71 (1H, s), 7.01 (3H, s), 7.90 (8H, dd), 9.11 (1H, s), 9.25 (8H, brs).

Example 119

4-Amino-cyclohexanecarboxylic acid[3,5-bis-(3-carbamimidoyl-benzyloxy)-phenyl]-amide Intermediates (a) and (b) are the same as in Example 77.

c) [3,5-Bis-(3-cyano-benzyloxy)-phenyl]-carbamic Acid Tert-butyl Ester

Using 3,5-bis-(3-cyano-benzyloxy)-benzoic acid (2.2 g, 5.7 mmol) and following the procedure of Example 105(c) afforded 0.85 g of the required product.

d) [3,5-Bis-(3-cyano-benzyloxy)-phenyl]-amine

Using [3,5-Bis-(3-cyano-benzyloxy)-phenyl]-carbamic acid tert-butyl ester (0.8 g, 1.76 mmol) and following the procedure of Example 9(d) afforded 0.6 g of the required product. Percentage purity (LCMS): 100.0%, (M+1)=355.0+1.

e) {4-[3,5-Bis-(3-cyano-benzyloxy)-phenylcarbamoyl]-cyclohexyl}-carbamic Acid Tert-butyl Ester Following the procedure of Example 107(e) trans-4-tert-butoxycarbonylamino-cyclohexanecarboxylic acid 0.41 g (1.68 mmol) and [3,5-Bis-(3-cyano-benzyloxy)-phenyl]-amine (0.6 g, 1.68 mmol) were used to afford 0.61 g of the required product. Percentage purity (LCMS): 79.8%, (M−1)= 580.0-1.

f) (4-{3,5-Bis-[3-(N-hydroxycarbamimidoyl)-benzyloxy]-phenylcarbamoyl}-cyclohexyl)-carbamic Acid Tert-butyl Ester {4-[3,5-Bis-(3-cyano-benzyloxy)-phenylcarbamoyl]-cyclohexyl}-carbamic acid tert-butyl ester 0.6 g (1.03 mmol) was subjected to form N-hydroxycarbamimidoyl using the procedure of Example 95(d) to afford 0.615 g of the required product. Percentage purity (LCMS): 100%, (M+1)=646.2+1.

g) {4-[3,5-Bis-(3-carbamimidoyl-benzyloxy)-phenylcarbamoyl]-cyclohexyl}-carbamic Acid Tert-butyl Ester Using (4-{3,5-bis-[3-(N-hydroxycarbamimidoyl)-benzyloxy]-phenylcarbamoyl}-cyclohexyl)-carbamic acid tert-butyl ester 0.61 g (0.94 mmol) and following the procedure of Example 118(g) afforded 0.6 g of the required product. Percentage purity (LCMS): 100%, (M−1)=614.-1.

h) 4-Amino-cyclohexanecarboxylic Acid[3,5-bis-(3-carbamimidoyl-benzyloxy)-phenyl]-amide {4-[3,5-Bis-(3-carbamimidoyl-benzyloxy)-phenylcarbamoyl]-cyclohexyl}-carbamic acid tert-butyl ester 0.6 g (0.97 mmol) was treated using the procedure of Example 9(d) to afford 0.3 g of the required product. Percentage purity (HPLC): 85.98%, (LCMS): 98.14%. $^1$H NMR (DMSO-$d_6$): δ 1.44 (4H, m), 1.82 (4H, m), 3.05 (1H, m), 3.31 (1H, m), 5.2 (4H, s), 6.71 (1H, s), 7.15 (2H, s), 7.88 (2H, m), 7.9 (8H, m), 9.11 (4H, brs), 9.25 (6H, brs), 10.01 (1H, s).

Example 120

Trans-4-methyl-cyclohexanecarboxylic Acid[3,5-bis-(4-carbamimidoyl-phenoxy)-phenyl]-amide

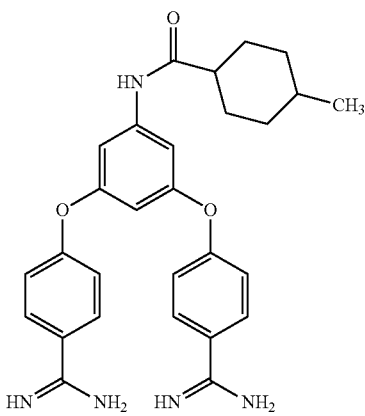 [SMILES: CC1CCC(C(=O)Nc2cc(Oc3ccc(C(=N)N)cc3)cc(Oc3ccc(C(=N)N)cc3)c2)CC1]

Intermediates (a) to (d) are the same as in Example 105.

e) Trans-4-methyl-cyclohexanecarboxylic Acid[3,5-bis-(4-cyano-phenoxy)-phenyl]-amide Following the procedure of Example 107(e) trans-4-methyl-cyclohexanecarboxylic acid 0.21 g (1.52 mmol) and

[3,5-bis-(4-cyano-phenoxy)-phenyl]-amine (0.50 g, 1.52 mmol) were used to afford 0.65 g of the required product. Percentage purity (LCMS): 85.4%, (M+1)=451.1+1.

f) Trans-4-methyl-cyclohexanecarboxylic Acid{3,5-bis-[4-(N-hydroxy-carbamimidoyl)-phenoxy]-phenyl}-amide Trans-4-methyl-cyclohexanecarboxylic acid[3,5-bis-(4-cyano-phenoxy)-phenyl]-amide 0.65 g (1.44 mmol) was subjected to form N-hydroxycarbamimidoyl using the procedure of Example 95(d) to afford 0.80 g of the required product. Percentage purity (LCMS): 82.7%, (M+1)=517.2+1.

g) Trans-4-methyl-cyclohexanecarboxylic acid{3,5-bis-[4-(N-acetylhydroxy-carbamimidoyl)-phenoxy]-phenyl}-amide Trans-4-methyl-cyclohexanecarboxylic acid{3,5-bis-[4-(N-hydroxy-carbamimidoyl)-phenoxy]-phenyl}-amide 0.80 g (1.54 mmol) was acetylated using the procedure of Example 2(e) to afford 1.00 g of the required product. Percentage purity (LCMS): 82.7%, (M+1)=601.2+1.

h) Trans-4-methyl-cyclohexanecarboxylic Acid[3,5-bis-(4-carbamimidoyl-phenoxy)-phenyl]-amide Trans-4-methyl-cyclohexanecarboxylic acid{3,5-bis-[4-(N-acetylhydroxy-carbamimidoyl)-phenoxy]-phenyl}-amide 1.00 g (1.66 mmol) was reduced using the procedure of Example 2(f) to afford 0.40 g of the required product. Percentage purity (HPLC): 98.4%, (LCMS): 98.2%. $^1$H NMR (DMSO-$d_6$): δ 0.9 (5H, m), 1.32 (3H, m), 1.7 (4H, m), 2.2 (1H, m), 3.05 (2H, m), 7.31 (6H, m), 7.92 (4H, d), 9.1 (4H, brs), 9.3 (4H, brs), 10.1 (1H, s).

Example 121

4-[3-[(4-Amino-cyclohexanecarbonyl)-amino]-5-(4-carbamimidoyl-phenoxy)-phenoxy]-benzamide Intermediates (a)-(e) are the same as in Example 117.

f) {Trans-4-[3-(4-cyano-phenoxy)-5-(4-formyl-phenoxy)-phenylcarbamoyl]-cyclohexyl}-carbamic Acid Tert-butyl Ester Following the procedure of Example 42(b) {trans-4-[3-(4-cyano-phenoxy)-5-hydroxy-phenylcarbamoyl]-cyclohexyl}-carbamic acid tert-butyl ester (1.0 g, 2.21 mmol) and 4-fluorobenzaldehyde (0.475 ml, 4.43 mmol) were used to afford 0.4 g of the required product. $^1$H NMR (DMSO-$d_6$): δ 1.11 (4H, m), 1.29 (9H, s), 1.8 (4H, m), 2.11 (1H, m), 3.15 (1H, m), 6.82 (1H, d), 7.34 (6H, m), 7.86 (2H, d), 7.92 (2H, d), 10.11 (1H, s).

g) 4-[3-[(Trans-4-tert-butoxycarbonylamino-cyclohexanecarbonyl)-amino]-5-(4-cyano-phenoxy)-phenoxy]-benzoic Acid Following the procedure of Example 92(e) {trans-4-[3-(4-cyano-phenoxy)-5-(4-formyl-phenoxy)-phenylcarbamoyl]-cyclohexyl}-carbamic acid tert-butyl ester (0.4 g, 0.72 mmol) was used to afford 0.15 g of the required product. NMR (DMSO-$d_6$): δ 1.21 (9H, s), 1.32 (4H, m), 1.8 (4H, m), 2.11 (1H, m), 2.62 (1H, m), 6.62 (1H, s), 6.81 (1H, m), 7.26 (5H, m), 7.92 (3H, dd), 10.1 (1H, s).

h) {Trans-4-[3-(4-carbamoyl-phenoxy)-5-(4-cyano-phenoxy)-phenylcarbamoyl]-cyclohexyl}-carbamic Acid Tert-butyl Ester Following the procedure of Example 94(f) 4-[3-[(trans-4-tert-butoxycarbonyl-amino-cyclohexanecarbonyl)-amino]-5-(4-cyano-phenoxy)-phenoxy]-benzoic acid (0.15 g, 0.26 mmol) was used to afford 0.12 g of the required product. Percentage purity (LCMS): 86.7%, (M+1)=570.2+1.

i) (Trans-4-{3-(4-carbamoyl-phenoxy)-5-[4-(N-hydroxycarbamimidoyl)-phenoxy]-phenylcarbamoyl}-cyclohexyl)-carbamic Acid Tert-butyl Ester {Trans-4-[3-(4-carbamoyl-phenoxy)-5-(4-cyano-phenoxy)-phenylcarbamoyl]-cyclohexyl}-carbamic acid tert-butyl ester 0.12 g (0.21 mmol) was subjected to form N-hydroxycarbamimidoyl using the procedure of Example 95(d) to afford 0.12 g of the required product. Percentage purity (LCMS): 55.5%, (M+1)=603.2+1.

j) (Trans-4-{3-(4-carbamoyl-phenoxy)-5-[4-(N-acetylhydroxycarbamimidoyl)-phenoxy]-phenylcarbamoyl}-cyclohexyl)-carbamic Acid Tert-butyl Ester (Trans-4-{3-(4-carbamoyl-phenoxy)-5-[4-(N-hydroxycarbamimidoyl)-phenoxy]-phenylcarbamoyl}-cyclohexyl)-carbamic acid tert-butyl ester 0.12 g (0.198 mmol) was acetylated using the procedure of Example 2(e) to afford 0.13 g of the required product. Percentage purity (LCMS): 50.0%, (M+1)=645+1.

k) {Trans-4-[3-(4-carbamimidoyl-phenoxy)-5-(4-carbamoyl-phenoxy)-phenyl-carbamoyl]-cyclohexyl}-carbamic Acid Tert-butyl Ester (Trans-4-{3-(4-carbamoyl-phenoxy)-5-[4-(N-acetylhydroxycarbamimidoyl)-phenoxy]-phenylcarbamoyl}-cyclohexyl)-carbamic acid tert-butyl ester 0.13 g (0.2 mmol) was reduced using the procedure of Example 2(f) to afford 0.1 g of the required product. Percentage purity (LCMS): 73.6%, (M+1)=587+1.

l) 4-[3-[(Trans-4-amino-cyclohexanecarbonyl)-amino]-5-(4-carbamimidoyl-phenoxy)-phenoxy]-benzamide {Trans-4-[3-(4-carbamimidoyl-phenoxy)-5-(4-carbamoyl-phenoxy)-phenyl-carbamoyl]-cyclohexyl}-carbamic acid tert-butyl ester 0.1 g (0.17 mmol) was treated using the procedure of Example 9(d) to afford 0.03 g of the required product. Percentage purity (HPLC): 97.1%, (LCMS): 100.0% (M+1). $^1$H NMR (DMSO-$d_6$): δ 1.44 (4H, m), 1.82 (4H, m), 2.2 (1H, t), 3.05 (1H, m), 6.71 (1H, s), 7.11 (2H, s), 7.30 (3H, m), 7.88 (7H, m), 9.1 (2H, brs), 9.25 (2H, brs), 10.1 (1H, s).

Example 122

3,5-Bis-(4-carbamimidoyl-phenoxy)-N-(1-cyclopropylmethyl-piperidin-4-yl)-benzamide Intermediates (a)-(d) are the same as in Example 32.

e) 3,5-Bis-(4-cyano-phenoxy)-N-(1-cyclopropylm-ethyl-piperidin-4-yl)-benzamide Following procedure of Example 11(e) 3,5-bis-(4-cyano-phenoxy)-N-piperidin-4-yl-benzamide 0.5 g (1.14 mmol) and bromomethyl-cyclopropane (0.231 g, 1.71 mmol) were used to afford 0.4 g of the required product. Percentage purity (LCMS): 45.0%, (M+1)=492.2+1 f) N-(1-Cyclopropylmethyl-piperidin-4-yl)-3,5-bis-[4-(N-hydroxycarbamimidoyl)-phenoxy]-benzamide 3,5-Bis-(4-cyano-phenoxy)-N-(1-cyclopropylmethyl-piperidin-4-yl)-benzamide 0.4 g (0.812 mmol) was subjected to form N-hydroxycarbamimidoyl using the procedure of Example 95(d) to afford 0.4 g of the required product. Percentage purity (LCMS): 100%, (M+1)=558+1.

g) N-(1-Cyclopropylmethyl-piperidin-4-yl)-3,5-bis-[4-(N-acetylhydroxy-carbamimidoyl)-phenoxy]-benzamide N-(1-Cyclopropylmethyl-piperidin-4-yl)-3,5-bis-[4-(N-hydroxycarbamimidoyl)-phenoxy]-benzamide 0.4 g (0.716 mmol) was acetylated using the procedure of Example 2(e) to afford 0.45 g of the required product. Percentage purity (LCMS): 29.1%, (M+1)=642.2+1.

h) 3,5-Bis-(4-carbamimidoyl-phenoxy)-N-(1-cyclopropylmethyl-piperidin-4-yl)-benzamide N-(1-Cyclopropylmethyl-piperidin-4-yl)-3,5-bis-[4-(N-acetylhydroxy-carbamimidoyl)-phenoxy]-benzamide 0.45 g (0.7 mmol) was reduced using the procedure of Example 2(f) to afford 0.25 g of the required product. Percentage purity (HPLC): 97.24%, (LCMS): 100%. $^1$H NMR (DMSO-$d_6$): δ 0.3 (2H, m), 0.6 (2H, d), 1.1 (1H, m), 1.82 (2H, m), 2.13 (3H, m), 3.05 (4H, m), 3.6 (2H, d), 7.15 (1H, m), 7.22 (2H, m), 7.40 (4H, d), 7.5 (2H, d), 7.9 (4H, d), 8.6 (1H, d), 9.21 (8H, brs), 9.6 (1H, brs).

Example 123

3,5-Bis-(4-carbamimidoyl-phenoxy)-N-[1-(2-hydroxy-ethyp-piperidin-4-yl]-benzamide Intermediates (a)-(d) are the same as in Example 32.

e) 3,5-Bis-(4-cyano-phenoxy)-N-[1-(2-hydroxy-ethyl)-piperidin-4-yl]-benzamide Following procedure of Example 11(e) 3,5-bis-(4-cyano-phenoxy)-N-piperidin-4-yl-benzamide 0.5 g (1.14 mmol) and 2-bromoethanol (0.214 g, 1.71 mmol) were used to afford 0.4 g of the required product. Percentage purity (LCMS): 76.2%, (M+1)=482+1.

f) 3,5-Bis-[4-(N-hydroxycarbamimidoyl)-phenoxy]-N-[1-(2-hydroxy-ethyl)-piperidin-4-yl]-benzamide 3,5-Bis-(4-cyano-phenoxy)-N-[1-(2-hydroxy-ethyl)-piperidin-4-yl]-benzamide 0.4 g (0.829 mmol) was subjected to form N-hydroxycarbamimidoyl using the procedure of Example 95(d) to afford 0.4 g of the required product. Percentage purity (LCMS): 100%, (M+1)=548.2+1.

g) 3,5-Bis-(4-carbamimidoyl-phenoxy)-N-[1-(2-hydroxy-ethyl)-piperidin-4-yl]-benzamide To a stirred solution of 3,5-bis-(4-carbamimidoyl-phenoxy)-N-[1-(2-hydroxy-ethyl)-piperidin-4-yl]-benzamide 0.35 g (0.638 mmol) in 15 ml of methanol, ammonium formate (201 mg, 3.192 mmol) followed by acetic acid (0.36 ml) were added. After 10 min stirring, under inert atmosphere of nitrogen Pd/C (102 mg, 0.957 mmol) was added and resulting mixture was further stirred for 5 h at 60° C. Reaction progress was monitored by TLC. Reaction mixture was cooled to RT and filtered through celite and washed with methanol (20 ml). Thus obtained filterate was concentrated under vacuo to afford 0.15 g of the required product. Percentage purity (HPLC): 95.4%, (LCMS): 100%. $^1$H NMR (DMSO-$d_6$): δ 1.82 (2H, m), 2.01 (2H, m), 3.2 (4H, m), 3.61 (4H, m), 4.01 (1H, m), 7.21 (1H, s), 7.35 (4H, d), 7.50 (2H, d), 7.91 (4H, d), 8.6 (1H, d), 9.2 (8H, brs), 9.4 (1H, brs).

Example 124

4-[3,5-Bis-(4-carbamimidoyl-phenoxy)-benzoylamino]-piperidine-1-carboxylic Acid Ethyl Ester Intermediates (a)-(d) are the same as in Example 32.

e) 4-[3,5-Bis-(4-cyano-phenoxy)-benzoylamino]-piperidine-1-carboxylic Acid Ethyl Ester Following procedure of Example 11(e) 3,5-bis-(4-cyano-phenoxy)-N-piperidin-4-yl-benzamide 0.5 g (1.14 mmol) and ethyl choroformate (0.186 g, 1.71 mmol) were used to afford 0.4 g of the required product. $^1$H NMR (DMSO-$d_6$): 81.21 (311, t), 1.42 (4H, m), 1.81 (3H, d), 2.92 (2H, m), 4.12 (2H, m), 7.26 (5H, d), 7.52 (2H, d), 7.92 (4H, d), 8.41 (1H, d).

f) 4-{3,5-Bis-[4-(N-hydroxycarbamimidoyl)-phenoxy]-benzoylamino}-piperidine-1-carboxylic Acid Ethyl Ester 4-[3,5-Bis-(4-cyano-phenoxy)-benzoylamino]-piperidine-1-carboxylic acid ethyl ester 0.4 g (0.784 mmol) was subjected to form N-hydroxycarbamimidoyl using the procedure of Example 95(d) to afford 0.40 g of the required product. Percentage purity (LCMS): 87.6%, (M+1)=576.2+1.

g) 3,5-Bis-(4-carbamimidoyl-phenoxy)-N-[1-(2-hydroxy-ethyl)-piperidin-4-yl]-benzamide 4-{3,5-Bis-[4-(N-hydroxycarbamimidoyl)-phenoxy]-benzoylamino}-piperidine-1-carboxylic acid ethyl ester 0.4 g (0.52 mmol) was subjected to reduction using the procedure of Example 123(g) to afford 0.2 g of the required product. Percentage purity (HPLC): 97.4%, (LCMS): 100%. $^1$H NMR (DMSO-$d_6$): δ 1.22 (3H, m), 1.41 (2H, m), 1.7 (2H, d), 2.81 (2H, brs), 4.1 (5H, q), 7.21 (1H, t), 7.35 (4H, d), 7.50 (2H, d), 7.9 (4H, d), 8.45 (1H, d), 9.2 (8H, brs).

Example 125

3,5-Bis-(4-carbamimidoyl-phenoxy)-N-cyclohexyl-benzamide

Intermediates (a) and (b) are the same as in Example 26.

c) 3,5-Bis-(4-cyano-phenoxy)-N-cyclohexyl-benzamide

Following the procedure of Example 9(e) 3,5-bis-(4-cyano-phenoxy)-benzoic acid 0.5 g (1.4 mmol) and cyclohexylamine (0.14 g, 1.4 mmol) were used to afford 0.61 g of the required product. Percentage purity (LCMS): 78.1%, (M+1)= 437.0+1.

d) N-Cyclohexyl-3,5-bis-[4-(N-hydroxycarbamimidoyl)-phenoxyl]-benzamide

Following the procedure of Example 95(d) 3,5-bis-(4-cyano-phenoxy)-N-cyclo-hexyl-benzamide 0.61 g (1.4 mmol) and other reagents were used to afford 0.65 g of the required product. Percentage purity (LCMS): 85.1.0%, (M+1)= 503.1+1.

e) N-Cyclohexyl-3,5-bis-[4-(N-acetylhydroxycarbamimidoyl)-phenoxy]-benzamide Following the procedure of Example 2(e) N-cyclohexyl-3,5-bis-[4-(N-hydroxy-carbamimidoyl)-phenoxy]-benzamide 0.65 g (1.29 mmol) was used to afford 0.76 g of the required product. Percentage purity (LCMS): 39.0%, (M+1)=587.2+1.

f) 3,5-Bis-(4-carbamimidoyl-phenoxy)-N-cyclohexyl-benzamide (4-{3,5-Bis-[4-(N-acetylhydroxycarbamimidoyl)-phenoxy]-benzoylamino}-cyclo-hexyl)-carbamic acid tert-butyl ester 0.76 g (1.29 mmol) was reduced using the procedure of Example 2(f) to afford 0.25 g of the required product. Percentage purity (HPLC): 95.01%, (LCMS): 100%. $^1$H NMR (DMSO-$d_6$): δ 1.22 (4H, m), 1.91 (6H, m), 3.11 (1H, t), 7.15 (1H, s), 7.2 (4H, d), 7.50 (2H, d), 7.78 (4H, d), 8.45 (1H, d), 9.21 (8H, brs).

Example 126

3,5-Bis-(4-carbamimidoyl-phenoxy)-N-cyclohexylmethyl-benzamide

Intermediates (a) and (b) are the same as in Example 26.

c) 3,5-Bis-(4-cyano-phenoxy)-N-cyclohexylmethyl-benzamide

Following the procedure of Example 9(e) 3,5-bis-(4-cyano-phenoxy)-benzoic acid 0.5 g (1.26 mmol) and cyclohexylmethylamine (0.143 g, 1.26 mmol) were used to afford 0.60 g of the required product. Percentage purity (LCMS): 97.6%, (M+1)=451.1+1.

d) N-Cyclohexylmethyl-3,5-bis-[4-(N-hydroxycarbamimidoyl)-phenoxy]-benzamide Following the procedure of Example 95(d) 3,5-bis-(4-cyano-phenoxy)-N-cyclo-hexylmethyl-benzamide 0.60 g (1.22 mmol) and other reagents were used to afford 0.65 g of the required product. Percentage purity (LCMS): 89.0%, (M+1)= 517.2+1.

e) N-Cyclohexylmethyl-3,5-bis-[4-(N-acetylhydroxycarbamimidoyl)-phenoxy]-benzamide Following the procedure of Example 2(e) N-cyclohexylmethyl-3,5-bis-[4-(N-hydroxycarbamimidoyl)-phenoxy]-benzamide 0.65 g (1.16 mmol) was used to afford 0.5 g of the required product. Percentage purity (LCMS): 72.0%, (M+1)= 601.2+1.

f) 3,5-Bis-(4-carbamimidoyl-phenoxy)-N-cyclohexylmethyl-benzamide

N-Cyclohexylmethyl-3,5-bis-[4-(N-acetylhydroxycarbamimidoyl)-phenoxy]-benzamide 0.5 g (0.78 mmol) was reduced using the procedure of Example 2(f) to afford 0.25 g of the required product. Percentage purity (HPLC) 98.9%, (LCMS): 100%. $^1$H NMR (DMSO-$d_6$): δ 0.8 (2H, t), 1.2 (3H, m), 1.62 (6H, d), 3.1 (2H, t), 7.15 (1H, s), 7.25 (4H, d), 7.50 (2H, d), 7.91 (4H, d), 8.61 (1H, t), 9.25 (4H, brs).

Example 127

3,5-Bis-(4-carbamimidoyl-phenoxy)-N-(4-methyl-cyclohexyl)-benzamide

Intermediates (a) and (b) are the same as in Example 26.

c) 3,5-Bis-(4-cyano-phenoxy)-N-(4-methyl-cyclohexyl)-benzamide

Following the procedure of Example 9(e) 3,5-bis-(4-cyano-phenoxy)-benzoic acid 0.5 g (1.26 mmol) and 4-methyl-cyclohexylamine (0.143 g, 1.26 mmol) were used to afford 0.6 g of the required product. Percentage purity (LCMS): 84.6%, (M+1)=451.1+1.

d) 3,5-Bis-[4-(N-hydroxycarbamimidoyl)-phenoxy]-N-(4-methyl-cyclohexyl)-benzamide Following the procedure of Example 95(d) 3,5-bis-(4-cyano-phenoxy)-N-(4-methyl-cyclohexyl)-benzamide 0.6 g (1.22 mmol) and other reagents were used to afford 0.65 g of the required product. Percentage purity (LCMS): 43.8%, (M+1)=517.2+1.

e) 3,5-Bis-[4-(N-acetylhydroxycarbamimidoyl)-phenoxy]-N-(4-methyl-cyclohexyl)-benzamide Following the procedure as in Example 2(e) 3,5-bis-[4-(N-hydroxycarbamimidoyl)-phenoxy]-N-(4-methyl-cyclohexyl)-benzamide 0.65 g (1.16 mmol) was used to afford 0.7 g of the required product. Percentage purity (LCMS): 75.2%, (M+1)=601.2+1.

f) 3,5-Bis-(4-carbamimidoyl-phenoxy)-N-(4-methyl-cyclohexyl)-benzamide 3,5-Bis-[4-(N-acetylhydroxycarbamimidoyl)-phenoxy]-N-(4-methyl-cyclohexyl)-benzamide 0.7 g (1.16 mmol) was reduced using the procedure of Example 2(f) to afford 0.25 g of required product. Percentage purity (HPLC): 97.7%, (LCMS): 97.1%. $^1$H NMR (DMSO-$d_6$): δ 0.9 (3H, d), 1.3 (4H, m), 1.52 (4H, m), 3.05 (1H, m), 3.61 (1H, m), 7.15 (1H, m), 7.42 (4H, d), 7.50 (2H, t), 7.91 (4H, d), 9.11 (4H, brs), 9.25 (4H, brs).

Example 128

N-(4-Amino-cyclohexyl)-3-(3-bromo-phenoxy)-5-(4-carbamimidoyl-phenoxy)-benzamide Intermediates (a) and (c) are the same as in Example 49.

d) {4-[3-(3-Bromo-phenoxy)-5-(4-cyano-phenoxy)-benzoylamino]-cyclohexyl}-carbamic Acid Tert-butyl Ester {4-[3-(4-Cyano-phenoxy)-5-hydroxy-benzoylamino]-cyclohexyl}-carbamic acid isopropyl ester (1.0 g, 2.2 mmol)

and copper acetate (0.4 g, 2.2 mmol), dissolved in 30 ml of dichloromethane, were charged in a 100 ml capacity seal-tube. 3-bromophenyl boronic acid (0.667 g, 3.32 mmol), 4 Å molecular sieves (3.0 g) and 0.438 g (5.53 mmol) of pyridine, in 20 ml of dichloromethane, was added to the reaction mixture in a sealed-tube and reaction mixture was stirred at RT for 20 h. After reaction completion 2.0 g of silica-gel was added and the mixture was filtered. Thus obtained filterate was concentrated under reduced pressure and subjected to column chromatography to afford 0.3 g of the required product. Percentage purity (LCMS): 86.0%, (M+1)=605.1+1.

e) (4-{3-(3-Bromo-phenoxy)-5-[4-(N-hydroxycarbamimidoyl)-phenoxy]-benzoyl-amino}-cyclohexyl)-carbamic acid tert-butyl ester Following the procedure of Example 95(d) {4-[3-(3-bromo-phenoxy)-5-(4-cyano-phenoxy)-benzoylamino]-cyclohexyl}-carbamic acid tert-butyl ester 0.3 g (0.49 mmol) and other reagents were used to afford 0.30 g of the required product. Percentage purity (LCMS): 72.0%, (M+1)=581.8+1 (Boc acid).

f) (4-{3-(3-Bromo-phenoxy)-5-[4-(N-acetylhydroxycarbamimidoyl)-phenoxy]-benzoylamino}-cyclohexyl)-carbamic Acid Tert-butyl Ester Following the procedure of Example 2(e) (4-{3-(3-bromo-phenoxy)-5-[4-(N-hydroxycarbamimidoyl)-phenoxy]-benzoylamino}-cyclohexyl)-carbamic acid tert-butyl ester 0.30 g (4.69 mmol) was used to afford 0.31 g of the required product. Percentage purity (LCMS): 71.0%, (M+1)=580.1+1 (de-Boc).

g) {4-[3-(3-Bromo-phenoxy)-5-(4-carbamimidoyl-phenoxy)-benzoylamino]-cyclohexyl}-carbamic Acid Tert-butyl Ester {4-[3-{4-[(acetyl-hydroxy-amino)-imino-methyl]-phenoxy}-5-(3-bromo-phenoxy)-benzoylamino]-cyclohexyl}-carbamic acid tert-butyl ester 0.31 g (4.55 mmol) was reduced using the procedure of Example 2(f) to afford 0.25 g of the required product. Percentage purity (LCMS): 60.0%, (M+1)=623.9+1 h) {4-[3-(3-Bromo-phenoxy)-5-(4-carbamimidoyl-phenoxy)-benzoylamino]-cyclohexyl}-carbamic Acid Tert-butyl Ester {4-[3-(3-Bromo-phenoxy)-5-(4-carbamimidoyl-phenoxy)-benzoylamino]-cyclo-hexyl}-carbamic acid tert-butyl ester 0.25 g (4.01 mmol) was treated using the procedure of Example 9(d) to afford 0.1 g of the required product. Percentage purity (HPLC): 96.2%, (LCMS): 97.8%. $^1$H NMR (DMSO-$d_6$): δ1.41 (4H, d), 1.9 (4H, m), 3.05 (1H, m), 7.15 (1H, m), 7.21 (1H, m), 7.42 (4H, d), 7.91 (5H, d), 8.5 (1H, d), 9.11 (2H, brs), 9.25 (2H, brs).

Example 129

N-(4-amino-cyclohexyl)-3-(4-bromo-phenoxy)-5-(4-carbamimidoyl-phenoxy)-benzamide Intermediates (a) and (c) are the same as in Example 49.

d) {4-[3-(4-Broino-phenoxy)-5-(4-cyano-phenoxy)-benzoylamino]-cyclohexyl}-carbamic Acid Tert-butyl Ester Following the procedure of Example 128(c) {4-[3-(4-cyano-phenoxy)-5-hydroxy-benzoylamino]-cyclohexyl}-carbamic acid tert-butyl ester (1.0 g, 2.21 mmol) and 4-bromo phenyl boronic acid (0.67 g, 3.32 mmol) were used to afford 0.32 g of the required product. Percentage purity (LCMS): 55.7%, (M+1)=605.1+1 (de-Boc; −100).

e) (4-{3-(4-Bromo-phenoxy)-5-[4-(N-hydroxycarbamimidoyl)-phenoxy]-benzoylamino}-cyclohexyl)-carbamic Acid Tert-butyl Ester Following the procedure of Example 95(d) 3{4-[3-(4-Bromo-phenoxy)-5-(4-cyano-phenoxy)-benzoylamino]-cyclohexyl}-carbamic acid tert-butyl ester 0.32 g (0.52 mmol) and other reagents were used to afford 0.30 g of the required product. Percentage purity (LCMS): 37.5%, (M+1)=640.1+1.

f) (4-{3-(4-Bromo-phenoxy)-5-[4-(N-acetylhydroxycarbamimidoyl)-phenoxy]-benzoylamino}-cyclohexyl)-carbamic Acid Tert-butyl Ester Following the procedure as in Example 2(e) (4-{3-(4-bromo-phenoxy)-5-[4-(N-hydroxycarbamimidoyl)-phenoxy]-benzoylamino}-cyclohexyl)-carbamic acid tert-butyl ester 0.30 g (4.69 mmol) was used to afford 0.31 g of the required product. Percentage purity (LCMS): 38.6%, (M+1)=584+1 (de-Boc; −100).

g) {4-[3-(4-Bromo-phenoxy)-5-(4-carbamimidoyl-phenoxy)-benzoylamino]-cyclohexyl}-carbamic Acid Tert-butyl Ester {4-[3-{4-[(Acetyl-hydroxy-amino)-imino-methyl]-phenoxy}-5-(4-bromo-phenoxy)-benzoylamino]-cyclohexyl}-carbamic acid tert-butyl ester 0.31 g (4.55 mmol) was reduced using the procedure of Example 2(f) to afford 0.25 g of the required product. Percentage purity (LCMS): 22.8%, (M+1)=522.1+1 (de-Boc; −100).

h) N-(4-amino-cyclohexyl)-3-(4-bromo-phenoxy)-5-(4-carbamimidoyl-phenoxy)-benzamide {4-[3-(4-Bromo-phenoxy)-5-(4-carbamimidoyl-phenoxy)-benzoylamino]-cyclo-hexyl}-carbamic acid tert-butyl ester 0.1 g (4.01 mmol) was treated using the procedure of Example 9(d) to afford 0.1 g of the required product. Percentage purity (HPLC): 93.6%, (LCMS): 100%. $^1$H NMR (DMSO-$d_6$): δ 1.41 (4H, d), 1.9 (4H, m), 3.05 (1H, m), 3.61 (1H, m), 7.15 (1H, m), 7.21 (1H, m), 7.42 (1H, d), 7.6 (1H, d), 7.91 (4H, d), 8.5 (1H, d), 9.11 (2H, brs), 9.25 (2H, brs).

ABBREVIATIONS

DMF—N,N-dimethylformamide
THF—Tetrahydrofuran
TEA—Triethyl Amine
EDC—1-ethyl-3-(3-dimethylaminopropyl)carbodiimide hydrochloride
HOBT—hydroxybenzotriazole
DIPEA—N,N-diisopropylethylamine
PyBop—Benzotriazol-1-yl-oxytripyrrolidinophosphonium hexafluorophosphate
$Na_2CO_3$—Sodium carbonate
RT—Room temperature

The invention claimed is:
1. A compound of formula (I)

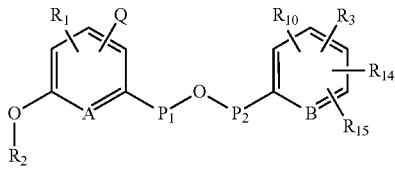

wherein
$P_1$ is a bond; $P_2$ is a bond or $C_{1-3}$ alkyl;
A is CH;
B is CH or N;
$R_1$ is —NH—$SO_2$—$ZR_9R_{13}$, —$NR_4$—CO—$ZR_9R_{13}$, —CO—$NR_7R_8$, —CO—O—$ZR_9R_{13}$, —CO—$NR_4$—$R^X$—$ZR_9R_{13}$, or a group of formula

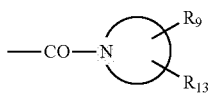

wherein the ring portion in formula (II) is a 5-12 membered saturated, partially saturated, or aromatic ring, which may be monocyclic or bicyclic, and which contains 0, 1, 2, or 3 heteroatoms selected from N, O, S, or combinations thereof;
$R_3$ is —C($NR_{17}$)$NH_2$ or amino $C_{1-7}$ alkyl;
$R_{10}$, $R_{14}$, and $R_{15}$ are independently hydrogen, halogen, hydroxy, $C_{1-7}$ alkyl, halogen $C_{1-7}$ alkyl, or —C($NR_{17}$)$NH_2$;
Q is hydrogen or halogen;
$R_4$ is hydrogen or $C_{1-7}$ alkyl;
Z is a 5-12 membered saturated, partially saturated, or aromatic ring, wherein said ring is monocyclic or bicyclic, and which contains 0, 1, 2, or 3 heteroatoms selected from N, O, S, or combinations thereof;
$R_9$ and $R_{13}$ are independently hydrogen, halogen, hydroxy, carboxy, $C_{1-7}$ alkyl, carboxy $C_{1-7}$ alkyl, hydroxy $C_{1-7}$ alkyl, $C_{1-7}$ alkoxycarbonyl, $R^A NH_2$, or —COR$^B$ $NH_2$;
$R^A$, $R^B$, and $R^X$ are independently a bond or $C_{1-7}$ alkyl;
$R_7$ and $R_8$ are independently hydrogen, amino $C_{1-7}$ alkyl, carboxy $C_{1-7}$ alkyl, or $C_{1-7}$ alkyl,
with a proviso that $R_7$ and $R_8$ are not simultaneously hydrogen;
$R_2$ is $C_{1-7}$ alkyl, amino $C_{1-7}$ alkyl, carboxy $C_{1-7}$ alkyl, $C_{1-7}$ alkoxycarbonyl $C_{1-7}$ alkyl, $C_{1-7}$ alkylamino, carboxy $C_{1-7}$ alkylamino, $R^D C(NR_{17})NH_2$, or a group of formula (III)

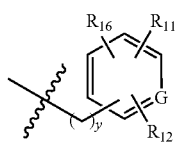

y=0-2; $R^D$ is a bond or $C_{1-7}$ alkyl; G is CH or N;
$R_{11}$ is hydrogen, halogen, amino, carboxy, amino $C_{1-7}$ alkyl, $C_{1-7}$ alkoxycarbonyl, halogen $C_{1-7}$ alkoxy, —C($NR_{17}$)$NH_2$, —NHCOR$^G NH_2$, R$^J$NHCOOR$^U$, or —CONR$_{19}$R$_{20}$;

$R^G$ is $C_{1-7}$ alkyl; $R^J$ is a bond or $C_{1-7}$ alkyl; $R^U$ is hydrogen or $C_{1-7}$ alkyl;
$R_{12}$ and $R_{16}$ are independently hydrogen, halogen or $C_{1-7}$ alkyl;
or $R_{12}$ and $R_{16}$ form, together with the carbon atoms to which they are attached, a 5 or 6 membered saturated, partially saturated, or aromatic ring, which contains 0, 1, 2, or 3 heteroatoms selected from N, O, S, or combinations thereof, wherein said ring is substituted or unsubstituted;
$R_{17}$ is hydrogen, —OH, $C_{1-7}$ alkoxy, —O(CO)OR$_{18}$, or —(CO)OR$_{18}$;
$R_{18}$ is $C_{1-7}$ alkyl;
$R_{19}$ and $R_{20}$ are independently hydrogen, $C_{1-7}$ alkyl, or $C_{1-7}$ alkoxy;
or a pharmaceutically acceptable salt or ester thereof.
2. The compound according to claim 1, wherein B is CH.
3. The compound according to claim 1, wherein $R_3$ is —C($NR_{17}$)$NH_2$ and $R_{10}$, $R_{14}$, and $R_{15}$ are hydrogen.
4. The compound according to claim 1, wherein $R_2$ is a group of formula (III), wherein G is CH, y is 0-1, $R_{11}$ is —C($NR_{17}$)$NH_2$ or amino $C_{1-7}$ alkyl, and $R_{12}$ and $R_{16}$ are hydrogen.
5. The compound according to claim 1, wherein $P_2$ is a bond.
6. The compound according to claim 1, wherein $R_1$ is —$NR_4$—CO—$ZR_9R_{13}$, —CO—O—$ZR_9R_{13}$, or —CO—$NR_4$—$R^X$—$ZR_9R_{13}$.
7. The compound according to claim 6, wherein Z is a 6 or 10 membered saturated, partially saturated, or aromatic ring.
8. The compound according to claim 7, wherein Z is cyclohexyl, piperidinyl, phenyl, naphthyl, or quinolinyl.
9. The compound according to claim 8, wherein Z is cyclohexyl or piperidinyl, $R_4$ is hydrogen, $R^X$ is a bond, $R_9$ is $R^A NH_2$, and $R_{13}$ is hydrogen.
10. A pharmaceutical composition comprising a compound of formula (I)

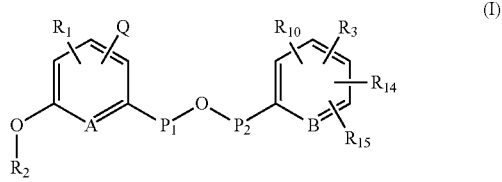

wherein
$P_1$ is a bond; $P_2$ is a bond or $C_{1-3}$ alkyl;
A is CH;
B is CH or N;
$R_1$ is —NH—$SO_2$—$ZR_9R_{13}$, —$NR_4$—CO—$ZR_9R_{13}$, —CO—$NR_7R_8$, —CO—O—$ZR_9R_{13}$, —CO—$NR_4$—$R^X$—$ZR_9R_{13}$, or a group of formula

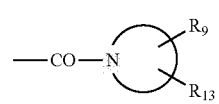

wherein the ring portion in formula (II) is a 5-12 membered saturated, partially saturated, or aromatic ring, which may be monocyclic or bicyclic, and which contains 0, 1, 2, or 3 heteroatoms selected from N, O, S, or combinations thereof;

$R_3$ is —C(NR$_{17}$)NH$_2$ or amino C$_{1-7}$ alkyl;

$R_{10}$, $R_{14}$, and $R_{15}$ are independently hydrogen, halogen, hydroxy, C$_{1-7}$ alkyl, halogen C$_{1-7}$ alkyl, or —C(NR$_{17}$)NH$_2$;

Q is hydrogen or halogen;

$R_4$ is hydrogen or C$_{1-7}$ alkyl;

Z is a 5-12 membered saturated, partially saturated, or aromatic ring, wherein said ring is monocyclic or bicyclic, and which contains 0, 1, 2, or 3 heteroatoms selected from N, O, S, or combinations thereof;

$R_9$ and $R_{13}$ are independently hydrogen, halogen, hydroxy, carboxy, C$_{1-7}$ alkyl, carboxy C$_{1-7}$ alkyl, hydroxy C$_{1-7}$ alkyl, C$_{1-7}$ alkoxycarbonyl, R$^A$NH$_2$, or —COR$^B$NH$_2$;

$R^A$, $R^B$, and $R^X$ are independently a bond or C$_{1-7}$ alkyl;

$R_7$ and $R_8$ are independently hydrogen, amino C$_{1-7}$ alkyl, carboxy C$_{1-7}$ alkyl, or C$_{1-7}$ alkyl, with a proviso that $R_7$ and $R_8$ are not simultaneously hydrogen;

$R_2$ is C$_{1-7}$ alkyl, amino C$_{1-7}$ alkyl, carboxy C$_{1-7}$ alkyl, C$_{1-7}$ alkoxycarbonyl C$_{1-7}$ alkyl, C$_{1-7}$ alkylamino, carboxy C$_{1-7}$ alkylamino, R$^O$C(NR$_{17}$)NH$_2$, or a group of formula (III)

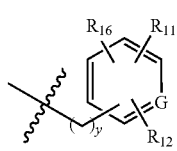

y=0-2; R$^D$ is a bond or C$_{1-7}$ alkyl; G is CH or N;

$R_{11}$ is hydrogen, halogen, amino, carboxy, amino C$_{1-7}$ alkyl, C$_{1-7}$ alkoxycarbonyl, halogen C$_{1-7}$ alkoxy, —C(NR$_{17}$)NH$_2$, —NHCOR$^G$NH$_2$, R$^J$NHCOOR$^U$, or —CONR$_{19}$R$_{20}$;

$R^G$ is C$_{1-7}$ alkyl; R$^J$ is a bond or C$_{1-7}$ alkyl; R$^U$ is hydrogen or C$_{1-7}$alkyl;

$R_{12}$ and $R_{16}$ are independently hydrogen, halogen or C$_{1-7}$ alkyl;

or $R_{12}$ and $R_{16}$ form, together with the carbon atoms to which they are attached, a 5 or 6 membered saturated, partially saturated, or aromatic ring, which contains 0, 1, 2, or 3 heteroatoms selected from N, O, S, or combinations thereof, wherein said ring is substituted or unsubstituted;

$R_{17}$ is hydrogen, —OH, C$_{1-7}$ alkoxy, —O(CO)OR$_{18}$, or —(CO)OR$_{18}$;

$R_{18}$ is C$_{1-7}$ alkyl;

$R_{19}$ and $R_{20}$ are independently hydrogen, C$_{1-7}$ alkyl, or C$_{1-7}$ alkoxy;

or a pharmaceutically acceptable salt or ester thereof together with a pharmaceutically acceptable carrier.

11. A method for the treatment of cancer, comprising administering to a subject in need thereof a therapeutically effective amount of a compound of formula (I)

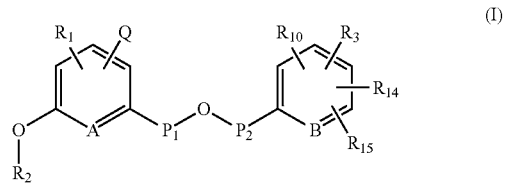

wherein $P_1$ is a bond; $P_2$ is a bond or C$_{1-3}$ alkyl;

A is CH;

B is CH or N;

$R_1$ is hydrogen, amino, —NH—SO$_2$—ZR$_9$R$_{13}$, —NR$_4$—CO—ZR$_9$R$_{13}$, —CO—NR$_7$R$_8$, —CO—O—ZR$_9$R$_{13}$, —CO—NR$_4$—R$^X$—ZR$_9$R$_{13}$, or a group of formula

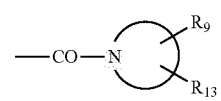

wherein the ring portion in formula (II) is a 5-12 membered saturated, partially saturated, or aromatic ring, which may be monocyclic or bicyclic, and which contains 0, 1, 2, or 3 heteroatoms selected from N, O, S, or combinations thereof;

$R_3$ is —C(NR$_{17}$)NH$_2$ or amino C$_{1-7}$ alkyl;

$R_{10}$, $R_{14}$, and $R_{15}$ are independently hydrogen, halogen, hydroxy, C$_{1-7}$ alkyl, halogen C$_{1-7}$ alkyl, or —C(NR$_{17}$)NH$_2$;

Q is hydrogen or halogen;

$R_4$ is hydrogen or C$_{1-7}$ alkyl;

Z is a 5-12 membered saturated, partially saturated, or aromatic ring, wherein said ring is monocyclic or bicyclic, and which contains 0, 1, 2, or 3 heteroatoms selected from N, O, S, or combinations thereof;

$R_9$ and $R_{13}$ are independently hydrogen, halogen, hydroxy, carboxy, C$_{1-7}$ alkyl, carboxy C$_{1-7}$ alkyl, hydroxy C$_{1-7}$ alkyl, C$_{1-7}$ alkoxycarbonyl, R$^A$NH$_2$, or —COR$^B$NH$_2$;

$R^A$, $R^B$, and $R^X$ are independently a bond or C$_{1-7}$ alkyl;

$R_7$ and $R_8$ are independently hydrogen, amino C$_{1-7}$ alkyl, carboxy C$_{1-7}$ alkyl, or C$_{1-7}$ alkyl, with a proviso that $R_7$ and $R_8$ are not simultaneously hydrogen;

$R_2$ is C$_{1-7}$ alkyl, amino C$_{1-7}$ alkyl, carboxy C$_{1-7}$ alkyl, C$_{1-7}$ alkoxycarbonyl C$_{1-7}$ alkyl, C$_{1-7}$ alkylamino, carboxy C$_{1-7}$ alkylamino, R$^D$C(NR$_{17}$)NH$_2$, or a group of formula (III)

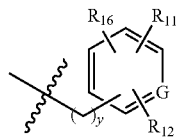

y=0-2; R$^D$ is a bond or C$_{1-7}$ alkyl; G is CH or N;

$R_{11}$ is hydrogen, halogen, amino, carboxy, amino C$_{1-7}$ alkyl, C$_{1-7}$ alkoxycarbonyl, halogen C$_{1-7}$ alkoxy, —C(NR$_{17}$)NH$_2$, —NHCOR$^G$NH$_2$, R$^J$NHCOOR$^U$, or —CONR$_{19}$R$_{20}$;

$R^G$ is $C_{1-7}$ alkyl; $R^J$ is a bond or $C_{1-7}$ alkyl; $R^U$ is hydrogen or $C_{1-7}$ alkyl;

$R_{12}$ and $R_{16}$ are independently hydrogen, halogen or $C_{1-7}$ alkyl;

or $R_{12}$ and $R_{16}$ form, together with the carbon atoms to which they are attached, a 5 or 6 membered saturated, partially saturated, or aromatic ring, which contains 0, 1, 2, or 3 heteroatoms selected from N, O, S, or combinations thereof, wherein said ring is substituted or unsubstituted;

$R_{17}$ is hydrogen, —OH, $C_{1-7}$ alkoxy, —O(CO)OR$_{18}$, or —(CO)OR$_{18}$;

$R_{18}$ is $C_{1-7}$ alkyl;

$R_{19}$ and $R_{20}$ are independently hydrogen, $C_{1-7}$ alkyl, or $C_{1-7}$ alkoxy;

or a pharmaceutically acceptable salt or ester thereof.

* * * * *

UNITED STATES PATENT AND TRADEMARK OFFICE
CERTIFICATE OF CORRECTION

PATENT NO. : 8,722,930 B2  
APPLICATION NO. : 13/321078  
DATED : May 13, 2014  
INVENTOR(S) : Rajeev Goswami et al.

Page 1 of 1

It is certified that error appears in the above-identified patent and that said Letters Patent is hereby corrected as shown below:

In the Claims

Claim 1, col. 134, line 14, "or$C_{1-7}$" should read as --or $C_{1-7}$--.

Signed and Sealed this  
Twelfth Day of August, 2014

Michelle K. Lee  
*Deputy Director of the United States Patent and Trademark Office*